(12) United States Patent
Audia et al.

(10) Patent No.: US 6,528,505 B1
(45) Date of Patent: Mar. 4, 2003

(54) CYCLIC AMINO ACID COMPOUNDS PHARMACEUTICAL COMPOSITIONS COMPRISING SAME AND METHODS FOR INHIBITING β-AMYLOID PEPTIDE RELEASE AND/OR ITS SYNTHESIS BY USE OF SUCH COMPOUNDS

(75) Inventors: James E. Audia, Indianapolis, IN (US); Bruce A. Dressman, Indianapolis, IN (US); Qing Shi, Carmel, IN (US)

(73) Assignees: Elan Pharmaceuticals, Inc., South San Francisco, CA (US); Eli Lilly & Company, Indianapolis, IN (US)

( * ) Notice: Subject to any disclaimer, the term of this patent is extended or adjusted under 35 U.S.C. 154(b) by 0 days.

(21) Appl. No.: 09/338,180

(22) Filed: Jun. 22, 1999

Related U.S. Application Data

(60) Provisional application No. 60/160,067, filed on Jun. 22, 1998, and provisional application No. 60/155,238, filed on Sep. 30, 1998.

(51) Int. Cl.⁷ .................. C07D 223/14; C07D 243/06; C07D 243/10; C07D 243/12; A61K 31/55

(52) U.S. Cl. ..................... 514/212.04; 514/212.07; 540/522; 540/523

(58) Field of Search ................ 540/522, 523; 514/212.04, 212.07

(56) References Cited

U.S. PATENT DOCUMENTS

| | | | |
|---|---|---|---|
| 3,598,859 A | 8/1971 | Yates et al. ................ 260/471 |
| 3,657,341 A | 4/1972 | Thorne ........................ 260/558 |
| 4,080,449 A | 3/1978 | Croisier et al. ............ 424/244 |
| 4,410,520 A | 10/1983 | Watthey .................... 424/244 |
| 4,473,575 A | 9/1984 | Watthey .................... 424/263 |
| 4,477,464 A | 10/1984 | Slade et al. ................. 424/275 |
| 4,666,829 A | 5/1987 | Glenner et al. ............... 435/6 |
| 4,977,168 A | 12/1990 | Bernat et al. ............... 514/330 |
| 5,015,639 A | 5/1991 | Berger et al. ............... 514/213 |
| 5,206,235 A | 4/1993 | Fisher et al. ............... 514/213 |
| 5,238,932 A | 8/1993 | Flynn et al. ................ 514/214 |
| 5,247,080 A | 9/1993 | Berger et al. ............... 540/523 |
| 5,283,241 A | 2/1994 | Bochis et al. ............... 514/183 |
| 5,284,841 A | 2/1994 | Chu et al. ................... 514/183 |
| 5,324,726 A | 6/1994 | Bock et al. .................. 514/221 |
| 5,360,802 A | 11/1994 | Chambers et al. .......... 514/221 |
| 5,420,271 A | 5/1995 | Warshawsky et al. ...... 540/521 |
| 5,478,857 A | 12/1995 | Clemens et al. ............ 514/381 |
| 5,486,541 A | 1/1996 | Sterling et al. ............. 514/657 |
| 5,502,048 A | 3/1996 | Chapdelaire et al. ....... 514/213 |
| 5,519,061 A | 5/1996 | Youdim et al. ............. 514/647 |
| 5,532,415 A | 7/1996 | Youdim et al. ............. 564/308 |
| 5,556,969 A | 9/1996 | Chambers et al. .......... 540/509 |
| 5,633,251 A | 5/1997 | Claremon et al. .......... 514/221 |
| 5,656,626 A | 8/1997 | Chapdelaine et al. ....... 514/213 |
| 5,658,901 A | 8/1997 | Claremon et al. .......... 514/221 |
| 5,672,598 A | 9/1997 | De et al. .................... 514/212 |
| 5,712,397 A | 1/1998 | Esser et al. ................... 546/90 |
| 5,770,573 A | 6/1998 | Arrhenius et al. ............ 514/18 |

FOREIGN PATENT DOCUMENTS

| | | |
|---|---|---|
| EP | 0 061 187 | 9/1982 |
| EP | 0 167 919 | 1/1986 |
| EP | 0 284 256 | 9/1988 |
| EP | 0 349 949 | 1/1990 |
| EP | 0 376 849 | 7/1990 |
| EP | 0 434 360 | 6/1991 |
| EP | 0 434 364 | 6/1991 |
| EP | 0 434 369 | 6/1991 |
| EP | 0 490 590 | 6/1992 |
| EP | 0 514 133 | 11/1992 |
| EP | 0 523 845 | 1/1993 |
| EP | 0 549 039 | 6/1993 |
| EP | 0 647 632 | 4/1995 |
| EP | 0 652 009 | 8/1995 |
| EP | 0 667 344 | 8/1995 |
| EP | 0 677 517 | 10/1995 |
| EP | 0 732 399 | 9/1996 |
| EP | 0 778 266 | 11/1997 |
| GB | 1 519 495 | 7/1978 |
| GB | 1 573 931 | 8/1980 |
| GB | 2 272 439 | 5/1994 |
| GB | 2 290 788 | 1/1996 |
| JP | 06145148 | 5/1994 |
| JP | 04210967 | 8/1994 |
| JP | 07304770 | 11/1995 |
| JP | 10072444 | 3/1998 |
| WO | 92/01683 | 2/1992 |
| WO | 92/16524 | 10/1992 |
| WO | 93/19052 | 9/1993 |
| WO | 93/19063 | 9/1993 |
| WO | 94/04531 | 3/1994 |
| WO | 94/05693 | 3/1994 |
| WO | 94/07486 | 4/1994 |
| WO | 94/10569 | 5/1994 |

(List continued on next page.)

OTHER PUBLICATIONS

Aquino, et al. "Discovery of 1,5–Benzodiazepines with Peripheral Cholecystokinin (CCK–A) Receptor Agonist Activity. 1. Optimization of the Agonist Trigger." *J. Med. Chem.* 39: 562–569 (1996).

Bock, et al. "Selective Non–Peptide Ligands for an Accommodating Peptide Receptor. Imidazobenzodiazepines as Potent Cholecystokinin Type B Receptor Antagonists." *Bioorg. and Med. Chem. Lets.* 2(9):987–998 (1994).

Bock, et al. "Synthesis and Resolution of 3–Amino–1, 3–dihydro–5–phenyl–2H–1,4–benzodiazepine–2–ones." *J. Org. Chem.* 52:3232–3239 (1987).

(List continued on next page.)

*Primary Examiner*—Bruck Kifle
(74) *Attorney, Agent, or Firm*—Burns, Doane, Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis as well as methods for treating Alzheimer's disease both prophylactically and therapeutically with such pharmaceutical compositions.

57 Claims, No Drawings

FOREIGN PATENT DOCUMENTS

| WO | 95/03289 | 2/1995 |
|---|---|---|
| WO | 95/03290 | 2/1995 |
| WO | 95/09838 | 4/1995 |
| WO | 95/14671 | 6/1995 |
| WO | 95/21840 | 8/1995 |
| WO | 95/23810 | 9/1995 |
| WO | 95/25118 | 9/1995 |
| WO | 95/32191 | 11/1995 |
| WO | 96/05839 | 2/1996 |
| WO | 96/16981 | 6/1996 |
| WO | 96/20725 | 7/1996 |
| WO | 96/22966 | 8/1996 |
| WO | 96/40146 | 12/1996 |
| WO | 96/40653 | 12/1996 |
| WO | 96/40654 | 12/1996 |
| WO | 96/40655 | 12/1996 |
| WO | 96/40656 | 12/1996 |
| WO | 97/30072 | 8/1997 |
| WO | 97/38705 | 10/1997 |
| WO | 98/00405 | 1/1998 |
| WO | 98/25930 | 6/1998 |
| WO | 98/28268 | 7/1998 |
| WO | 98/38177 | 9/1998 |

OTHER PUBLICATIONS

Bock, et al. "An Expedient Synthesis of 3–Amino–1, 3–Dihydro–5–Phenyl–2H–1,4–Benzodiazepine–2–one." *Tet. Lets.* 28(9):939–942 (1987).

Chambers, et al. L–708,474: the C5–Cyclohexyl Analogue of L–365,260, A Selective High Affinity Ligand for the CCKB/Gastrin Receptor. *Bioorg. and Med. Chem. Letts.* 3(10):1919–1924 (1993).

Chartier–Harlin, et al. "Early–onset Alzheimer's disease caused by mutations at codon 717 of the βAmyloid precursor protein gene." *Nature.* 353: 884–846 (1991).

Citron, et al. "Mutation of the β–amyloid precursor protein in familial Alzheimer's disease increases β–amyloid protein production." *Nature* 360:672–674 (1992).

Cordell. "B–Amyloid Formation as a Potential Therapeutic Target for Alzheimer's Disease." *Ann. Rev. Pharmacol. Toxicol.* 34:69–89 (1994).

Evans, et al. "Methods for Drug Discovery: Development of Potent, Selective Orally Effective Cholecystokinin Antagonists." *J. Med. Chem.* 31:2235–2246 (1988).

Evans, et al. "Molecular Mimicry and the Design of Peptidomimetrics." *Molecular Mimicry in Health and Disease.* (A. Lernmark, et al., eds.) Elsevier Science Publishers B.v. (Biomedical Division) (1988) pp. 23–34.

Finizia, et al. "Synthesis and Evaluation of Novel 1,–5–Benzodiazepines as potent and selective CCK–B Ligands, Effect of the Substitution of the N–5 Phenyl with Alkyl Groups." *Bioorg. & Medicinal Chemistry Letters.* 6(24):2957–2962 (1996).

Glenner, et al. "Alzheimer's disease: Initial Report of the Purification and Characterization of a Novel Cerebrovascular Amyloid Protein." *Biochem. Biophys. Res. Commun.* 120(3):885–890 (1984).

Goate, et al. "Segregation of a missense mutation in the amyloid precursor protein gene with familial Alzheimer's disease." *Nature.* 349: 704–706 (1991).

Hirst, et al. "Discovery of 1,5–Benzodiazepines with Peripheral Cholecystokinin (CCK–A) Receptor Agonists Activity (II): Optimization of the C3 Amino Substituent." *J. Med. Chem.* 39:5236–5245 (1996).

Hofmann, et al. "Interactions of Benzodiazepine Derivatives with Annexins." *J. Biol. Chem.* 273(5):2885–2894 (1998).

Johnson–Wood, et al. "Amyloid precursor protein processing and A$\beta_{42}$ deposition in a transgenic mouse model of Alzheimer's disease." *PNAS USA.* 94: 1550–1555 (1997).

Ksander, G.M., et al. "Dual Angiotensin Converting Enzyme/Thromboxane Synthase Inhibitors." *J. Med. Chem.* 37: 1823–1832 (1994).

Lowe, et al. "A Water Soluble Benzazepine Cholecystokinin–B–Receptor Antagonist." *Bioorg. and Med. Chem. Lets.* 5(17): 1933–1936 (1995).

Lowe, et al. "5–Phenyl–3–ureidobenzzazepin–2–ones as Cholecystokinin–B Receptor Antagonists." *J. Med. Chem.* 37: 3789–3811 (1994).

Mullan, et al. "A pathogenic mutation for probable Alzheimer's diseae in the APP gene at the N–terminus of β–amyloid." *Nature Genet.* 1: 345–347 (1992).

Murrell, et al. "A Mutation in the Amyloid Precursor Protein Associate with Hereditary Alzheimer's Disease." *Science.* 254:97–99 (1991).

Papadopoulos, et al. Anodic Oxidation of N–Acyl and N–Alkoxylcarbonyl Dipeptide Esters as a Key Step for the Formation of Chiral Heterocyclic Synthetic Building Blocks. *Tetrahedron* 47(4/5):563–572 (1991).

Patel, et al. "Biological Preperties of the Benzodiazepine Amidine Derivative L–740,093, a Choleycystokinin–B/Gastrin Receptor Antagonist with High Affinity in vitro and High Potency in vivo." *Molecular Pharmacology.* 46:943–948 (1994).

Rittle, et al. "A New Amine Resolution Method and its Application to 3–Aminobenzodiazepines." *Tet. Lets.* 28(5):521–522 (1987).

Satoh, et al. "New 1,4–Benzodiazepine–2–one Derivatives as Gastrin/Cholecystokinin–B Antagonists." *Chem. Pharm. Bull.* 43(12): 2159–2167 (1995).

Selkoe, et al. "Amyloid Protein and Alzheimer's Disease." *Scientific American.* 68–78 (1991).

Selkoe, et al. "The Molecular Pathology of Alzheimer's Disease." *Neuron.* 6:487–498 (1991).

Semple, et al. "Design, Synthesis, and Evolution of a Novel, Selective, and Orally Bioavailable Class of Thrombin Inhibitors: P1–Argininal Derivatives Incorporating P3–P4 Lactam Sulfoamide Moieties." *J. Med. Chem.* 39: 4531–4536 (1996).

Semple, et al. "A Facile Large Scale Synthesis of Optically Active 3–Amino–5–(2–Pyridyl)–1, 4–Benzodiazepin–2–One Derivatives." *Synthetic Communications.* 26(4): 721–727 (1996).

Seubert, et al. "Isolation and quanitification of soluble Alzherimer's peptide from biological fluids." *Nature.* 359: 325–327 (1992).

Sherrill, et al. "An Improved Synthesis and Resolution of 3–Amino–1,3 dihydro–5–phenyl–2H–1, 4–benzodiazepine–2–ones." *J. Org. Chem.* 60:730–734 (1995).

Showell, et al. "High Affinity and Potent, Water–Soluble 5–Amino–1,4–Benzodiazepine CCKB/Gastrin Receptor Antagonists Containing a Cationic Solubilizing Group." *J. Med. Chem.* 37:719–721 (1994)

Smith, et al. "β–APP Processing as a Therapeutic Target for Alzheimer's Disease." *Current Pharmaceutical Design.* 3:439–445 (1997).

Van Niel, et al. "CCKB Selective Receptor Ligands: Novel 1,3,5–Trisubstituted Benzazepin–2–ones." *Bioorganic & Medicinal Chemistry Letters.* 5(13):1421–1426 (1995).

Varnavas, et al. "Synthesis of New Benzodiazepine Derivatives as Potential Cholecystokinin Antagonists." *Il Farmaco.* 46(2):391–401 (1991).

CYCLIC AMINO ACID COMPOUNDS PHARMACEUTICAL COMPOSITIONS COMPRISING SAME AND METHODS FOR INHIBITING β-AMYLOID PEPTIDE RELEASE AND/OR ITS SYNTHESIS BY USE OF SUCH COMPOUNDS

CROSS-REFERENCE TO RELATED APPLICATIONS

This application claims the benefit of U.S. Provisional Patent Application Serial No. 60/160,067 which was converted from U.S. patent application Ser. No. 09/102,507 filed on Jun. 22, 1998, and U.S. Provisional Patent Application Serial No. 60/155,238 which was converted from U.S. patent application Ser. No. 09/164,451 filed on Sep. 30, 1998; which applications are incorporated herein by reference in their entirety.

BACKGROUND OF THE INVENTION

1. Field of the Invention

This invention relates to compounds which inhibit β-amyloid peptide release and/or its synthesis, and, accordingly, have utility in treating Alzheimer's disease.

2. References

The following publications, patents and patent applications are cited in this application as superscript numbers:

1. Glenner, et al., *Biochem. Biophys. Res. Commun.*, 120 (3):885–890 (1984).
2. U.S. Pat. No. 4,666,829, issued May 19, 1987
3. Selkoe, *Neuron*, 6:487–498 (1991).
4. Goate, et al., *Nature*, 349:704–706 (1991).
5. Chartier Harlan, et al., *Nature*, 353:844–846 (1991).
6. Murrell, et al., *Science*, 254:97–99 (1991).
7. Mullan, et al., *Nature Genet.*, 1:345–347 (1992.
8. Schenk, et al., International Patent Application Publication No. WO 94/10569, published May 11, 1994.
9. Selkoe, Scientific American, "Amyoid Protein and Alzheimer's Disease", pp. 2–8, November, 1991.
10. Yates et al., U.S. Pat. No. 3,598,859.
11. *Tetrahedron Letters* 1993, 34(48), 7685.
12. R. F. C. Brown et al., *Tetrahedron Letters* 1971, 8, 667–670.
13. A. O. King et al., *J. Org. Chem.* 1993, 58, 3384–3386.
14. U.S. Provisional Application Serial No. 60/019,790, filed Jun. 14, 1996.
15. R. D. Clark et al., *Tetrahedron* 1993, 49(7), 1351–1356.
16. Citron, et al., *Nature* (1992) 360:672–674.
17. P. Seubert, *Nature* (1992) 359:325–327.
18. Hansen, et al., *J. Immun. Meth.*(1989) 119:203–210.
19. Games et al., *Nature* (1995) 373:523–527.
20. Johnson-Wood et al., *PNAS USA* (1997) 94:1550–1555.

All of the above publications, patents and patent applications are herein incorporated by reference in their entirety to the same extent as if each individual publication, patent or patent application was specifically and individually indicated to be incorporated by reference in its entirety.

State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyzes have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

Compounds which inhibit β-amyloid peptide release and/or its synthesis in vivo are disclosed in U.S. patent application Ser. No. 08/996,422, filed Dec. 22, 1997 and entitled "Cycloalkyl, Lactam, Lactone and Related Compounds, Pharmaceutical Compositions Comprising Same, and Methods for Inhibiting β-Amyloid Peptide Release, and/or its Synthesis by Use of Such Compounds," the disclosure of which is incorporated herein by reference in its entirety. The present invention is directed to novel N-terminal cyclic amino acid derivatives of such compounds.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition.

Accordingly, in one of its composition aspects, the present invention provides compounds of formula I and Ia:

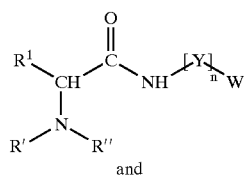

and

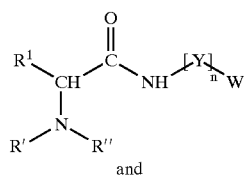

wherein

W is a cyclic group selected from the group consisting of:

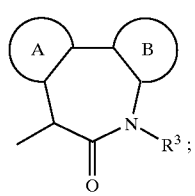 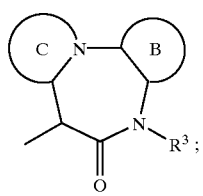

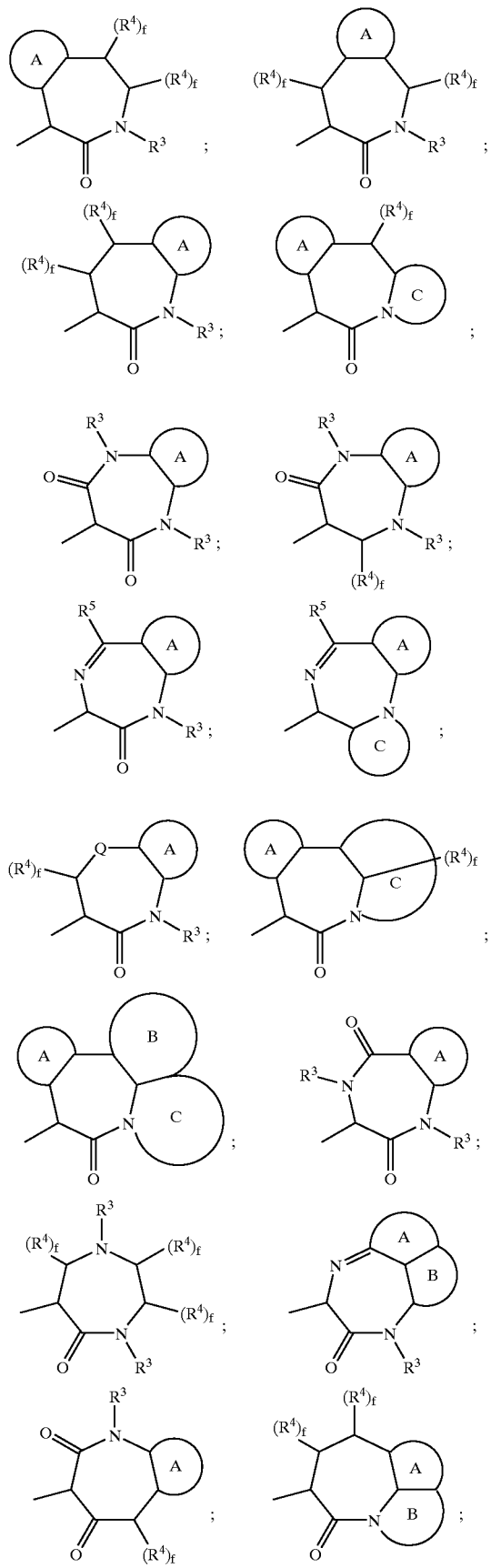

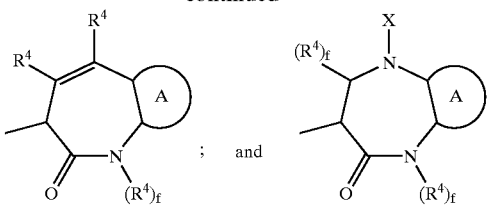

wherein
ring A, together with the atoms to which it is attached, forms a carbocyclic or hetercyclic ring selected from the group consisting of aryl, cycloalkyl, heteroaryl, substituted cycloalkyl, cycloalkenyl, substituted cycloalkenyl, and heterocyclic;
ring B, together with the atoms to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;
ring C, together with the atoms to which it is attached, forms a heteroaryl or heterocyclic ring;
Y is represented by the formula:

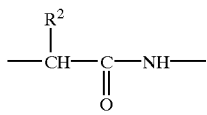

$R^1$, together with R' and the carbon and nitrogen atoms attached thereto, respectively, form a nitrogen containing heterocyclic in formula I or a nitrogen containing unsaturated heterocyclic or heteroaryl group in formula Ia;
R" is selected from the group consisting of hydrogen, alkyl, substituted alkyl and aryl;
each $R^2$ is independently selected from the group consisting of alkyl, substituted alkyl, alkenyl, substituted alkenyl, alkynyl, substituted alkynyl, cycloalkyl, aryl, heteroaryl and heterocyclic;
each $R^3$ is independently selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;
each $R^4$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic;
$R^5$ is selected from the group consisting of hydrogen, alkyl, substituted alkyl, alkoxy, substituted alkoxy, alkenyl, substituted alkenyl, alkynyl, substituted alkynyl, substituted amino, aryl, aryloxy, cycloalkyl, substituted cycloalkyl, cycloalkenyl, substituted cycloalkenyl, heteroaryl, heterocyclic, thioalkoxy and substituted thioalkoxy;
Q is selected from the group consisting of oxygen, sulfur, —S(O)—, —S(O)—, —C(O)— and —C(S)—;
X is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic; or X and one of $R^4$ and the atoms to which they are attached form a double bond;
each f is independently an integer from 0 to 2;
t is an integer from 0 to 2;
n is an integer equal to 1 or 2; and
pharmaceutically acceptable salts thereof.

This invention also provides for novel pharmaceutical compositions comprising a pharmaceutically acceptable carrier and a compound of the formula I or Ia above.

Additionally, in one of its method aspects, this invention is directed to a method for inhibiting β-amyloid peptide release and/or its synthesis in a cell which method comprises administering to such a cell an amount of a compound or a mixture of compounds of formula I/Ia above effective in inhibiting the cellular release and/or synthesis of β-amyloid peptide.

Because the in vivo generation of β-amyloid peptide is associated with the pathogenesis of AD[8,9], the compounds of formula I/Ia can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically acceptable inert carrier and an effective amount of a compound or a mixture of compounds of formula I/Ia above.

In yet another of its method aspects, this invention is directed to a therapeutic method for treating a patient with AD in order to inhibit further deterioration in the condition of that patient which method comprises administering to said patient a pharmaceutical composition comprising a pharmaceutically acceptable inert carrier and an effective amount of a compound or a mixture of compounds of formula I/Ia above.

In formula I or Ia above, rings A and B may be the same or different and are preferably independently selected from the group consisting of aryl, cycloalkyl, cycloalkenyl, heteroaryl and heterocyclic. More preferably, rings A and B are independently selected from the group consisting of aryl and cycloalkyl. Still more preferably, rings A and B are independently aryl.

Particularly preferred A and B rings include, by way of example, phenyl, substituted phenyl, including fluoro-substituted phenyl, cyclohexyl and the like.

Preferred C rings include, by way of example, pyrrolidinyl, piperidinyl, morpholino and the like.

Preferred heterocycles defined by $R^1$, R' and the nitrogen and carbon atoms attached thereto, respectively, include by way of example,
monocyclic nitrogen-containing heterocycles optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like;
bicyclic heterocycles wherein the second cyclic group is selected from the group consisting of aryl, cycloalkyl, cycloalkenyl, heteroaryl and heterocyclic wherein the bicyclic group includes fused bicyclics, bridged bicyclics and spiro bicyclics and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like; and tricyclic heterocycles wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like.

Particularly preferred nitrogen-containing heterocycles defined by $R^1$, R' and the nitrogen and carbon atoms attached thereto, respectively, include by way of example, pyrrolidinyl, 4-hydroxypyrrolidinyl, azetidinyl, thiazolidinyl, piperidinyl, piperizinyl, dihydroindolyl (e.g., 2,3-dihydroindol-2-yl), tetrahydroquinolinyl (e.g., 1,2,3,4-tetrahydroquinolin-2-yl, 1,2,3,4-tetrahydroquinolin-1-yl, 1,2,3,4-tetrahydroquinolin-3-yl,), morpholinyl, thiomorpholinyl, 4-halopyrrolidinyl, 3-phenylpyrrolidinyl, 4-aminopyrrolidinyl, 3-methoxypyrrolidinyl, 4,4-dimethylpyrrolidinyl, 5,5-dimethylthiazolindin-4-yl, 2,3,4,5-tetrahydrooxazol-4-yl, perhydroindolyl-2-yl and the like.

Preferred nitrogen-containing heteroaryl groups defined by $R^1$, R' and the nitrogen and carbon atoms attached thereto, respectively, include by way of example, monocyclic heteroaryls optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like;

bicyclic heteroaryls wherein the second cyclic group is selected from the group consisting of aryl, cycloalkyl, cycloalkenyl, heteroaryl and heterocyclic wherein the bicyclic group includes fused bicyclics and bridged bicyclics and further wherein each ring is optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like and, in addition, when the second cyclic group is a cycloalkyl, cycloalkenyl or a heterocyclic group, keto and thioketo groups; and tricyclic heteroaryls wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, alkyl, substituted alkyl, alkoxy, substituted alkoxy, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and the like, and, in addition, when the second and/or third cyclic group is a cycloalkyl, cycloalkenyl or a heterocyclic group, keto and thioketo groups.

Particularly preferred heteroaryls defined by $R^1$, R' and the nitrogen and carbon atoms attached thereto, respectively, include by way of example, pyridinyl, 2-quinoxalinyl, indolyl, N-methylindolyl, 3-amino-2-pyrazinyl, 3-amino-5,6-dichloro-2-pyrazinyl, 4-methoxyindolyl, 3-isoquinolinyl, and the like.

$R^2$ is preferably selected from the group consisting of alkyl, substituted alkyl, alkenyl, cycloalkyl, aryl, heteroaryl and heterocyclic.

Particularly preferred $R^2$ substituents include, by way of example, methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, n-butyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, -2-methylcyclopentyl, -cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl (e.g., 2-pyridyl, 3-pyridyl and 4-pyridyl), pyridyl (2-pyridyl, 3-pyridyl and 4-pyridyl), —CH$_2$-naphthyl (e.g., 1-naphthyl and 2-naphthyl), —CH$_2$—(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, thien-3-yl, and the like.

Preferably, $R^3$ is selected from the group consisting of hydrogen, alkyl, substituted alkyl and cycloalkyl.

Particularly preferred $R^3$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

When present, $R^4$ is preferably alkyl or substituted alkyl.

$R^5$ is preferably hydrogen; alkyl; substituted alkyl; phenyl; substituted phenyl, such as 2-fluorophenyl, 3-fluorophenyl, 4-fluorophenyl, 2-chlorophenyl and the like; cycloalkyl, such as cyclohexyl and the like; or heteroaryl or heterocyclic, such as 1-piperdinyl, 2-pyridyl, 2-thiazyl, 2-thienyl and the like.

Preferably, f is 0 or 1. More preferably, f is 0 and when f is 0 then a methylene group or a methenylene group is defined.

Preferably, n is 1.

In one preferred embodiment of this invention, W is a cyclic group of the formula:

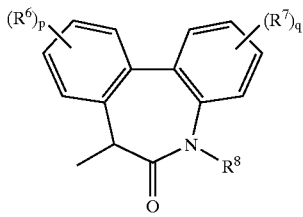

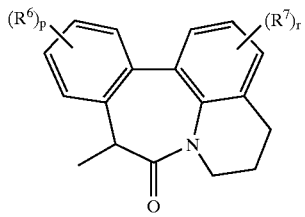

wherein $R^6$, $R^7$, and p are as defined herein and r is an integer from 0 to 3.

wherein each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

each $R^7$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

$R^8$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

p is an integer from 0 to 4; q is an integer from 0 to 4.

Preferably, $R^6$ and $R^7$ are independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy. More preferably, when present, $R^6$ and $R^7$ are fluoro.

$R^8$ is preferably selected from the group consisting of hydrogen, alkyl, substituted alkyl, acyl, aryl, cycloalkyl and substituted cycloalkyl. More preferably, $R^8$ is selected from the group consisting of hydrogen, alkyl, substituted alkyl and cycloalkyl.

Particularly preferred $R^8$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

In another preferred embodiment of this invention, W is a cyclic group of the formula:

In still another preferred embodiment of this invention, W is a cyclic group of the formula:

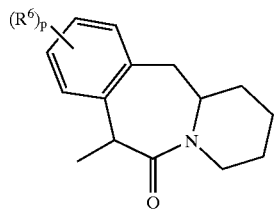

wherein $R^6$ and p are as defined herein.

In yet another preferred embodiment of this invention, W is a cyclic ring of the formula:

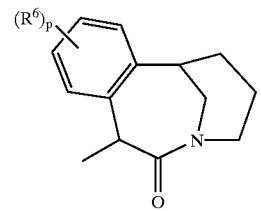

wherein $R^6$ and p are as defined herein.

In still another preferred embodiment of this invention, W is a cyclic ring of the formula:

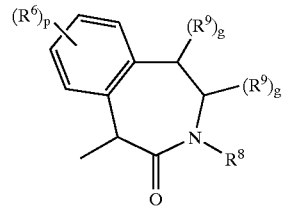

wherein $R^6$, $R^8$ and p are as defined herein; and each $R^9$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic; and g is an integer from 0 to 2.

When present, $R^9$ is preferably alkyl or substituted alkyl.

In another preferred embodiment of this invention, W is a cyclic ring of the formula:

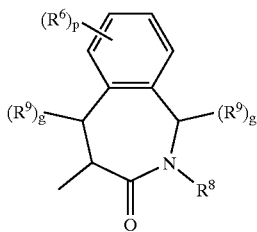

wherein $R^6$, $R^8$, $R^9$, g and p are as defined herein.

In yet another preferred embodiment of this invention, W is a cyclic ring of the formula:

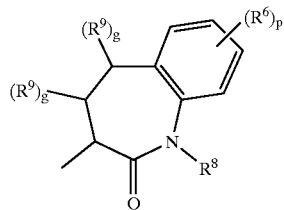

wherein $R^6$, $R^8$, $R^9$, g and p are as defined herein.

In still another preferred embodiment of this invention, W is a cyclic ring of the formula:

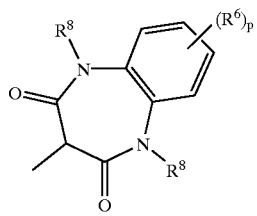

wherein $R^6$, $R^8$ and p are as defined herein.

In another preferred embodiment of this invention, W is a cyclic ring of the formula:

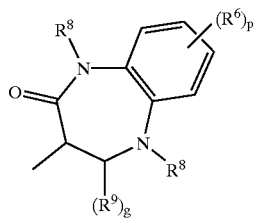

wherein $R^6$, $R^8$, $R^9$, g and p are as defined herein.

In another preferred embodiment of this invention, W is a cyclic ring of the formula:

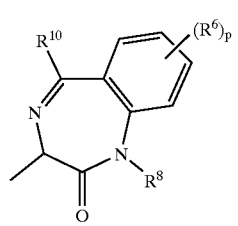

wherein $R^6$, $R^8$ and p are as defined herein; and
$R^{10}$ is selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic.

In another preferred embodiment of this invention, W is a cyclic ring of the formula:

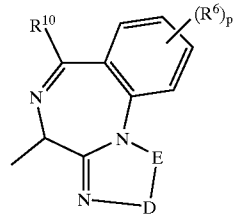

wherein $R^6$, $R^{10}$ and p are as defined herein; and

D-E is selected from the group consisting of alkylene, alkenylene, substituted alkylene, substituted alkenylene and —N=CH—.

In another preferred embodiment of this invention, W is a cyclic ring of the formula:

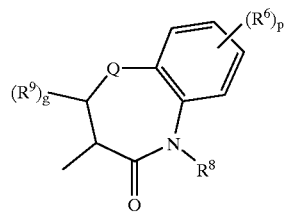

wherein $R^6$, $R^8$, $R^9$, g and p are as defined herein; and

Q is oxygen, sulfur, —S(O)—, —S(O)—, —C(O)— or —C(S)—.

In another preferred embodiment of this invention, W is a cyclic ring of the formula:

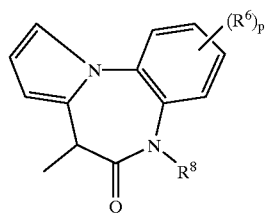

wherein $R^6$, $R^8$ and p are as defined herein.

In another preferred embodiment of this invention, W is a cyclic ring of the formula:

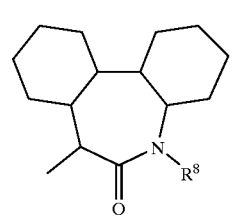

wherein $R^8$ is as defined herein.

In another preferred embodiment of this invention, W is a cyclic ring of the formula:

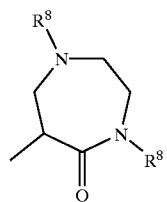

wherein $R^8$ is as defined herein.

In another preferred embodiment of this invention, W is a cyclic ring of the formula:

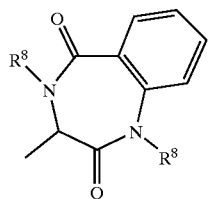

wherein $R^8$ is as defined herein.

In another preferred embodiment of this invention, W is a cyclic ring of the formula:

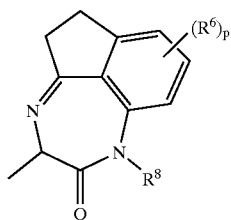

wherein $R^8$, $R^8$ and p are as defined herein.

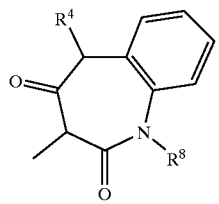

In another preferred embodiment of this invention, W is a cyclic ring of the formula: wherein $R^4$ and $R^8$ are as defined herein.

In another preferred embodiment of this invention, W is a cyclic ring of the formula:

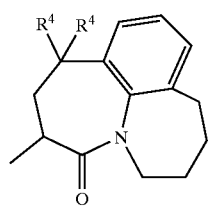

wherein $R^4$ is as defined herein.

In another preferred embodiment of this invention, W is a cyclic ring of the formula:

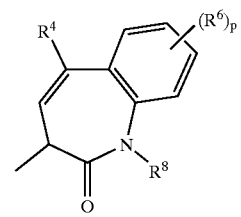

wherein $R^4$, $R^6$, $R^8$ and p are as defined herein.

In another preferred embodiment of this invention, W is a cyclic ring of the formula:

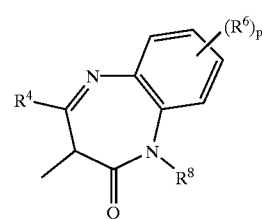

wherein $R^4$, $R^6$, $R^8$ and p are as defined herein.

Compounds of this invention include, by way of example, the following:

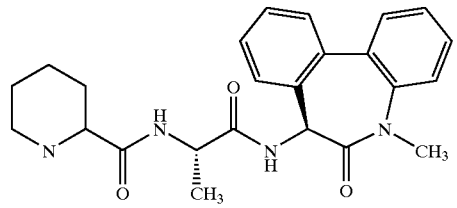

e.g., 5-(S)-[N'-homoprolyl)-L-alaninyl]amino-7-methyl-5,7-dihydro-6H-dibenz[b,d]azepin-6-one;

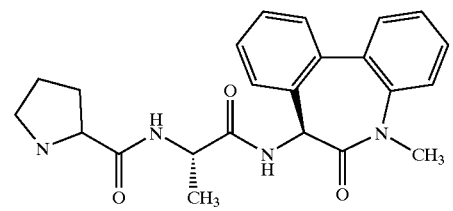

e.g., 5-(S)-[L-prolyl-L-alaninyl]amino-7-methyl-5,7-dihydro-6H-dibenz[b,d]azepin-6-one;

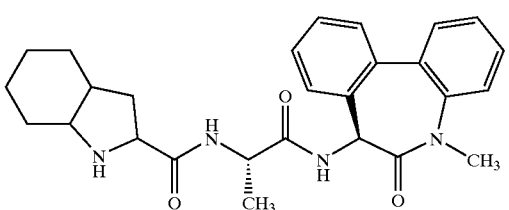

e.g., 5-(S)-[(N'-octahydroindolyl-2-oyl)-L-alaninyl]amino-7-methyl-5,7-dihydro-6H-dibenz[b,d]azepin-6-one;

e.g., 5-[N'-(decahydro-quinolyl-2-oyl)-L-alaninyl]-amino-7-methyl-5,7-dihydro-6H-dibenz[b,d]azepin-6-one;

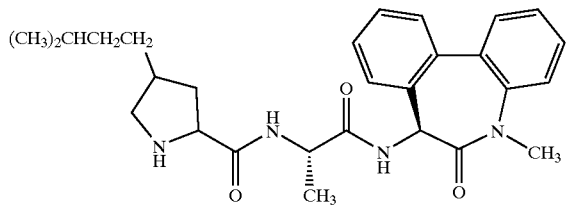

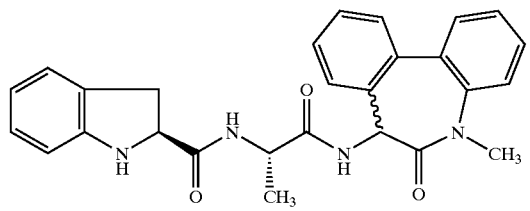

e.g., 5-(S)-[L-(4-(3-methylbutyl)prolyl)-L-alaninyl]amino-7-methyl-5,7-dihydro-6H-dibenz[b,d]azepin-6-one;

e.g., 5-{N'-[(S)-indolyl-2-oyl]-L-alaninyl}-amino-7-methyl-5,7-dihydro-6H-dibenz[b,d]azepin-6-one;

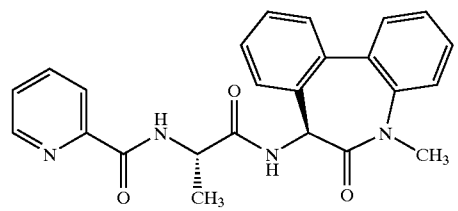

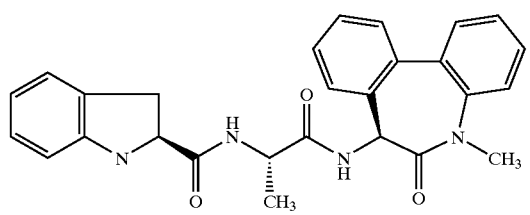

e.g., 5-(S)-[N'-picolinyl-L-alaninyl]amino-7-methyl-5,7-dihydro-6H-dibenz[b,d]azepin-6-one;

e.g., 5-(S)-{N'-[(S)-indolyl-2-oyl]-L-alaninyl}-amino-7-methyl-5,7-dihydro-6H-dibenz[b,d]azepin-6-one;

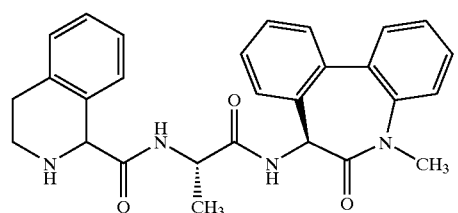

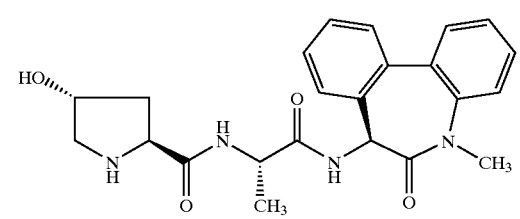

e.g., 5-(S)-[N'-(1,2,3,4-tetrahydroisoquinolin-1-oyl)-L-alaninyl]amino-7-methyl-5,7-dihydro-6H-dibenz[b,d]azepin-6-one;

e.g., 5-(S)-[N'-(L-trans-4-hydroxyprolyl)-L-alaninyl]-amino-7-methyl-5,7-dihydro-6H-dibenz[b,d]azepin-6-one;

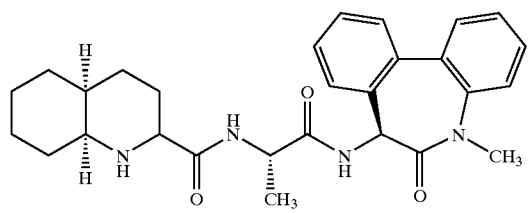

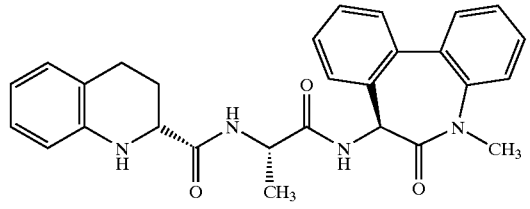

e.g., 5-(S)-[N'-(decahydro-quinolyl-2-oyl)-L-alaninyl]-amino-7-methyl-5,7-dihydro-6H-dibenz[b,d]azepin-6-one;

e.g., 5-(S)-[N'-(1,2,3,4-tetrahydroquinolyl-2-oyl)-L-alaninyl]-amino-7-methyl-5,7-dihydro-6H-dibenz[b,d]azepin-6-one;

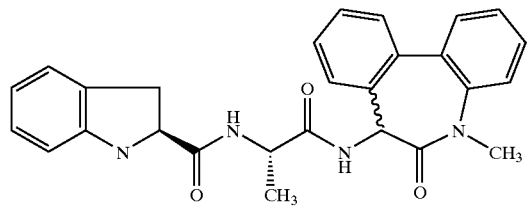

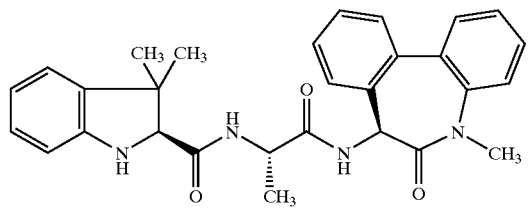

e.g., 5-(S)-[N'-(3,3-dimethylindolyl-2-oyl)-L-alaninyl]-amino-7-methyl-5,7-dihydro-6H-dibenz[b,d]azepin-6-one

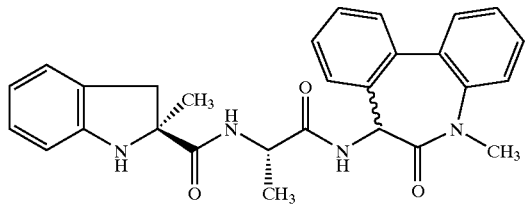

e.g., 5-{N'-[(S)-2-methylindolyl-2-oyl]-L-alaninyl}-amino-7-methyl-5,7-dihydro-6H-dibenz[b,d]azepin-6-one;

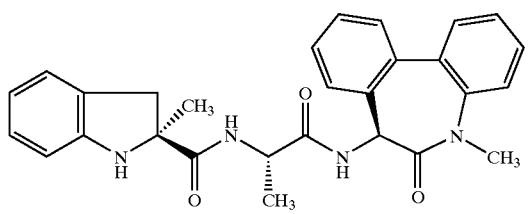

e.g., 5-(S)-{N'-[(S)-2-methylindolyl-2-oyl]-L-alaninyl}-amino-7-methyl-5,7-dihydro-6H-dibenz[b,d]azepin-6-one

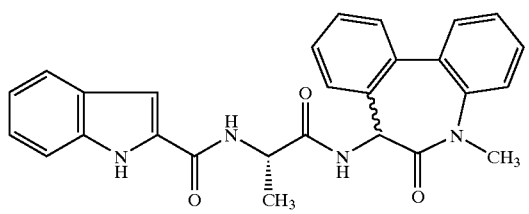

e.g., 5-[N'-(indole-2-oyl)-L-alaninyl]-amino-7-methyl-5,7-dihydro-6H-dibenz[b,d]azepin-6-one;

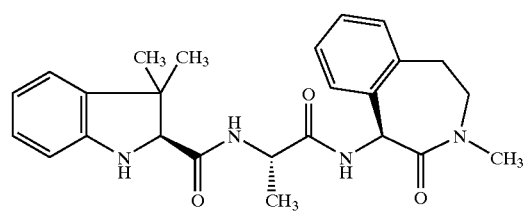

e.g., 1-(S)-[N'-(3,3-dimethylindolyl-2-oyl)-L-alaninyl]-amino-3-methyl-4,5,6,7- tetrahydro-2H-3-benzazepin-2-one;

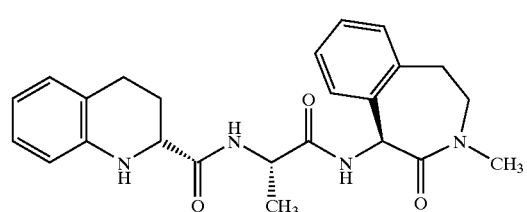

e.g., 1-(S)-[N'-(1,2,3,4-tetrahydroquinolyl-2-oyl)-L-alaninyl]-amino-3-methyl-4,5,6,7-tetrahydro-2H-3-benzazepin-2-one;
3-[(N'-(3-pyridinoyl)-L-alaninyl)]amino-2,3-dihydro-1-methyl-5-phenyl-1H-1,4-benzodiazepin-2-one, 5-{N'-(2-piperidine carboxyl)-L-alaninyl}-amino-7-methyl-5,7-dihydro 6H-dibenz[b,d]azepin-6-one (both enantiomers), and

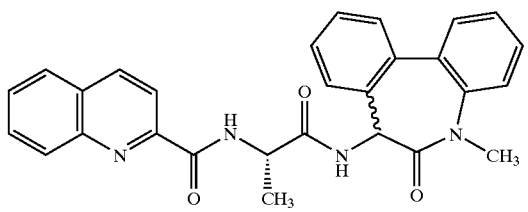

e.g., 5-[N'-(quinolyl-2-oyl)-L-alaninyl]-amino-7-methyl-5,7-dihydro-6H-dibenz[b,d]azepin-6-one.

As is appreciated by the skilled person, compounds of the present invention exist as isomers. Herein, the Cahn-Prelog-Ingold designations of (R)— and (S)— and, for amino acid derived portions of the compounds, the L— and D— designations of stereochemistry relative to the isomers of glyceraldehyde are used to refer to specific isomers where designated. The specific isomers can be prepared by stereospecific synthesis or can be resolved and recovered by techniques known in the art, such as, chromatography on chiral stationary phases, and fractional recrystallization of addition salts formed by reagents used for that purpose. Useful methods of resolving and recovering specific stereoisomers are known in the art and described, for example, in Stereochemistry of Organic Compounds, E. L. Eliel and S. H. Wilen (Wiley-Interscience 1994), Enantiomers, Racemates and Resolutions, J. Jacques, A. Collet and S. J. Wilen (Wiley-Interscience 1981), and European Patent Application No. EP-A-838448, published Apr. 29, 1998. It is to be understood that the invention extends to all of the isomeric forms of the compounds of the present invention, including the diastereomeric, enantiomeric and racemic forms of the compounds.

Also included within the scope of this invention are prodrugs of the compounds of formula I or Ia above including acylated forms of alcohols and thiols, aminals of one or more amines, and the like.

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

1 Asp Ala Glu Phe Arg His Asp Ser Gly Tyr
11 Glu Val His His Gln Lys Leu Val Phe Phe
21 Ala Glu Asp Val Gly Ser Asn Lys Gly Ala

31 Ile Ile Gly Leu Met Val Gly Gly Val Val
41 Ile Ala Thr (SEQ ID NO: 1)

or a sequence which is substantially homologous thereto.

"Alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, decyl, dodecyl, hexadecyl, and the like.

"Substituted alkyl" refers to an alkyl group, preferably of from 1 to 20 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl,—SO-heteroaryl, —SO$_2$-alkyl, —SO$_2$-substituted alkyl, —SO$_2$-aryl and —SO$_2$-heteroaryl.

"Alkylene" refers to divalent alkylene groups preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to an alkylene group, preferably of from 1 to 20 carbon atoms and more preferably of from 1 to 6 carbon atoms, having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl,—SO-aryl,—SO-heteroaryl,—SO$_2$-alkyl, —SO$_2$-substituted alkyl, —SO$_2$-aryl, and —SO$_2$-heteroaryl. Additionally, such substituted alkylene groups include those where 2 substituents on the alkylene group are fused to form one or more cycloalkyl, aryl, heterocyclic or heteroaryl groups fused to the alkylene group. Preferably such fused cycloalkyl groups contain from 1 to 3 fused ring structures.

"Alkenylene" refers to divalent alkenylene groups preferably having from 2 to 20 carbon atoms and more preferably 2 to 6 carbon atoms. This term is exemplified by groups such as ethenylene (—CH=CH—), the propenylene isomers (e.g., —CH$_2$CH=CH— and —C(CH$_3$)=CH—) and the like.

"Substituted alkenylene" refers to an alkenylene group, preferably of from 2 to 20 carbon atoms and more preferably of from 2 to 6 carbon atoms, having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Additionally, such substituted alkylene groups include those where 2 substituents on the alkylene group are fused to form one or more cycloalkyl, aryl, heterocyclic or heteroaryl groups fused to the alkylene group.

"Alkaryl" refers to -alkylene-aryl groups preferably having from 1 to 20 carbon atoms and more preferably 1 to 6 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O-" where "alkyl" is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-" where substituted alkyl is as defined above.

"Alkylalkoxy" refers to the group "-alkylene-O-alkyl" wherein alkylene and alkyl are as defined above and which includes by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

"Alkylthioalkoxy" refers to the group "-alkylene-S-alkyl" wherein alkylene and alkyl are as defined above and which includes by way of example, methylenethiomethoxy (—CH$_2$SCH$_3$), ethylenethiomethoxy (—CH$_2$CH$_2$SCH$_3$), n-propylene-thio-iso-propoxy (—CH$_2$CH$_2$CH$_2$SCH(CH$_3$)$_2$), methylenethio-t-butoxy (—CH$_2$SC(CH$_3$)$_3$) and the like.

"Alkenyl" refers to alkenyl groups preferably having from 2 to 20 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

"Substituted alkenyl" refers to an alkenyl group as defined above having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyl" refers to alkynyl groups preferably having from 2 to 20 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH) and the like.

"Substituted alkynyl" refers to an alkynyl group as defined above having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

"Acylamino" refers to the group —C(O)NRR where each R is independently selected from the group consisting of hydrogen, alkyl, substituted alkyl, aryl, heteroaryl, heterocyclic and where both R groups are joined to form a heterocyclic group, wherein alkyl, substituted alkyl, aryl, heteroaryl and heterocyclic are as defined herein.

"Amino" refers to the group —NH$_2$.

"Substituted amino" refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, heteroaryl, heterocyclic and where both R groups are joined to form a heterocyclic group. When both R groups are hydrogen, —N(R)$_2$ is an amino group. Examples of substituted amino groups include, by way of illustration, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

The term "amino-blocking group" or "amino-protecting group" refers to any group which, when bound to an amino group, prevents undesired reactions from occurring at the amino group and which may be removed by conventional chemical and/or enzymatic procedures to reestablish the amino group. Any known amino-blocking group may be used in this invention. Typically, the amino-blocking group is selected so as to render the resulting blocked-amino group unreactive to the particular reagents and reaction conditions employed in a subsequent pre-determined chemical reaction or series of reactions. After completion of the reaction(s), the amino-blocking group is selectively removed to regenerate the amino group. Examples of suitable amino-blocking groups include, by way of illustration, tert-butoxycarbonyl (Boc), benzyloxycarbonyl (Cbz), acetyl, 1-(1'-adamantyl)-1-methylethoxycarbonyl (Acm), allyloxycarbonyl (Aloc), benzyloxymethyl (Bom), 2-p-biphenylisopropyloxycarbonyl (Bpoc), tert-butyldimethylsilyl (Bsi), benzoyl (Bz), benzyl (Bn), 9-fluorenyl-methyloxycarbonyl (Fmoc), 4-methylbenzyl, 4-methoxybenzyl, 2-nitrophenylsulfenyl (Nps), 3-nitro-2-pyridinesulfenyl (NPys), trifluoroacetyl (Tfa), 2,4,6-trimethoxybenzyl (Tmob), trityl (Trt), and the like. If desired, amino-blocking groups covalently attached to a solid support may also be employed.

"Aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

"Acyloxy" refers to the groups alkyl-C(O)O—, substituted alkyl-C(O)O—, cycloalkyl-C(O)O—, substituted cycloalkyl-C(O)—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

"Aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Carboxyalkyl" refers to the groups "—C(O)Oalkyl" and "C(O)O-substituted alkyl" where alkyl is as defined above.

"Cycloalkyl" refers to cyclic alkyl groups of from 3 to 20 carbon atoms and preferably 3 to 12 carbon atoms having a single cyclic ring or multiple rings including condensed rings, bridged rings, spiro rings and combinations thereof. Such cycloalkyl groups include, by way of example, single ring structures such as cyclopropyl, cyclobutyl, cyclopentyl, cyclooctyl, and the like, or multiple ring structures such as adamantanyl, and the like.

"Substituted cycloalkyl" refers to cycloalkyl groups having from 1 to 5 (preferably 1 to 3) substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Cycloalkenyl" refers to cyclic alkenyl groups of from 4 to 20 carbon atoms and preferably 4 to 12 carbon atoms having a single cyclic ring or multiple rings including condensed rings, bridged rings, spiro rings and combinations thereof and at least one point of internal unsaturation. Examples of suitable cycloalkenyl groups include, for instance, cyclobut-2-enyl, cyclopent-3-enyl, cyclooct-3-enyl and the like.

"Substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Halo" or "halogen" refers to fluoro, chloro, bromo and iodo and preferably is either fluoro or chloro.

"Heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

Such heteroaryl groups can have a single ring (e.g., pyridyl or furyl) or multiple rings including condensed and bridged ring structures (e.g., indolizinyl or benzothienyl).

"Monocyclic heteroaryls" refer to single ring heteroaryl groups which are exemplified by, for example, pyridyl, pyrrolyl and pyrimidine.

"Bicyclic heteroaryls" refer to heteroaryl groups comprised of two ring systems which may be fused or bridged wherein at least one of the rings contains a heteroatom and the other ring is selected from the group consisting of cycloalkyl, cycloalkenyl, aryl, heteroaryl and heterocyclic. Examples of fused bicyclic heteroaryl ring systems include, for instance, 3-isoquinoline and the like.

"Tricyclic heteroaryls" refer to heteroaryl groups comprised of three ring systems wherein each of the ring systems are independently fused or bridged wherein at least one of the rings contains a heteroatom and the remaining two rings are selected from the group consisting of cycloalkyl, cycloalkenyl, aryl, heteroaryl and heterocyclic. When the remaining two rings are cycloalkyl, cycloalkenyl or heterocyclic, these rings may optionally be spiro linked.

"Heteroaryloxy" refers to the group "—O-heteroaryl".

"Heterocycle" or "heterocyclic" refers to a monovalent saturated or unsaturated group having a single ring or multiple rings, from 1 to 15 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Such heterocyclic groups can have a single ring or multiple rings including condensed rings, bridged rings, spiro rings and combinations thereof. Preferred heterocyclics include morpholino, piperidinyl, and the like.

"Nitrogen containing heterocycles" refer to heterocyclic groups described above (including saturated and unsaturated heterocyclic groups) wherein at least one of the heteroatoms in the heterocyclic group is nitrogen.

"Monocyclic heterocyclics" refer to single ring heterocycle groups which are exemplified by, for example, pyrrolidinyl, morpholino, and the like.

"Bicyclic heterocyclics" refer to heterocyclic groups comprised of two ring systems which may be fused, spiro or bridged wherein at least one of the rings contains a heteroatom and the other ring is selected from the group consisting of cycloalkyl, cycloalkenyl, aryl, heteroaryl and heterocyclic. Examples of fused bicyclic heterocyclic ring systems include, for instance, 3-(1,2,3,4-tetrahydro-isoquinolinyl) and the like.

"Tricyclic heterocyclics" refer to heterocyclic groups comprised of three ring systems wherein each of the ring systems is independently fused, spiro or bridged wherein at least one of the rings contains a heteroatom and the remaining two rings are selected from the group consisting of cycloalkyl, cycloalkenyl, aryl, heteroaryl and heterocyclic. When the remaining two rings are cycloalkyl, cycloalkenyl or heterocyclic, these rings may optionally be spiro linked.

Examples of heterocycles and heteroaryls include, but are not limited to, pyrrole, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heterocyclooxy" refers to the group "—O-heterocycle".

"Keto" or "oxo" refers to the group ">C=O".

"Oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

"Thioketo" refers to the group ">C=S".

The term "5,7-dihydro-6H-dibenz[b,d]azepin-6-one" refers to a polycyclic ε-caprolactam ring system having the formula:

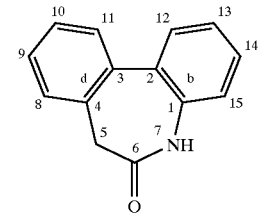

wherein, for nomenclature purposes, the atoms and bonds are numbered and lettered, respectively, as shown.

The term "5,6-dihydro-4H-quino[8,1-ab][3]benzazepin-8(9H)-one" refers to a polycyclic ε-caprolactam ring system having the formula:

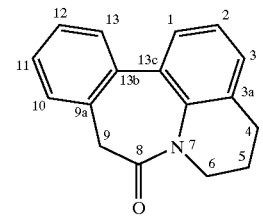

wherein, for nomenclature purposes, the atoms and bonds are numbered and lettered, respectively, as shown.

The term "1,3,4,7,12,12a-hexahydropyrido[2,1-b][3]benzazepin-6(2H)-one" refers to a polycyclic ε-caprolactam ring system having the formula:

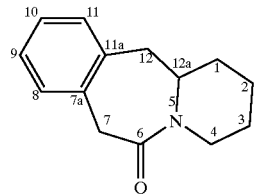

wherein, for nomenclature purposes, the atoms and bonds are numbered and lettered, respectively, as shown.

The term "4,5,6,7-tetrahydro-3,7-methano-3H-3-benzazonin-2(1H)-one" refers to a polycyclic ε-caprolactam ring system having the formula:

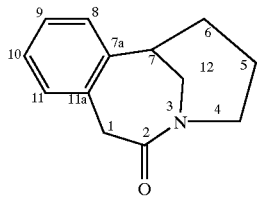

wherein, for nomenclature purposes, the atoms and bonds are numbered and lettered, respectively, as shown.

As to any of the above groups which contain 1 or more substituents, it is understood that such groups do not contain any substitution or substitution pattern which are sterically impractical and/or synthetically non-feasible.

"Pharmaceutically acceptable salt" refers to pharmaceutically acceptable salts of a compound of formula I or Ia which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more amino, hydroxyl, thiol, carboxyl groups or other protectable functional group of the compounds which prevents reactions from occurring at these groups and which protecting group can be removed by conventional chemical or enzymatic steps to reestablish the unprotected functional group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred carboxyl protecting groups include esters such as methyl, ethyl, propyl, t-butyl etc. which can be removed by mild hydrolysis conditions compatible with the nature of the product.

Compound Preparation

When n is one, the compounds of formula I (and by correlation thereto, the compounds of formula Ia) are readily prepared by conventional acylation reactions as illustrated in Scheme 1 below:

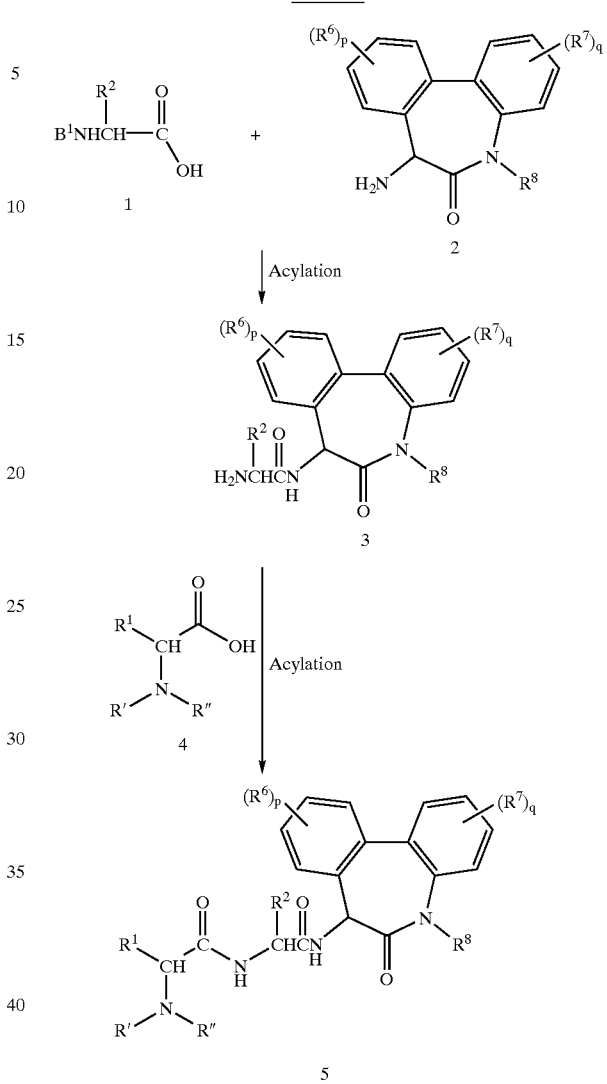

As shown in Scheme 1, protected carboxylic acid 1 (where $B^1$ is an amino protecting group and $R^2$ is as defined herein) can be coupled with an amine compound, such as 2 (where $R^6$, $R^7$, $R^8$, p and q are as defined herein), by conventional acylation reaction conditions well known in peptide chemistry to provide, after deprotection, intermediate 3.

In Scheme 1, amine 2 is merely representative and those skilled in the art will recognize that amino derivatives of any of the other ring systems described herein may be employed in this reaction to provide for compounds of formula I. Similarly, amino acid 4 can be replaced with an unsaturated heterocyclic or heteroaryl amino acid, such as picolinic acid (pyrid-2-yl carboxylic acid) which would provide for compounds of formula Ia.

Intermediate 3 can then be acylated or coupled with a cyclic amino acid, e.g., 4 (where R', R" and $R^1$ are as defined herein), to provide compound 5. If necessary, the amino group of cyclic amino acid 4 can be blocked with a removable blocking group such as with BOC, CBZ and the like and.

Both acylation reactions are typically conducted using conventional coupling reagents and procedures and at least a stoichiometric amount of intermediate 2 and carboxylic acid I in the first acylation reaction and intermediate 3 and carboxylic acid 4 in the second acylation reaction. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, tetrahydrofuran and the like. Alternatively, the acid halide of compounds 1 and/or 4 can be employed in the acylation reactions of scheme (1) and, when so employed, it is typically employed in the presence of a suitable base to scavenge the acid generated during the reaction. Suitable bases include, by way of example, triethylamine, diisopropylethylamine, N-methylmorpholine and the like.

Alternatively, compound 5 can be prepared by acylation of a compound of formula 6:

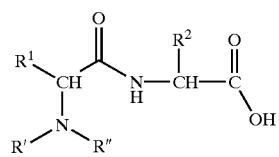

where R', R'', $R^1$, and $R^2$ as defined herein, with amine 2, under conventional acylation conditions as described above.

When n is two, the compounds of this invention can be prepared merely by incorporating a second acylation reaction which couples a compound of formula 1 with intermediate 3 followed by removal of the blocking group and then coupling amino acid 4 under conventional acylation conditions. Alternatively, a triamino acid analogue of compound 6 can be prepared which is then coupled via conventional conditions, as discussed above, with amine 2, to afford compounds of formula I or Ia.

Synthesis of Amino Acids Starting Materials

Amino acids 1 and 4 employed in the above reactions are well known in the art and many of these amino acids are commercially available. In addition, these amino acids can be readily prepared by several divergent synthetic routes with the particular route selected relative to the ease of compound preparation, commercial availability of starting materials, whether n is one or two, etc.

Amino acids, such as 1 and 4, c an also be coupled to amines prepared by use of polymer supported forms of carbodiimide peptide coupling reagents. A polymer supported form of EDC, for example, has been described (*Tetrahedron Letters*, 34(48), 7685 (1993))[11]. Additionally, a new carbodiimide coupling reagent, PEPC, and its corresponding polymer supported forms have been discovered and are very useful for the preparation of such compounds.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethylphenylacetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer supported forms are outlined in Scheme 2.

Scheme 2

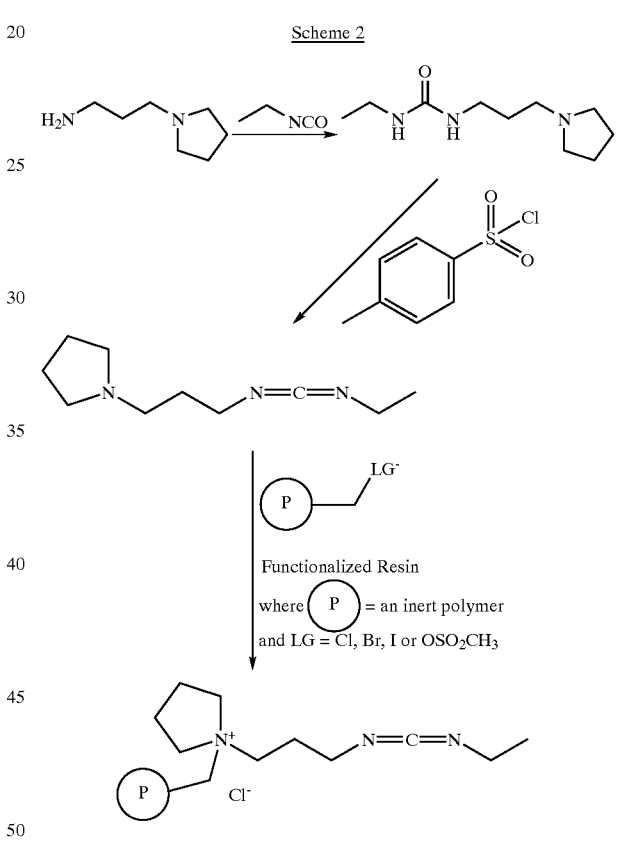

Such methods are described more fully in U.S. patent application Ser. No. 60/019,790[14] filed Jun. 14, 1996 which application is incorporated herein by reference in its entirety. Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient to about 45° C., for from about 3 to 120 hours. Typically, the product may be isolated by washing the reaction with $CHCl_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Preparation of Cyclic Compounds (e.g. Benzaepinones, Dibenzazepinones, Benzodiazepines and Related Compounds)

The cyclic compounds and amino-substituted derivatives thereof, such as 2, employed in the reactions described above are either known in the art or can be prepared by art-recognized procedures using commercially available starting materials and reagents.

For example, 5,7-dihydro-6H-dibenz[b,d]azepin-6-one may be prepared by cyclizing a chloromethyl amide intermediate using the procedures set forth in R. F. C. Brown et al., Tetrahedron Letters 1971, 8, 667–670[12] and references cited therein.

Additionally, the synthesis of a representative cyclic compuond, i.e., a 5,7-dihydro-6H-dibenz[b,d]azepin-6-one, is illustrated in Scheme 3. As will be readily apparent to those of ordinary skill in the art, the synthetic procedure illustrated in Scheme 3 and the reaction conditions described below can be modified by selecting the appropriate starting materials and reagents to allow the preparation of other cyclic amines suitable for use in this invention.

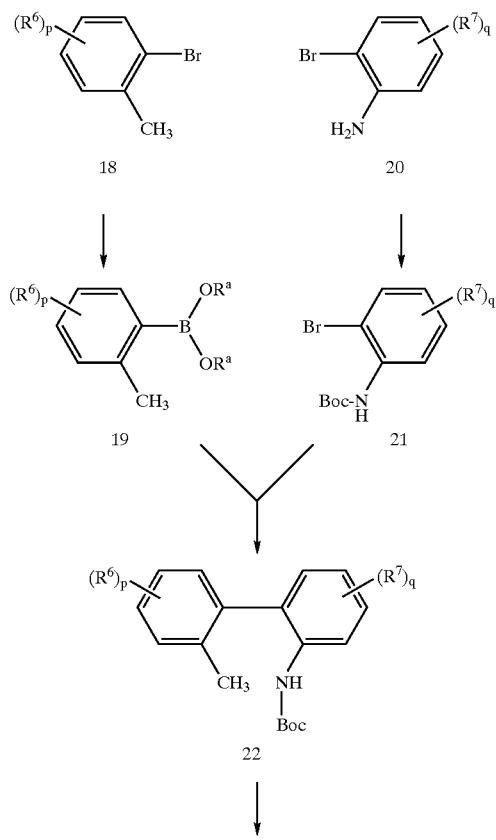

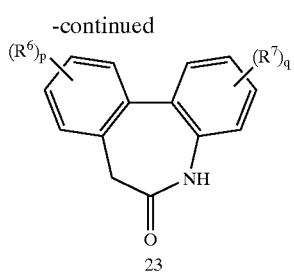

As shown in Scheme 3,5,7-dihydro-6H-dibenz[b,d]azepin-6-one derivatives, 23, wherein $R^6$, $R^7$, p and q are as defined above, can be readily prepared in several steps from a 2-bromotoluene derivative 18 and a 2-bromoaniline derivative 20. In this synthetic procedure the 2-bromotoluene derivative, 18, is first converted into the corresponding 2-methylphenylboronate ester, 19. This reaction is typically conducted by treating 18 with about 1.0 to about 2.1 equivalents of an alkyl lithium reagent, preferably sec-butyl lithium or tert-butyl lithium, in an inert diluent, such as THF, at a temperature ranging from about –80° C. to about –60° C. for about 0.25 to about 1 hour. The resulting lithium anion is then treated in situ with an excess, preferably 1.5 equivalents, of a trialkylborate, such as trimethylborate [$(CH_3O)_3B$]. This reaction is initially conducted at –80° C. to about –60° C. and then allowed to warm to about 0° C. to about 30° C. for about 0.5 to about 3 hours. The resulting methyl boronate ester is typically not isolated, but is preferably converted in situ into the pinacol ester by treating the reaction mixture with an excess, preferably about 2.0 equivalents, of pinacol. This reaction is typically conducted at ambient temperature for about 12 to about 24 hours to afford the 2-methylphenylboronate ester, 19, in which both $R^a$ groups are preferably joined together to form —$C(CH_3)_2C(CH_3)_2$—.

In a separate reaction, the amino group of a 2-bromoaniline derivative, 20, is converted into the N-Boc derivative 21 by treating 20 with about 1.0 to about 1.5 equivalents of di-tert-butyl-dicarbonate. Typically, this reaction is conducted at a temperature ranging from 25° C. to about 100° C. for about 12 to 48 hours to afford the N-Boc-2-bromoaniline derivative 21.

As further illustrated in Scheme 3, the 2-methylphenylboronate ester, 19, and the N-Boc-2-bromoaniline derivative 21 can then be coupled to form the biphenyl derivative 22. This reaction is typically conducted by contacting 21 with about 1.0 to about 1.2 equivalents of 19 and about 1.0 to about 1.2 equivalents of potassium carbonate in the presence of a pallidium catalyst, preferably tetrakis(triphenylphosphine)pallidium(0). Generally, this coupling reaction is conducted in a diluent, preferably 20% water/dioxane, under an inert atmosphere at a temperature ranging from about 50° C. to about 100° C. for about 6 to 24 hours.

Biphenyl derivative 22 is then readily converted into the 5,7-dihydro-6H-dibenz[b,d]azepin-6-one 23 by carboxylation of the 2-methyl group, followed by cyclization to form the ε-caprolactam. The carboxylation reaction is typically conducted by contacting 22 with about 2.0 to about 2.5 equivalents of a suitable base, such as sec-butyllithium, tert-butyllithium and the like, in an inert diluent, such as THF, at a temperature ranging from about –100° C. to about –20° C. for about 0.5 to 6 hours. The resulting dianion is then treated with excess anhydrous carbon dioxide to form the carboxylate. Treatment of the carboxylate with excess hydrogen chloride in a suitable diluent, such as methanol, at a temperature ranging from about 25° C. to about 100° C. then affords the 5,7-dihydro-6H-dibenz[b,d]azepin-6-one 23. Various other cyclic compounds can be prepared by routine modifications of the above described procedures.

Preferred synthetic procedures for aminating a representative compound are illustrated in Scheme 4. It will be readily apparent to those of ordinary skill in the art that the synthetic procedure illustrated in Scheme 4 and the following reaction conditions can be modified by selecting the appropriate starting materials and reagents to allow the preparation of other amino compounds suitable for use in this invention.

Scheme 4

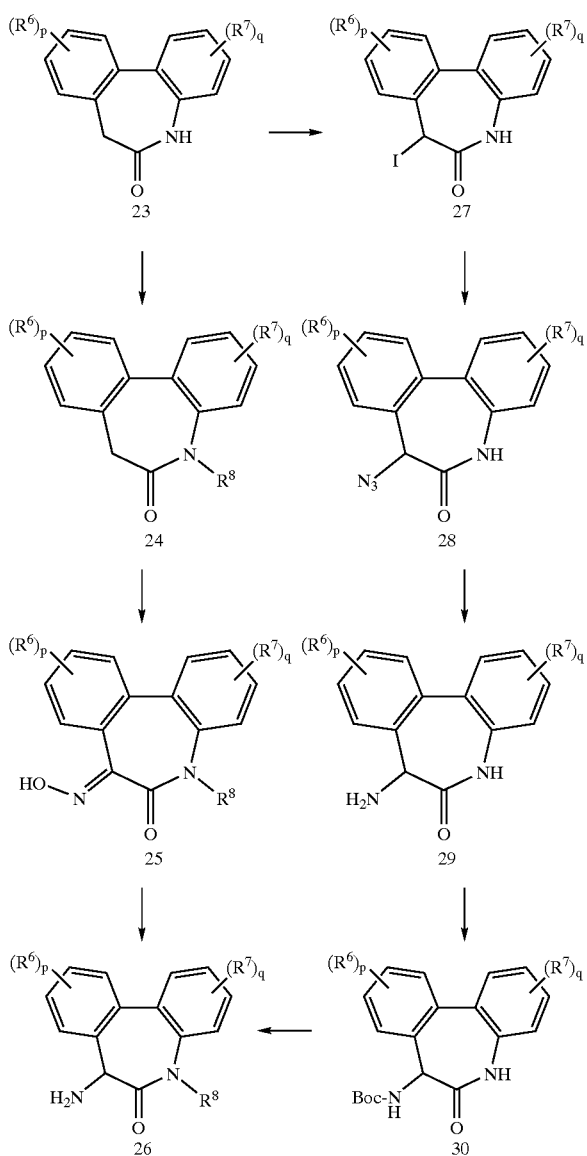

As shown in Scheme 4, 5,7-dihydro-6H-dibenz[b,d] azepin-6-one, 23, is optionally N-alkylated using conventional reagents and conditions to provide a 7-alkyl-5,7-dihydro-6H-dibenz[b,d]azepin-6-one derivative, 24. Typically, this reaction is conducted by first contacting 23 with about 1.0 to 1.5 equivalents of a suitable base, such as sodium hydride, sodium bis(trimethysilyl)amide and the like, in an inert diluent, such as DMF, THF and the like, at a temperature ranging from about −78° C. to about 50° C. for about 0.25 to about 6 hours. The resulting anion is then treated in situ with an excess, preferably about 1.1 to about 2.0 equivalents, of an alkyl, substituted alkyl, cycloalkyl halide, etc., typically a chloride, bromide or iodide. This reaction is typically conducted at a temperature ranging from about 0° C. to about 60° C. for about 1.0 to about 48 hours to afford the 7-alkyl-5,7-dihydro-6H-dibenz[b,d] azepin-6-one derivative, 24. It is understood, however, that if a substituted alkyl or cycloalkyl halide is used in this reaction, the 7-substituent will be substituted alkyl or cycloalkyl rather than the alkyl group recited herein.

The 7-alkyl-5,7-dihydro-6H-dibenz[b,d]azepin-6-one 24 is then oximated by contacting 24 with an excess, preferably with about 1.0 to 1.5 equivalents of a suitable base, such as sodium bis(trimethysilyl)amide and the like, in the presence of about 1.0 to about 2.0 equivalents of an alkyl nitrite. Suitable alkyl nitrites for use in this reaction include, by way of example, butyl nitrite, isoamyl nitrite and the like. This reaction is typically conducted in an inert diluent, such as THF and the like, at a temperature ranging from about −10° C. to about 20° C. for about 0.5 to about 6 hours to afford the 7-alkyl-5-oximo-5,7-dihydro-6H-dibenz[b,d]azepin-6-one derivative 25.

Reduction of 25 using conventional reagents and conditions then affords the 5-amino-7-alkyl-5,7-dihydro-6H-dibenz[b,d]azepin-6-one 26. Preferably, this reduction reaction is conducted by hydrogenating the oxime 25 in the presence of a catalyst, such as Raney nickel. This reaction is typically conducted under about 200 psi to about 600 psi of hydrogen at a temperature of about 70° C. to about 120° C. for about 8 to 48 hours in a diluent, preferably a mixture of ethanol and ammonia (about 20:1). Alternatively, in another preferred procedure, the oxime may be reduced using 10% Pd/C and between about 30 to about 60 psi of hydrogen at a temperature ranging from about 20° C. to about 50° C. for about 4 hours. The resulting 5-amino-7-alkyl-5,7-dihydro-6H-dibenz[b,d]azepin-6-one 26 is generally purified using well known procedures, such as recrystallization and/or chromatography.

Alternatively, 5-amino-7-alkyl-5,7-dihydro-6H-dibenz[b, d]azepin-6-ones, 26, can be prepared by first forming the 5-iodo derivative 27 of 5,7-dihydro-6H-dibenz[b,d]azepin-6-one, 23. This reaction is typically conducted as described in A. O. King et al.[13] by treating 23 with an excess, preferably about 1.2 to about 2.5 equivalents, of trimethylsilyl iodide in the presence of an excess of a trialkyamine, such as triethylamine, diisopropylethylamine, TMEDA and the like, at a temperature ranging from about −20° C. to about 0° C. for about 3 to 30 minutes and then adding about 1.1 to about 2.0 equivalents of iodine ($I_2$). Typically, after addition of the iodide, the reaction is stirred at a temperature ranging from about 0° C. to about 20° C. for about 2 to about 4 hours to afford 5-iodo-5,7-dihydro-6H-dibenz[b,d]azepin-6-one, 27.

Displacement of iodide from 27 using an alkali metal azide then affords 5-azido-5,7-dihydro-6H-dibenz[b,d] azepin-6-one, 28. Typically, this reaction is conducted by contacting 27 with about 1.1 to about 1.5 equivalents of sodium azide in an inert diluent, such as DMF, at a temperature ranging from about 0° C. to about 50° C. for about 12 to about 48 hours.

The azido derivative 28 is then reduced to the corresponding amino derivative 29 using conventional procedures and reagents. For example, the azido group is preferably reduced by contacting 28 with an excess, preferably with about 3 equivalents, of triphenylphosphine in a diluent, preferably a mixture of THF and water. This reduction reaction is typically conducted at a temperature ranging from about 0° C. to about 50° C. for about 12 to 48 hours to afford 5-amino-5,7-dihydro-6H-dibenz[b,d]azepin-6-one, 29.

The amino group of 29 is then protected or blocked using a conventional amino blocking group. Preferably, compound 29 is treated with about 1.0 to about 1.1 equivalents of di-tert-butyl dicarbonate in the presence of an excess, preferably about 2 to about 3 equivalents, of a trialkylamine, such as triethylamine. This reaction is typically conducted in an inert diluent, such as THF, at a temperature ranging from about 0° C. to about 50° C. for 3 to about 24 hours to provide 5-(N-Boc-amino)-5,7-dihydro-6H-dibenz[b,d]azepin-6-one, 30.

Compound 30 is then optionally N-alkylated to afford, after de-blocking of the amino group, a 5-amino-7-alkyl-5,7-dihydro-6H-dibenz[b,d]azepin-6-one, 26. The N-alkylation reaction is typically conducted by treating 30 with about 1.0 to 1.5 equivalents of an alkyl halide, a substituted alkyl halide or a cycloalkyl halide in the presence of about 1.0 to about 1.5 equivalents of a suitable base, such as cesium carbonate and the like. This reaction is generally conducted in an inert diluent, such as DMF and the like, at a temperature ranging from about 25° C. to about 100° C. for about 12 to about 48 hours.

Representative alkyl, substituted alkyl and cycloalkyl halides suitable for use in this N-alkylation reaction include, by way of illustration, 1-iodo-2-methylpropane, methyl bromoacetate, 1-chloro-3,3-dimethyl-2-butanone, 1-chloro-4-phenylbutane, bromomethylcyclopropane, 1-bromo-2,2,2-trifluoroethane, bromocyclohexane, 1-bromohexane and the like.

The N-Boc protecting group is then removed using conventional procedures and reagents to afford the 5-amino-7-alkyl-5,7-dihydro-6H-dibenz[b,d]azepin-6-one, 26. This deblocking reaction is typically conducted by treating the N-Boc compound 30 with anhydrous hydrogen chloride in an inert diluent, such as 1,4-dioxane, at a temperature ranging from about 0° C. to about 50° C. for about 2 to about 8 hours. The resulting 5-amino-7-alkyl-5,7-dihydro-6H-dibenz[b,d]azepin-6-one 26 is generally purified using well known procedures, such as recrystallization and/or chromatography.

The 5-amino-7-alkyl-5,7-dihydro-6H-dibenz[b,d]azepin-6-ones, 26, can also be prepared via an azide transfer reaction as illustrated in Scheme 5.

Scheme 5

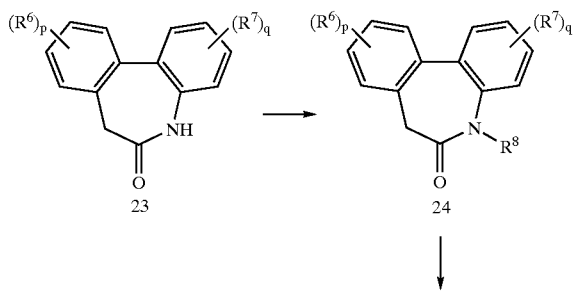

-continued

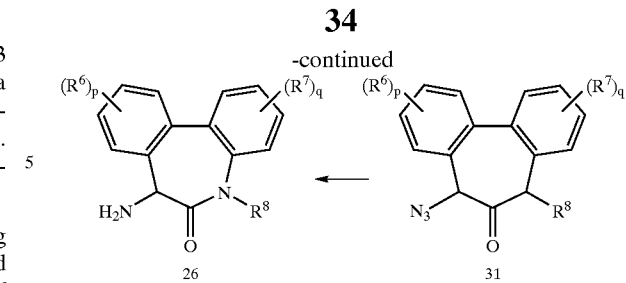

As shown in Scheme 5, 5,7-dihydro-6H-dibenz[b,d]azepin-6-one, 23, is first N-alkylated as described above using conventional reagents and conditions to provide a 7-alkyl-5,7-dihydro-6H-dibenz[b,d]azepin-6-one derivative, 24.

The 7-alkyl-5,7-dihydro-6H-dibenz[b,d]azepin-6-one 24 is then reacted with an azide transfer reagent to afford 5-azido-7-alkyl-5,7-dihydro-6H-dibenz[b,d]azepin-6-one 31. Typically, this reaction is conducted by first contacting 24 with an excess, preferably with about 1.0 to 1.5 equivalents of a suitable base, such as lithium diisopropylamide and the like, in an inert diluent such as THF, at a temperature ranging from about −90° C. to about −60° C. for about 0.25 to about 2.0 hours. The resulting anion is then treated with an excess, preferably with about 1.1 to about 1.2 equivalents, of an azide transfer reagent, such as 2,4,6-triisopropylbenzenesulfonyl azide (trisyl azide). This reaction is typically conducted at a temperature ranging from about −90° C. to about −60° C. for about 0.25 to about 2.0 hours. The reaction mixture is then typically treated with an excess of glacial acetic acid and the mixture is allowed to warm to ambient temperature and then heated at about 35° C. to about 50° C. for about 2 to 4 hours to afford the 5-azido-7-alkyl-5,7-dihydro-6H-dibenz[b,d]azepin-6-one derivative 31. Reduction of 31 as described above using conventional reagents and conditions then affords the 5-amino-7-alkyl-5,7-dihydro-6H-dibenz[b,d]azepin-6-one 26.

If desired, the aryl rings of 5-amino-7-alkyl-5,7-dihydro-6H-dibenz[b,d]azepin-6-ones, 26, and similar or related compounds may be partially or fully saturated by treatment with hydrogen in the presence of a hydrogention catalyst. Typically, this reaction is conducted by treating 26 with hydrogen at a pressure of about 10 to about 100 psi in the presence of a catalyst, such as rhodium on carbon. This reaction is typically conducted at a temperature ranging from about 20° C. to about 100° C. for about 12 to 96 hours in a suitable diluent, such as ethyl acetate/acetic acid (1:1) and the like.

Other methods for preparing intermediates useful in this invention are described in U.S. patent application Ser. No. 09/102,726, filed Jun. 22, 1998 as entitled "Polycyclic β-Amino-ε-caprolactams and Related Compounds", the disclosure of which is incorporated herein by reference in its entirety.

Additionally, the synthesis of various benzapinones and related compounds are described in Busacca et al., *Tetrahedron Lett.*, 33, 165–168 (1992); Crosisier et al., U.S. Pat. No. 4,080,449; J. A. Robl et al. *Tetrahedron Lett.*, 36(10), 1593–1596 (1995); Flynn et al. *J. Med. Chem.* 36, 2420–2423 (1993); Orito et al. *Tetrahedron*, 36, 1017–1021 (1980); Kawase et al., *J. Org. Chem.*, 54, 3394–3403 (1989); Lowe et al., *J. Med. Chem.* 37, 3789–3811 (1994); Robl et al., *Bioorg. Med. Chem. Lett.*, 4, 1789–1794 (1994); Skiles et al., *Bioorg. Med. Chem. Lett.*, 3, 773–778 (1993); Grunewald et al., *J. Med. Chem.*, 39(18), 3539-(1996);

Warshawsky et al., *Bioorg. Med. Chem. Lett.*, 6, 957–962 (1996); Ben-Ishai, et al., *Tetrahedron*, 43, 439–450 (1987); van Neil et al, *Bioorg. Med. Chem.* 5, 1421–1426 (1995); and reference cited therein. These publications and patents are incorporated herein by reference in their entirety.

Similarly, various benzodiazepine derivatives suitable for use in this invention can be prepared using conventional procedures and reagents. For example, a 2-aminobenzophenone can be readily coupled to α-(isopropylthio)-N-(benzyloxycarbonyl)glycine by first forming the acid chloride of the glycine derivative with oxayl chloride, and then coupling the acid chloride with the 2-aminobenzophenone in the presence of a base, such as 4-methylmorpholine, to afford the 2-[α-(isopropylthio)-N-(benzyloxycarbonyl)glycinyl]-aminobenzo-phenone. Treatment of this compound with ammonia gas in the presence of an excess, preferably about 1.1 to about 1.5 equivalents, of mercury (II) chloride then affords the 2-[N-(α-amino)-N'-(benzyloxycarbonyl)-glycinyl]aminobenzophenone. This intermediate can then be readily cyclized by treatment with glacial acetic acid and ammonium acetate to provide the 3-(benzyloxycarbonyl)amino-2,3-dihydro-5-phenyl-1H-1,4-benzodiazepin-2-one. Subsequent removal of the Cbz group affords the 3-amino-2,3-dihydro-5-phenyl-1H-1,4-benzodiazepin-2-one.

Alternatively, 2,3-dihydro-5-phenyl-1H-1,4-benzodiazepin-2-ones can be readily aminated at the 3-position using conventional azide transfer reactions followed by reduction of the resulting azido group to form the corresponding amino group. The conditions for these and related reactions are described in the examples set forth below. Additionally, 2,3-dihydro-5-phenyl-1H-1,4-benzodiazepin-2-ones are readily alkylated at the 1-position using conventional procedures and reagents. For example, this reaction is typically conducted by first treating the benzodiazepinone with about 1.1 to about 1.5 equivalents of a base, such as sodium hydride, potassium tert-butoxide, potassium 1,1,1,3,3,3-hexamethyldisilazane, cesium carbonate, in an inert diluent, such as DMF. This reaction is typically conducted at a temperature ranging from about −78° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

Additionally, the 3-amino-2,4-dioxo-2,3,4,5-tetrahydro-1H-1,5-benzodiazepines employed in this invention are typically prepared by first coupling malonic acid with a 1,2-phenylenediamine. Conditions for this reaction are well known in the art and are described, for example, in PCT Application WO 96-US8400 960603. Subsequent alkylation and amination using conventional procedures and reagents affords various 3-amino-1,5-bis(alkyl)-2,4-dioxo-2,3,4,5-tetrahydro-1H-1,5-benzodiazepines. Such procedures are described in further detail in the example set forth below.

The synthesis of additional ring structures is provided in the examples below.

In the synthesis of compounds of formula I or Ia using the synthetic methods described herein, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enantiomers. Preferably, however, when a chiral product is desired, the chiral product corresponds to the L-amino acid derivative. Alternatively, chiral products can be obtained via purification techniques which separates enantiomers from a R,S mixture to provide for one or the other stereoisomer. Such techniques are well known in the art.

Pharmaceutical Formulations

When employed as pharmaceuticals, the compounds of formula I or Ia are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I or Ia above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I or Ia above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

FORMULATION EXAMPLE 9

A subcutaneous formulation may be prepared as follows:

| Ingredient | Quantity |
| --- | --- |
| Active Ingredient | 1.0 mg |
| corn oil | 1 mL |

(Depending on the solubility of the active ingredient in corn oil, up to about 5.0 mg or more of the active ingredient may be employed in this formulation, if desired).

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier. Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in diagnosing and treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The compounds described herein are also suitable for use in the administration of the compounds to a cell for diagnostic and drug discovery purposes. Specifically, the compounds may be used in the diagnosis of cells releasing and/or synthesizing β-amyloid peptide. In addition the compounds described herein are useful for the measurement and evaluation of the activity of other candidate drugs on the inhibition of the cellular release and/or synthesis of β-amyloid peptide.

The following synthetic and biological examples are offered to illustrate this invention and are not to be construed in any way as limiting the scope of this invention.

EXAMPLES

In the examples below, the following abbreviations have the following meanings. If an abbreviation is not defined, it has its generally accepted meaning.

Boc=t-butoxycarbonyl
BOP=benzotriazol-1-yloxy-tris(dimethylamino) phosphonium hexafluorophosphate
bd=broad doublet
bs=broad singlet
bt=broad triplet
CBZ=benzyloxycarbonyl
d=doublet
dd=doublet of doublets
DIC=diisopropylcarbodiimide
DIPEA=diisopropylethylamine
DMF=dimethylformamide
DMSO=dimethylsulfoxide
EDC=ethyl-1-(3-dimethyaminopropyl)carbodiimide
eq.=equivalents
EtOAc=ethyl acetate
g=grams
HMDS=1,1,1,3,3,3-hexamethyldisilazane
HOBT=1-hydroxybenzotriazole hydrate
Hunig's base=diisopropylethylamine
L=liter
LDA=lithium diisopropylamide
m=multiplet
M=molar
max=maximum
mg=milligram
mL=milliliter
mm=millimeter
mmol=millimole
N=normal
ng=nanogram
nm=nanometers
OD=optical density
PEPC=1-(3-(1-pyrrolidinyl)propyl)-3-ethylcarbodiimide
psi=pounds per square inch
φ=phenyl
q=quartet quint.=quintet
rpm=rotations per minute
RT=room temperature
s=singlet
sat.=saturated
t=triplet
TFA=trifluoroacetic acid
THF=tetrahydrofuran
tlc=thin layer chromatography
TMSI=trimethylsilyl iodide
µL=microliter
UV=ultra-violet In the examples below, all temperatures are in degrees Celsius (unless otherwise indicated). The compounds set forth in the examples below were prepared using the following general procedures as indicated.

In the following examples and procedures, the term "Aldrich" indicates that the compound or reagent used in the procedure is commercially available from Aldrich Chemical Company, Inc., 1001 West Saint Paul Avenue, Milwaukee, Wis. 53233 USA; the term "Fluka" indicates that the compound or 20 reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa.; the term "Bachem" indicates that the compound or reagent is commercially available from Bachem Biosciences Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; the term "TCI" indicates that the compound or reagent is commercially available from TCI America, 9211 North Harborgate Street, Portland Oreg. 97203; the term "Alfa" indicates that the compound or reagent is commercially available from Johnson Matthey Catalog Company, Inc., 30 Bond Street, Ward Hill, Mass. 01835–0747; the term "Novabiochem" indicates that the compound or reagent is commercially available from Calbiochem-Novabiochem Corp. 10933 North Torrey Pines Road, P.O. Box 12087, La Jolla Calif. 92039–2087;the term "Oakwood" indicates that the compound or reagent is commercially available from Oakwood, Columbia, S.C.; the term "Advanced Chemtech" indicates that the compound or reagent is commercially available from Advanced Chemtech, Louisville, Ky.; and the term "Pfaltz & Bauer" indicates that the compound or reagent is commercially available from Pfaltz & Bauer, Waterbury, Conn., USA.

I. COUPLING PROCEDURES

The following procedures may be used to prepare compounds of this invention wherein an amine compound, e.g., an amino acid ester or an amine compound 2 as depicted above, is reacted with a carboxylic acid compound.

General Procedure A

First EDC Coupling Procedure

To a 1:1 mixture of the corresponding carboxylic acid and the corresponding amine, amine hydrochloride or amino acid ester or amide in $CH_2Cl_2$ at 0° C. was added 1.5 eq. triethylamine, followed by 2.0 eq. hydroxybenzotriazole monohydrate and then 1.25 eq. of ethyl-3-(3-dimethylamino)propyl carbodiimide HCl. The reaction mixture was stirred overnight at room temperature and then transferred to a separatory funnel. The mixture was washed with water, saturated aqueous $NaHCO_3$, 1N HCl and saturated aqueous NaCl, and then dried over $MgSO_4$. The resulting solution was stripped free of solvent on a rotary evaporator to yield the crude product.

General Procedure B

Second EDC Coupling Procedure

A mixture of the corresponding acid (1 eq.), N-1-hydroxybenzotriazole (1.6 eq.), the corresponding amine (1 eq.), N-methylmorpholine (3 eq.) and dichloromethane (or DMF for insoluble substrates) was cooled in an ice-water bath and stirred until a clear solution was obtained. EDC (1.3 eq.) was then added to the reaction mixture. The cooling bath was then allowed to warm to ambient temperature over 1–2 hours and the reaction mixture was stirred overnight. The reaction mixture was then evaporated to dryness under vacuum. To the residue was added 20% aqueous potassium carbonate and the mixture was shaken throughly and then allowed to stand until the oily product solidified (overnight if necessary). The solid product was then collected by filteration, washed thoroughly with 20% aqueous potassium carbonate, water, 10% HCl, and water to give the product, usually in pure state. No racemization was observed.

General Procedure C

Third EDC Coupling Procedure

The carboxylic acid was dissolved in methylene chloride. The corresponding amine or amino acid ester or amide (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product.

General Procedure D

Fourth EDC Coupling Procedure

A round bottom flask was charged with the corresponding carboxylic acid (1.0 eq.), hydroxybenzotriazole hydrate (1.1 eq.) and the corresponding amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the product.

General Procedure E

BOP Coupling Procedure

To a stirred solution of the carboxylic acid (2 mmol) in DMF, cooled in an ice-water bath, was added BOP (2.4 mmol) and N-methylmorpholine (6 mmol). The reaction mixture was stirred for 50 minutes and then a solution of α-amino-γ-lactam (2 mmol) in DMF cooled at 0° C. was added. The cooling bath was allowed to warm to ambient temperature over 1–2 hours and the reaction mixture was then stirred overnight. A 20% aqueous potassium carbonate solution (60 mL) was added and this mixture shaken throughly. No solid formed. The mixture was then washed with ethyl acetate (150 mL) and evaporated to dryness under vacuum to give a white solid. Water (50 mL) was then added and this mixture shaken throughly. The precipitate that formed was collected by filtration, then washed thoroughly with water, followed by 1 mL of diethyl ether to give the product (51 mg, 0.16 mmol, 7.8%).

General Procedure F

Coupling of an Acid Chloride with an Amino Acid Ester

To a stirred solution of amine or amino acid ester or amide (4.6 mmol) in 5 mL of pyridine was added 4.6 mmol of the carboxylic acid chloride. Precipitation occurred immediately. The mixture was stirred for 3.5 hours, dissolved in 100 mL of diethyl ether, washed with 10% HCl three times, brine once, 20% potassium carbonate once and brine once. The solution was dried over magnesium sulfate, filtered, and evaporated to yield the product.

General Procedure G

Coupling of a Carboxylic Acid with an Amino Acid Ester

A solution of the carboxylic acid (3.3 mmol) and 1,1'-carbodiimidazole (CDI) in 20 mL THF was stirred for 2 hours. (D,L)-alanine isobutyl ester hydrochloride (3.6 mmol) was added, followed by 1.5 mL (10.8 mmol) of triethylamine. The reaction mixture was stirred overnight. The reaction mixture was dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure H

Fifth EDC Coupling Procedure

In a round bottom flask was added a carboxylic acid (1.1 eq.) in THF, an amine hydrochloride (1.0 eq.), 1-hydroxybenzotriazole hydrate (1.1 eq.), N,N-diisopropylethylamine (2.1 eq.), followed by 1-(3-dimethylaminopropyl)-3-ethylcarbodiimide hydrochloride (EDC) (1.1 eq.). The reaction mixture stirred at room temperature for 10–20 hours under an atmosphere of nitrogen. The mixture was diluted with EtOAc and washed with 0.1 M HCl (1×10 mL), saturated NaHCO$_3$ (1×10 mL), H$_2$O (1×10 mL), and brine and dried over MgSO$_4$. The drying agent was removed by filtration and the filtrate was concentrated in vacuo. The residue was purified by flash column chromatography on silica gel followed by trituration from EtOAc and hexanes.

General Procedure I

Sixth EDC Coupling Procedure

To a solution or suspension of the amine or amine hydrochloride (1.0 eq.) in THF (0.05–0.1 M) under N$_2$ at 0° C. was added the carboxylic acid (1.0–1.1 eq.), hydroxybenzotriazole monohydrate (1.1–1.15 eq.), Hunig's base (1.1 eq. for free amines and 1.1–2.3 eq. for hydrochloride amine salts), followed by 1-(3-dimethylaminopropyl)-3-ethylcarbodiimide hydrochloride (1.1–1.15 eq.). The cooling bath was removed and the mixture allowed to warm to room temperature for 10–24 hours. The solution or mixture was diluted with EtOAc, in a 3–5 volume multiple of the initial THF volume, and washed with 0.1–1.0 M aq. HCl (1 or 2×), dilute NaHCO$_3$ (1 or 2×), and brine (1×). Then, the organic phase was dried over either MgSO$_4$ or Na$_2$SO$_4$, filtered, concentrated to provide the crude product, which was either further purified or utilized without further purification.

General Procedure J

EEDQ Coupling Procedure

To a solution of the amine in THF (1.0 eq., 0.05–0.08 M, final molarity) under N$_2$ at room temperature was added the N-t-Boc protected amino acid (1.1 eq., either as a solid or in THF via cannula), followed by EEDQ (Aldrich, 1.1 eq.). The pale yellow solution was stirred at room temperature for 16–16.5 hours, then diluted with EtOAc (in a 3–5 volume multiple of the initial THF volume), and washed with 1M aq. HCl (2×), dilute aq. NaHCO$_3$ (2×), and brine (1×). The organic phase was dried over either Na$_2$SO$_4$ or MgSO$_4$, filtered, and concentrated.

II. CARBOXYLIC ACIDS

The following procedures may be used to prepare carboxylic acid intermediates useful in the present invention:

General Procedure II-A

Ester Hydrolysis to Free Acid

Ester hydrolysis to the free acid was conducted by conventional methods. Below are two examples of such conventional de-esterification methods.

Method A: To a carboxylic ester compound in a 1:1 mixture of CH$_3$OH/H$_2$O was added 2–5 equivalents of K$_2$CO$_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over MgSO$_4$. The solution was stripped free of solvent on a rotary evaporator to yield the product.

Method B: The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was dissolved in water and washed with ether. The layers were separated and the aqueous layer was acidified to pH 2. The aqueous layer was extracted with ethyl acetate. The ethyl acetate extracts were dried over Na$_2$SO$_4$ and the solvent was removed under reduced pressure after filtration. The residue was purified by conventional methods (e.g., recrystallization).

General Procedure II-B

Acid Chloride Preparation

Carboxylic acid (0.174 mol) was dissolved in dichloromethane and this solution was cooled to 0° C. DMF (0.5 mL, catalytic) was added followed by the dropwise addition of oxalyl chloride (18 mL, 0.20 mol) over a 5 minute period. The reaction was stirred for 3 hours and then rotoevaporated at reduced pressure to give an oil which was placed on a high vacuum pump for 1 hour to afford the corresponding acid chloride.

General Procedure II-C

Schotten-Baumann Procedure

Carboxylic acid chloride (from General Procedure II-B) was added dropwise to a 0° C. solution of an amino acid (0.187 mol) in 2 N sodium hydroxide (215 mL, 0.43 mol). The reaction was stirred for 1 hour at 0° C. and then overnight at room temperature. The reaction was diluted with water (100 mL), then extracted with ethyl acetate (3×150 mL). The organic layer was then washed with brine (200 mL), dried over $MgSO_4$, and rotoevaporated at reduced pressure to a residue. Recrystallization of the residue from ethyl acetate/hexanes afforded the desired product (34.5 g, 82% yield).

The following procedures illustrate the synthesis of cyclic intermediates useful in preparing compounds of this invention:

III. CYCLIC COMPOUNDS

The following procedures illustrate the synthesis of various cyclic compound intermediates useful for preparing compounds of this invention:

A. Benzazepinone Derivatives and Related Compounds

General Procedure 1-A

Alkylation of 1-Amino-1,3,4,5-tetrahydro-2H-3-benzazepin-2-one

Step A: 1-Ethoxycarbonylamino-1,3,4,5-tetrahydro-2H-3-benzazepin-2-one was prepared according to the procedure of Ben-Ishai et al., *Tetrahedron*, 1987, 43, 430.

Step B: 1-Ethoxycarbonylamino-1,3,4,5-tetrahydro-2H-3-benzazepin-2-one (2.0 g, 100M %) was dissolved in DMF (30 mL) and NaH (95%, 0.17 g, 100M %) was added in one portion. The reaction mixture was stirred for 1 hour and then the appropriate alkyl iodide (300M %) was added and the mixture was stirred for 12 hours. The reaction was poured into water and extracted with ethyl acetate (3×). The ethyl acetate extracts were then washed with water (3×) and brine (1×). Treatment with $MgSO_4$, rotoevaporation, and chromatography (30% EtOAc/hexanes) yielded 1-ethoxycarbonylamino-3-alkyl-1,3,4,5-tetrahydro-2H-3-benzazepin-2-one in 87% yield.

Step C: 1-Ethoxycarbonylamino-3-alkyl-1,3,4,5-tetrahydro-2H-3-benzazepin-2-one (1.0 g, 100M %) was suspended in 30 mL of 30% HBr/HOAc and heated to 100° C. The reaction mixture was stirred for 5 hours at this temperature and then the reaction was cooled and rotoevaporated to yield 1-amino-3-alkyl-1,3,4,5-tetrahydro-2H-3-benzazepin-2-one as the hydrobromide salt (100% yield).

General Procedure 1-B

Alkylation of 3-Amino-1,3,4,5-tetrahydro-2H-1-benzazepin-2-one

Step A: 3-Amino-1,3,4,5-tetrahydro-2H-1-benzazepin-2-one was prepared from α-tetralone using the methods described in Armstrong et al. *Tetrahedron Letters*, 1994, 35, 3239. The following compounds were as prepared by this procedure for use in the following steps:

5-methyl-3-amino-1,3,4,5-tetrahydro-2H-1-benzazepin-2-one (from 4-methyl-α-tetralone (Aldrich)); and 5,5-dimethyl-3-amino-1,3,4,5-tetrahydro-2H-1-benzazepin-2-one (from 4,4-dimethyul-α-tetralone (Aldrich)).

Step B: 3-Amino-1,3,4,5-tetrahydro-2H-1-benzazepin-2-one (4.43 g, 100M %) was suspended in t-butanol (30 mL) and BOC-anhydride (7.5 mL, 130M %) was added dropwise. The reaction was stirred for 2 hours and then it was rotoevaporated to a residue which was chromatographed with 60% ethyl acetate/hexanes to yield BOC-protected 3-amino-1,3,4,5-tetrahydro-2H-1-benzazepin-2-one in 87% yield.

Step C: BOC-protected 3-amino-1,3,4,5-tetrahydro-2H-1-benzazepin-2-one (1.5 g, 100M %) was dissolved in DMF (20 mL) and NaH (95%, 0.13 g, 100M %) was added in one portion. The reaction mixture was stirred for 1 hour and then the appropriate alkyl iodide (300M %) was added and stirring was continued for 12 hours. The reaction was poured into water and extracted with ethyl acetate (3×). The ethyl acetate extracts were washed with water (3×) and then brine (1×). Treatment with $MgSO_4$, rotoevaporation, and chromatography (30% EtOAc/hexanes) yielded a BOC-protected 3-amino-1-alkyl-1,3,4,5-tetrahydro-2H-1-benzazepin-2-one in 80% yield.

Step D: The BOC-protected 3-amino-1-alkyl-1,3,4,5-tetrahydro-2H-1-benzazepin-2-one (1.0 g, 100M %) was suspended in 30 mL of 1:1 $CH_2Cl_2$/triflouroacetic acid and the mixture was stirred for 4 hours. The reaction was then rotoevaporated to yield the 3-amino-1-alkyl-1,3,4,5-tetrahydro-2H-1-benzazepin-2-one (100% yield).

Example 1-A

Synthesis of 3-Amino-1,5-dimethyl-1,3,4,5-tetrahydro-2H-1-benzazepin-2-one

Step A: 3-Amino-5-methyl-1,3,4,5-tetrahydro-2H-1-benzazepin-2-one was prepared from 4-methyl-α-tetralone using the methods described in Armstrong et al. *Tetrahedron Letters*, 1994, 35, 3239.

Step B: 3-Amino-5-methyl-1,3,4,5-tetrahydro-2H-1-benzazepin-2-one (9.3 g 100M%) was dissolved in dioxane (300 mL) and the solution was chilled to 0° C. BOC-anhydride (13.89 g 130M %) was added and the ice bath was removed allowing the solution to come to room temperature and stirring was continued for 16 hours. The solution was rotory evaporated to remove dioxane to provide an off white solid. This solid was recrystallized from $CHCl_3$ to yield BOC-protected 3-amino-5-methyl-1,3,4,5-tetrahydro-2H-1-benzazepin-2-one in 55% yield.

Step C: BOC-protected 3-amino-5-methyl-1,3,4,5-tetrahydro-2H-1-benzazepin-2-one (100 M %) was dissolved in DMF (20 mL) and NaH (95%, 100M %) was added in one portion and the reaction mixture was stirred for 1 hour. Methyl iodide (300 M %) was added and this mixture was stirred for 12 hours. The reaction was then poured into water and extracted with ethyl acetate (3×) then backwashed with water (3×) and then brine (1×). Treatment with $MgSO_4$, rotoevaporation, and chromatography (5% MeOH/$CH_2Cl_2$) yielded BOC-protected 3-amino-1,5-dimethyl-1,3,4,5-tetrahydro-2H-1-benzazepin-2-one in 75% yield.

Step D: BOC-protected 3-amino-1,5-dimethyl-1,3,4,5-tetrahydro-2H-1-benzazepin-2-one (100 M %) was suspended in 30 mL of 1:1 CH$_2$Cl$_2$/triflouroacetic acid. The reaction mixture was stirred for 4 hours. The reaction was then rotoevaporated to yield 3-amino-1,5-dimethyl-1,3,4,5-tetrahydro-2H-1-benzazepin-2-one (100% yield).

Example 1-B

Synthesis of 5-(L-Alaninyl)-amino-3,3,7-trimethyl-5,7-dihydro-6H-benz[b]azepin-6-one Hydrochloride Following the procedure of Example 2-I and using 5-amino-3,3,7-trimethyl-5,7-dihydro-6H-benz[b]azepin-6-one hydrochloride (Example 1-C), the title compound was prepared.

Example 1-C

Synthesis of 5-Amino-3,3,7-trimethyl-5,7-dihydro-6H-benz[b]azepin-6-one Hydrochloride Step A: General Procedure
 N-Alkylation of Lactams
  To a stirred solution of a BOC-protected (α-aminocaprolactam (6.87 g, 30 mmol) in DMF (150 mL) was added in portions 97% NaH (1.08 g, 45 mmol). Bubbling occured immediately and followed by heavy precipitation. After 10 minutes, benzyl bromide (3.93 mL, 33 mmol) was added. The precipitate dissolved quickly and in about 10 min. a clear solution was obtained. The reaction mixture was stirred overnight and then evaporated as completely as possible on a rotovap at 30° C. Ethyl acetate (100 mL) was added to the residue and this mixture was washed with water, brine, and dried over magnesium sulfate. After filtration and concentration, a thick liquid (10 g) was obtained which was then chromatographed over silica gel with 1:3 ethyl acetate/hexane as the eluant to provide 5.51 g (58%) of the N-benzylated product as an oil. Other lactams and alkylating agents may be used in this procedure to obtain a wide variety of N-alkylated lactams. Various bases, such as LiN(SiMe$_3$), may also be employed.
  Following this General Procedure and using N-t-Boc-5-amino-3,3-dimethyl-5,7-dihydro-6H-benz[b]azepin-6-one (General Procedure 1-B, followed by Boc protection) and methyl iodide, N-t-Boc-5-amino-3,3,7-trimethyl-5,7-dihydro-6H-benz[b]azepin-6-one was prepared.

Step B: General Procedure
 BOC Removal Procedure
  A stream of anhydrous HCl gas was passed through a stirred solution of the N-t-Boc protected amino acid in 1,4-dioxane (0.03–0.09 M), chilled in a ice bath to ~10° C. under N$_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in CH$_2$Cl$_2$ then re-concentrated and placed in vacuum oven at 60–70° C. to remove most of the residual dioxane) and used without further purification.
  Following this General Procedure and using N-t-Boc-5-amino-3,3,7-trimethyl-5,7-dihydro-6H-benz[b]azepin-6-one, the title compound was prepared.

Example 1-D

Synthesis of 3-(S)-Amino-1-methyl-5-oxa-1,3,4,5-tetrahydro-2H-1-benzazepin-2-one Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following the General Procedure of Step A of Example 1-C and using the product from Step A of this example, the title compound was prepared.

Example 1-E

Synthesis of 3-(S)-Amino-1-ethyl-5-oxa-1,3,4,5-tetrahydro-2H-1-benzazepin-2-one

Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following the General Procedure of Step A of Example 1-C and using the product from Step A of this example, the title compound was prepared.

Example 1-F

Synthesis of 3-(S)-Amino-1-methyl-5-thia-1,3,4,5-tetrahydro-2H-1-benzazepin-2-one The title compound was prepared from N-Boc-cystine (Novabio) and 2-fluoro-1-nitrobenzene (Aldrich) using the method of R. J. DeVita et al., *Bioorganic and Medicinal Chemistry Lett.* 1995, 5(12) 1281–1286, followed by the General Procedure of Step A of Example 1-C.

Example 1-G

Synthesis of 7-Amino-1,3,4,7,12,12a-hexahydropyrido[2,1-b][3]-benzazepin-6(2H)-one Step A—Synthesis of N-Chloroacetyl-2-benzylpiperidine
 Following General Procedure F and using 2-benzylpyridine, the title compound was prepared.
 Physical data were as follows:
 (MW=251.8); mass spectroscopy (MH+) 252.0.

Step B—Synthesis of 1,3,4,7,12,12a-hexahydropyrido[2,1-b][3]benzazepin-6(2H)-one
 Following General Procedure G and using N-chloroacetyl-2-benzylpiperidine, the title compound was prepared.
 Physical data were as follows:
 $^1$H-nmr (CDCl$_3$): δ=1.3–1.9 (6H); 2.42 (t, 1H); 3.08 (m, 2H); 3.47 (m, 1H); 3.96 (q, 2H); 4.66 (d, 1H); 7.2 (m, 4H). (MW=215.3); mass spectroscopy (MH+) 216.1.

Step C—Synthesis of 7-Oximo-1,3,4,7,12 12a-hexahydropyrido[2,1-b][3]benzazepin-6(2H)-one
 Following General Procedure 3A (Step B) and using 1,3,4,7,12,12a-hexahydropyrido[2,1-b][3]benzazepin-6(2H)-one (from Step B above), the title compound was prepared.
 Physical data were as follows:
 (MW=244.3); mass spectroscopy (MH+) 245.0.

Step D—Synthesis of 7-Amino-1,3,4,7,12,12a-hexahydropyrido[2,1-b][3]benzazepin-6(2H)-one
 Following General Procedure 3A (Step C) and using 7-oximo-1,3,4,7,12,12a-hexahydropyrido[2,1-b][3]benzazepin-6(2H)-one (from Step C above), the title compound was prepared.
 Physical data were as follows:
 $^1$H-nmr (CDCl$_3$): δ=1.3–1.9 (6H); 2.42 (t, 1H); 3.08 (m, 2H); 3.47 (m, 1H); 3.96 (q, 2H); 4.66 (d, 1H); 7.2 (m, 4H). (MW=230.3); mass spectroscopy (MH+) 231.1.

Example 1-H

Synthesis of 1-(N'-L-Alaninyl)amino-4,5,6,7-tetrahydro-3,7-methano-3H-3-benzazonin-2(1H)-one Step A—Synthesis of N-Chloroacetyl-3-phenylpiperidine Following General Procedure F and using 3-phenylpyridine hydrochloride (Aldrich), the title compound was prepared.

Step B—Synthesis of 4,5,6,7-Tetrahydro-3,7-methano-3H-3-benzazonin-2(1H)-one

Following General Procedure G and using N-chloroacetyl-3-phenyl-piperidine, the title compound was prepared.

Physical data were as follows:

$^1$H-nmr (CDCl$_3$): d=1.32–1.57 (2H); 2.08 (m, 2H); 2.81 (t, 1H); 3.13 (bs, 1H); 3.37 (m, 2H); 4.36 (m, 2H); 4.50 (d, 1H). (MW=201.3); mass spectroscopy (MH+) 202.1.

Step C—Synthesis of 1-Oximo-4,5,6,7-tetrahydro-3.7-methano-3H-3-benzazonin-2(1H)-one Following General Procedure 3A (Step B) and using the product from Step B above, the title compound was prepared.

Step D—Synthesis of 1-Amino-4,5,6,7-tetrahydro-3,7-methano-3H-3-benzazonin-2(1H)-one Following General Procedure 3A (Step C) and using the product from Step C above, the title compound was prepared.

Physical data were as follows:

$^1$H-nmr (CDCl$_3$): δ=2.86 (t, 1H); 3.17 (bs, 1H); 3.39 (dd, 1H); 4.40 (d, 1H); 4.50 (d, 1H); 5.39 (s, 1H). (MW=216.3); mass spectroscopy (MH+) 217.4.

Step E—Synthesis of 1-(N'-Boc-L-Alaninyl)amino-4,5,6,7-tetrahydro-3,7-methano-3H-3-benzazonin-2(1H)-one Following General Procedure D and using N-tert-Boc-L-alanine (Aldrich) and the product from Step D above, the title compound was prepared.

Physical data were as follows:

(MW=387.48); mass spectroscopy (MH+) 388.1.

Step F—Synthesis of 1-(N'-L-Alaninyl)amino-4,5,6,7-tetrahydro-3,7-methano-3H-3-benzazonin-2(1H)-one Following General Procedure E and using the product from Step E, the title compound was prepared.

Physical data were as follows:

$^1$H-nmr (CDCl$_3$): δ=2.85 (t, 1H); 3.16 (bs, 1H); 3.40 (dd, 1H); 3.67 (m, 1H); 4.35 (d, 1H); 4.56 (d, 1H); 6.40 (d, 1H). (MW=287.4); mass spectroscopy (MH+) 288.1.

Example 2-A

Synthesis of 5-Amino-5,7-dihydro-6H-dibenzo[a,c]cyclohepten-6-ol Hydrochloride

Step A—Synthesis of 5-Oximo-5,7-dihydro-6H-dibenzo[a,c]cyclohepten-6-one

A round bottom flask was charged with 5,7-dihydro-6H-dibenzo[a,c]cyclohepten-6-one (1.0 g, 4.81 mmol)(CAS #1139-82-8, prepared as described in *Tetrahedron Letters*, Vol. 28, No. 23, (1987), pp 2633–2636) and butyl nitrite (0.673 mL, 5.77 mmol) (Aldrich) in Et$_2$O. The solution was cooled to 0° C. and treated drop-wise with a saturated solution of HCl(g)/Et$_2$O. After 5 hours at 0° C., the resulting precipitate was filtered, rinsed with cold Et$_2$O and vacuum dried to give the title compound as a colorless solid.

NMR data was as follows:

$^1$H-nmr (CDCl$_3$): δ=7.26–7.74 (m, 8H), 3.84 (m, 2H). C$_{15}$H$_{11}$NO$_2$ (MW=237.26); mass spectroscopy (MH+) 238. Anal. Calcd for C$_{15}$H$_{11}$NO$_2$; C, 75.93 H, 4.67 N, 5.90. Found: C, 75.67 H, 4.83 N, 5.67.

Step B—Synthesis of 5-Amino-5,7-dihydro-6H-dibenzo[a,c]cyclohepten-6-ol Hydrochloride The compound isolated above (0.489 g, 2.04 mmol) was dissolved in THF and added drop-wise to a well-stirred mixture of LAH (10.2 mL, 10.2 mmol)/THF. After heating to reflux for 25 hours under N$_2$ atmosphere the solution was quenched and worked-up according to Fieser's method. The resulting solid was rinsed with NH$_3$ sat/CHCl$_3$, the filtrate evaporated and the title compound purified by chromatography (SiO$_2$, CHCl$_3$).

C$_{15}$H$_{15}$NO (MW=225.290); mass spectroscopy (MH+) 226. Anal. Calcd for C$_{15}$H$_{15}$NO; C, 79.97 H, 6.71 N, 6.22. Found: C, 80.19 H, 6.71 N, 5.91.

Example 2-B

Synthesis of 5-[L-alaninyl]-amino-5,7-dihydro-6H-dibenzo[a,c]cyclohepten-6-one

Following General Procedure D above using Boc-L-alanine (Aldrich) and 5-amino-5,7-dihydro-6H-dibenzo[a,c]cyclohepten-6-ol hydrochloride (Example 2-A), the compound was prepared as a tan foam.

The resulting alcohol was oxidized as follows. To a stirred mixture of oxalyl chloride (0.1.5 mL, 1.2 mmol) in 10 mL of dichloromethane cooled to −78° C. was added DMSO (0.106 mL, 1.5 mmol) and the mixture was stirred for 10 minutes. A solution of the alcohol (0.1828 g, 0.60 mmol) in 20 mL of chloroform was added dropwise. The reaction mixture was stirred at −78° C. for 2 hours, and then 0.5 mL (3.6 mmol) of triethylamine was added. Stirring was continued for 1 hour and then the mixture was allowed to warm to room temperature and stirring was continued at ambient temperature overnight. The mixture was then diluted with 50 mL of dichloromethane, washed with brine (3×), dried over magnesium sulfate, filtered and evaporated to dryness to give the crude product which as typically purified by column chromatography.

The Boc group was removed using 2.0 M HCl/dioxane. The title compound was isolated as an orange foam.

C$_{18}$H$_{18}$N$_2$O$_2$HCl (MW=330.4); mass spectroscopy (MH+ of freebase) 295.

C. Dibenzazepinone Derivatives and Related Compounds

General Procedure 3-A

Preparation of 5-Amino-7-alkyl-5,7-dihydro-6H-dibenz[b,d]azepin-6-one Derivatives Step A: Following the General Procedure of Step A of Example 1-C and using 5,7-dihydro-6H-dibenz[b,d]azepin-6-one and an alkyl halide, the 7-alkyl-5,7-dihydro-6H-dibenz[b,d]azepin-6-one was prepared.

Step B: The 7-alkyl-5,7-dihydro-6H-dibenz[b,d]azepin-6-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1N HCl and extracted with EtOAc. The organic portion was dried and concentrated to yield a crude product which was purified by silica gel chromatography.

Step C: The resulting oxime was dissolved in EtOH/NH$_3$ (20:1) and hydrogenated in a bomb using Raney nickel and hydrogen (500 psi) at 100° C. for 10 hours. The resulting mixture was filtered and concentrated to provide an oil which was purified by silica gel chromatography to yield the title compound.

General Procedure 3-B

Preparation of Fluoro-substituted 5,7-Dihydro-6H-dibenz[b,d]azepin-6-one Derivatives A modification of the procedure of Robin D. Clark and Jahangir, *Tetrahedron*, Vol. 49, No. 7, pp. 1351–1356, 1993[15] was used. Specifically, an appropriately substituted N-t-Boc-2-amino-2'-methylbiphenyl was dissolved in THF and cooled to −78° C. s-Butyl lithium (1.3M in cyclohexane, 2.2 eq.) was added slowly so that the temperature remained below −65° C. The resulting mixture was allowed to warm to −25° C. and was stirred at that temperature for 1 hour. The mixture was cooled to −78° C. Dry $CO_2$ was bubbled through the mixture for 30 seconds. The mixture was allowed to warm to ambient temperature then was carefully quenched with water. The mixture was concentrated under reduced pressure then was adjusted to pH 3 with 1N HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

General Procedure 3-C

Resolution of 5-Amino-7-methyl-5,7-dihydro-6H-dibenz[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% $H_2O$ with 0.1% trifluoroacetic acid and a flow rate of 1.0 mL/minutes at 35° C. The resolved di-p-toluoyl-D-tartaric salt was then dissolved in EtOAc and saturated $NaHCO_3$ until pH 9–10 was reached. The layers were separated and the organic layer was washed again with saturated $NaHCO_3$, $H_2O$, and brine. The organic layer was dried over $MgSO_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC.

Example 3-A

Synthesis of 5-Amino-7-methyl-5,7-dihydro-6H-dibenz[b,d]azepin-6-one Hydrochloride Step A—Synthesis of 7-Methyl-5,7-dihydro-6H-dibenz[b,d]azepin-6-one A round bottom flask was charged with sodium hydride (0.295 g, 7.46 mmol) in 9.0 mL of DMF and treated with 5,7-dihydro-6H-dibenz[b,d]azepin-6-one (1.3 g, 6.22 mmol) (CAS #20011-90-9, prepared as described in Brown, et. al., *Tetrahedron Letters*, No. 8, 667–670, (1971) and references cited therein). After stirring at 60° C. for 1 hour, the solution was treated with methyl iodide (1.16 mL, 18.6 mmol) and stirring continued for 17 hours with the exclusion of light. After cooling, the reaction was diluted with $CH_2Cl_2/H_2O$, washed with $NaHSO_4$ solution, $H_2O$, and dried over $Na_2SO_4$. Evaporation and flash chromatography ($SiO_2$, $CHCl_3$) gave 0.885 g (63%) of the title compound as a colorless solid.

NMR data was as follows:
$^1$H-nmr (CDCl$_3$): δ=7.62 (d, 2H), 7.26–7.47 (m, 6H), 3.51 (m, 2H), 3.32 (s, 3H). $C_{15}H_{13}NO$ (MW=223.27); mass spectroscopy (MH+) 223. Anal. Calcd for $C_{15}H_{13}NO$; C, 80.69 H, 5.87 N, 6.27. Found: C, 80.11 H, 5.95 N, 6.23.

Step B—Synthesis of 7-Methyl-5-oximo-5,7-dihydro-6H-dibenz[b,d]azepin-6-one

The compound isolated above (0.700 g, 3.14 mmol) was dissolved in 20 mL of toluene and treated with butyl nitrite (0.733 mL, 6.28 mmol). The reaction temperature was lowered to 0° C. and the solution was treated with KHMDS (9.42 mL, 0.5 M) under $N_2$ atmosphere. After stirring for 1 hour the reaction was quenched with a saturated solution of $NaHSO_4$, diluted with $CH_2Cl_2$ and separated. The organic layer was dried over $Na_2SO_4$ and the title compound purified by chromatography ($SiO_2$, 98:2 $CHCl_3$/MeOH) giving 0.59 g (80%) as a colorless solid.

$C_{15}H_{12}N_2O_2$ (MW=252.275); mass spectroscopy (MH+) 252. Anal. Calcd for $C_{15}H_{12}N_2O_2$; C, 71.42 H, 4.79 N, 11.10. Found: C, 71.24 H, 4.69 N, 10.87.

Step C—Synthesis of 5-Amino-7-Methyl-5,7-dihydro-6H-dibenz[b,d]azepin-6-one Hydrochloride The oxime isolated above (0.99 g, 3.92 mmol) was hydrogenated in a Parr apparatus at 35 psi over 10% Pd/C (0.46 g) in 3A ethanol. After 32 hours, the reaction mixture was filtered through a plug of celite, the filtrate evaporated to a foam and treated with a saturated solution of HCl (g) in $Et_2O$. The resulting colorless solid was filtered, rinsed with cold $Et_2O$ and vacuum dried to give 0.66 g (61%) of the title compound.

NMR data was as follows:
$^1$H-nmr (DMSOd6): δ=9.11 (bs, 3H), 7.78–7.41 (m, 8H), 4.83 (s, 1H), 3.25 (s, 3H). $C_{15}H_{14}N_2O$ HCl (MW=274.753); mass spectroscopy (MH+free base) 238. Anal. Calcd for $C_{15}H_{14}N_2O$ HCl; C, 65.57 H, 5.50 N, 10.19 Found: C, 65.27 H, 5.67 N, 10.13.

Example 3-B

Synthesis of (S)- and (R)-5-(L-Alaninyl)-amino-7-methyl-5,7-dihydro-6H-dibenz[b,d]azepin-6-one Step A—Synthesis of (S)- and (R)-5-(N-Boc-L-Alaninyl)-amino-7-methyl-5,7-dihydro-6H-dibenz[b,d]azepin-6-one Boc-L-Alanine (0.429 g, 2.26 mmol) (Aldrich) was dissolved in THF and treated with HOBt hydrate (0.305 g, 2.26 mmol), and 5-amino-7-methyl-5,7-dihydro-6H-dibenz[b,d]azepin-6-one (0.45 g, 1.89 mmol) (Example 3-A). The temperature was lowered to 0° C. and the reaction mixture treated with EDC (0.449 g, 2.26 mmol) (Aldrich) and stirred 17 hours under $N_2$. The reaction mixture was evaporated, the residue diluted with EtOAc/$H_2O$, washed 1.0 N HCl, sat. $NaHCO_3$, brine and dried over $Na_2SO4$. The diastereomers were separated on a Chiralcel OD column using 10% IPA/heptane at 1.5 mL/minute.

Isomer 1: Retention time 3.37 minutes.
NMR data was as follows:
$^1$H-nmr (CDCl$_3$): δ=7.62–7.33 (m, 9H), 5.26 (d, 1H), 5.08 (m, 1H), 4.34 (m, 1H), 3.35 (s, 3H), 1.49 (s, 9H), 1.40 (d, 3H). Optical Rotation: [α]$_{20}$=−96 @ 589 nm (c=1, MeOH). $C_{23}H_{27}N_3O_4$ (MW=409.489); mass spectroscopy (MH+) 409. Anal. Calcd for $C_{23}H_{27}N_3O_4$; C, 67.46 H, 6.64 N, 10.26. Found: C, 68.42 H, 7.02 N, 9.81.

Isomer 2: Retention time 6.08 minutes.
NMR data was as follows:
$^1$H-nmr (CDCl$_3$): δ=7.74 (bd, 1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H). Optical Rotation: [α]$_{20}$=69 @ 589 nm (c=1, MeOH). C$_{23}$H$_{27}$N$_3$O$_4$ (MW=409.489); mass spectroscopy (MH+) 409. Anal. Calcd for C$_{23}$H$_{27}$N$_3$O$_4$; C, 67.46 H, 6.64 N, 10.26. Found: C, 67.40 H, 6.62 N, 10.02.

Step B—Synthesis of (S)- and (R)-5-(L-Alaninyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
C$_{18}$H$_{19}$N$_3$O$_2$.HCl (MW=345.832); mass spectroscopy (MH+free base) 309. Optical Rotation: [α]$_{20}$=−55 @ 589 nm (c=1, MeOH).

Isomer 2:
C$_{18}$H$_{19}$N$_3$O$_2$.HCl (MW=345.832); mass spectroscopy (MH+free base) 309. Optical Rotation: [α]$_{20}$=80 @ 589 nm (c=1, MeOH).

Example 3-C

Synthesis of (S)- and (R)-5-(L-Valinyl)-amino-7-methyl-5,7-dihydro-6H-dibenz[b,d]azepin-6-one Step A—Synthesis of (S)- and (R)-5-(N-Boc-L-Valinyl)-amino-7-methyl-5,7-dihydro-6H-dibenz[b,d]azepin-6-one Boc-L-Valine (0.656 g, 3.02 mmol) (Aldrich) was dissolved in THF and treated with HOBt hydrate (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 3-A). The temperature was lowered to 0° C. and the reaction mixture treated with EDC (0.601 g, 3.02 mmol) (Aldrich) and stirred 17 hours under N$_2$. The reaction mixture was evaporated, the residue diluted with EtOAc/H$_2$O, washed 1.0 N HCl, sat. NaHCO$_3$, brine and dried over Na$_2$SO$_4$. The diastereomers were separated on a Chiralcel OD column using 10% IPA/heptane at 1.5 mL/minute.

Isomer 1: Retention time 3.23 minutes.
Optical Rotation: [α]$_{20}$=−120 @ 589 nm (c=1, MeOH). C$_{25}$H$_{31}$N$_3$O$_4$ (MW=437.544); mass spectroscopy (MH+) 438.

Isomer 2: Retention time 6.64 minutes.
Optical Rotation: [α]$_{20}$=50 @ 589 nm (c=1, MeOH). C$_{25}$H$_{31}$N$_3$O$_4$ (MW=437.544); mass spectroscopy (MH+) 438.

Step B—Synthesis of (S)- and (R)-5-(L-Valinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
C$_{20}$H$_{23}$N$_3$O$_2$.HCl (MW=373.88); mass spectroscopy (MH+free base) 338. Optical Rotation: [α]$_{20}$=−38 @ 589 nm (c=1, MeOH).

Isomer 2:
C$_{20}$H$_{23}$N$_3$O$_2$.HCl (MW=373.88); mass spectroscopy (MH+free base) 338. Optical Rotation: [α]$_{20}$=97 @ 589 nm (c=1, MeOH).

Example 3-D

Synthesis of (S)- and (R)-5-(L-tert-Leucine)-amino-7-methyl-5,7-dihydro-6H-dibenz[b,d]azepin-6-one Step A—Synthesis of (S)- and (R)-5-(N-Boc-L-tert-Leucinyl)-amino-7-methyl-5,7-dihydro-6H-dibenz[b,d]azepin-6-one Boc-L-tert-Leucine (0.698 g, 3.02 mmol) (Fluka) was dissolved in THF and treated with HOBt hydrate (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 3-A). The temperature was lowered to 0° C. and the reaction mixture treated with EDC (0.601 g, 3.02 mmol) (Alrich) and stirred 17 hours under N$_2$. The reaction mixture was evaporated, the residue diluted with EtOAc/H$_2$O, washed 1.0 N HCl, sat. NaHCO$_3$, brine and dried over Na$_2$SO$_4$. The diastereomers were separated on a Chiralcel OD column using 10% IPA/heptane at 1.5 mL/minute.

Isomer 1: Retention time 3.28 minutes.
Optical Rotation: [α]$_{20}$=−128 @ 589 nm (c=1, MeOH). C$_{26}$H$_{33}$N$_3$O$_4$ (MW=451.571); mass spectroscopy (MH+) 452.

Isomer 2: Retention time 5.52 minutes.
Optical Rotation: [α]$_{20}$=26 @ 589 nm (c=1, MeOH). C$_{26}$H$_{33}$N$_3$O$_4$ (MW=451.571); mass spectroscopy (MH+) 452.

Step B—Synthesis of (S)- and (R)-5-(L-tert-Leucinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
C$_{21}$H$_{25}$N$_3$O$_2$.HCl (MW=387.91); mass spectroscopy (MH+free base) 352. Optical Rotation: [α]$_{20}$=−34 @ 589 nm (c=1, MeOH).

Isomer 2:
C$_{21}$H$_{25}$N$_3$O$_2$.HCl (MW=387.91); mass spectroscopy (MH+free base) 352. Optical Rotation: [α]$_{20}$=108 @ 589 nm (c=1, MeOH).

Example 3-E

Synthesis of 5-(N-Boc-Amino)-5,7-dihydro-6H,7H-dibenz[b,d]azepin-6-one

Step A—Synthesis of 5-Iodo-5,7-dihydro-6H-dibenz[b,d]azepin-6-one

A solution of 5,7-dihydro-6H-dibenz[b,d]azepin-6-one (1.0 g, 4.77 mmol) (Example 3-A) and Et$_3$N (2.66 mL, 19.12 mmol) were stirred for 5.0 minutes at −15° C. in CH$_2$Cl$_2$ and treated with TMSI (1.36 mL, 9.54 mmol). After stirring for 15 minutes I$_2$ (1.81 g, 7.16 mmol) was added in a single portion and the reaction allowed to warm to 5–10° C. over 3 h. The reaction was quenched with sat. Na$_2$SO$_3$, diluted with CH$_2$Cl$_2$ and separated. The organics were washed with Na$_2$SO$_3$ and NaHSO$_3$ and dried over MgSO$_4$. After filtration, the organics were concentrated to approximately 20 mL and diluted with an additional 20 mL of hexanes. The title compound was isolated as a tan precipitate by filtration.

Step B—Synthesis of 5-Azido-5,7-dihydro-6H-dibenz[b,d]azepin-6-one

The iodide isolate above was dissolved in DMF and treated with 1.2 equivalents of NaN$_3$. After stirring 17 hour at 23° C., the mixture was diluted with EtOAc/H$_2$O, separated, washed with brine and dried over MgSO$_4$. The title compound was triturated from hot EtOAc as a tan powder.

Step C—Synthesis of 5-(N-Boc-Amino)-5,7-dihydro-6H, 7H-dibenz[b,d]azepin-6-one

The azide was dissolved in THF/H$_2$O and stirred at 23° C. for 17 hours in the presence of 3.0 equivalents of Ph$_3$P. The reaction was diluted with 50% HOAc/toluene, separated, the aqueous layer extracted with toluene and evaporated to an oily residue. This was taken to pH 7.0 by the addition of 1 N NaOH, the resulting HOAc salt was collected and vacuum dried. Finally, the compound was treated with Boc anhydride (1.05 equivalents) and Et$_3$N (2.1 equivalents) in THF. After stirring for 5 hours at 23° C., the reaction was filtered and the title compound isolated as a colorless powder.

Example 3-F

Synthesis of 5-Amino-7-(2-methylpropyl)-5,7-dihydro-6H-dibenz[b,d]azepin-6-one Hydrochloride Step A—Synthesis of 5-(N-Boc-Amino)-7-(2-methylpropyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3-E) in DMF was treated with Cs$_2$CO$_3$ (0.22 g, 0.678 mmol) and warmed to 60° C. To the reaction mixture was added 1-iodo-2-methylpropane (0.078 mL, 0.678 mmol) and stirring continued for 17 hours. After cooling to 23° C. the mixture was diluted with CH$_2$Cl$_2$, washed with several portions of brine and dried over Na$_2$SO$_4$. The title compound was purified by chromatography (SiO$_2$, CHCl$_3$/MeOH 9:1).

C$_{23}$H$_{28}$N$_2$O$_3$ (MW=380.41); mass spectroscopy (MH+) 381Anal. Calcd for C$_{23}$H$_{28}$N$_2$O$_3$; C, 72.61 H, 7.42 N, 7.36. Found: C, 72.31 H, 7.64 N, 7.17.

Step B—Synthesis of 5-Amino-7-(2-methylpropyl)-5,7-dihydro-6H-dibenz[b,d]azepin-6-one Hydrochloride The compound isolated in Part A was deprotected in dioxane saturated with gaseous HCl. The title compound was isolated as a slightly colored solid after evaporation and vacuum drying.

Example 3-G

Synthesis of 5-Amino-7-(methoxyacetyl)-5,7-dihydro-6H-dibenz[b,d]azepin-6-one Hydrochloride Step A—Synthesis of 5-(N-Boc-Amino)-7-(methoxyacetyl)-5,7-dihydro-6H-dibenz[b,d]azepin-6-one A solution of 5-(N-Boc-amino)-5,7-dihydro-6H-dibenz[b,d]azepin-6-one (1.03, 3.08 mmol) (Example 3-E) in DMF was treated with Cs$_2$CO$_3$ (1.10 g, 3.39 mmol) and warmed to 60° C. To the reaction mixture was added bromomethyl acetate (0.321 mL, 3.39 mmol) (Aldrich) and stirring continued for 17 hours. After cooling to 23° C., the mixture was diluted with CH$_2$Cl$_2$, washed with several portions of brine and dried over Na$_2$SO$_4$. The title compound was purified by chromatography (SiO$_2$, CHCl$_3$).

C$_{22}$H$_{24}$N$_2$O$_5$ (MW=396.44); mass spectroscopy (MH+) 397Anal. Calcd for C$_{22}$H$_{24}$N$_2$O$_5$; C, 66.65 H, 6.10 N, 7.07. Found: C, 66.28 H, 5.72 N, 6.50.

Step B—Synthesis of 5-Amino-7-(methoxyacetyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

C$_{17}$H$_{16}$N$_2$O$_3$ HCl (MW=332.78); mass spectroscopy (MH+free base) 297.

Example 3-H

Synthesis of 5-Amino-7-(3,3-dimethyl-2-butanonyl)-5,7-dihydro-6H-dibenz [b,d]azepin-6-one Hydrochloride Step A—Synthesis of 5-(N-Boc-Amino)-7-(3,3-dimethyl-butanonyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3-E) in DMF was treated with Cs$_2$CO$_3$ (0.3 g, 0.925 mmol) and warmed to 60° C. To the reaction mixture was added 1-chloro-3,3-dimethyl-2-butanone (0.096 mL, 0.74 mmol) (Aldrich) and stirring continued for 17 hours. After cooling to 23° C., the mixture was diluted with CH$_2$Cl$_2$, washed with several portions of brine and dried over Na$_2$SO$_4$. The title compound was isolated as a colorless solid.

C$_{25}$H$_{30}$N$_2$O$_4$ (MW=422.522); mass spectroscopy (MH+) 423.

Step B—Synthesis of 5-Amino-7-(3,3-dimethyl-2-butanonyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

Example 3-I

Synthesis of L-Alaninyl-5-amino-7-methyl-5,7-dihydro-6H-dibenz[b,d]azepin-6-one Hydrochloride Step A: Following General Procedure D and using N-t-Boc-L-alanine and 5-amino-7-methyl-5,7-dihydro-6H-dibenz[b,d]azepin-6-one, N-t-Boc-L-alaninyl-5-amino-7-methyl-5,7-dihydro-6H-dibenz[b,d]azepin-6-one was prepared.

Step B: Following the General Procedure of Step B of Example 1-C and using the N-t-Boc-L-alaninyl-5-amino-7-methyl-5,7-dihydro-6H-dibenz[b,d]azepin-6-one, the title compound was prepared. Other substituted N-t-Boc-L-alaninyl-5-amino-7-methyl-5,7-dihydro-6H-dibenz[b,d]azepin-6-ones can also be prepared by this procedure.

Example 3-J

Synthesis of L-Valinyl-5-amino-7-methyl-5,7-dihydro-6H-dibenz[b,d]azepin-6-one Hydrochloride Step A: Following General Procedure D and using N-t-Boc-L-valine and 5-amino-7-methyl-5,7-dihydro-6H-dibenz[b,d]azepin-6-one, N-t-Boc-L-valinyl-5-amino-7-methyl-5,7-dihydro-6H-dibenz[b,d]azepin-6-one was prepared.

Step B: Following the General Procedure of Step B of Example 1-C and using the N-t-Boc-L-valinyl-5-amino-7-methyl-5,7-dihydro-6H-dibenz[b,d]azepin-6-one, the title compound was prepared. Other substituted N-t-Boc-L-valinyl-5-amino-7-methyl-5,7-dihydro-6H-dibenz[b,d]azepin-6-ones can also be prepared by this procedure.

Example 3-K

Synthesis of 5-Amino-7-phenbutyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein) and 1-chloro-4-phenylbutane (Aldrich), the title compound was prepared.

Example 3-L

Synthesis of 5-Amino-7-cyclopropymethyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein) and (bromomethyl)cyclopropane (Aldrich), the title compound was prepared.

Example 3-M

Synthesis of 5-Amino-7-(2',2',2'-trifluoroethyl)-5,7-dihydro-6H-dibenz[b,d]azepin-6-one Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein) and 1-bromo-2,2,2-trifluoroethane (Aldrich), the title compound was prepared.

Example 3-N

Synthesis of 5-Amino-7-cyclohexyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, pp. 667–670, (1971) and references cited therein) and bromocyclohexane (Aldrich), the title compound was prepared.

Example 3-O

Synthesis of 5-(L-Alaninyl)amino-9-fluoro-7-methyl-5,7-dihydro-6H-dibenz[b,d]azepin-6-one Hydrochloride Step 1: 2-Bromo-5-fluorotoluene was stirred in THF at −78C. s-BuLi (1.05 eq., 1.3 M in cyclohexane) was slowly added and the mixture was stirred for 45 minutes. Trimethylborate (1.5 eq.) was added and the mixture was allowed to warm to ambient temperature. After stirring for 1 hour, pinacol (2 eq.) was added. The mixture was stirred for 16 hours then was concentrated under reduced pressure. The resulting residue was slurried in $CH_2Cl_2$ and filtered through Celite. The filtrate was concentrated to yield an oil which was purified by chromatography on deactivated silica gel ($Et_3N$) to yield the arylboronate ester.

Step 2: 2-Bromoaniline (1 eq.) and di-t-butyl-dicarbonate (1.1 eq.) were stirred at 80° C. for 20 hours. The resulting mixture was allowed to cool and was directly distilled using house vacuum to provide N-t-Boc-2-bromoaniline.

Step 3: N-t-Boc-2-bromoaniline (Step 2, 1 eq.), the arylboronate ester (Step 1, 1.1 eq.), $K_2CO_3$ (1.1 eq.) and tetrakis(triphenylphosphine)palladium(0) (0.02 eq.) were stirred in 20% water/dioxane under nitrogen. The solution was heated at reflux for 10 hours. The mixture was allowed to cool then was concentrated. The resulting residue was partitioned between water and chloroform. The organic portion was dried and concentrated to yield an oil which was purified by silica gel chromatography using 1:1 $CH_2Cl_2$/hexanes.

Step 4: Following General Procedure 3-B and using the substituted biphenyl from step 3, the 9-fluoro-5,7-dihydro-6H-dibenz[b,d]azepin-6-one was prepared.

Step 5: 9-Fluoro-5,7-dihydro-6H-dibenz[b,d]azepin-6-one (1 eq., Step 4), cesium carbonate (1.1 eq., Aldrich) and methyl iodide (1.1 eq., Aldrich) were stirred in dry DMF at ambient temperature for 16 hours. The mixture was concentrated under reduced pressure to provide a residue which was partitioned between EtOAc and water. The organic portion was dried and concentrated to yield an oil which was purified by silica gel chromatography to 9-fluoro-7-methyl-5,7-dihydro-6H-dibenz[b,d]azepin-6-one.

Step 6: Following General Procedure 3-A, Step B and 9-fluoro-7-methyl-5,7-dihydro-6H-dibenz[b,d]azepin-6-one from Step 5, 5-amino-9-fluoro-7-methyl-5,7-dihydro-6H-dibenz[b,d]azepin-6-one was prepared.

Step 7: Following the procedure of Example 3-I and using 5-amino-9-fluoro-7-methyl-5,7-dihydro-6H-dibenz[b,d]azepin-6-one from Step 6, the title compound was prepared.

Example 3-P

Synthesis of 5-(L-Alaninyl)amino-13-fluoro-7-methyl-5,7-dihydro-6H-dibenz[b,d]azepin-6-one Hydrochloride Following the procedure of Example 3-O and using 2-bromo-4-fluoroaniline (Step 2, Lancaster) and o-tolylboronic acid (Step 3, Aldrich), the title compound was prepared.

Example 3-Q

Synthesis of 5-(L-Alaninyl)amino-10-fluoro-7-methyl-5,7-dihydro-6H-dibenz[b,d]azepin-6-one Hydrochloride Following the procedure of Example 3-O and using 2-bromo-4-fluorotoluene (Step 1), the title compound was prepared.

Example 3-R

Synthesis of 5-(L-Alanyl)-amino-7-cyclopropylmethyl-5,7-dihydro-6H-dibenz[b,d]azepin-6-one Hydrochloride Following the procedure of Example 3-I and using 5-amino-7-cyclopropylmethyl-5,7-dihydro-6H-dibenz[b,d]azepin-6-one (Example 3-L), the title compound was prepared.

Example 3-S

Synthesis of 5-(L-Alaninyl)amino-7-phenbutyl-5,7-dihydro-6H-dibenz[b,d]azepin-6-one Hydrochloride Following the procedure of Example 3-I and using 5-amino-7-phenbutyl-5,7-dihydro-6H-dibenz[b,d]azepin-6-one (Example 3-K), the title compound was prepared.

Example 3-T

Synthesis of 5-(L-Valinyl)amino-7-cyclopropylmethyl-5,7-dihydro-6H-dibenz[b,d]azepin-6-one Hydrochloride Following the procedure of Example 3-J and using 5-amino-7-cyclopropylmethyl-5,7-dihydro-6H-dibenz[b,d]azepin-6-one (Example 3-L), the title compound was prepared.

Example 3-U

Synthesis of 5-(L-Valinyl)amino-7-phenbutyl-5,7-dihydro-6H-dibenz[b,d]azepin-6-one Hydrochloride Following the procedure of Example 3-J and using 5-amino-7-phenbutyl-5,7-dihydro-6H-dibenz[b,d]azepin-6-one (Example 3-U), the title compound was prepared.

Example 3-V

Synthesis of 5-(L-Valinyl)amino-7-hexyl-5,7-dihydro-6H-dibenz[b,d]azepin-6-one Hydrochloride Step A: Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein) and 1-bromohexane (Aldrich), 5-amino-7-hexyl-5,7-dihydro-6H-dibenz[b,d]azepin-6-one was prepared.

Step B: Following the procedure of Example 3-J and using 5-amino-7-hexyl-5,7-dihydro-6H-dibenz[b,d]azepin-6-one, the title compound was prepared.

Example 3-W

Synthesis of 5-(L-Valinyl)amino-10-fluoro-7-methyl-5,7-dihydro-6H-dibenz[b,d]azepin-6-one Hydrochloride Following the procedure of Example 3-J and using 5-amino-10-fluoro-7-methyl-5,7-dihydro-6H-dibenz[b,d]azepin-6-one (as prepared in Example 3-Q), the title compound was prepared.

Example 3-X

Synthesis of 5-(L-Valinyl)amino-13-fluoro-7-methyl-5,7-dihydro-6H-dibenz[b,d]azepin-6-one Hydrochloride Following the procedure of Example 3-J and using the 5-amino-13-fluoro-7-methyl-5,7-dihydro-6H-dibenz[b,d]azepin-6-one (as prepared in Example 3-P), the title compound was prepared.

Example 3-Y

Synthesis of 5-(L-Valinyl)amino-13-fluoro-7-methyl-5,7-dihydro-6H-dibenz[b,d]azepin-6-one Hydrochloride Following the procedure of Example 3-J and using the 5-amino-9-fluoro-7-methyl-5,7-dihydro-6H-dibenz[b,d]azepin-6-one (as prepared in Example 3-O), the title compound was prepared.

Example 3-Z

Synthesis of (5-Amino-7-methyl-1,2,3,4,5,7-hexahydro-6H-dicyclohexyl[b,d]azepin-6-one The 5-amino-7-methyl-5,7-dihydro-6H-dibenz[b,d]azepin-6-one hydrochloride (Example 3-A) was dissolved in a 1:1 mixture of EtOAc/HOAc. 5% Rh/C was added and the mixture was stirred at 60° C. under 60 psi of hydrogen. After 3 days, the mixture was filtered and the filtrate was concentrated to provide an oil which was purified by SCX-cation exchange chromatography to yield the title compound.

Example 3-AA

Synthesis of 5-(S)-Amino-7-methyl-5,7-dihydro-6H-dibenz[b,d]azepin-6-one Hydrochloride Following General Procedure 3-C using racemic 5-amino-7-methyl-5,7-dihydro-6H-dibenz[b,d]azepin-6-one (1.0 eq.) and di-p-toluoyl-D-tartaric acid monohydrate (1.0 eq.) in methanol, the title compound was prepared as a solid. The product was collected by filtration. Enantiomeric excess was determined by chiral HPLC.

Desired enantiomer 1: retention time of 9.97 minutes.
Undesired enantiomer 2: retention time of 8.62 minutes.
NMR data was as follows:
$^1$H-nmr (CDCl$_3$): δ=9.39 (s, 2H), 7.75–7.42 (m, 8H), 4.80 (s, 1H), 3.30 (s, 3H). C$_{15}$H$_{15}$ClN$_2$O (MW=274.75); mass spectroscopy (MH$^-$) 239.1. Anal Calcd for C$_{15}$H$_{15}$ClN$_2$O$_3$; C, 65.57; H, 5.50; N, 10.20; Found: C, 65.51, H, 5.61; N, 10.01.

Example 3-AB

Synthesis of 9-Amino-5,6-dihydro-4H-quino[8,1-ab][3]benzazepin-8(9H)-one Hydrochlororide Step A—Synthesis of 8-Phenylquinoline A degassed solution of 8-bromoquinoline (1.0 g, 4.81 mmol) (Aldrich) in dioxane (50 mL)/H$_2$O (10 mL) was treated with phenylboronic acic (0.64 g, 5.29 mmol) (Aldrich), Pd(Ph$_3$P)$_4$ (0.050 g, 0.04 mmol) and K$_2$CO$_3$ (0.73 g, 5.29 mmol). After refluxing for 4 hours under a N$_2$ atmosphere the reaction was allowed to cool, diluted with EtOAc and separated. After drying over Na$_2$SO$_4$ and SiO$_2$ chromatography (95:5 Hexanes/EtOAc) the titled compound was isolated as a colorless oil.

Physical data were as follows:
$^1$H-nmr (CDCl$_3$): δ=8.97 (d, 1H), 8.22 (dd, 1H), 7.87–7.39 (m, 9H). C$_{15}$H$_{11}$N (MW=205); mass spectroscopy (MH+) 206.

Step B—Synthesis of 8-Phenyl-1,2,3,4-tetrahydroquinoline

The product from Step A (0.99 g, 4.82 mmol) was hydrogenated according to the procedure described by Honel, M., et. al., J. C. S. Perkin I, (1980), 1933–1938.

Physical data were as follows:
$^1$H-nmr (CDCl$_3$): δ=7.46 (m, 3H), 7.38 (m, 2H), 6.98 (m, 2H), 6.70 (m, 1H), 3.27 (t, 2H), 2.86 (t, 2H), 1.96 (m, 2H). C$_{15}$H$_{15}$N (MW=209); mass spectroscopy (MH+) 210.

Step C—Synthesis of 1-Chloromethylacetyl-8-phenyl-1,2,3,4-tetrahydroquinoline

The product from Step B (1.0 g, 4.78 mmol) was dissolved in CH$_2$Cl$_2$ (20 mL)/H$_2$O (20 mL) and treated with NaHCO$_3$ (0.602 g, 7.18 mmol) followed by chloroacetyl chloride (0.478 mL, 5.26 mmol). After stirring for 17 h at 23° C., the reaction was diluted with CH$_2$Cl$_2$, washed with saturated NaHCO$_3$, dried over Na$_2$SO$_4$ and purified by SiO$_2$ chromatography (CHCl$_3$/Hexanes 9:1). The product was isolated as a colorless solid.

Physical data were as follows:
C$_{17}$H$_{16}$ClNO (MW=286.77); mass spectroscopy (MH+) 287. Anal. Calcd for C$_{17}$H$_{16}$ClNO; C, 71.45 H, 5.64 N, 4.90. Found: C, 71.63 H, 5.60 N, 4.87.

Step D—Synthesis of 5,6-Dihydro-4H-quino[8,1-ab][3]benzazepin-8(9H)-one

The product from Step C (0.89 g, 3.11 mmol) was mixed thoroughly with AlCl$_3$ (0.87 g, 6.54 mmol) at 23° C. and the mixture heated neat at 100° C. for 5–7 minutes. After vigorous gas evolution, the molten mixture was allowed to cool and extracted with several portions of CH$_2$Cl$_2$/NaHCO$_3$ (sat). The combined organic layers were dried over Na$_2$SO$_4$ and the title compound was purified by chromatography (SiO$_2$, CHCl$_3$/hexanes 9:1), yielding a colorless oil which solidified upon standing.

Physical data were as follows:
C$_{17}$H$_{15}$NO (MW=249.312); mass spectroscopy (MH+) 250. Anal. Calcd for C$_{17}$H$_{15}$NO; C, 81.90 H, 6.06 N, 5.62. Found: C, 81.75 H, 6.11 N, 5.86.

Step E—Synthesis of 9-Oximo-5,6-Dihydro-4H-quino[8,1-ab][3]benzazepin-8(9H)-one

The product from Step D (0.490 g, 1.97 mmol) was dissolved in THF and butyl nitrite (0.46 mL, 3.93 mmol) and treated with KHMDS (0.5 M, 4.52 mL, 2.26 mmol) at 0° C. After stirring for 1 h, the reaction was quenched with cold 1 N HCl, extracted with EtOAc, the combined organic layers dried over $Na_2SO_4$ and the product purified by $SiO_2$ chromatography ($CHCl_3$/MeOH, 99:1). The title compound was isolated as a colorless solid.

Physical data were as follows:

$C_{17}H_{14}N_2O_2$ (MW=278.3); mass spectroscopy (MH+) 279. Anal. Calcd for $C_{17}H_{14}N_2O_2 \cdot 0.3317$ mol $H_2O$; C, 71.82 H, 5.19 N, 9.85. Found: C, 71.85 H, 5.09 N, 9.59.

Step F—Synthesis of 9-Amino-5,6-dihydro-4H-quino[8,1-ab][3]benzazepin-8(9H-one

The product from Step E (0.360 g, 1.29 mmol) was hydrogenated over Ra/Ni (0.05 g) in EtOH (50 mL)/$NH_3$ (anhydrous) (5.0 mL) at 100° C. and 500 psi for 10 h. The catalyst was removed by filtration and the resulting filtrate chromatographed over $SiO_2$ ($CHCl_3$/MeOH, 98:2) yielding the titled compound as a colorless oil which solidified upon standing.

Physical data were as follows:

$C_{17}H_{16}N_2O$ (MW=264.326); mass spectroscopy (MH+) 266. Anal. Calcd for $C_{17}H_{16}N_2O$; C, 77.25 H, 6.10 N, 10.60. Found: C, 77.23 H, 6.15N, 10.49.

Example 3-AC

Synthesis of 9-(N'-L-Alaninyl)amino-5,6-dihydro-4H-quino[8,1-ab][3]benzazepin-8(9H)-one Hydrochloride Step A—Synthesis of 9-(N'-Boc-L-Alaninyl)amino-5,6-Dihydro-4H-quino[8,1-ab][3]benzazepin-8(9H)-one Following General Procedure D and using N-Boc-Alanine (Aldrich) and 9-amino-5,6-dihydro-4H-quino[8,1-ab][3]benzazepin-8(9H)-one (from Example 3-AB), the title compound was prepared.

Physical data were as follows:

$C_{25}H_{29}N_3O_4$ (MW=435.521); mass spectroscopy (MH+) 436. Anal. Calcd for $C_{25}H_{29}N_3O_4 \cdot 0.4102$ mol $H_2O$; C, 67.79 H, 6.79 N, 9.49; Found: C, 67.83 H, 6.91 N, 9.29.

Step B—Synthesis of 9-(N'-L-Alaninyl)amino-5,6-dihydro-4H-quino[8,1-ab][3]benzazepin-8(9H)-one Hydrochloride Following General Procedure E and using the product from Step A, the title compound was prepared.

Physical data were as follows:

$C_{20}H_{21}N_3O_2$HCl (MW=371.6); mass spectroscopy (MH+ free base) 335.

Example 3-AD

Synthesis of 5-[L-alaninyl]-amino-7-(2-methylpropyl)-5,7-dihydro-6H-dibenz[b,d]azepin-6-one Hydrochloride Following General Procedure D above using Boc-L-alanine (Aldrich) and 5-amino-7-(2-methylpropyl)-5,7-dihydro-6H-dibenz[b,d]azepin-6-one hydrochloride (Example 3-F), the compound was prepared as a tan foam. The resulting Boc group was removed using 2.0 M HCl/dioxane. The title compound was isolated as a slightly colored solid after evaporation and vacuum drying.

$C_{21}H_{24}N_3O_2$HCl (MW 386); mass spectroscopy (MH+of freebase) 351.

Example 3-AE

Synthesis of 5-[L-alaninyl]-amino-5,7-dihydro-6H,7H-dibenz[b,d]azepin-6-one Hydrochloride Step A—Synthesis of 5-Amino-5,7-dihydro-6H,7H-dibenz[bd]azepin-6-one Hydrochloride 5-(N-Boc-Amino)-5,7-dihydro-6H,7H-dibenz[b,d]azepin-6-one (Example 3-E) was treated with 2.0 M HCl/dioxane. After stirring for 17 h at 23° C., the title compound was isolated as a slightly colored solid after filtration and vacuum drying.

$C_{14}H_{12}N_2$OHCl (MW=260.72); mass spectroscopy (MH+of freebase) 225. Anal. Calcd for $C_{14}H_{12}N_2$OHCl, C, 64.50 H, 5.03 N, 10.74. Found: C, 64.35 H, 4.99 N, 10.51.

Step B—Synthesis of 5-[N-Boc-L-alaninyl]-amino-5,7-dihydro-6H,7H-dibenz[b,d]azepin-6-one The compound isolated above was coupled with Boc-L-alanine (Aldrich) following General Procedure D. The title compound was used without further purification.

$C_{22}H_{25}N_4O_4$ (MW=395.45); mass spectroscopy (MH+) 396. Anal. Calcd for $C_{22}H_{25}N_4O_4$ C, 66.82H, 6.37 N, 10.63. Found: C, 65.53 H, 6.16 N, 10.38.

Step C—Synthesis of 5-[L-alaninyl]-amino-5,7-dihydro-6H,7H-dibenz[b,d]azepin-6-one Hydrochloride The compound isolated above was deprotected using HCl/dioxane. The title compound was used without further purification after stirring for 17 h at 23 C and vacuum drying.

D. Benzodiazepine Derivatives and Related Compounds

General Procedure 4-A

N-1-Methylation of Benzodiazepines

A solution of benzodiazepine (1 eq.) in DMF (0.1 M concentration) at 0° C. was treated with potassium tert-butoxide (1.0 eq., 1.0 M solution in THF). After stirring for 30 minutes at 0° C., iodomethane (1.3 eq.) was added and stirring continued for 25 minutes. The mixture was diluted with methylene chloride and washed with water and brine. The organic phase was dried over $Na_2SO_4$, filtered, and concentrated. The crude product was then either purified by trituration with 1:1 ether/hexanes or chromatographed via HPLC using ethyl acetate/hexanes as the eluent.

General Procedure 4-B

Cbz Removal Procedure

A flask was charged with the Cbz-protected 3-aminobenzodiazepine (1 eq.). To this was added HBr (34 eq.; 30% solution in acetic acid). Within 20 minutes all of the starting material dissolves. The reaction was stirred for 5 hours at ambient temperature. Ether was added to the orange solution causing the HBr.amine salt to precipitate. The mixture was decanted. This process of adding ether and decanting was repeated thrice in an effort to remove acetic acid and benzyl bromide. Toluene was added and the mixture concentrated in vacuo. This step was also repeated. The HBr salt was partitioned between ethyl acetate and 1 M $K_2CO_3$. The aqueous layer was back-extracted with ethyl acetate. The combined organics were washed with brine, dried over $Na_2SO_4$, filtered, and concentrated.

General Procedure 4-C

Boc Removal Procedure

A solution of Boc-protected amine (1 eq.) in methylene chloride (0.15 M concentration) was cooled to 0° C. and treated with trifluoroacetic acid (30 eq.). After 10 minutes at 0° C., the cooling bath was removed and stirring continued at ambient for 20 minutes to 1 hour. The mixture was concentrated in vacuo to remove excess trifluoroacetic acid. The residue was dissolved in methylene chloride and washed with saturated aqueous $NaHCO_3$ or 1 M $K_2CO_3$ and brine. The organic layer was dried over $Na_2SO_4$, filtered, and concentrated.

General Procedure 4-D

Azide Transfer Reaction Using KHMDS

The azido derivative was prepared using the procedure described in John W. Butcher et al., *Tet. Lett.*, 37, 6685–6688 (1996).

General Procedure 4-E

Azide Transfer Reaction Using LDA

To a solution of diisopropylamine (1.1 eq.) in 1 mL of dry THF cooled to –78° C. was added n-butyl lithium (1.6M in hexane) (1.1 eq.) dropwise maintaining the reaction temperature at –78° C. The reaction mixture was stirred for 30 minutes at –78° C. and then the lactam (0.471 mM) was added dropwise as a solution in 1 mL of dry THF. The reaction mixture was stirred at –78° C. for 30 minutes and then a pre-cooled solution of trisyl azide (1.2 eq.) was added as a solution in 1 mL of dry THF. The reaction mixture was stirred at –78° C. for 20 minutes and then quenched with acetic acid (4.0 eq.). The reaction mixture was then stirred at 40° C. for 2 hours. The reaction was then poured into EtOAc and washed with water, sodium bicarbonate and brine, and then dried over sodium sulfate, filtered and concentrated. The residue was purified by LC 2000 chromatography.

General Procedure 4-F

Azido Group Reduction

The azido group was reduced to the corresponding primary amine using the procedure described in John W. Butcher et al., *Tet. Lett.*, 37, 6685–6688 (1996).

General Procedure 4-G

N-Alkylation of Amides or Lactams Using Sodium Hydride or Potassium tert-Butoxide To a slurry of sodium hydride or potassium tert-butoxide (1.1 eq) in 15 mL of dry DMF was added the appropriate amide (0.0042 moles) as a solution in 10 mL of DMF. The alkyl iodide was then added and a thick slurry resulted. The reaction became less thick as time elapsed and when complete by TLC the reaction had become homogeneous. The reaction mixture was poured over ice and extracted into ethyl acetate. The organic layer was washed with water, followed by brine. The organic layer was then dried over sodium sulfate, filtered and concentrated under reduced pressure. The residue was purified by HPLC (LC 2000), eluting with an ethyl acetate/hexane system.

General Procedure 4-H

N-Alkylation of Amides or Lactams Using KHMDS

To the appropriate amide or lactam in THF cooled to –78° C. was added KHMDS dropwise and the reaction mixture was stirred for 30 min. at –78° C. The alkyl iodide was then added dropwise while maintaining the temperature at –70° C. The cooling bath was then removed and reaction was allowed to warm to room temperature and stirring was continued for 2 hours. The reaction mixture was then poured over ice and extracted into ethyl acetate. The organic extracts were washed with water, followed by brine. The organic layer was then dried over sodium sulfate, filtered and concentrated under reduced pressure. The residue was purified by HPLC (LC 2000), eluting with an ethyl acetate/hexane system.

General Procedure 4-I

N-Alkylation of Amides or Lactams Using Cesium Carbonate

To a solution of the amide or lactam in DMF was added cesium carbonate (1.05 eq) and an alkyl iodide (1.1 eq). The mixture was allowed to stir overnight at room temperature and then the reaction mixture was dilluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

General Procedure 4-J

BOC Removal Procedure

To an N-Boc protected compound was added $CH_2Cl_2$/ TFA (4:1) at room temperature. The reaction mixture was stirred at room temperature for 3 hours and then concentrated. The residue was extracted into dichloromethane and washed with water, saturated sodium bicarbonate, dried over $Na_2SO_4$, filtered and concentrated to give the free amine.

General Procedure 4-K

Azide Transfer Procedure

This azide transfer procedure is a modification of the procedure described in Evans, D. A.; Britton, T. C.; Ellman, J. A.; Dorow, R. L. *J. Am. Chem. Soc.* 1990, 112, 4011–4030. To a solution of the lactam substrate (1.0 eq.) in THF (~0.1 M) under $N_2$ at –78° C. was added a solution of $KN(TMS)_2$ (1.1 eq. of 0.5 M in Toluene, Aldrich) dropwise over a period of 2–10 minutes. A slight exotherm was often observed by an internal thermometer, and the resulting solution was stirred for 5–15 minutes, while re-cooling to –78° C. Then, trisyl azide (1.1–1.5 eq., CAS No. 36982-84-0, prepared as described by references in the Evans reference above) in THF (~0.5 M), either precooled to –78° C. or at room temperature, was added via cannula over a period of 0.5–5 minutes. Again, a slight exotherm was generally noted. The resulting solution was stirred for from 5–10 minutes, while re-cooling to –78° C. Then, AcOH (4.5–4.6 eq., glacial) was added, the cooling bath removed and the mixture allowed to warm to room temperature with stirring for 12–16 hours. The mixture was diluted with EtOAc, in a 2–5 volume multiple of the initial THF volume, and washed with dilute aq. $NaHCO_3$ (1–2×), 0.1–1.0 M aq. HCl (0–2×), and brine (1×). The organic phase was then dried over $MgSO_4$, filtered, concentrated to provide the crude product.

General Procedure 4-L

Azide Reduction to an Amine

A mixture of the azide in absolute EtOH (0.03–0.07 M) and 10% Pd/C (~1/3 by weight of the azide) was shaken in a Parr apparatus under $H_2$ (35–45 psi) at room temperature for 3–6 hours. The catalyst was removed by filtration through a plug of Celite, rinsing with absolute EtOH, and the filtrate concentrated to provide the crude amine product.

General Procedure 4-M

Amide Alkylation Using Cesium Carbonate

This procedure is a modification of the procedure described in Claremon, D. A.; et al, PCT Application: WO 96/406555. To a mixture of 2,4-dioxo-2,3,4,5-tetrahydro-1H-1,5-benzodiazepine (CAS No. 49799-48-6) in DMF (1.0 eq., 0.7 M) under $N_2$ at room temperature was added $Cs_2CO_3$ (2.2 eq.) and the appropriate alkyl halide (2.2 eq.). The mixture was stirred at room temperature for 5.5–16 hours. The mixture was partitioned between EtOAc and sat. $NaHCO_3$. The aqueous layer was extracted with EtOAc (1–2x) and the combined EtOAc extracts were dried over $Na_2SO_4$, filtered, and concentrated to provide the crude product.

General Procedure 4-N

BOC Removal Procedure

A stream of anhydrous HCl gas was passed through a stirred solution of the N-t-Boc protected amino acid in 1,4-dioxane (0.03–0.09 M), chilled in a ice bath to ~-10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then reconcentrated and placed in vacuum oven at 60–70° C. to remove most of the residual dioxane) and used without further purification.

Example 4-A

Synthesis of 3-Amino-1,3-dihydro-5-(1-piperidinyl)-2H-1,4-benzodiazepin-2-one

Step A—Preparation of 1,2-Dihydro-3H-1-methyl-5-(1-piperidinyl)-1,4-benzodiazepin-2-one A solution of phosphorous pentachloride (1.2 eq) in methylene chloride was added dropwise to a solution of 1-methyl-1,2,3,4-tetrahydro-3H-1,4-benzodiazepin-2,5-dione (Showell, G. A.; Bourrain, S.; Neduvelil, J. G.; Fletcher, S. R.; Baker, R.; Watt, A. P.; Fletcher, A. E.; Freedman, S. B.; Kemp, J. A.; Marshall, G. R.; Patel, S.; Smith, A. J.; Matassa, V. G. *J. Med. Chem.* 1994, 37, 719.) in methylene chloride. The resultant yellowish-orange solution was stirred at ambient temperature for 2.5 hours; the solvent was removed in vacuo. The orange residue was redissolved in methylene chloride, cooled to 0° C., and treated with a solution of piperidine (2 eq) and triethylamine (2 eq) in methylene chloride. The cooling bath was removed and the reaction stirred for 18 hours. The reaction mixture was washed with saturated aqueous $NaHCO_3$ (back-extracted with methylene chloride) and brine. The organic phase was dried over $Na_2SO_4$, filtered, and concentrated. The residue was purified via HPLC eluting with a gradient of 4 to 10% methanol/methylene chloride affording the title intermediate as a yellow solid having a melting point of 103–105° C.

$C_{15}H_{19}N_3O$ (MW 257.37); mass spectroscopy 257. Anal. Calcd for $C_{15}H_{19}N_3O$: C, 70.01; H, 7.44; N, 16.33. Found: C, 69.94; H, 7.58; N, 16.23.

Step B—Preparation of 1,2-Dihydro-3H-1-methyl-3-oximido-5-(1-piperidinyl)-1,4-benzodiazepin-2-one Potassium tert-butoxide (2.5 eq) was added in two portions to a -20° C. solution of 1,2-dihydro-3H-1-methyl-5-(1-piperidinyl)-1,4-benzodiazepin-2-one (1 eq.) in toluene. After stirring at -20° C. for 20 minutes, isoamyl nitrite (1.2 eq.; Aldrich) was added to the red reaction mixture. The reaction was stirred at -20° C. for 5 hours at which time the reaction was done by TLC. The cooling bath was removed and the reaction quenched with 0.5 M citric acid. After stirring for 10 minutes, diethyl ether was added. The suspension was stirred at ambient temperature overnight then filtered washing with ether. The resultant cream colored solid had a melting point of 197–200° C.

$^1$H NMR data of the E/Z isomers was as follows:
$^1$H NMR (300 MHz, $CDCl_3$): δ=7.64 (1H, bs), 7.48 (2H, d, J=7.4 Hz), 7.35–7.20 (6H, m), 6.75 (1H, bs), 3.8–3.2 (8H, m), 3.46 (3H, s), 3.42 (3H, s), 1.90–1.40 (12H, m). $C_{15}H_{18}N_4O_2$ (MW=286.37); mass spectroscopy 286.

Step C—Preparation of 1,2-dihydro-3H-1-methyl-3-[O-(ethylaminocarbonyl)oximido]-5-(1-piperidinyl)-1,4-benzodiazepin-2-one A mixture of 1,2-dihydro-3H-1-methyl-3-oximido-5-(1-piperidinyl)-1,4-benzodiazepin-2-one (1 eq.) in THF was treated with ethyl isocyanate (1.7 eq) and triethylamine (0.6 eq). The mixture was heated to 64° C. for 4 hours. The mixture was concentrated and the residue purified by HPLC eluting with 5% methanol/methylene chloride.

$^1$H NMR data of the E/Z isomers was as follows:
$^1$H NMR (300 MHz, $CDCl_3$): δ=7.50 (2H, dd, J=8.4, 1.5 Hz), 7.35–7.22 (6H, m), 6.42 (1H, bt), 6.20 (1H, bt), 3.7–3.4 (8H, m), 3.46 (3H, s), 3.44 (3H, s), 3.25 (4H, m), 1.9–1.4 (12H, m), 1.12 (3H, t, J=6.3 Hz), 1.10 (3H, t, J=6.3 Hz). $C_{18}H_{23}N_5O_3$ (MW=357.46); mass spectroscopy 357.

Step D—Preparation of 3-Amino-1,3-dihydro-2H-1-methyl-5-(1-piperidinyl)-1,4-benzodiazepin-2-one The 1,2-dihydro-3H-1-methyl-3-[O-(ethylaminocarbonyl)oximido]-5-(1-piperidinyl)-1,4-benzodiazepin-2-one (1 eq.) was hydrogenated in methanol over 5% palladium on carbon (0.15 eq.) at 43 psi for 3.25 hours. The reaction was filtered through celite and concentrated in vacuo. The residue was taken up in methylene chloride and filtered a second time through celite. The filtrate was concentrated and the resultant foam was used immediately.

Example 4-B

Synthesis of 3-(L-Alaninyl)-amino-2,3-dihydro-1-methyl-5-phenyl-1H-1,4-benzodiazepin-2-one Step A—Preparation of (S)-3-Amino-1,3-dihydro-1-methyl-5-phenyl-2H-1,4-benzodiazepin-2-one, (1S)-7,7-Dimethyl-2-oxobicyclo[2,2,1]heptane-1-methanesulfonate The title intermediate was prepared according to Reider, P. J.; Davis, P.; Hughes, D. L.; Grabowski, E. J. J. *J. Org. Chem.* 1987, 52, 955 using 3-amino-1,3-dihydro-1-methyl-5-phenyl-2H-1,4-benzodiazepin-2-one (Bock M. G.; DiPardo, R. M.; Evans, B. E.; Rittle, K. E.; Veber, D. F.; Freidinger, R. M.; Hirshfield, J.; Springer, J. P. *J. Org. Chem.* 1987, 52, 3232.) as the starting material.

Step B—Preparation of 3-[N'-(tert-Butylcarbamate)-L-alaninyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2,2,1]heptane-1-methanesulfonate was free based by partitioning between methylene chloride and 1M potassium carbonate. The free amine was then coupled with N-Boc-alanine following General Procedure D.

$C_{24}H_{28}N_4O_4$ (MW=436.56); mass spectroscopy 436. Anal. Calc. for $C_{24}H_{28}N_4O_4$: C, 66.03; H, 6.47; N, 12.84. Found: C, 65.79; H, 6.68; N, 12.80.

Step C—Preparation of 3-(L-Alaninyl)-amino-2,3-dihydro-1-methyl-5-phenyl-1H-1,4-benzodiazepin-2-one Following General Procedure 4-C using 3-[N'-(tert-butylcarbamate)-L-alaninyl]-amino-2,3-dihydro-1-methyl-5-phenyl-1H-1,4-benzodiazepin-2-one, the title compound was prepared as a white foam.

Anal. Calc. for $C_{19}H_{19}N_4O_2$: C, 69.21; H, 6.64; N, 15.37. Found: C, 70.11; H, 6.85; N, 15.01.

Example 4-C

Synthesis of 3-(L-Alaninyl)-amino-7-chloro-2,3-dihydro-1-methyl-5-phenyl-1H-1,4-benzodiazepin-2-one Step A—Preparation of 3-(Benzyloxycarbonyl)-amino-7-chloro-2,3-dihydro-1-methyl-5-phenyl-1H-1,4-benzodiazepin-2-one A solution of 3-(benzyloxycarbonyl)-amino-7-chloro-2,3-dihydro-5-phenyl-1H-1,4-Benzodiazepin-2-one (1 eq; Neosystem) in DMF was cooled to 0° C. and treated with potassium tert-butoxide (1 eq; 1.0M solution in THF). The resultant yellow solution was stirred at 0° C. for 30 minutes then quenched with methyl iodide (1.3 eq.). After stirring an addition 25 minutes the reaction was diluted with methylene chloride and washed with water and brine. The organic phase was dried over $Na_2SO_4$, filtered, and concentrated. The residue was purified via HPLC chromatography eluting with a gradient of 20→30% ethyl acetate/hexanes.

$C_{24}H_{20}ClN_3O_3$ (MW=433.92); mass spectroscopy 433. Anal. calcd for $C_{24}H_{20}ClN_3O_3$: C, 66.44; H, 4.65; N, 9.68. Found: C, 66.16; H, 4.50; N, 9.46.

Step B—Preparation of 3-Amino-7-chloro-1,3-dihydro-1-methyl-5-phenyl-2H-1,4-benzodiazepin-2-one Following General Procedure 4-B using 3-(benzyloxycarbonyl)-amino-7-chloro-2,3-dihydro-1-methyl-5-phenyl-1H-1,4-benzodiazepin-2-one, the title intermediate was prepared as a white foam which was used immediately in Step C.

Step C—Preparation of 3-[N'-tert-Butylcarbamate)-L-alaninyl]-amino-7-chloro-1,3-dihydro-1-methyl-5-phenyl-2H-1,4-benzodiazepin-2-one Following General Procedure D using N-Boc-L-alanine and 3-amino-7-chloro-1,3-dihydro-1-methyl-5-phenyl-2H-1,4-benzodiazepin-2-one, the title intermediate was prepared as a white foam.

$C_{24}H_{28}ClN_4O_4$ (MW=471.18); mass spectroscopy 471; Anal. calcd for $C_{24}H_{21}ClN_4O_4$: C, 61.21; H, 5.78; N, 11.90. Found: C, 61.24; H, 5.59; N, 11.67.

Step D—Preparation of 3-(L-Alaninyl)amino-7-chloro-1,3-dihydro-1-methyl-5-phenyl-2H-1,4-benzodiazepin-2-one Following General Procedure 4-C using 3-[N'-tert-butylcarbamate)-L-alaninyl]-amino-7-chloro-1,3-dihydro-1-methyl-5-phenyl-2H-1,4-benzodiazepin-2-one, the title intermediate was prepared as a white foam. The crude material was used immediately.

Example 4-D

Synthesis of 3-(L-Alaninyl)amino-7-bromo-2,3-dihydro-1-methyl-5-(2-fluorophenyl)-1H-1,4-benzodiazepin-2-one Step A—Preparation of 3-(Benzyloxycarbonyl)-amino-7-bromo-2,3-dihydro-1-methyl-5-(2-fluorophenyl)-1H-1,4-benzodiazepin-2-one Following General Procedure 4-A using 3-(benzyloxycarbonyl)-amino-7-bromo-2,3-dihydro-5-(2-fluorophenyl)-1H-1,4-benzodiazepin-2-one (Neosystem), the title intermediate was prepared as a white foam.

$C_{24}H_{19}BrFN_3O_3$ (MW=496.36); mass spectroscopy 497. Anal. calcd for $C_{24}H_{19}BrFN_3O_3$: C, 58.08; H, 3.86; N, 8.47. Found: C, 57.90; H, 4.15; N, 8.20.

Step B—Preparation of 3-Amino-7-bromo-1,3-dihydro-1-methyl-5-(2-fluorophenyl)-2H-1,4-benzodiazepin-2-one Following General Procedure 4-B using 3-(benzyloxycarbonyl)-amino-7-bromo-2,3-dihydro-1-methyl-5-(2-fluorophenyl)-1H-1,4-benzodiazepin-2-one, the title intermediate was prepared as a white foam which was used immediately in Step C.

Step C—Preparation of 3-[N'-(tert-Butylcarbamate)-L-alaninyl]-amino-7-bromo-1,3-dihydro-1-methyl-5-(2-fluorophenyl)-2H-1,4-benzodiazepin-2-one Following General Procedure D using N-Boc-L-alanine (Novo) and 3-amino-7-bromo-1,3-dihydro-1-methyl-5-(2-fluorophenyl)-2H-1,4-benzodiazepin-2-one, the title intermediate was prepared as a white foam.

$C_{24}H_{26}BrFN_4O_4$ (MW=533.12); mass spectroscopy 533.2. Anal. calcd for $C_{24}H_{26}BrFN_4O_4$: C, 54.04; H, 4.91; N, 10.50. Found: C, 53.75; H, 4.92; N, 10.41.

Step D—Preparation of 3-(L-Alaninyl)-amino-7-bromo-1,3-dihydro-1-methyl-5-(2-fluorophenyl)-2H-1,4-benzodiazepin-2-one Following General Procedure 4-C using 3-[N'-(tert-butylcarbamate)-L-alaninyl]-amino-7-bromo-1,3-dihydro-1-methyl-5-(2-fluorophenyl)-2H-1,4-benzodiazepin-2-one, the title intermediate was prepared as a white foam. The crude material was used immediately.

Example 4-E

Synthesis of 3-(N'-Methyl-L-alaninyl)-amino-2,3-dihydro-1-methyl-5-phenyl-1H-1,4-benzodiazepin-2-one Step A—Preparation of 3-[N'-(tert-Butylcarbamate)-N'-methyl-L-alaninyl]-amino-2,3-dihydro-1-methyl-5-phenyl-1H-1,4-benzodiazepin-2-one Following General Procedure D and using (S)-3-amino-1,3-dihydro-1-methyl-5-phenyl-2H-1,4-benzodiazepin-2-one (Example 4-B) and N-tert-Boc-N-methyl-alanine (Sigma), the title intermediate was obtained as a white solid.

$C_{25}H_{30}N_4O_4$ (MW=450.2); mass spectroscopy (M+1) 451.2. Anal. calcd for $C_{25}H_{30}N_4O_4$: C, 66.65; H, 6.71; N, 12.44. Found: C, 66.66; H, 6.89; N, 12.21.

Step B—Preparation of 3-(N'-Methyl-L-alaninyl)-amino-2,3-dihydro-1-methyl-5-phenyl-1H-1,4-benzodiazepin-2-one Following General Procedure 4-C and using 3-[N'-(tert-butylcarbamate)-N'-methyl-L-alaninyl]-amino-2,3-dihydro-1-methyl-5-phenyl-1H-1,4-benzodiazepin-2-one, the title intermediate was prepared as a white foam.

$C_{20}H_{22}N_4O_2$ (MW=350.46); mass spectroscopy (M+1) 351.4. Anal. calcd for $C_{20}H_{22}N_4O_2$: C, 68.55; H, 6.33; N, 15.99. Found, C, 68.36; H, 6.20; N, 15.79.

Example 4-F

Synthesis of 3-(L-Alaninyl)amino-7-chloro-2,3-dihydro-1-methyl-5-(2-chlorophenyl)-1H-1,4-benzodiazepin-2-one Step A—Preparation of 3-(Benzyloxycarbonyl)-amino-7-chloro-2,3-dihydro-1-methyl-5-(2-chlorophenyl)-1H-1,4-benzodiazepin-2-one Following General Procedure 4-A using 3-(benzyloxycarbonyl)-amino-7-chloro-2,3-dihydro-5-(2-chlorophenyl)-1H-1,4-benzodiazepin-2-one (Neosystem), the title intermediate was prepared as a white solid having a melting point of 232–233° C.

$C_{24}H_{19}Cl_2N_3O_3$ (MW 468.36); mass spectroscopy 468. $^1$H NMR (300 MHz, CDCl$_3$): δ=7.67 (1H, m), 7.52 (1H, dd, J=2.4, 8.7 Hz), 7.42–7.26 (9H, m), 7.07 (1H, d, J=2.4 Hz), 6.70 (1H, d, J=8.3 Hz), 5.35 (1H, d, J=8.4 Hz), 5.14 (2H, ABq, J=19.6 Hz), 3.47 (3H, s). $^{13}$C NMR (75 MHz, CDCl$_3$): δ=166.66, 165.65, 155.72, 140.52, 136.99, 136.0, 132.87, 131.99, 131.47, 131.40, 131.38, 131.16, 130.54, 130.06, 128.45, 128.08, 128.03, 127.72, 127.22, 123.28, 122.01, 68.95, 67.02, 35.32.

Step B—Preparation of 3-Amino-7-chloro-1,3-dihydro-1-methyl-5-(2-chlorophenyl)-2H-1,4-benzodiazepin-2-one Following General Procedure 4-B using 3-(benzyloxycarbonyl)-amino-7-chloro-2,3-dihydro-1-methyl-5-(2-chlorophenyl)-1H-1,4-benzodiazepin-2-one, the title intermediate was prepared as a white foam which was used immediately in Step C.

Step C—Preparation of 3-[N'-(tert-Butylcarbamate)-L-alaninyl]-amino-7-chloro-1,3-dihydro-1-methyl-5-(2-chlorophenyl)-2H-1,4-benzodiazepin-2-one Following General Procedure D using N-Boc-L-alanine and 3-amino-7-chloro-1,3-dihydro-1-methyl-5-(2-chlorophenyl)-2H-1,4-benzodiazepin-2-one, the title intermediate was prepared as a white foam.

$C_{24}H_{26}Cl_2N_4O_4$ (MW=505.44); mass spectroscopy 505.2.

Step D—Preparation of 3-(L-Alaninyl)-amino-7-chloro-1,3-dihydro-1-methyl-5-(2-chlorophenyl)-2H-1,4-benzodiazepin-2-one Following General Procedure 4-C using 3-[N'-(tert-butylcarbamate)-L-alaninyl]-amino-7-chloro-1,3-dihydro-1-methyl-5-(2-chlorophenyl)-2H-1,4-benzodiazepin-2-one, the title intermediate was prepared as a white foam. The crude material was used immediately.

Example 4-G

Synthesis of 3-(L-Alaninyl)amino-5-cyclohexyl-2,3-dihydro-1-methyl-1H-1,4-Benzodiazepin-2-one Step A—Preparation of 3-(Berzyloxycarbonyl)-amino-5-cylclohexyl-2,3-dihydro-1-methyl-1H-1,4-benzodiazepin-2-one Following General Procedure 4-A using 3-(benzyloxycarbonyl)-amino-5-cyclohexyl-2,3-dihydro-1H-1,4-benzodiazepin-2-one (Neosystem), the title intermediate was prepared as a white solid having a melting point of 205–206° C.

$C_{24}H_{27}N_3O_3$ (MW 405.54); mass spectroscopy 405. $^1$H NMR (300 MHz, CDCl$_3$): δ=7.54 (1H, d, J=7.9 Hz), 7.48 (1H, d, J=7.7 Hz), 7.36–7.26 (7H, m), 6.54 (1H, d, J=8.3 Hz), 5.15 (1H, d, J=8.0 Hz), 5.09 ( 2H, ABq, J=17.1 Hz), 3.39 (3H, s), 2.77 (1H, m), 2.01 (1H, bd, J=13.6 Hz), 1.85 (1H, bd, J=12.4 Hz), 1.68–1.49 (4H, m), 1.34–1.02 (4H, m).

Step B—Preparation of 3-Amino-5-cyclohexyl-1,3-dihydro-1-methyl-2H-1,4-benzodiazepin-2-one Following General Procedure 4-B using 3-(benzyloxycarbonyl)-amino-5-cyclohexyl-2,3-dihydro-1-methyl-1H-1,4-benzodiazepin-2-one, the title intermediate was prepared as a white foam which was used immediately in Step C.

$C_{16}H_{21}N_3O$ (MW+H=272.1763); mass spectroscopy 272.1766.

Step C—Preparation of 3-[N'-(tert-Butylcarbamate)-L-alaninyl]-amino-5-cyclohexyl-1,3-dihydro-1-methyl-2H-1,4-benzodiazepin-2-one Following General Procedure D using N-Boc-L-alanine and 3-amino-5-cyclohexyl-1,3-dihydro-1-methyl-2H-1,4-benzodiazepin-2-one, the title intermediate was prepared as a white foam.

$C_{24}H_{34}N_4O_4$ (MW=442.62); mass spectroscopy (M+H) 443.2.

Step D—Preparation of 3-(L-Alaninyl)amino-5-cyclohexyl-1,3-dihydro-1-methyl-2H-1,4-benzodiazepin-2-one Following General Procedure 4-C using 3-[N'-(tert-butylcarbamate)-L-alaninyl]-amino-5-cyclohexyl-1,3-dihydro-1-methyl-2H-1,4-benzodiazepin-2-one, the title intermediate was prepared as a white foam. The crude material was used immediately.

$C_{19}H_{26}N_4O_2$ (M+H=343.2136); mass spectroscopy found 343.2139.

Example 4-H

Synthesis of 3-(L-Alaninyl)amino-2,3-dihydro-1-methyl-7-nitro-5-phenyl-1H-1,4-benzodiazepin-2-one Step A—Preparation of 2-[N-(α-Isopropylthio)-N'-(benzyloxycarbonyl)-glycinyl]-amino-5-nitrobenzophenone A solution of α-(isopropylthio)-N-(benzyloxycarbonyl) glycine (1 eq; prepared according to Zoller, V.; Ben-Ishai, D. Tetrahedron 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-5-nitrobenzophenone (0.9 eq.; Acros) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous NaHCO$_3$, and brine. The organic phase was dried over Na$_2$SO$_4$, filtered, and concentrated. The residue was purified via preparative LC2000 eluting with a gradient of 15→20% ethyl acetate/hexanes giving an off-white foam.

$C_{26}H_{25}N_3O_6S$ (MW=507.61); mass spectroscopy found 507.9. Anal. calcd for $C_{26}H_{25}N_3O_6S$: C, 61.53; H, 4.96; N, 8.28. Found: C, 61.70; H, 4.99; N, 8.22.

Step B—Preparation of 2-[N-(α-Amino)-N'-(benzyloxycarbonyl)-glycinyl]-amino-5-nitrobenzophenone Ammonia gas was bubbled into a solution 2-[N-(α-isopropylthio)-N'-(benzyloxycarbonyl)-glycinyl]-amino-5-nitrobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C—Preparation of 3-(Benzyloxycarbonyl)-amino-2,3-dihydro-7-nitro-5-phenyl-1H-1,4-benzodiazepin-2-one 2-[N-(α-Amino)-N'-(benzyloxycarbonyl)-glycinyl]-amino-5-nitrobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over Na$_2$SO$_4$, filtered, and concentrated. The residue was purified via flash chromatography eluting with a gradient of 2–3% isopropyl alcohol/methylene chloride.

$C_{23}H_{18}N_4O_5$ (MW=430.45); mass spectroscopy found (M+H) 431.2. Anal. calcd for $C_{23}H_{18}N_4O_5$: C, 64.18; H, 4.22; N, 13.02. Found: C, 64.39; H, 4.30; N, 13.07.

Step D—Preparation of 3-(Benzyloxycarbonyl)-amino-2,3-dihydro-1-methyl-7-nitro-5-phenyl-1H-1,4-benzodiazepin-2-one Following General Procedure 4-A and using 3-(benzyloxycarbonyl)-amino-2,3-dihydro-7-nitro-5-phenyl-1H-1,4-benzodiazepin-2-one, the title intermediate was prepared as a yellow foam.

$C_{24}H_{20}N_4O_5$ (MW=444.48); mass spectroscopy found (M+H) 445.2. Anal. calcd for $C_{24}H_{20}N_4O_5$: C, 64.86; H, 4.54; N, 12.60. Found: C, 65.07; H, 4.55; N, 12.46.

Step E—Preparation of 3-Amino-1,3-dihydro-1-methyl-7-nitro-5-phenyl-2H-1,4-benzodiazepin-2-one Following General Procedure 4-B and using 3-(benzyloxycarbonyl)-amino-2,3-dihydro-1-methyl-7-nitro-5-phenyl-1H-1,4-benzodiazepin-2-one, the title intermediate was prepared as a yellow foam which was used immediately in Step F.

Step F—Preparation of 3-[N'-(tert-Butylcarbamate)-L-alaninyl]-amino-2,3-dihydro-1-methyl-7-nitro-5-phenyl-1H-1,4-benzodiazepin-2-one Following General Procedure D using N-Boc-L-alanine and 3-amino-1,3-dihydro-1-methyl-7-nitro-5-phenyl-2H-1,4-benzodiazepin-2-one, the title intermediate was prepared as a yellow solid.

$C_{24}H_{27}N_5O_6$ (MW=481.56); mass spectroscopy found (M+H) 482.3. Anal. calcd for $C_{24}H_{27}N_5O_6$: C, 59.88; H, 5.61; N, 14.55. Found: C, 60.22; H, 5.75; N, 13.91.

Step G—Preparation of 3-(L-Alaninyl)-amino-2,3-dihydro-1-methyl-7-nitro-5-phenyl-1H-1,4-benzodiazepin-2-one Following General Procedure 4-C using 3-[N'-(tert-butylcarbamate)-L-alaninyl]-amino-2,3-dihydro-1-methyl-7-nitro-5-phenyl-1H-1,4-benzodiazepin-2-one, the title intermediate was prepared as a yellow foam. The crude material was used immediately.

Example 4-I

Synthesis of 3-(L-Alaninyl)amino-2,3-dihydro-1-methyl-5-(2-fluorophenyl)-1H-1,4-benzodiazepin-2-one Step A—Preparation of 3-Amino-1,3-dihydro-1-methyl-5-(2-fluorophenyl)-2H-1,4-benzodiazepin-2-one A flask was charged with 3-(benzyloxycarbonyl)-amino-7-bromo-2,3-dihydro-1-methyl-5-(2-fluorophenyl)-1H-1,4-benzodiazepin-2-one (1 eq.; Example 4-D, Step A) and 10% palladium on carbon. Methanol was added, and the flask was placed under a balloon of $H_2$. The reaction was stirred for 21 hours. The mixture was filtered through celite washing with methanol. The filtrate was concentrated to a white solid.

$C_{16}H_{14}FN_3O$ (MW=283.33); mass spectroscopy found (M+H) 284.1.

Step B—Preparation of 3-[N'-(tert-Butylcarbamate)-L-alaninyl]-amino-3-dihydro-1-methyl-5-(2-fluorophenyl)-2H-1,4-benzodiazepin-2-one Following General Procedure D using N-Boc-L-alanine and 3-amino-1,3-dihydro-1-methyl-5-(2-fluorophenyl)-2H-1,4-benzodiazepin-2-one, the title intermediate was prepared as a white solid.

$C_{24}H_{27}FN_4O_4$ (MW=454.50); mass spectroscopy found (M+H) 455.4. Anal. calcd for $C_{24}H_{27}FN_4O_4$: C, 63.44; H, 5.95; N, 12.33. Found: C, 63.64; H, 6.08; N, 12.16.

Step C—Preparation of 3-(L-Alaninyl)-amino-7-bromo-1,3-dihydro-1-methyl-5-(2-fluorophenyl)-2H-1,4-benzodiazepin-2-one Following General Procedure 4-C using 3-[N'-(tert-butylcarbamate)-L-alaninyl]-amino-1,3-dihydro-1-methyl-5-(2-fluorophenyl)-2H-1,4-benzodiazepin-2-one, the title intermediate was prepared as a white foam. The crude material was used immediately.

Example 4-J

Synthesis of 3-(L-Alaninyl)-amino-2,3-dihydro-1-methyl-5-(3-fluorophenyl)-1H-1,4-benzodiazepin-2-one Step A—Preparation of 2-Amino-3'-fluorobenzophenone A solution of 3-bromofluorobenzene (1 eq.) in THF was cooled to −78° C. under nitrogen and treated with tert-butyllithium (2.05 eq., 1.6 M solution in pentane) at a rate of 40 mL/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3. $^1H$ NMR (300 MHz, $CDCl_3$) d 7.44–7.19 (6H, m), 6.74 (1H, d, J=8.0 Hz), 6.61 (1H, dd, J=0.94, 7.9 Hz), 6.10 (2H, bs).

Step B—Preparation of 2-[N-(α-Isopropylthio)-N'-(benzyloxycarbonyl)-glycinyl]-amino-3'-fluorobenzophenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-3'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found (M+$NH_4^+$) 498.3. $^1H$ NMR (300 MHz, $CDCl_3$) d 11.39 (1H, s), 8.59 (1H, d, J=6.0 Hz), 7.63–7.55 (2H, m), 7.48–7.27 (9H, m), 7.14 (1H, dt, J=1.2, 8.4 Hz), 5.94 (1H, d, J=7.2 Hz), 5.58 (1H, d, J=8.7 Hz), 5.17 (2H, ABq, J=14.7 Hz), 3.25 (1H, sep, J=6.6 Hz), 1.44 (3H, d, J=6.0 Hz), 1.28 (3H, d, J=6.6 Hz).

Step C—Preparation of 2-[N-(α-Amino)-N'-(benzyloxycarbonyl)-glycinyl]-amino-3'-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)-amino-2,3-dihydro-5-(3-fluorophenyl)-1H-1,4-benzodiazepin-2-one 2-[N-(α-Amino)-N'-(benzyloxycarbonyl)-glycinyl]-amino-3'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}FN_3O_3$ (MW=403.44); mass spectroscopy found (M+H) 404.4. Anal. calcd for $C_{23}H_{18}FN_3O_3 \cdot 0.5H_2O$: C, 66.98; H, 4.64; N, 10.18. Found: C, 67.20; H, 4.64; N, 9.77.

Step E—Preparation of 3-(Benzyloxycarbonyl)-amino-2,3-dihydro-1-methyl-5-(3-fluorophenyl)-1H-1,4-benzodiazepin-2-one Following General Procedure 4-A and using 3-(benzyloxycarbonyl)-amino-2,3-dihydro-5-(3-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.3. Anal. calcd for $C_{24}H_{20}FN_3O_3$: C, 69.06; H, 4.83; N, 10.07. Found: C, 69.33; H, 4.95; N, 9.82.

Step F—Preparation of 3-Amino-1,3-dihydro-1-methyl-5-(3-fluorophenyl)-2H-1,4-benzodiazepin-2-one Following General Procedure 4-B and using 3-(benzyloxycarbonyl)-amino-2,3-dihydro-1-methyl-5-(3-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.3. Anal. calcd for $C_{24}H_{27}FN_4O_4$: C, 63.42; H, 5.99; N, 12.33. Found: C, 63.34; H, 6.01; N, 12.08.

Step H—Preparation of 3-(L-Alaninyl)-amino-2,3-dihydro-1-methyl-5-(3-fluorophenyl)-1H-1,4-benzodiazepin-2-one Following General Procedure 4-C using 3-[N'-(tert-butylcarbamate)-L-alaninyl]-amino-2,3-dihydro-1-methyl-5-(3-fluorophenyl)-1H-1,4-benzodiazepin-2-one, the title intermediate was prepared as a yellow foam. The crude material was used immediately.

Example 4-K

Synthesis of 3-(L-Alaninyl)amino-2,3-dihydro-1-methyl-5-(4-fluorophenyl)-1H-1,4-benzodiazepin-2-one Step A—Preparation of 2-Amino-4'-fluorobenzophenone A solution of 4-bromofluorobenzene (1 eq.) in THF was cooled to −78° C. under nitrogen and treated with tert-butyllithium (2.05 eq., 1.6 M solution in pentane) at a rate of 40 mL/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3. Anal. calcd for $C_{13}H_{10}FNO$: C, 72.55; H, 4.68; N, 6.51. Found: C, 72.80; H, 4.51; N, 6.74.

Step B—Preparation of 2-[N-(α-Isopropylthio)-N'-(benzyloxycarbonyl)-glycinyl]-amino-4'-fluorobenzophenone A solution of α-(isopropylthio)-N-(benzyloxycarbonyl) glycine (1 eq; prepared according to Zoller, V.; Ben-Ishai, D. Tetrahedron 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-4'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found (M+$NH_4^+$) 498.2. $^1H$ NMR (300 MHz, $CDCl_3$) d 11.28 (1H, s), 8.56 (1H, d, J=8.4 Hz), 7.78–7.73 (2H, m), 7.61–7.53 (2H, m), 7.36–7.32 (5H, m), 7.20–7.14 (3H, m), 5.98 (1H, d, J=7.5 Hz), 5.57 (1H, d, J=7.8 Hz), 5.16 (2H, ABq, J=14.7 Hz), 3.25 (1H, sep, J=6.0 Hz), 1.43 (3H, d, J=6.3 Hz), 1.27 (3H, d, J=6.6 Hz).

Step C—Preparation of 2-[N-(α-Amino)-N'-(benzyloxycarbonyl)-glycinyl]-amino-4'-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)amino-2,3-dihydro-5-(4-fluorophenyl)-1H-1,4-benzodiazepin-2-one 2-[N-(α-Amino)-N'-(benzyloxycarbonyl)-glycinyl]-amino-4'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}FN_3O_3$ (MW=403.44); mass spectroscopy found (M+H) 404.4. Anal. calcd for $C_{23}H_{18}FN_3O_3 \cdot 1.25H_2O$: C, 64.85; H, 4.85. Found: C, 64.80; H, 4.55.

Step E—Preparation of 3-(Benzyloxycarbonyl)-amino-2,3-dihydro-1-methyl-5-(4-fluorophenyl)-1H-1,4-benzodiazepin-2-one Following General Procedure 4-A and using 3-(benzyloxycarbonyl)-amino-2,3-dihydro-5-(4-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.2. Anal. calcd for $C_{24}H_{20}FN_3O_3$: C, 69.06; H, 4.83; N, 10.07. Found: C, 69.35; H, 4.93; N, 9.97.

Step F—Preparation of 3-Amino-1,3-dihydro-1-methyl-5-(4-fluorophenyl)-2H-1,4-benzodiazepin-2-one Following General Procedure 4-B and using 3-(benzyloxycarbonyl)-amino-2,3-dihydro-1-methyl-5-(4-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.4. Anal. calcd for $C_{24}H_{27}FN_4O_4 \cdot 1.5H_2O$: C, 59.86; H, 6.28; N, 11.64. Found: C, 60.04; H, 5.62; N, 11.27.

Step H—Preparation of 3-(L-Alaninyl)-amino-2,3-dihydro-1-methyl-5-(4-fluorophenyl)-1H-1,4-benzodiazepin-2-one Following General Procedure 4-C using 3-[N'-(tert-butylcarbamate)-L-alaninyl]-amino-2,3-dihydro-1-methyl-5-(4-fluorophenyl)-1H-1,4-benzodiazepin-2-one, the title intermediate was prepared as a yellow foam. The crude material was used immediately.

Example 4-L

Synthesis of 3-(N'-L-Alaninyl)amino-2,3-dihydro-1-isobutyl-5-phenyl-1H-1,4-benzodiazepin-2-one Step A: 1,3-Dihydro-5-phenyl-2H-1,4-benzodiazepin-2-one (prepared according to the procedure of M. G. Bock et al., *J. Org. Chem.* 1987, 52, 3232–3239) was alkylated with isobutyl iodide using General Procedure 4-G to afford 1,3-dihydro-1-isobutyl-5-phenyl-2H-1,4-benzodiazepin-2-one.

Step B: Following General Procedures 4-D and 4-F and using the product from Step A, 3-amino-1,3-dihydro-1-isobutyl-5-phenyl-2H-1,4-benzodiazepin-2-one was prepared.

Step C: The product from Step B and N-Boc-L-alanine (Sigma) were coupled using General Procedure D, followed by removal of the Boc group using General Procedure 4-J, to afford 3-(N'-L-alaninyl)amino-1,3-dihydro-1-isobutyl-5-phenyl-2H-1,4-benzodiazepin-2-one.

By substituting isopropyl iodide, n-propyl iodide, cyclopropylmethyl iodide and ethyl iodide for isobutyl iodide in Step A above, the following additional intermediates were prepared:

3-(N'-L-alaninyl)amino-1,3-dihydro-1-isopropyl-5-phenyl-2H-1,4-benzodiazepin-2-one 3-(N'-L-alaninyl)amino-1,3-dihydro-1-propyl-5-phenyl-2H-1,4-benzodiazepin-2-one 3-(N'-L-alaninyl)amino-1,3-dihydro-1-cyclopropylmethyl-5-phenyl-2H-1,4-benzodiazepin-2-one 3-(N'-L-alaninyl)amino-1,3-dihydro-1-ethyl-5-phenyl-2H-1,4-benzodiazepin-2-one.

Example 4-M

Synthesis of 3-(N'-L-Alaninyl)amino-1-methyl-5-phenyl-1,3,4,5-tetrahydro-2H-1,5-benzodiazepin-2-one Step A: 1,3,4,5-Tetrahydro-5-phenyl-2H-1,5-benzodiazepin-2-one (CAS No. 32900-17-7) was methylated using General Procedure 4-I to afford 1-methyl-5-phenyl-1,3,4,5-tetrahydro-2H-1,5-benzodiazepin-2-one.

Step B: Following General Procedures 4-E and 4-F and using the product from Step A, 3-amino-1-methyl-5-phenyl-1,3,4,5-tetrahydro-2H-1,5-benzodiazepin-2-one was prepared.

Step C: The product from Step B and N-Boc-L-alanine (Sigma) were coupled using General Procedure D, followed by removal of the Boc group using the General Procedure of Step B of Example 1-C, to afford 3-(N'-L-alaninyl)amino-1-methyl-5-phenyl-1,3,4,5-tetrahydro-2H-1,5-benzodiazepin-2-one.

Example 4-N

Synthesis of 3-(N'-L-Alaninyl)amino-2,4-dioxo-1-methyl-5-phenyl-2,3,4,5-tetrahydro-1H-1,5-benzodiazepine 3-Amino-2,4-dioxo-1-methyl-5-phenyl-2,3,4,5-tetrahydro-1H-1,5-benzodiazepine (CAS No. 131604-75-6) was coupled with N-Boc-L-alanine (Sigma) using General Procedure D, followed by removal of the Boc group using General Procedure 4-N, to afford the title compound.

Example 4-O

Synthesis of 3-((R)-Hydrazinopropionyl)amino-2,3-dihydro-1-methyl-5-phenyl)-1H-1,4-benzodiazepin-2-one Part 1—Synthesis of (R)-N,N'-Di-BOC-2-Hydrazinopropionic Acid Step A: To (S)-(−)-4-benzyl-2-oxazolidanone (Aldrich) in THF cooled to −50° C. was added n-butyl lithium 1.1 eq. (1.6 M in hexane) dropwise. The reaction mixture was allowed to warm to −20° C. and then was re-cooled to −78° C. and propionyl chloride (1.1 eq) was added in one portion. The reaction mixture was allowed to stir an additional 15 min. at −78° C. and then was allowed to warm to room temperature. The reaction was then quenched with a saturated solution of sodium bicarbonate and extracted with ethyl acetate. The organic extracts were washed with water, followed by brine and then dried over sodium sulfate, filtered and concentrated to give (S)-(−)-3-propionyl-4-benzyl-2-oxazolidanone.

Step B: To a solution of (S)-(−)-3-propionyl-4-benzyl-2-oxazolidanone in THF at −78° C. was added KHMDS (1.05 eq.) (Aldrich) dropwise. The reaction mixture was allowed to stir at −78° C. for 30 min. and then a precooled solution of di-tert-butyl-azodicarboxylate (Aldrich) was added via a cannula. After 5 min. 2.6 eq. of acetic acid was added. The reaction mixture was then extracted with dichloromethane and the organic layer was washed with 1 M potassium phosphate. The organic layer was then dried over sodium sulfate, filtered and concentrated to give (S)-(−)-3-[(R)-N,N'-di-BOC-2-hydrazinopropionyl]-4-benzyl-2-oxazolidanone.

Step C: To (S)-(−)-3-[(R)-N,N'-di-BOC-2-hydrazinopropionyl]-4-benzyl-2-oxazolidanone (0.49 moles) at 0° C. in 8 mL of THF and 3 mL of water was added LiOH (1.7 eq.) and $H_2O_2$ (3.0 eq.) and the reaction mixture was stirred at room temperature for 3 hours. The reaction mixture was then poured into a seraratory funnel and diluted with water. The aqueous mixture was extracted with ethyl acetate and then acidified to pH 2.0 with 1N HCl and extracted with ethyl acetate. The organic layer was then dried over sodium sulfate, filtered and solvent removed to give (R)-N,N'-di-BOC-2-hydrazinopropionic acid which was used without further purification.

Part B

3-Amino-2,3-dihydro-1-methyl-5-phenyl-1H-1,4-benzodiazepin-2-one was coupled to (R)-N,N'-di-BOC-2-hydrazinopropionic acid using General Procedure D. The Boc group was removed by dissolving the Boc-protected compound in a 1:1–2:1 mixture of $CH_2Cl_2$ and trifluoroacetic acid. The resulting solution was stirred until tlc indicated complete conversion, typically 2 hours. The solution was then stripped to dryness and the residue was taken up in ethyl acetate or $CH_2Cl_2$. The solution was washed with saturated aqueous $NaHCO_3$ and the aqueous phase was adjusted to a basic pH, then extracted with ethyl acetate or $CH_2Cl_2$. The organic phase was washed with saturated aqueous NaCl and dried over $MgSO_4$. The solution was stripped free of solvent on a rotary evaporator to afford the title compound.

Example 4-P

Synthesis of 3-Amino-2,4-dioxo-1,5-bis-(1-methylethyl)-2,3,4,5-tetrahydro-1H-1,5-benzodiazepine Step A:—Synthesis of 2,4-Dioxo-2,3,4,5-tetrahydro-1H-1,5-benzodiazepine 2,4-Dioxo-2,3,4,5-tetrahydro-1H-1,5-benzodiazepine (CAS No. 49799-48-6) was prepared from 1,2-phenylenediamine (Aldrich) and malonic acid (Aldrich) using the procedure of Claremon, D. A.; et al, PCT Application: WO 96/40655.

Step B:—Synthesis of 2,4-Dioxo-1,5-bis-(1-methylethyl)-2,3,4,5-tetrahydro-1H-1,5-benzodiazepine 2,4-Dioxo-1,5-bis-(1-methylethyl)-2,3,4,5-tetrahydro-1H-1,5-benzodiazepine (CAS No. 113021-84-4) was prepared following General Procedure 4-M using the product from Step A and 2-iodopropane (Aldrich). Purification was by flash chromatography eluting with EtOAc/hexanes (3:7 gradient to 1:1), then recrystalization from EtOAc/hexanes.

Step C:—Synthesis of 3-Azido-2,4-dioxo-1,5-bis-(1-methylethyl)-2,3,4,5-tetrahydro-1H-1,5-benzodiazepine Following General Procedure 4-K using the product from Step B, 3-azido-2,4-dioxo-1,5-bis-(1-methylethyl)-2,3,4,5-tetrahydro-1H-1,5-benzodiazepine (CAS No. 186490-50-6) was prepared as a white solid. The product was purified by flash chromatography eluting with hexanes/EtOAc (4:1) to provide a separable 23:1 mixture of pseudo-axial/pseudo-equatorial azides. The pure pseudo-axial azide was used in the next step.

Step D:—Synthesis of 3-Amino-2,4-dioxo-1,5-bis-(1-methylethyl)-2,3,4,5-tetrahydro-1H-1,5-benzodiazepine Following General Procedure 4-L using the product from Step C, 3-amino-2,4-dioxo-1,5-bis-(1-methylethyl)-2,3,4,5-tetrahydro-1H-1,5-benzodiazepine (CAS No. 186490-51-7) was prepared as a white solid. Purification was by flash chromatography eluting with $CH_2Cl_2$/MeOH (98:2 gradient to 95:5). The isolated pseudo-axial amine atropisomer was completely converted to the pseudo-equatorial amine atropisomer by heating in toluene to 100–105° C. for 15 minutes, and the pseudo-equatorial amine atropisomer was used in the next step. The isomers were distinguished by $^1$H-NMR in $CDCl_3$. Selected $^1$H-NMR ($CDCl_3$): Pseudo-axial amine 4.40 (s, 1H); Pseudo-equatorial amine 3.96 (s, 1H).

Example 4-Q

Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Step A:—Synthesis of N-(t-Butoxycarbonyl)-R-2-thienylglycine N-(t-Butoxycarbonyl)-R-2-thienylglycine (CAS No. 74462-03-1) was prepared from L-α-(2-thienyl)glycine (Sigma) by the procedure described in Bodansky, M. et al; *The Practice of Peptide Synthesis*; Springer Verlag; 1994, p. 17.

Step B:—Synthesis of 3-[N'-(t-Butoxycarbonyl)-R-2-thienylglycinyl]-amino-2,4-dioxo-1,5-bis-(1-methylethyl)-2,3,4,5-tetrahydro-1H-1,5-benzodiazepine Following General Procedure J above using the product from Example 4-P and the product from Step A above, 3-[N'-(t-butoxycarbonyl)-R-2-thienylglycinyl]-amino-2,4-dioxo-1,5-bis-(1-methylethyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step C:—Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Following General Procedure 4-N above using the product from Step B, the title compound was prepared as a white solid.

Example 4-R

Synthesis of 3-(L-Alaninyl)-amino-2,4-dioxo-1,5-bis-methyl-2,3,4,5-tetrahydro-1H-1,5-benzodiazepine Hydrochloride Step A:—Synthesis of 2,4-Dioxo-1,5-bis-methyl-2,3,4,5-tetrahydro-1H-1,5-benzodiazepine 2,4-Dioxo-1,5-bis-methyl-2,3,4,5-tetrahydro-1H-1,5-benzodiazepine (CAS No. 23954-54-3) was prepared following General Procedure 4-M using the product from Example 4-P, Step A and iodomethane (Aldrich). The white solid product precipitated during partial concentration of the reaction after work-up, and was isolated by filtration.

Step B:—Synthesis of 3-Azido-2,4-dioxo-1,5-bis-methyl-2,3,4,5-tetrahydro-1H-1,5-benzodiazepine For this substrate, General Procedure 4-K was modified in the following manner. Initially the product from Step A was suspended (not a solution) in THF at −78° C., and following addition of the $KN(TMS)_2$ solution, this suspension was allowed to warm to −35° C. over a period of 12 minutes, during which the suspension became a solution, and was re-cooled to −78° C.; then treated as described in the General Procedure. 3-Azido-2,4-dioxo-1,5-bis-methyl-2,3,4,5-tetrahydro-1H-1,5-benzodiazepine was purified by flash chromatography eluting with $CHCl_3$/EtOAc (7:1), then trituration from hot $CHCl_3$ with hexanes and cooled to −23° C. The product was isolated as a white solid.

Step C:—Synthesis of 3-Amino-2,4-dioxo-1,5-bis-methyl-2,3,4,5-tetrahydro-1H-1,5-benzodiazepine Following General Procedure 4-L using the product from Step B, 3-amino-2,4-dioxo-1,5-bis-methyl-2,3,4,5-tetrahydro-1H-1,5-benzodiazepine was prepared as a white solid. The crude product was used without further purification.

Step D:—Synthesis of 3-[N'-(t-Butoxycarbonyl)-L-alaninyl]-amino-2,4-dioxo-1,5-bis-methyl-2,3,4,5-tetrahydro-1H-1,5-benzodiazepine Following General Procedure I above using N-Boc-L-alanine (Novabiochem) and the product from Step C, 3-[N'-

(t-butoxycarbonyl)-L-alaninyl]-amino-2,4-dioxo-1,5-bis-methyl-2,3,4,5-tetrahydro-1H-1,5-benzodiazepine was prepared as a white foam. Purification was by flash chromatography eluting with CH$_2$Cl$_2$/EtOAc (2:1 gradient to 1:1).

Step E:—Synthesis of 3-(L-Alaninyl)-amino-2,4-dioxo-1,5-bis-methyl-2,3,4,5-tetrahydro-1H-1,5-benzodiazepine Hydrochloride Following General Procedure 4-N above using the product from Step D, the title compound was prepared as an off-white amorphous solid.

Example 4-S

Synthesis of 3-(L-Alaninyl)amino-2,4-dioxo-1,5-bis-(2-methylpropyl)-2,3,4,5-tetrahydro-1H-1,5-benzodiazepine Hydrochloride Step A:—Synthesis of 2,4-Dioxo-1,5-bis-(2-methylpropyl)-2,3,4,5-tetrahydro-1H-1,5-benzodiazepine 2,4-Dioxo-1,5-bis-(2-methylpropyl)-2,3,4,5-tetrahydro-1H-1,5-benzodiazepine was prepared following General Procedure 4-M using the product from Example 4-P, Step A and 1-iodo-2-methylpropane (Aldrich). Purification was by flash chromatography eluting with EtOAc/hexanes (3:7 gradient to 1:1), then recrystalization from EtOAc/hexanes.

Step B:—Synthesis of 3-Azido-2,4-dioxo-1,5-bis-(2-methylpropyl)-2,3,4,5-tetrahydro-1H-1,5-benzodiazepine Following General Procedure 4-K (a precipitate formed during the addition of the KN(TMS)$_2$, but dissolved upon addition of the trisyl azide) using the product from Step A, 3-azido-2,4-dioxo-1,5-bis-(2-methylpropyl)-2,3,4,5-tetrahydro-1H-1,5-benzodiazepine was prepared as a white solid. The product was purified by flash chromatography eluting with hexanes/EtOAc (4:1) and a second flash chromatography eluting with CH$_2$Cl$_2$/hexanes/EtOAc (10:10:1 gradient to 8:6:1).

Step C:—Synthesis of 3-Amino-2,4-dioxo-1,5-bis-(2-methylpropyl)-2,3,4,5-tetrahydro-1H-1,5-benzodiazepine Following General Procedure 4-L using the product from Step B, 3-amino-2,4-dioxo-1,5-bis-(2-methylpropyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH).

Step D:—Synthesis of 3-[N'-(t-Butoxycarbonyl)-L-alaninyl]-amino-2,4-dioxo-1,5-bis-(2-methylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2-methylpropyl)-2,3,4,5-tetrahydro-1H-1,5-benzodiazepine was prepared as a white foam. Purification was by flash chromatography eluting with CH$_2$Cl$_2$/EtOAc (3:1 gradient to 3:2).

Step E:—Synthesis of 3-(L-Alaninyl)-amino-2,4-dioxo-1,5-bis-(2-methylpropyl)-2,3,4,5-tetrahydro-1H-1,5-benzodiazepine Hydrochloride Following General Procedure 4-N above using the product from Step D, the title compound was prepared as an amorphous white solid.

Example 4-T

Synthesis of 3-(S-Phenylglycinyl)amino-2,4-dioxo-1,5-bis-(2-methylpropyl)-2,3,4,5-tetrahydro-1H-1,5-benzodiazepine Hydrochloride Step A:—Synthesis of 3-[N'-(t-Butoxycarbonyl)-S-phenylglycinyl]-amino-2,4-dioxo-1,5-bis-(2-methylpropyl)-2,3,4,5-tetrahydro-1H-1,5-benzodiazepine Following General Procedure J above using the product from Example 4-S, Step C and the Boc-L-phenylglycine (Novabiochem, CAS No. 2900-27-8), 3-[N'-(t-butoxycarbonyl)-S-phenylglycinyl]-amino-2,4-dioxo-1,5-bis-(2-methylpropyl)-2,3,4,5-tetrahydro-1H-1,5-benzodiazepine was prepared as a white foam. Purification was by flash chromatography eluting with CH$_2$Cl$_2$/EtOAc (9:1 gradient to 5:1).

Step B:—Synthesis of 3-(S-Phenylglycinyl)-amino-2,4-dioxo-1,5-bis-(2-methylpropyl)-2,3,4,5-tetrahydro-1H-1,5-benzodiazepine Hydrochloride Following General Procedure 4-N above using the product from Step A, 3-(S-phenylglycinyl)-amino-2,4-dioxo-1,5-bis-(2-methylpropyl)-2,3,4,5-tetrahydro-1H-1,5-benzodiazepine hydrochloride was prepared as an off-white solid.

Example 4-U

Synthesis of 3-(L-Alaninyl)amino-2,4-dioxo-1,5-bis-(cyclopropylmethyl)-2,3,4,5-tetrahydro-1H-1,5-benzodiazepine Hydrochloride Step A:—Synthesis of 2,4-Dioxo-1,5-bis-(cyclopropylmethyl)-2,3,4,5-tetrahydro-1H-1,5-benzodiazepine 2,4-Dioxo-1,5-bis-(cyclopropylmethyl)-2,3,4,5-tetrahydro-1H-1,5-benzodiazepine was prepared following General Procedure 4-M using the product from Example 4-P, Step A, and (bromomethyl)cyclopropane (Lancaster). Purification was by flash chromatography eluting with EtOAc/hexanes (3:7 gradient to straight EtOAc), then recrystalization from EtOAc/hexanes.

Step B:—Synthesis of 3-Azido-2,4-dioxo-1,5-bis-(cyclopropylmethyl)-2,3,4,5-tetrahydro-1H-1,5-benzodiazepine For this substrate General Procedure 4-K was modified in the following manner. Initially the product from Step A was suspended (not a solution) in THF at −78° C., and following addition of the KN(TMS)$_2$ solution, this suspension was allowed to warm to −30° C., during which the suspension became a solution, and was re-cooled to −78° C. Upon re-cooling to −78° C. a precipitate began to form, therefore the reaction flask containing the mixture was partially raised above the cooling bath until the internal temperature rose to −50° C.; then the trisyl azide solution was added. The cooling bath was removed and the mixture allowed to warm to −20° C. whereupon the mixture had become a nearly homogenous solution, and the AcOH was added. Then, treated as described in the general procedure. 3-Azido-2,4-dioxo-1,5-bis-(cyclopropylmethyl)-2,3,4,5-tetrahydro-1H-1,5-benzodiazepine was purified by trituration with hot to room temperature EtOAc, followed by recrystallization from hot to −23° C. CHCl$_3$/EtOAc/EtOH (5:5:1) and isolated as a white solid.

Step C:—Synthesis of 3-Amino-2,4-dioxo-1,5-bis-(cyclopropylmethyl)-2,3,4,5-tetrahydro-1H-1,5-benzodiazepine Following General Procedure 4-L using the product from Step B, 3-amino-2,4-dioxo-1,5-bis-(cyclopropylmethyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH) followed by recrystalization from warm CH$_2$Cl$_2$/hexanes (1:1) to −23° C.

Step D:—Synthesis of 3-[N'-(t-Butoxycarbonyl)-L-alaninyl]-amino-2,4-dioxo-1,5-bis-(cyclopropylmethyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(cyclopropylmethyl)-2,3,4,5-tetrahydro-1H-1,5-benzodiazepine was prepared as a white foam. Purification was by flash chromatography eluting with CH$_2$Cl$_2$/EtOAc (3:1 gradient to 2:1).

Step E:—Synthesis of 3-(L-Alaninyl)-amino-2,4-dioxo-1,5-bis-(cyclopropylmethyl)-2,3,4,5-tetrahydro-1H-1,5-benzodiazepine Hydrochloride Following General Procedure 4-N above using the product from Step D, the title compound was prepared as an off-white solid.

Example 4-V

Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Step A:—Synthesis of 2,4-Dioxo-1,5-bis-(2,2-dimethylpropyl)-2,3,4,5-tetrahydro-1H-1,5-benzodiazepine To a stirred suspension of the product from Example 4-P, Step A (1.0 eq., 17.08 g) in DMSO (500 mL) at room temperature was added neopentyl iodide (43.01 g, 2.24 eq., Aldrich) and Cs$_2$CO$_3$ (72.65 g, 2.3 eq., Aldrich). The resulting mixture was heated to 75° C. for 30 minutes, then additional Cs$_2$CO$_3$ (31.59 g, 1.0 eq.) was added and the mixture rapidly stirred at 75° C. for 6 hours. The mixture was allowed to cool and H$_2$O (500 mL) and EtOAc (1000 mL) were added. The phases were partitioned and the organic phase washed with H$_2$O (1×500 mL), 1 M aq. HCl (2×500 mL), and brine (1×500 mL). Then, the organic phase was dried over MgSO$_4$, filtered, concentrated, and purified by flash chromatography eluting with hexanes/EtOAc (3:2 gradient to 2:3) to provide 2,4-dioxo-1,5-bis-(2,2-dimethylpropyl)-2,3,4,5-tetrahydro-1H-1,5-benzodiazepine as a white solid.

Step B:—Synthesis of 3-Azido-2,4-dioxo-1,5-bis-(2,2-dimethylpropyl)-2,3,4,5-tetrahydro-1H-1,5-benzodiazepine Following General Procedure 4-K using the product from Step A, 3-azido-2,4-dioxo-1,5-bis-(2,2-dimethylpropyl)-2,3,4,5-tetrahydro-1H-1,5-benzodiazepine was prepared as a white solid. The product was purified by flash chromatography eluting with hexanes/CH$_2$Cl$_2$/EtOAc (10:5:1 gradient to 5:5:1) to provide a separable 13:1 mixture of pseudo-axial/pseudo-equatorial azides. The pure pseudo-axial azide was used in the next step. Selected $^1$H-NMR (CDCl$_3$): Pseudo-axial azide 5.12 (s, 1H); Pseudo-equatorial azide 4.03 (s, 1H).

Step C:—Synthesis of 3-Amino-2,4-dioxo-1,5-bis-(2,2-dimethylpropyl)-2,3,4,5-tetrahydro-1H-1,5-benzodiazepine Following General Procedure 4-L using the product from Step B, 3-amino-2,4-dioxo-1,5-bis-(2,2-dimethylpropyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH). The isolated white solid product was identified as a ~4:1 mixture of pseudo-axial and pseudo-equatorial amines atropisomers by $^1$H-NMR. The mixture was heated in toluene to 100° C. for 20 minutes, then re-concentrated to provide the pure pseudo-equatorial amine atropisomer, as a white solid, and this was for the next step. Selected $^1$H-NMR (CDCl$_3$): Pseudo-axial amine 4.59 (s, 1H); Pseudo-equatorial amine 4.03 (s, 1H).

Step D:—Synthesis of 3-[N'-(t-Butoxycarbonyl)-L-alaninyl]-amino-2,4-dioxo-1,5-bis-(2,2-dimethylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2,2-dimethylpropyl)-2,3,4,5-tetrahydro-1H-1,5-benzodiazepine was prepared as a white foam. Purification was by flash chromatography eluting with CH$_2$Cl$_2$/EtOAc (4:1 gradient to 5:2).

Step E:—Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Following General Procedure 4-N above using the product from Step D, the title compound was prepared as an off-white solid.

Example 4-W

Synthesis of 3-(L-Alaninyl)amino-2,4-dioxo-1,5-bis-phenyl-2,3,4,5-tetrahydro-1H-1,5-benzodiazepine Hydrochloride Step A:—Synthesis of 2,4-Dioxo-1,5-bis-phenyl-2,3,4,5-tetrahydro-1H-1,5-benzodiazepine This procedure is a modification of the procedure described in Chan, D. M. T. *Tetrahedron Lett.* 1996, 37, 9013–9016. A mixture of the product from Example 4-P, Step A (1.0 eq., 7.50 g), Ph$_3$Bi (2.2 eq., 41.26 g, Aldrich), Cu(OAc)$_2$ (2.0 eq., 15.48 g, Aldrich), Et$_3$N (2.0 eq., 8.62 g) in CH$_2$Cl$_2$ (100 mL) was stirred under N$_2$ at room temperature for 6 days (monitoring by TLC). The solids were removed by filtration through a plug of Celite rinsing with CH$_2$Cl$_2$/MeOH (3×75 mL). The filtrate was concentrated, dissolved in hot CH$_2$Cl$_2$/MeOH (9:1) and filtered through a large plug of silica gel eluting with CH$_2$Cl$_2$/MeOH (9:1, 2 L). The filtrate was concentrated and the residue purified by flash chromatography eluting with straight CH$_2$Cl$_2$ gradient to CH$_2$Cl$_2$/MeOH (9:1). 2,4-Dioxo-1,5-bis-phenyl-2,3,4,5-tetrahydro-1H-1,5-benzodiazepine crystallized during concentration of the fractions containing the product, and was isolated by filtration as a white solid.

Step B:—Synthesis of 3-Azido-2,4-dioxo-1,5-bis-phenyl-2,3,4,5-tetrahydro-1H-1,5-benzodiazepine For this substrate, General Procedure 4-K was modified in the following manner. Initially the product from Step A was suspended (not a solution) in THF at −70° C., and following addition of the KN(TMS)$_2$ solution, this suspension was allowed to warm to −20° C. over a period of 10 minutes, during which the suspension became a solution, and was re-cooled to −70° C.; then treated as described in the general procedure. The title compound was purified by trituration with hot CHCl$_3$/hexanes (1:1) to yield 3-azido-2,4-dioxo-1,5-bis-phenyl-2,3,4,5-tetrahydro-1H-1,5-benzodiazepine as a white solid.

Step C:—Synthesis of 3-Amino-2,4-dioxo-1,5-bis-phenyl-2,3,4,5-tetrahydro-1H-1,5-benzodiazepine Following General Procedure 4-L using the product from Step B, 3-amino-2,4-dioxo-1,5-bis-phenyl-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH).

Step D:—Synthesis of 3-[N'-(t-Butoxycarbonyl)-L-alaninyl]-amino-2,4-dioxo-1,5-bis-phenyl-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-phenyl-2,3,4,5-tetrahydro-1H-1,5-benzodiazepine was prepared as a white foam. Purification was by flash chromatography eluting with $CH_2Cl_2$/EtOAc (4:1 gradient to 3:1).

Step E:—Synthesis of 3-(L-Alaninyl)-amino-2,4-dioxo-1,5-bis-phenyl-2,3,4,5-tetrahydro-1H-1,5-benzodiazepine Hydrochloride Following General Procedure 4-N above using the product from Step D, the title compound was prepared as a white amorphous solid.

Example 4-X

Synthesis of 3-Amino-2,3-dihydro-1-methyl-5-phenyl-1H-1,4-benzodiazepin-2-one

Following the method of R. G. Sherrill et al., *J. Org. Chem.*, 1995, 60, 730–734 and using glacial acetic acid and HBr gas, the title compound was prepared.

Example 4-Y

Synthesis of 3-(L-Valinyl)-amino-2,3-dihydro-1-methyl-5-phenyl-1H-1,4-benzodiazepin-2-one Step A—Synthesis of 3-[N'-(tert-Butylcarbamate)-L-valinyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 4-B, Step A) was free based by partitioning between methylene chloride and 1 M potassium carbonate. The free amine was then coupled with N-Boc-valine following General Procedure D to give the title compound.

$C_{26}H_{32}N_4O_4$ (MW 464.62); mass spectroscopy 464.3. Anal. Calcd for $C_{26}H_{32}N_4O_4$: C, 67.22; H, 6.94; N, 12.06. Found: C, 67.29; H, 6.79; N, 11.20.

Step B—Synthesis of 3-(L-Valinyl)-amino-2,3-dihydro-1-methyl-5-phenyl-1H-1,4-benzodiazepin-2-one Following General Procedure 4-C and using 3-[N'-(tert-butylcarbamate)-L-alaninyl]-amino-2,3-dihydro-1-methyl-5-phenyl-1H-1,4-benzodiazepine-2-one, the title compound was prepared as a white foam.

$C_{21}H_{23}N_4O_2$ (MW 363.48); mass spectroscopy (M+H) 364.2.

Example 4-Z

Synthesis of 3-(L-tert-Leucinyl)-amino-2,3-dihydro-1-methyl-5-phenyl-1H-1,4-benzodiazepin-2-one Step A—Synthesis of 3-[N'-(tert-Butylcarbamate)-L-tert-leucinyl]-amino-2,3-dihydro-1-methyl-5-phenyl-1H-1,4-benzodiazepin-2-one (S)-3-amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 4-B, Step A) was free based by partitioning between methylene chloride and 1M potassium carbonate. The free amine was then coupled with N-Boc-tert-leucine following General Procedure D to give the title compound.

$C_{27}H_{35}N_4O_4$ (MW 479.66); mass spectroscopy 479.

Step B—Synthesis of 3-(L-tert-Leucinyl)-amino-2,3-dihydro-1-methyl-5-phenyl-1H-1,4-benzodiazepin-2-one Following General Procedure 4-C and using 3-[N'-(tert-butylcarbamate)-L-tert-leucinyl]-amino-2,3-dihydro-1-methyl-5-phenyl-1H-1,4-benzodiazepine-2-one, the title compound was prepared as a white foam.

Anal. Calcd for $C_{22}H_{25}N_4O_2.0.5H_2O$: C, 68.19; H, 7.02; N, 14.40. Found: C, 68.24; H, 7.00; N, 14.00.

Example 4-AA

Synthesis of 3-(L-Alaninyl)-amino-2,3-dihydro-1,5-dimethyl-1H-1,4-benzodiazepine 2,3-Dihydro-1,5-dimethyl-1H-1,4-benzodiazepine was prepared following General Procedures 4-I (using methyl iodide), 4-D and 4-F. Coupling of this intermediate with Boc-L-alanine (Novo) using General Procedure D.

The Boc group was removed by dissolving the Boc-protected compound in a 1:1–2:1 mixture of $CH_2Cl_2$ and trifluoroacetic acid. The resulting solution was stirred until tlc indicated complete conversion, typically 2 hours. The solution was then stripped to dryness and the residue was taken up in ethyl acetate or $CH_2Cl_2$. The solution was washed with saturated aqueous $NaHCO_3$ and the aqueous phase was adjusted to a basic pH, then extracted with ethyl acetate or $CH_2Cl_2$. The organic phase was washed with saturated aqueous NaCl and dried over $MgSO_4$. The solution was stripped free of solvent on a rotary evaporator to afford the title compound which was used without further purification.

Example 4-AB

Synthesis of 3-(L-3-Thienylglycinyl)amino-2,4-dioxo-1,5-bis-(2,2-dimethylpropyl)-2,3,4,5-tetrahydro-1H-1,5-benzodiazepine Step A:—Synthesis of N-(t-Butoxycarbonyl)-L-3-thienylglycine N-(t-Butoxycarbonyl)-L-3-thienylglycine was prepared from L-α-(3-thienyl)glycine (Sigma) by the procedure described in Bodansky, M. et al; *The Practice of Peptide Synthesis*; Springer Verlag; 1994, p. 17.

Step B:—Synthesis of 3-[N'-(t-Butoxycarbonyl)-L-3-thienylglycinyl]-amino-2,4-dioxo-1,5-bis-(2,2-dimethylpropyl)-2,3,4,5-tetrahydro-1H-1,5-benzodiazepine Following General Procedure D above using the product from Example 4-V, Step C and the product from Step A above, 3-[N'-(t-butoxycarbonyl)-L-3-thienylglycinyl]-amino-2,4-dioxo-1,5-bis-(2,2-dimethylpropyl)-2,3,4,5-tetrahydro-1H-1,5-benzodiazepine was prepared.

Step C:—Synthesis of 3-(L-3-Thienylglycinyl)amino-2,4-dioxo-1,5-bis-(2,2-dimethylpropyl)-2,3,4,5-tetrahydro-1H-1,5-benzodiazepine Following General Procedure 4-N above using the product from Step B, the title compound was prepared.

Example 4-AC

Synthesis of 2-(L-Alaninyl)-amino-3H-fluoreno[1,9-ef]-2,4-dihydro-1-methyl-1H-1,4-diazepin-3-one Step A—Preparation of 1-[N-(α-Isopropylthio)-N'-(benzyloxycarbonyl)-glycinyl]-amino-9-fluorenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 1-amino-9-fluorenone (0.9 eq.; Aldrich) and 4-methylmorpholine (2.0 eq., Aldrich) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was triturated with 1:1 diethyl ether/hexanes giving the title compound and a yellow solid.

MS Calcd for $C_{26}H_{25}N_2O_4S$: 461.15 (MH$^+$), found 461.3; Anal. Calcd for $C_{26}H_{24}N_2O_4S$: C, 67.81; H, 5.25; N, 6.08. Found: C, 67.97; H, 5.26; N, 6.14.

Step B—Preparation of 1-[N-(α-Amino)-N'-(benzyloxycarbonyl)-glycinyl]-amino-9-fluorenone Ammonia gas was bubbled into a solution 1-[N-(α-isopropylthio)-N'-(benzyloxycarbonyl)-glycinyl]-amino-9-fluorenone (1 eq) in THF at 0° C. After 35 minutes mercury (II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C—Preparation of 2-(Benzyloxycarbonyl)-amino-3H-fluoreno[1,9-ef]-2,4-dihydro-1H-1,4-diazepin-3-one 1-[N-(α-Amino)-N'-(benzyloxycarbonyl)-glycinyl]-amino-9-fluorenone (1 eq.) was treated with glacial acetic acid and ammonium acetate (4.7 eq.). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was triturated with 3:1 diethyl ether/methylene chloride.

Anal. Calcd for $C_{23}H_{17}N_3O_3 \cdot 0.25H_2O$: C, 71.22; H, 4.55; N, 10.83. Found: C, 71.50; H, 4.44; N, 10.84.

Step D—Preparation of 2-(Benzyloxycarbonyl)-amino-3H-fluoreno[1,9-ef]-2,4-dihydro-1-methyl-1H-1,4-diazepin-3-one Following General Procedure 4-A above using 2-(benzyloxycarbonyl)-amino-3H-fluoreno[1,9-ef]-2,4-dihydro-1H-1,4-diazepin-3-one, the title intermediate was prepared as a yellow solid.

Anal. Calcd for $C_{24}H_{19}N_3O_3$: C, 72.53; H, 4.82; N, 10.57. Found: C, 72.37; H, 5.01; N, 10.36.

Step E—Preparation of 2-Amino-3H-fluoreno[1,9-ef]-2,4-dihydro-1-methyl-1H-1,4-diazepin-3-one Following General Procedure 4-B above using 2-(benzyloxycarbonyl)-amino-3H-fluoreno[1,9-ef]-2,4-dihydro-1-methyl-1H-1,4-diazepin-3-one, the title intermediate was prepared as a yellow foam which was used immediately in Step F.

Step F—Preparation of 2-[N'-(tert-Butylcarbamate)-L-alaninyl]-amino-3H-fluoreno[1,9-ef]-2,4-dihydro-1-methyl-1H-1,4-diazepin-3-one Following General Procedure D using N-Boc Alanine (Novabiochem) and 2-amino-3H-fluoreno[1,9-ef]-2,4-dihydro-1-methyl-1H-1,4-diazepin-3-one, the title intermediate was prepared as a yellow solid.

MS Calcd for $C_{24}H_{27}N_4O_4$: 435.21 (MH$^+$); found 435.29.

Step G—Preparation of 2-(L-Alaninyl)-amino-3H-fluoreno[1,9-ef]-2,4-dihydro-1-methyl-1H-1,4-diazepin-3-one Following General Procedure 4-C using 2-[N'-(tert-butylcarbamate)-L-alaninyl]-amino-3H-fluoreno[1,9-ef]-2,4-dihydro-1-methyl-1H-1,4-diazepin-3-one, the title intermediate was prepared as a yellow foam.

Example 4-AD

Synthesis of 5-(L-Alaninyl]-amino-7-methyl-1,2,4-triazolo[4,3-d][1,4]benzodiazepin-6(7H)-one Step A—Preparation of 1,3-Dihydro-5-(ethylthio)-1-methyl-2H-1,4-benzodiazepin-2-one A rapidly stirred solution of 1-methyl-1,2,3,4-tetrahydro-3H-1,4-benzodiazepin-2,5-dione (Showell, G. A.; Bourrain, S.; Neduvelil, J. G.; Fletcher, S. R.; Baker, R.; Watt, A. P.; Fletcher, A. E.; Freedman, S. B.; Kemp, J. A.; Marshall, G. R.; Patel, S.; Smith, A. J.; Matassa, V. G. *J. Med. Chem.* 1994, 37, 719.) (1 eq.) and pyridine (1.1 eq., Aldrich) in $CH_2Cl_2$ (0.16 M in dione), cooled to −40 to −45° C. under $N_2$ in an oven-dried flask, was treated dropwise with trifluoromethanesulfonic anhydride (1.1 eq., Aldrich). The resulting mixture (light yellow color; precipitate) was stirred at −40 to −35° C. for 20 minutes and then at 0° C. (ice bath) to 10° C. for 14.5 hours (note: ice in Dewar melted slowly overnight). The resulting orange solution (some precipitate) was recooled to 0° C. and treated dropwise with ethanethiol (1.2 eq., Aldrich). The resulting mixture was stirred at 0 to 4° C. under $N_2$ for 8 hours then partitioned between $CH_2Cl_2$ and saturated aqueous $NaHCO_3$. The aqueous phase was extracted thrice with $CH_2Cl_2$. The organic extracts were combined, dried over $Na_2SO_4$, and evaporated in vacuo. The mixture was purified via flash chromatography using a gradient from $CH_2Cl_2$ to 30:70 $CH_2Cl_2$/Ethyl acetate as the eluent.

MS Calcd for $C_{12}H_{15}NOS$: 235.09 (MH+), found 235.0. Anal. Calcd for $C_{12}H_{14}NOS$: C, 61.51; H, 6.02; N, 11.96. Found: C, 61.55; H, 5.99; N, 11.74.

Step B: Preparation of 7-Methyl-1,2,4-triazolo[4,3-d][1,4]benzodiazepin-6(7H)-one A mixture of 1,3-dihydro-5-(ethylthio)-1-methyl-2H-1,4-benzodiazepin-2-one (1 eq.) and formic hydrazide (5.8 eq. Aldrich) in n-butanol (0.1 M in benzodiazepine) was stirred at reflux under $N_2$ for 24 hours. An additional 1.67 eq. of formic hydrazide was added and refluxing continued an additional 16 hours. The yellow solution was evaporated in vacuo and the residue was purified via flash chromatography eluting with a gradient from 98:2® 96:4 $CH_2Cl_2$/MeOH. The product was obtained as a white solid.

MS Calcd for $C_{11}H_{11}N_4O$: 215.09, found 215.3. Anal Calcd for $C_{11}H_{10}N_4O$: C, 61.67; H, 4.71; N, 26.15. Found: C, 61.56; H, 4.71; N, 26.08.

Step C: Preparation of 5(5H)-Azido-7-methyl-1,2,4-triazolo[4,3-d][1,4]benzodiazepin-6(7H)-one Following General Procedure 4-K using 5H-7-methyl-1,2,4-triazolo[4,3-d][1,4]benzodiazepin-6(7H)-one, the title compound was prepared as a pale yellow solid.

MS Calcd for C11H9N7O: 255.09, FDMS found 255.0. IR (solution in $CHCl_3$) 2138, 2115 cm$^{-1}$.

Step D: Preparation of 5(5H)-Amino-7-methyl-1,2,4-triazolo[4,3-d][1,4]benzodiazepin-6(7H)-one A mixture of 5(5H)-azido-7-methyl-1,2,4-triazolo[4,3-d][1,4]benzodiazepin-6(7H)-one in ethyl acetate (0.1 M) under $N_2$ was treated with 10% Pd on carbon (0.4 equiv., Engelhard). The reaction vessel was flushed with $H_2$ and stirring continued for 3 hours under a balloon of $H_2$. The vessel was flushed with $N_2$ and the contents filtered through celite 545 washing with ethyl acetate. The filtrate was concentrated in vacuo to give a white powder.

MS Calcd for $C_{11}H_{12}N_5O$: 230.10 (MH$^+$), found 230.1.

Step E: Preparation of 5(5H)-[N'-(tert-Butylcarbamate)-L-alaninyl]-amino-7-methyl-1,2,4-triazolo[4,3-d][1,4]benzodiazepin-6(7H)-one Following General Procedure D using 5(5H)-amino-7-methyl-1,2,4-triazolo[4,3-d][1,4]benzodiazepin-6(7H)-one and N-Boc Alanine (Novabiochem), the title intermediate was prepared as a white foam.

MS Calcd for $C_{19}H_{25}N_6O_4$: 401.19 (MH+), found 401.1. Anal. Calcd for $C_{19}H_{24}N_6O_4$: C, 55.74; H, 6.15; N, 20.53. Found: C, 56.06; H, 6.42; N, 20.20.

Step F: Preparation of 5(5H)-(L-Alaninyl)-amino-7-methyl-1,2,4-triazolo[4,3-d][1,4]benzodiazepin-6(7H)-one Following General Procedure 4-C using 5(5H)-[N'-(tert-butylcarbamate)-L-alaninyl]-amino-7-methyl-1,2,4-triazolo[4,3-d][1,4]benzodiazepin-6(7H)-one, the title compound was prepared as a white foam.

MS Calcd for $C_{14}H_{17}N_6O_2$: 301.14 (MH$^+$), found 301.1.

Example 4-AE

Synthesis of 3-(L-Alaninyl)-amino-2,3-dihydro-1-methyl-5-piperidinyl-1H-1,4-benzodiazepin-2-one Step A—Preparation of 3-[N'-tert-Butylcarbamate)-L-alaninyl]-amino-2,3-dihydro-1-methyl-5-(1-piperidinyl)-1H-1,4-benzodiazepin-2-one Following General Procedure D above using 3-amino-1,3-dihydro-1-methyl-5-(1-piperidinyl)-2H-1,4-benzodiazepin-2-one (Example 4-A) and N-Boc Alanine (Novabiochem), the title compound was prepared as a white foam.

MS Calcd for $C_{23}H_{33}N_5O_4$ 444.26 (MH$^+$), found 444.4. Anal. Calcd for $C_{23}H_{33}N_5O_4.0.5H_2O$: C, 61.04; H, 7.57; N, 15.47. Found: C, 61.09; H, 7.29; N, 15.21.

Step B—Preparation of 3-(L-Alaninyl)-amino-2,3-dihydro-1-methyl-5-(1-1-piperidinyl)-1H-1,4-benzodiazepin-2-one Following General Procedure 4-C using 3-[N'-tert-butylcarbamate)-L-alaninyl]-amino-2,3-dihydro-1-methyl-5-(1-piperidinyl)-1H-1,4-benzodiazepin-2-one, the title compound was prepared.

Example 4-AF

Synthesis of 3-(L-Alaninyl)-amino-2,3-dihydro-5-isopropyl-1-methyl-1H-1,4-benzodiazepin-2-one Step A: Preparation of 3-(Benzyloxycarbonyl)-amino-2,3-dihydro-5-isopropyl-1H-1,4-benzodiazepin-2-one A slurry of 2-(benzotriazol-1-yl)-N-(benzyloxycarbonyl) glycine (1.1 equiv.; Katritzky, A. R.; Urogdi, L.; Mayence, A. *J. Org. Chem.* 1990, 55, 2206) in THF (0.3 M) was cooled to 0° C. and treated with oxalyl chloride (1.1 equiv.) in a dropwise manner. To the slurry was added dropwise DMF (0.1 equiv.); stirring was continued at 0° C. for 1 hour. A solution of 1-(2-aminophenyl)-2-methyl-1-propanone (1.0 equiv.; Robl, J. A. *Synthesis* 1991, 56.) and N-methylmorpholine (2.2 equiv.) in THF (1 M in propanone), pre-cooked to 0° C., was added via cannula. Upon completion of the addition, the reaction was warmed to ambient temperature. The mixture was filtered, washing the filter cake with THF. The filtrate was transferred to a three-neck flask and treated with ammonia gas through a dispersion tube for 15 minutes. Methanol (0.3 M in propanone) was added and the ammonia continued to be bubbled through the solution for 1 hour. The reaction was concentrated, diluted with ethyl acetate, and re-concentrated; this was repeated again. The residue was diluted with ethyl acetate and washed twice with 1 N NaOH. The aqueous washes were back-extracted with ethyl acetate. The combined organics were washed with brine, dried over $Na_2SO_4$, filtered, and concentrated. Acetic acid was added and concentrated in vacuo. The syrup was dissolved in acetic acid (0.6 M in propanone) and treated with ammonium acetate (4.0 equiv.). The reaction was stirred at ambient temperature for 18 hours. The resultant solid was filtered, washing with $H_2O$.

MS Calcd for $C_{20}H_{22}N_3O_3$: 352.17, found 352.5.

Step B: Preparation of 3-(Benzyloxycarbonyl)-amino-2,3-dihydro-5-isopropyl-1-methyl-1H-1,4-benzodiazepin-2-one Following General Procedure 4-A using 3-(benzyloxycarbonyl)-amino-2,3-dihydro-5-isopropyl-1H-1,4-benzodiazepin-2-one, the title compound was prepared as a white solid.

MS Calcd for $C_{21}H_{24}N_3O_3$: 366.18 (MH+), found 366.2. Anal. Calcd for $C_{21}H_{23}N_3O_3.0.25H_2O$: C, 68.18; H, 6.40; N, 11.36. Found: C, 68.36; H, 6.28; N, 11.48.

Step C: Preparation of 3-Amino-2,3-dihydro-5-isopropyl-1-methyl-1H-1,4-benzodiazepin-2-one Following General Procedure 4-B using 3-(benzyloxycarbonyl)-amino-2,3-dihydro-5-isopropyl-1-methyl-1H-1,4-benzodiazepin-2-one, the title compound was prepared as a white foam.

MS Calcd for $C_{13}H_{18}N_3O$: 232.14 (MH+), found 232.19.

Step D: Preparation of 3-[N'-(tert-Butylcarbamate)-L-alaninyl]HhhhhhH))

dkdkdjakfj:asldjf:alsjf:lksajf:lkasfl:jkflkj:fjl:kfsjl:kf-amino-2,3-dihydro-5-isopropyl-1-methyl-1H-1,4-benzodiazepin-2-one Following General Procedure D using 3-amino-2,3-dihydro-5-isopropyl-1-methyl-1H-1,4-benzodiazepin-2-one and N-Boc alanine (Novabiochem), the title compound was prepared as a white solid.

MS Calcd for $C_{21}H_{31}N_4O_4$: 403.23 (MH+), found 403.46.

Step E: Preparation of 3-(L-Alaninyl)-amino-2,3-dihydro-5-isopropyl-1-methyl-1H-1,4-benzodiazepin-2-one Following General Procedure 4-C using 3-[N'-(tert-butylcarbamate)-L-alaninyl]-amino-2,3-dihydro-5-isopropyl-1-methyl-1H-1,4-benzodiazepin-2-one, the title compound was prepared as a white foam.

MS Calcd for $C_{16}H_{23}N_4O_2$: 303.18 (MH+), found 303.21. Anal Calcd for $C_{16}H_{22}N_4O_2.0.3H_2O$: C, 62.44; H, 7.40; N, 18.20. Found: C, 62.58; H, 7.10; N, 17.79.

Example 4-AG

Synthesis of 3-(L-Alaninyl)-amino-2,3-dihydro-5-n-propyl-1-methyl-1H-1,4-benzodiazepin-2-one Step A: Preparation of 1-(2-Aminophenyl)-1-butanone A solution of anthranilonitrile (1 equiv., Aldrich) in diethyl ether (2.4 M) was cooled to 0° C. and treated with propylmagnesium chloride (2.5 equiv., Aldrich; 2.0 M in $Et_2O$) in a dropwise manner over the course of an hour. After addition of 25% of the Grignard reagent, an additional 1/10 volume of $Et_2O$ was added. The cooling bath was removed and stirring of the suspension continued for 5 hours. The reaction was returned to 0° C. and cautiously quenched with 3 N HCl. The cooling bath was removed and stirring continued for 30 minutes. The mixture was made basic by the addition of solid NaOH. The contents were extracted thrice with ethyl acetate; brine was added to help break up the suspension. The combined extracts were washed with brine, dried over $Na_2SO_4$, filtered, and concentrated. The crude residue was chromatographed eluting with 95:5 hexanes/ethyl acetate.

MS Calcd for $C_{10}H_{13}NO$: 163.10, found 163.18. Anal. Calcd for $C_{10}H_{13}NO.0.2H_2O$: C, 72.00; H, 8.10; N, 8.40. Found: C, 72.36; H, 8.25; N, 8.76.

Step B: Preparation of 3-(Benzyloxycarbonyl)-amino-2,3-dihydro-5-isopropyl-1H-1,4-benzodiazepin-2-one A slurry of 2-(benzotriazol-1-yl)-N-(benzyloxycarbonyl) glycine (1.1 equiv.; Katritzky, A. R.; Urogdi, L.; Mayence, A. J. Org. Chem. 1990, 55, 2206) in THF (0.3 M) was cooled to 0° C. and treated with oxalyl chloride (1.1 equiv.) in a dropwise manner. To the slurry was added dropwise DMF (0.1 equiv.); stirring was continued at 0° C. for 1 hour. A solution of 1-(2-aminophenyl)-1-butanone and N-methylmorpholine (2.2 equiv.) in THF (1 M in butanone), pre-cooled to 0° C., was added via cannula. Upon completion of the addition, the reaction was warmed to ambient temperature. The mixture was filtered, washing the filter cake with THF. The filtrate was transferred to a three-neck flask and treated with ammonia gas through a dispersion tube for 15 minutes. Methanol (0.3 M in butanone) was added and the ammonia continued to be bubbled through the solution for 1 hour. The reaction was concentrated, diluted with ethyl acetate, and re-concentrated; this was repeated again. The residue was diluted with ethyl acetate and washed twice with 1 N NaOH. The aqueous washes were back-extracted with ethyl acetate. The combined organics were washed with brine, dried over $Na_2SO_4$, filtered, and concentrated. Acetic acid was added and concentrated in vacuo. The syrup was dissolved in acetic acid (0.6 M in butanone) and treated with ammonium acetate (4.0 equiv.). The reaction was stirred at ambient temperature for 18 hours. The resultant solid was filtered, washing with $H_2O$.

MS Calcd for $C_{20}H_{22}N_3O_3$: 352.17, found 352.4.

Step C: Preparation of 3-(Benzyloxycarbonyl)-amino-2,3-dihydro-5-n-propyl-1-methyl-1H-1,4-benzodiazepin-2-one Following General Procedure 4-A using 3-(benzyloxycarbonyl)-amino-2,3-dihydro-5-n-propyl-1H-1,4-benzodiazepin-2-one, the title compound was prepared as a white solid.

MS Calcd for $C_{21}H_{24}N_3O_3$: 366.18 (MH+), found 366.2.

Step D: Preparation of 3-Amino-2,3-dihydro-5-n-propyl-1-methyl-1H-1,4-benzodiazepin-2-one Following General Procedure 4-B using 3-(benzyloxycarbonyl)-amino-2,3-dihydro-5-n-propyl-1-methyl-1H-1,4-benzodiazepin-2-one, the title compound was prepared as a white foam. This compound was used immediately in Step E.

Step E: Preparation of 3-[N'-(tert-Butylcarbamate)-L-alaninyl]-amino-2,3-dihydro-5-n-propyl-1-methyl-1H-1,4-benzodiazepin-2-one Following General Procedure D using 3-amino-2,3-dihydro-5-n-propyl-1-methyl-1H-1,4-benzodiazepin-2-one and N-Boc alanine (Novabiochem), the title compound was prepared as a white solid.

MS Calcd for $C_{21}H_{31}N_4O_4$: 403.23 (MH+), found 403.4.

Step F: Preparation of 3-(L-Alaninyl)-amino-2,3-dihydro-5-n-propyl-1-methyl-1H-1,4-benzodiazepin-2-one Following General Procedure 4-C using 3-[N'-(tert-butylcarbamate)-L-alaninyl]-amino-2,3-dihydro-5-n-propyl-1-methyl-1H-1,4-benzodiazepin-2-one the title compound was prepared as a white foam.

Example 4-AH

Synthesis of 3-(L-Alaninyl)amino-4-n-butyl-3,4-dihydro-1-methyl-1H-1,4-benzodiazepin-2,5-dione Step A—Preparation of 4-n-Butyl-3,4-dihydro-1-methyl-1H-1,4-benzodiazepin-2,5-dione A solution of 13 mmol of 3,4-dihydro-1-methyl-1H-1,4-benzodiazepin-2,5-dione (Tett. Lett. 1994, 50(30), 9051) in 30 mL dry dimethylformamide is treated, dropwise at 0° C. under nitrogen cover, with one equivalent of potassium-t-butoxide (Aldrich; 1.0 M in THF). After forty-five minutes at 0° C., iodobutane is introduced via syringe over several minutes. The reaction mixture is stirred at ambient temperature seventy-five minutes, diluted with methylene chloride, and then washed with water and saturated sodium chloride. The organic solution is dried over anhydrous sodium sulfate, filtered and concentrated in vacuo to give a yellow oil. Flash column chromatography (silica gel; ethyl acetate/hexane (7/1) eluent) provides pure material as a colorless oil (90% yield).

$C_{14}H_{18}N_2O_2$ (MW=246.3) Anal. Calcd for $C_{14}H_{18}N_2O_2$: C, 68.27; H, 7.37; N, 11.37. Found: C, 68.53; H, 7.11; N, 11.41.

Step B—Preparation of 3-Azido-4-n-butyl-3,4-dihydro-1-methyl-1H-1,4-benzodiazepine-2,5-dione Following General Procedure 4-K using 4-n-butyl-3,4-dihydro-1-methyl-1H-1,4-benzodiazepin-2,5-dione the title intermediate was prepared as a waxy solid.

$C_{14}H_{17}N_5O_2$ (MW=287.3); Exact Mass FAB+ Theory 288.1461 Found 288.1459.

Step C—Preparation of 3-Amino-4-n-butyl-3,4-dihydro-1-methyl-1H-1,4-benzodiazepine-2,5-dione A solution of 0.4 mmol of azide (see Step B above) in ethyl acetate is treated with 170 mg of 10% Pd/C (Englehard) and hydrogenated overnight via the static pressure of a hydrogen-filled balloon attached to the reaction flask via a syringe and septum. The catalyst is removed by filtration and the filtrate concentrated in vacuo to give a yellow oil. This was purified via chromatography (silica gel; 1 mil Chromatotron plate; 95/5 methylene chloride/methanol[7N ammonia])

Anal. Calcd for $C_{14}H_{19}N_3O_2$: C, 64.35; H, 7.33; N, 16.08. Found: C, 64.58; H, 7.19; N, 15.94.

Step D—Preparation of 3-(N-tert-Butylcarbamate-L-alaninyl)amino-4-n-butyl-3,4-dihydro-1-methyl-1H-1,4-benzodiazepin-2,5-dione Following General Procedure D using N-Boc-alanine and the aminobenzodiazepinedione from Step C above, the title intermediate was obtained as an amorphous white solid.

Anal. Calcd. for $C_{22}H_{32}N_4O_5$: C, 61.09; H, 7.46; N, 12.95. Found: C, 60.83; H, 7.51; N, 12.69.

Step E—Preparation of 3-(L-Alaninyl)amino-4-n-butyl-3,4-dihydro-1-methyl-1,4-benzodiazepin-2,5-dione Following General Procedure 4-C using the Boc-protected intermediate from Step D above, the title intermediate is obtained as a white solid.

$C_{17}H_{24}N_4O_3$ (MW=332.4) Exact Mass FAB+ Theory MW=333.1927 Found MW=333.1924.

Example 4-AI

Synthesis of 3-(L-Alaninyl)amino-1,3-dihydro-5-ethylthio-1-methyl-2H-1,4-benzodiazepin-2-one Step A—Preparation of 1,3-Dihydro-5-ethylthio-1-methyl-2H-1,4-benzodiazepin-2-one A solution of 1.0 mmol of 3,4-dihydro-1-methyl-1H-1,4-benzodiazepin-2,5-dione (Tett. Lett. 1994, 50(30), 9051) in 8 mL dry dichloromethane (Aldrich Sure Seal), in an oven-dried round bottom flask under nitrogen cover, is treated with 1.1 equivalents of anhydrous pyridine (Mallinkrodt). The reaction is cooled to −51° C. in a dry ice/acetone bath and treated, dropwise via syringe over three minutes, with 1.1 equivalents of trifluoromethanesulfonic anhydride (Aldrich; sealed ampules). The reaction mixture is allowed to stir twenty minutes while maintaining a reaction temperature between −47 and −35° C. The temperature is brought to 0° C. over 1–2 minutes and then maintained at that temperature for one hour. Ethanethiol (3.4 equivalents) is introduced via syringe and the mixture allowed to stir overnight, still immersed in an ice water-filled Dewar. The temperature had risen to 16° C. by morning. The reaction mixture is partitioned between methylene chloride and aqueous sodium bicarbonate. The aqueous is further extracted three times with methylene chloride and the combined extracts dried over anhydrous sodium sulfate, filtered and concentrated in vacuo to give a yellow oil. Purification is effected by flash chromatography (silica gel; gradient elution using methylene chloride/ethyl acetate in 100/1, 95/5, 90/10 and 85/15. The title compound is obtained as a colorless oil which crystallizes on standing.

Anal. Calcd for $C_{12}H_{14}N_2OS$: C, 61.51; H, 6.02; N, 11.96. Found: C, 61.55; H, 5.99; N, 11.74.

Step B—Preparation of 3-Azido-1,3-dihydro-5-ethylthio-1-methyl-2H-1,4-benzodiazepin-2-one Following General Procedure 4-K using the ethylthiobenzodiazepine intermediate from Step A above, the title intermediate was prepared as a white solid.

Anal. Calcd. for $C_{12}H_{13}N_5OS$: C, 52.35; H, 4.76; N, 25.44. Found: C, 52.63; H, 4.67; N, 25.39.

Step C—Preparation of 3-Amino-1,3-dihydro-5-ethylthio-1-methyl-2H-1,4-benzodiazepin-2-one A solution of 1.90 mmol of azide (see Step B above) in 13 mL of tetrahydrofuran to which had been added 1 mL of water is treated with an excess of triphenyphospine (2.8 equivalents) added in one portion as a solid. The reaction is stirred at room temperature under nitrogen cover for twenty hours and then diluted with ethyl acetate. The solution is extracted with 1 N HCl three times, and the combined extracts are rendered basic by the addition of 5N NaOH. This is extracted three times with ethyl acetate and the combined extracts washed once with saturated aqueous sodium chloride, dried over anhydrous sodium sulfate, filtered and concentrated in vacuo on a rotary evaporator at 20° C. The resulting oil is used immediately.

$C_{12}H_{15}N_3OS$ (MW=249.3) FAB+ Exact Mass: Theory 250.1014 Found 250.1011.

Step D—Preparation of 3-(N-tert-Butylcarbamate-L-alaninyl)amino-1,3-dihydro-5-ethylthio-1-methyl-2H-1,4-benzodiazepin-2-one Following General Procedure D using N-Boc-alanine and the aminobenzodiazepin-2-one from Step C above, the title intermediate was obtained as an amorphous white solid.

Anal. Calcd. for $C_{20}H_{28}N_4O_4S$: C, 57.12; H, 6.71; N, 13.32. Found: C, 56.85; H, 6.77; N, 13.12.

Step E—Preparation of 3-(L-Alaninyl)amino-4-n-butyl-3,4-dihydro-1-methyl-1,4-benzodiazepin-2,5-dione Following General Procedure 4-C using the Boc-protected intermediate from Step D above, the title intermediate is obtained as a colorless oil.

$C_{15}H_{20}N_4O_2S$ (MW=320.4) FAB+ Exact Mass Theory 321.1385 Found 321.1388.

Example 4-AJ

Synthesis of 3-L-Alaninyl-amino-5-phenyl-1-methyl-2H-1,5-diazepin-2-one

Step A: Preparation of 1-Phenyl-4-piperidinone (CAS #19125-34-9)

The title intermediate was prepared from aniline (Aldrich) and methyl acrylate (Aldrich) by the literature procedure of Hermant, R. M., et al. *J. Am. Chem. Soc.*, 1990, 112, 1214–1221.

Step B: Preparation of 5-Phenyl-2H-1,5-diazepin-2-one

To the product from Step A (12.54 g, 71.56 mmols) in glacial acetic acid (60 mL) and concentrated sulfuric acid (30 mL) at 0° C. was added sodium azide (5.12 g, 78.7 mmols) in five portions of 1.024 g over a period of 4 hours. The resultant pale yellow mixture was allowed to warm to room temperature with stirring under nitrogen for 17 hours. The mixture was poured onto ice and neutralized to pH 7 with 5 M aq. NaOH. The product was extracted into methylene chloride (2×400 mL) and the combined organic extracts were dried over sodium sulfate, filtered, and concentrated to a pale yellow solid. Flash chromatography purification eluting with EtOAc gradient to EtOAc/MeOH (95:5) yielded 12.37 g (91%) of the title intermediate as a pale yellow solid.

$C_{11}H_{14}N_2O$ (MW. 190.25), mass spectroscopy (MH$^+$), 191.4. Anal. Calcd. For $C_{11}H_{14}N_2O$: C, 69.45; H, 7.42; N, 14.72, Found: C, 69.74; H, 7.23; N, 15.00.

Step C: Preparation of 5-Phenyl-1-methyl-2H-1,5-diazepin-2-one

Following General Procedure 4-G using the product from Step B, methyl iodide, and potassium tert-butoxide, the title intermediate was prepared. HPLC purification eluting with EtOAc yielded the product as a white solid.

$C_{12}H_{16}N_2O$ (MW. 204.27), mass spectroscopy (MH$^+$), 205.2. Anal. Calcd. For $C_{12}H_{16}N_2O$: C, 70.56; H, 7.90; N, 13.71, Found: C, 70.65; H, 7.70; N, 13.95.

Step D: Preparation of 3-Azido-5-phenyl-1-methyl-2H-1,5-diazepin-2-one

Following the General Procedure 4-E using the product from Step C, the title intermediate was prepared. HPLC purification eluting with EtOAc/hexanes (60:40), and a second HPLC purification eluting with methylene chloride/methanol (98:2), yielded the product as a light yellow solid.

$C_{12}H_{15}N_5O$ (MW. 245), mass spectroscopy (MH$^+$), 246.4.

Step E: Preparation of 3-Amino-5-phenyl-1-methyl-2H-1,5-diazepin-2-one

Following the General Procedure 4-F using the product from Step D, the title intermediate was prepared as yellow oil which upon standing solidified.

$C_{12}H_{17}N_3O$ (MW. 219), mass spectroscopy(MH$^+$), 220.3. Anal. Calcd. For $C_{12}H_{17}N_3O$: C, 65.73; H, 7.81; N, 19.16, Found: C, 65.94; H, 7.37; N, 18.85.

Step F: Preparation of 3-[N'-(t-Butoxycarbonyl)-L-alaninyl]-amino-5-phenyl-1-methyl-2H-1,5-diazepin-2-one Following General Procedure D using the product from Step E and Boc-L-Alanine (Nova Biochem) the title intermediate was prepared. HPLC purification eluting with EtOAc/hexanes (1:1) afforded the title compound as a white solid.

Exact Mass, anal. cacld. for $C_{20}H_{31}N_4O_4$: Theory, 391.2345, Found, 391.2342.

Step G: Preparation of 3-(L-Alaninyl)-amino-5-phenyl-1-methyl-2H-1,5-diazepin-2-one Following the General Procedure 4-N using the product from Step F the title intermediate was prepared. HPLC purification eluting with 95:5 methylene chloride/methanol gave the title intermediate.

Exact mass anal. calcd. Form. $C_{15}H_{23}N_4O_2$, Theory, 291.182 1; Found, 291.1816.

Example 4-AK

Synthesis of 3-(S)-Phenylglycinyl]-amino-5-phenyl-1-methyl-2H-2,3,4,5-tetrahydro-1,5-benzodiazepine-2-one Step A: Preparation of 3-[N'-(t-Butoxycarbonyl)-(S)-phenylglycinyl]-amino-1-methyl-5-phenyl-1,3,4,5-tetrahydro-2H-1,5-benzodiazepine 2-one Following modified General Procedure J using the product from Example 4-M, Step B, and Boc-L-Phenylglycine (Nova Biochem), the title intermediate was prepared. The modification was that the reaction was only stirred for 6 hours. HPLC purification eluting with 80/20 hexanes/EtOAc afforded the separated diastereomers; isomer 1 (first eluting) and isomer 2 (second eluting).

$C_{29}H_{32}N_4O_4$ (MW 500.60); mass spectroscopy for isomer 1: MH⁺ 501.2; MH⁺, 499.3; mass spectroscopy for isomer 2: MH⁺501.2; MH⁺, 499.3.

Step B: Synthesis of 3-((S)-Phenylglycinyl)-amino-1-methyl-5-phenyl-1,3,4,5-tetrahydro-2H-1,5-benzodiazepine 2-one Following the General Procedure 4-N using the products (Isomers 1 and 2 brought through reaction sequence separately) from Step A, the title intermediates were prepared. HPLC purification eluting with 95/5 methylene chloride/methanol afforded the title intermediates as a light yellow oils.

$C_{24}H_{24}N_4O_2$ (MW 400.48); mass spectroscopy for isomer 1: MH⁺, 401.3; MH⁺, 399.2; mass spectroscopy for isomer 2: MH⁺, 401.2; MH⁺, 399.3.

Example 4-AL

Synthesis of 3-(L-Norvalinyl)-amino-2,4-dioxo-1,5-bis-methyl-2,3,4,5-tetrahydro-1H-1,5-benzodiazepine Step A: Preparation of 3-[N'-(t-Butoxycarbonyl)-L-norvalinyl]-amino-2,4-dioxo-1,5-bis-methyl-2,3,4,5-tetrahydro-1H-1,5-benzodiazepine Following General Procedure D using the product from Example 4-R, Step C and Boc-L-norvaline (BACHEM) the title intermediate was prepared. HPLC purification eluting with EtOAc/Hexanes (60:40) afforded the title intermediate as a white solid.

$C_{21}H_{30}N_4O_5$ (MW 418.49). Anal. Calcd. for $C_{21}H_{30}N_4O_5$ hemihydrate: C, 59.00; H, 7.39; N, 13.10. Found: C, 59.35; H, 7.58; N, 12.86. Exact Mass calcd. for $C_{21}H_{31}N_4O_5$: Theory 419.2294, Found 419.2289.

Step B: Preparation of 3-(L-Norvalinyl)-amino-2,4-dioxo-1,5-bis-methyl-2,3,4,5-tetrahydro-1H-1,5-benzodiazepine Following General Procedure 4-N using the product from Step A, the title intermediate was prepared and used without further purification.

$C_{16}H_{22}N_4O_3$ (MW 318.38) Exact Mass calcd. for $C_{16}H_{23}N_4O_3$: Theory 319.1770, Found 319.1774.

Example 4-AM

Synthesis of 3-(L-Norvalinyl)-amino-2,4-dioxo-1-methyl-5-phenyl-2,3,4,5-tetrahydro-1H-1,5-benzodiazepine Step A: Preparation of 3-[N'-(t-Butoxycarbonyl)-L-norvalinyl)-amino-2,4-dioxo-1-methyl-5-phenyl-2,3,4,5-tetrahydro-1H-1,5-benzodiazepine Following General Procedure D using 3-amino-2,4-dioxo-1-methyl-5-phenyl-2,3,4,5-tetrahydro-1H-1,5-benzodiazepine (CAS No. 131604-75-6) and Boc-L-norvaline (BACHEM) the title intermediate was prepared. HPLC purification with EtOAc/hexanes (1:1) afforded the title intermediate as a white solid.

$C_{26}H_{32}N_4O_5$ (MW 480.57); mass spectroscopy, MH⁺ 481.2. Anal. Calcd. for $C_{26}H_{32}N_4O_5$: C, 64.98; H, 6.71; N, 11.66. Found: C, 64.87; H, 6.83; N, 11.53.

Step B: Preparation of 3-(L-Norvalinyl)-amino-2,4-dioxo-1-methyl-5-phenyl-2,3,4,5-tetrahydro-1H-1,5-benzodiazepine Following General Procedure 4-N using the product from Step A, the title intermediate was prepared. HPLC purification eluting with methylene chloride/methanol (9:1) afforded the title intermediate as an off white solid.

$C_{21}H_{24}N_4O_3$ (MW 380.45); mass spectroscopy, MH⁺ 381.1. Exact Mass calcd. for $C_{21}H_{25}N_4O_3$: Theory 381.1889, Found 381.1928.

Example 4-AN

Synthesis of 3-(L-Alaninyl)-amino-1,5-bis-methyl-2H-2,3,4,5-tetrahydro-1,5-benzodiazepine-2-one Step A: Preparation of N,N'-Dimethyl-1,2-phenylenediamine (CAS No. 3213-79-4)

Following the literature procedures of Stetter, H., Chem. Ber.,1953, 86, 161. and Cheeseman, G. W. H.,J. Chem. Soc., 1955, 3308, the title intermediate was prepared from 1,2-phenylenediamine (Aldrich) as a low melting solid.

$C_8H_{12}N_2$ (MW 136); mass spectroscopy, 136.1. Exact mass anal. Cacld. for $C_8H_{13}N_2$: Theory, 137.1079, Found, 137.081.

Step B: Preparation of 1,5-bis-Methyl-2,3,4,5-tetrahydro-2H-1,5-benzadiazepine-2-one To a solution of the product from Step A (400 mg, 2.94 mmols) in 5M Aq. HCl (30 mL) was added acrylic acid (0.202 mL, 3.23 mmols, Aldrich) and the mixture heated to reflux for 18 hours. The black mixture was allowed to cool, then poured onto ice and the pH adjusted to 10 with 5M Aq. NaOH. The product was extracted into $CH_2Cl_2$ (200 mL) and washed with water (100 mL) and brine (100 mL). The organic phase was dried over $Na_2SO_4$, filtered, and concentrated to give a black oil. HPLC purification eluting with hexanes/EtOAc (1:1) afforded 364 mg of the title intermediate as a brown oil.

$C_{11}H_{14}N_2O$ (MW 190.25); mass spectroscopy, MH⁺ 191.4; Anal. Calcd. for $C_{11}H_{14}N_2O$: Theory, C, 69.45; H, 7.42; N, 14.72; Found, C, 69.26; H, 7.40; N, 14.64.

Step C: Preparation of 3-Azido-1,5-bis-methyl-2,3,4,5-tetrahydro-2H-1,5-benzadiazepine-2-one Following General Procedure 4-E using the product from Step B, the title intermediate was prepared. HPLC purification eluting with hexanes/EtOAc (7:3) afforded the title intermediate as a light brown oil.

$C_{11}H_{13}N_5O$ (MW 231.26), mass spectroscopy, MH⁺ 232.2; Exact mass Anal. Calcd. for $C_{11}H_{14}N_5O$: Theory, 232.1198; Found, 232.1196.

Step D: Preparation of 3-Amino-1,5-bis-methyl-2,3,4,5-tetrahydro-2H-1,5-benzadiazepine-2-one Following procedure 4-F using the product from Step C, the title intermediate was prepared and used without chromatographic purification.

$C_{11}H_{15}N_3O$ (MW 205.26), mass spectroscopy MH⁺ 206.2. Exact mass Anal. Calcd. for $C_{11}H_{16}N_3O$: Theory, 206.1293; Found, 206.1295.

Step E: Preparation of 3-[N'-(t-Butoxycarbonyl)-L-alaninyl]-amino-1,5-bis-methyl-2,3,4,5-tetrahydro-2H-1,5-benzadiazepine-2-one Following General Procedure D using the product from Step D and Boc-L-Alanine (Nova Biochem), the title intermediate was prepared. HPLC purification eluting with EtOAc/hexanes (6:4) afforded the title intermediate as a white foamy solid.

$C_{19}H_{28}N_4O_4$ (MW 376.45), mass spectroscopy MH⁺, 377.4, MH⁺, 375.3. Anal. Calcd. for $C_{19}H_{28}SN_4O_4$: Theory, C, 60.62; H, 7.50; N, 14.88. Found, C, 60.68; H, 7.42; N, 14.38.

Step F: Preparation of 3-(L-Alaninyl)-amino-1,5-bis-methyl-2,3,4,5-tetrahydro-2H-1,5-benzadiazepine-2-one Following the procedure 4-N using the product from Step E, the title intermediate was prepared. HPLC purification eluting with EtOAc/hexanes (6:4) afforded the title intermediate as a thick yellow oil.

$C_{14}H_{20}N_4O_2$: (MW 276.34), mass spectroscopy, MH⁺, 277.2.

Using the following procedures, the following additional intermediates can be prepared for use in this invention.

GENERAL PROCEDURE C–H

The intermediates shown in Table C-1 were synthesized in parallel in using the following procedure:

Step A: To a solution of 3-(tert-butoxycarbonyl)amino-2,3-dihydro-5-phenyl-1H-1,4-benzodiazepin-2-one (CA No. 125:33692: 100 mg, 0.28 mmol) in 1 mL of anhydrous DMF was added 600 μL of a solution of 0.5 M potassium bis(trimethylsilyl)amide (0.30 mmol) in toluene. Neat alkyl halide (0.56 mmol; as indicated in Table C-1) was added immediately in one portion and the reaction mixture was left undisturbed overnight. When an alkyl chloride was used, 1 equivalent of sodium iodide was added to the reaction mixture. After concentration under reduced pressure, the crude reaction residue was partitioned between methylene chloride (2 mL) and aqueous saturated bicarbonate (2 mL) and then passed through a 5 g Extralut QE cartridge (EM Science; Gibbstown, N.J.) using 10 mL of methylene chloride. The resulting filtrate was concentrated under reduced pressure and the crude product was further purified using automated semi-preparative HPLC (YMC 20×50 mm Silica column; gradient elution; 0–5% (5.5 min.), 5–20% (3.5 min.), 20–100% (2 min.), 100% (4 min.) ethyl acetate/methylene chloride, flow rate of 25 mL/min.). Product provided the expected M+1 peak by IEX MS and were carried on without further purification and characterization.

Step B: The product obtained from Step A was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product was eluted from the column using 6 mL of 2.0 M solution of ammonia/methanol. After concentration under reduced pressure, the product were characterized by IEX MS and carried on without further purification.

Step C: To the crude product obtained from Step B (1.05 equiv.) was added sequentially a 0.3 mM stock solution of HOBt.H$_2$O (1.05 equiv.) in DMF, a 0.3 mM stock solution of N-t-BOC-L-alanine (1.0 equiv.) in THF and 0.3 mM stock solution of 1-(3-dimethylaminopropyl)-3-ethyl carbodiimide (1.05 equiv.) in THF. After standing undisturbed for 24 h, the reaction mixture was concentrated and the residue redissolved in 2 mL of a 10% methanol/methylene chloride solution. This solution was then filtered through a pre-washed (methanol) 1 g SCX (Varian Sample Preparation) column using an additional 8 mL of the same solvent. For Example C-V a 1 g Si column (Varian Sample Preparation) was used). The filtrate was concentrated under a stream of nitrogen to approximately ⅓ its original volume and then passed over a plug (500 mg) of AG 1–8× anion exchange resin (BioRad; Hercules, Calif.; Columns were pre-washed with 1N NaOH, water and methanol) using an additional 10 mL of methanol. The resulting filtrate was concentrated under reduced pressure and the crude product was carried on without further purification after characterization by IEX MS.

Step D: The crude product obtained from Step C was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product were eluted from the column using 6 mL of 2.0 M solution of ammonia/methanol. After concentration under reduced pressure, the product were characterized by IEX MS and carried on without further purification. The intermediates prepared by this method are shown

TABLE C-A

Intermediates

| Ex. | Alkyl Halide | Intermediate | MS |
| --- | --- | --- | --- |
| C-A | 3-Fluorobenzyl bromide (Aldrich) | 3-(L-alaninyl)amino-5-phenyl-2,3-dihydro-1-(3-fluorobenzyl)-1H-1,4-benzodiazepin-2-one | 431.1 |
| C-B | Benzyl bromide (Aldrich) | 3-(L-alaninyl)amino-5-phenyl-2,3-dihydro-1-(benzyl)-1H-1,4-benzodiazepin-2-one | 513.2 |
| C-C | tert-Butylbenzyl bromide (Aldrich) | 3-(L-alaninyl)amino-5-phenyl-2,3-dihydro-1-(4-tert-butylbenzyl)-1H-1,4-benzodiazepin-2-one | 469.2 |
| C-D | 2-Bromoethyl-cyclohexane (Fairfield) | 3-(L-alaninyl)amino-5-phenyl-2,3-dihydro-1-(2-cyclohexylethyl)-1H-1,4-benzodiazepin-2-one | 433.2 |
| C-E | 1-Bromo-3,3-dimethylbutane (Wiley) | 3-(L-alaninyl)amino-5-phenyl-2,3-dihydro-1-(3,3-dimethylbutyl)-1H-1,4-benzodiazepin-2-one | 407.2 |
| C-F | Methyl alpha-bromophenylacetate (Aldrich) | 3-(L-alaninyl)amino-5-phenyl-2,3-dihydro-1-(1-methoxycarbonyl-1-phenylmethyl)-1H-1,4-benzodiazepin-2-one | 471.2 |
| C-G | 1-Bromo-2-ethyl-butane (Aldrich) | 3-(L-alaninyl)amino-5-phenyl-2,3-dihydro-1-(2-ethylbutyl)-1H-1,4-benzodiazepin-2-one | 407.2 |
| C-H | Bromomethyl-cyclohexane (Aldrich) | 3-(L-alaninyl)amino-5-phenyl-2,3-dihydro-1-(cyclohexylmethyl)-1H-1,4-benzodiazepin-2-one | 419.2 |
| C-I | 2-(Bromoethyl)ben-zene (Aldrich) | 3-(L-alaninyl)amino-5-phenyl-2,3-dihydro-1-(2-phenylethyl)-1H-1,4-benzodiazepin-2-one | 427.2 |
| C-J | 3-(Bromopropyl)ben-zene (K and K Laboratories) | 3-(L-alaninyl)amino-5-phenyl-2,3-dihydro-1-(3-phenylpropyl)-1H-1,4-benzodiazepin-2-one | 441.2 |
| C-K | N-(2-Bromoethyl)-phthalimide (Aldrich) | 3-(L-alaninyl)amino-5-phenyl-2,3-dihydro-1-(2-N-phthalimidyl)ethyl)-1H-1,4-benzodiazepin-2-one | 496.2 |
| C-L | 2-Phenylbenzyl bromide (Aldrich) | 3-(L-alaninyl)amino-5-phenyl-2,3-dihydro-1-(2-biphenylmethyl)-1H-1,4-benzodiazepin-2-one | 489.2 |
| C-M | Tetrahydrofurfuryl bromide (Lancaster) | 3-(L-alaninyl)amino-5-phenyl-2,3-dihydro-1-((2-tetrahydrofuranyl)methyl)-1H-1,4-benzodiazepin-2-one | 407.2 |
| C-N | 2-Bromomethyl-1,4-benzodioxane (Acros) | 3-(L-alaninyl)amino-5-phenyl-2,3-dihydro-1-(2-(1,4-benzodioxanyl)methyl)-1H-1,4-benzodiazepin-2-one | 471.2 |
| C-O | 3-Bromomethyl-5-chlorobenzo[b]thiophene (Maybridge) | 3-(L-alaninyl)amino-5-phenyl-2,3-dihydro-1-((3-(5-chlorobenzo[b]thienyl))methyl)-1H-1,4-benzodiazepin-2-one | 503.1 |
| C-P | 1-Bromopinacolone (Lancaster) | 3-(L-alaninyl)amino-5-phenyl-2,3-dihydro-1-(3,3-dimethyl-2-oxo-propyl)-1H-1,4-benzodiazepin-2-one | 421.1 |
| C-Q | 5-(Bromomethyl)ben-zofurazan (Maybridge) | 3-(L-alaninyl)amino-5-phenyl-2,3-dihydro-1-(5-benzofurazanylmethyl)-1H-1,4-benzodiazepin-2-one | 455.2 |
| C-R | 3-Phenoxypropyl bromide (Aldrich) | 3-(L-alaninyl)amino-5-phenyl-2,3-dihydro-1-(3-phenoxypropyl)-1H-1,4-benzodiazepin-2-one | 457.2 |
| C-S | 6-(Bromomethyl)-2-(trifluoromethyl)-quinoline (Maybridge) | 3-(L-alaninyl)amino-5-phenyl-2,3-dihydro-1-(6-(2-trifluoromethylquinolinyl)methyl)-1H-1,4-benzodiazepin-2-one | 533.2 |
| C-T | 1-Bromo-2-methyl-butane (Aldrich) | 3-(L-alaninyl)amino-5-phenyl-2,3-dihydro-1-(2-methylbutyl)-1H-1,4-benzodiazepin-2-one | 393.2 |
| C-U | Ethyl bromide (Aldrich) | 3-(L-alaninyl)amino-5-phenyl-2,3-dihydro-1-(ethyl)-1H-1,4-benzodiazepin-2-one | 351.2 |

TABLE C-A-continued

Intermediates

| Ex. | Alkyl Halide | Intermediate | MS |
|---|---|---|---|
| C-V | 3-Picolyl chloride hydrochloride (Aldrich) | 3-(L-alaninyl)amino-5-phenyl-2,3-dihydro-1-(3-pyridylmethyl)-1H-1,4-benzodiazepin-2-one | 414.1 |
| C-W | 1-(2-Chloroacetyl)-indoline (Maybridge) | 3-(L-alaninyl)amino-5-phenyl-2,3-dihydro-1-(2-oxo-2-N-indolinyl)ethyl)-1H-1,4-benzodiazepin-2-one | 482.2 |
| C-Y | 4-(Chloromethyl)-3,5-dimethylisoxazole (Aldrich) | 3-(L-alaninyl)amino-5-phenyl-2,3-dihydro-1-((4-(3,5-dimethyl)isoxazolyl)methyl)-1H-1,4-benzodiazepin-2-one. | 432.2 |
| C-Z | 2-Bromoethyl methyl ether (Aldrich) | 3-(L-alaninyl)amino-5-phenyl-2,3-dihydro-1-(2-methoxyethyl)-1H-1,4-benzodiazepin-2-one | 381.2 |

Example C-AA

Synthesis of (S)-3-(L-Phenylglycinyl)amino-2,3-dihydro-1-methyl-5-phenyl-1H-1,4-benzodiazepin-2-one Step A: Synthesis of (S)-3-(N'-(tert-Butoxycarbonyl)-L-phenylglycinyl)amino-2,3-dihydro-1-methyl-5-phenyl-1H-1,4-benzodiazepin-2-one To a solution of triethyl amine (519 uL, 3.8 mmol) and (S)-3-amino-5-phenyl-2-oxo-1,4-benzodiazepine (1.0 g, 3.8 mmol) (prepared according to the procedure of M. G. Bock et al., *J. Org. Chem.* 1987, 52, 3232–3239) in 100 mL of anhydrous methylene chloride at −20° C. was added N-Boc-L-phenylglycine fluoride (Carpino et al, *J. Org. Chem.* 1991, 56, 2611–2614) in one portion. The reaction mixture was stirred for 15 min. and quenched with saturated aqueous bicarbonate (10 mL). The layers were seperated, the organic layer washed sequentially with saturated aqueous bicarbonate, water and brine and then dried over sodium sulfate. Purification of the crude product using silica gel chromatography (10–50% ethyl acetate/hexane) gave 1.3 g (69%) of a hydroscopic white foam.

NMR data was as follows:

$^1$H NMR (300 MHz, CDCl$_3$): δ=1.35 (br s, 9H), 3.41 (s, 3H), 5.30–5.45 (m, 2H), 5.75–5.95 (m, 1H), 7.15–7.75 (m, 15H). IR (CDCl$_3$): 1709.7, 1676.6, 1489, 1166.3 cm$^{-1}$. IEX MS (M+1): 498.0.

Step B: Synthesis of (S)-3-(L-Phenylglycinyl)amino-2,3-dihydro-1-methyl-5-phenyl-1H-1,4-benzodiazepin-2-one (S)-3-(N'-(tert-Butoxycarbonyl)-L-phenylglycinyl) amino-2,3-dihydro-1-methyl-5-phenyl-1H-1,4-benzodiazepin-2-one (1.27 g, 2.55 mmol) was added to 50 mL of a stirring solution of 15% TFA in methylene chloride in one portion. After stirring 1 h, the reaction mixture was concentrated under reduced pressure and the residue dissolved in 100 mL of methylene chloride. This solution was washed twice with saturated sodium bicarbonate, once with brine and then dried over sodium sulfate. Purification of the crude product using silica gel column chromatography (5–10% methanol/methylene chloride) gave 743 mg (73%) of a very light green foam.

NMR data was as follows:

$^1$H NMR (CDCl$_3$): δ=2.05 (br s, 1H), 3.45 (s, 3H), 5.51 (d, J=8.39 Hz, 1H), 7.15–7.70 (m, 14H), 8.60 (d, J=830 Hz, 1H). IR (CDCl$_3$): 1673.3, 1601.1, 1506.1 cm$^{-1}$. IEX MS (M+1): 399.2.

Example C-AB

Synthesis of 3-(L-Alaninyl)amino-2,3-dihydro-1-(2-oxo-2-phenylethyl)-5-phenyl-1H-1,4-benzodiazepin-2-one Step A: Synthesis of 3-(Benzoxycarbonyl)amino-2,3-dihydro-1-(2-oxo-2-phenylethyl)-5-phenyl-1H-1,4-benzodiazepin-2-one To a solution of 3-(Benzoxycarbonyl)amino-2,3-dihydro-5-phenyl-1H-1,4-benzodiazepin-2-one (Bock, M. G. et al, *Tetrahedron Lett.* 1987, 28, 939; 4.0 g, 10.4 mmol) in 40 mL of anhydrous DMF at 0° C. was added potassium tert-butoxide (1.51 g, 13.5 mmol) in one portion. The reaction mixture was stirred 20 min. and α-bromoacetophenone (Lancaster; Windham, N.H.; 2.9 g, 14.6 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–5% ethyl acetate/methylene chloride) gave 4.2 g (81%) of an off white foam.

NMR data was as follows:

$^1$H NMR (300 MHz, CDCl$_3$): δ=5.16 (s, 2H), 5.34 (s, 2H), 5.50 (d, J=8.33 Hz, 1H), 6.70 (d, J=8.28 Hz, 1H), 7.20–7.70 (m, 12H), 7.91 (d, J=7.54 Hz, 2H). IR (CHCl$_3$): 1706.04, 1685.3, 1505.9, 1489.1, 1450.3, 1244.7 cm$^{-1}$. IEX MS (M+1): 504.3.

Step B: Synthesis of 3-Amino-2,3-dihydro-1-(2-oxo-2-phenylethyl)-5-phenyl-1H-1,4-benzodiazepin-2-one A solution of 3-(Benzoxycarbonyl)amino-2,3-dihydro-1-(2-oxo-2-phenylethyl)-5-phenyl-1H-1,4-benzodiazepin-2-one (3.7 g, 7.36 mmol) in 100 mL of anhydrous methylene chloride was cooled to 0° C. under nitrogen. A stream of anhydrous HBr gas was then bubbled through this solution for 1 h. The bubbler was removed and the reaction was warmed to room temperature under nitrogen. After stirring 1 h the reaction was concentrated under vacuum and the residue was redissolved in 20 mL of methylene chloride. The crude HBr salt of the product was precipitated from solution using 300 mL of anhydrous ether and collected by filtration as a light yellow solid. After washing with ether, the solid was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 2.27 g of the product was obtained as an orange foam which was carried on without further purification.

NMR data was as follows:

$^1$H NMR (300 MHz, CDCl$_3$): δ=2.60 (br s, 2H), 4.72 (s, 1H), 5.34 (s, 2H), 7.10–7.70 (m, 12H), 7.91 (d, J=7.60 Hz, 2H). IEX MS (M+1): 370.2

Step C: Synthesis of 3-(N'-(tert-Butoxycarbonyl)-L-alaninyl)amino-2,3-dihydro-1-(2-oxo-2-phenylethyl)-5-phenyl-1H-1,4-benzodiazepin-2-one To a solution of HOBt·H$_2$O (697 mg, 5.16 mmol), N,N-diisopropylethylamine (900 uL, 5.16 mmol) and N-t-BOC-L-alanine (975 mg, 5.16 mmol) in 20 mL of anhydrous THF at 0° C. was added 1-(3-dimethylaminopropyl)-3-ethyl carbodiimide hydrochloride (EDCI; 986 mg, 5.16 mmol) in one portion. After stirring 5 min., a solution of 3-amino-2,3-dihydro-1-(2-oxo-2-phenylethyl)-5-phenyl-1H-1,4-benzodiazepin-2-one (2.0 g, 5.43 mmol) in 20 mL of anhydrous THF was added via syringe and the reaction mixture was warmed to room temperature and stirred overnight. The reaction mixture was diluted with 200 mL methylene chloride, extracted sequentially with 10% citric acid, saturated sodium bicarbonate, water and brine and then dried over sodium sulfate. Purification of the crude product using silica gel chromatography (10%–30% ethyl acetate/ methylene chloride) gave 2.59 g (93%) of a white foam.

NMR data was as follows:

$^1$H NMR (300 MHz, CDCl$_3$): δ=1.30–1.60 (m, 12H), 4.35 (br s, 1H), 5.00–5.50 (m, 3H), 5.65–5.70 (m, 1H), 7.15–7.65 (m, 12H), 7.70–7.80 (m, 1H), 7.85–7.95 (m, 1H). IR (CHCl$_3$): 1705.8, 1678.8, 1488.7, 1450.2, 1230.4, 1164.4 cm$^{-1}$. IEX MS (M+1): 541.2.

Step D: Synthesis of 3-(L-Alaninyl)amino-2,3-dihydro-1-(2-oxo-2-phenylethyl)-5-phenyl-1H-1,4-benzodiazepin-2-one 3-(N'-(tert-Butoxycarbonyl)-L-alaninyl)amino-2,3-dihydro-1-(2-oxo-2-phenylethyl)-5-phenyl-1H-1,4-benzodiazepin-2-one (2.5 g, 4.63 mmol) was added to 100 mL of a stirring solution of 15% TFA/methylene chloride in one portion. After stirring 2 h, the reaction mixture was concentrated under reduced pressure and the residue was dissolved in 150 mL of methylene chloride. This solution was washed twice with saturated sodium bicarbonate, once with brine and then dried over sodium sulfate. Purification of the crude product using silica gel column chromatography (1–10% methanol/methylene chloride) gave 1.91 g (94%) of the title compound as a white foam.

NMR data was as follows:

$^1$H NMR (300 MHz, CDCl$_3$): δ=1.30–1.50 (m, 3H), 1.80–2.20 (br s, 2H), 3.55–3.75 (m, 1H), 5.20–5.45 (m, 2H), 5.67 (t, J=7.48 Hz, 1H), 7.20–7.65 (m, 12H), 7.90 (d, J=7.7 Hz, 2H), 8.80 (dd, J=25.09 Hz, J$_2$=8.33 Hz, 1H). EX MS (M+1): 441.2.

Example C-AC

Synthesis of 3-(L-Alaninyl)amino-2,3-dihydro-1-(4,4,4-trifluorobutyl)-5-phenyl-1H-1,4-benzodiazepin-2-one Step A: Synthesis of 3-(Benzoxycarbonyl)amino-2,3-dihydro-1-(4,4,4-trifluorobutyl)-5-phenyl-1H-1,4-benzodiazepin-2-one To a solution of 3-(benzoxycarbonyl)amino-2,3-dihydro-5-phenyl-1 H-1,4-benzodiazepin-2-one (3.7 g, 9.61 mmol) in 40 mL of anhydrous DMF at 0° C. was added potassium tert-butoxide (1.6 g, 14.4 mmol) in one portion. The reaction mixture was stirred 20 min. and 4,4,4-trifluoro-1-bromobutane (Lancaster; Windham, N.H.; 2.6 g, 13.4 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–3% ethyl acetate/ methylene chloride) gave 1.52 g (32%) of an off white foam.

NMR data was as follows:

$^1$H NMR (300 MHz, CDCl$_3$): δ=1.50–2.10 (m, 4H), 3.70–3.90 (m, 1H), 4.35–4.55 (m, 1H), 5.15 (s, 2H), 5.33 (d, J=8.47 Hz, 1H), 6.67 (d, J=8.40 Hz, 1H), 7.2–7.70 (m, 14H). IR (CHCl$_3$): 1720.4, 1683.0, 1604.8, 1505.5, 1451.1, 1323.9, 1254.5, 1148.4 cm$^{-1}$. IEX MS (M+1): 496.3.

Step B: Synthesis of 3-Amino-2,3-dihydro-1-(4,4,4-trifluorobutyl)-5-phenyl-1H-1,4-benzodiazepin-2-one A solution of 3-(benzoxycarbonyl)amino-2,3-dihydro-1-(4,4,4-trifluorobutyl)-5-phenyl-1H-1,4-benzodiazepin-2-one (1.42 g, 2.87 mmol) in 50 mL of anhydrous methylene chloride was cooled to 0° C. under nitrogen. A stream of anhydrous HBr gas was slowly bubbled through the solution for 1 h. The bubbler was removed and the reaction was warmed to room temperature under nitrogen. After stirring for 1 h, the reaction was concentrated under vacuum and the residue was redissolved in 10 mL of methylene chloride. The crude HBr salt of the product was precipitated from solution using 90 mL of anhydrous ether and collected by filtration. After washing with ether, the HBr salt was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 1.06 g (100%) of the product was obtained as a white foam which was carried on without further purification.

NMR data was as follows:

$^1$H NMR (300 MHz, CDCl$_3$): δ=1.60–2.10 (m, 4H), 2.76 (br s, 2H), 3.75–3.85 (m, 1H), 4.40–4.60 (m, 2H), 7.20–7.70 (m, 9H). IEX MS (M+1): 362.1.

Step C: Synthesis of 3-(N'-(tert-Butoxycarbonyl)-L-alaninyl)amino-2,3-dihydro-1-(4,4,4-trifluorobutyl)-5-phenyl-1H-1,4-benzodiazepin-2-one To a solution of HOBt-H$_2$O (373 mg, 2.76 mmol), N,N-diisopropylethylamine (481 uL, 2.76 mmol) and N-t-BOC-L-alanine (522 mg, 2.76 mmol) in 10 mL of anhydrous THF at 0° C. was added 1-(3-dimethylaminopropyl)-3-ethyl carbodiimide hydrochloride (EDCI; 527 mg, 2.76 mmol) in one portion. After stirring 5 min., a solution of 3-amino-2,3-dihydro-1-(4,4,4-trifluorobutyl)-5-phenyl-1H-1,4-benzodiazepin-2-one (1.05 g, 2.91 mmol) in 10 mL of anhydrous THF was added via syringe and the reaction mixture was warmed to room temperature and stirred overnight. The reaction mixture was diluted with 100 mL methylene chloride, extracted sequentially with 10% citric acid, saturated sodium bicarbonate, water and brine and then dried over sodium sulfate. Purification of the crude product using silica gel chromatography (10%–30% ethyl acetate/ methylene chloride) gave 1.28 g (83%) of a white foam.

NMR data was as follows:

$^1$H NMR (300 MHz, CDCl$_3$): δ=1.40–2.10 (m, 16H), 3.70–3.85 (m, 1H), 4.30–4.55 (m, 2H), 5.10 (br s, 1H), 5.45–5.55 (m, 1H), 7.25–7.80 (m, 10H). IR (CDCl$_3$): 1676.6, 1605.2, 1488.6, 1450.9, 1393.2, 1338.7, 1324.9, 1253.8, 1150.4 cm$^{-1}$. IEX MS (M+1): 533.1.

Step D: Synthesis of 3-(L-Alaninyl)amino-2,3-dihydro-1-(4,4,4-trifluorobutyl)-5-phenyl-1H-1,4-benzodiazepin-2-one 3-(N'-(tert-Butoxycarbonyl)-L-alaninyl)amino-2,3-dihydro-1-(4,4,4-trifluorobutyl)-5-phenyl-1H-1,4-benzodiazepin-2-one (1.21 g, 2.27 mmol) was added to 50 mL of a stirring solution of 15% TFA/methylene chloride in one portion. After stirring 2 h, the reaction mixture was concentrated under reduced pressure and the residue was dissolved in 100 mL of methylene chloride. This solution was washed twice with saturated sodium bicarbonate, once with brine and then dried over sodium sulfate. Purification of the crude product using silica gel column chromatography (1–5% methanol/methylene chloride) gave 670 mg (68%) of a light pink foam.

NMR data was as follows:

$^1$H NMR (300 MHz, CDCl$_3$): δ=1.43 (t, J=7.0 Hz, 3H), 1.60–2.20 (m, 7H), 3.60–3.85 (m, 2H), 4.35–4.55 (m, 1H), 5.51 (dd, J$_1$=8.36 Hz, J$_2$=2.48 Hz, 1H), 7.20–7.70 (m, 9H), 8.80 (dd, J$_1$=27.73 Hz, J$_2$=8.34 Hz, 1H). IEX MS (M+1): 433.2.

Example C-AE

Synthesis of 3-[(L-Alaninyl)amino]-2,3-dihydro-1-methyl-5-(2-pyridyl)-1H-1,4-benzodiazepin-2-one Step A: Synthesis of 3-Amino-2,3-dihydro-1-methyl-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-methyl-5-(2-pyridyl)-1H-1,4-benzodiazepin-2-one A solution of L-Boc-alanine (1.74 g, 9.20 mmol), HOBt monohydrate (1.24 g, 9.20 mmol), diisopropylethylamine (1.6 mL, 9.20 mmol) and $CH_2Cl_2$ (30 mL) was purged with nitrogen and cooled in an ice bath. To the cold solution was added 1-(3-dimethylaminopropyl)-3-ethylcarbodiimide hydrochloride (1.76 g, 9.20 mmol) followed by a solution of 3-amino-2,3-dihydro-1-methyl-5-(2-pyridyl)-1H-1,4-benzodiazepin-2-one (2.45 g, 9.20 mmol) dissolved in $CH_2Cl_2$ (15 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a tan foam. The title compound was crystallized from $CH_2Cl_2$/EtOAc to give 3.47 g (86% yield) of white crystals, mp. 228–229° C.

Anal. Calcd for $C_{23}H_{27}N_5O_4$: C, 63.14; H, 6.22; N, 16.01. Found: C, 63.25; H, 6.15; N, 15.95. MS (FD$^-$) 437 m/z.

Step C: Synthesis of 3-[(L-Alaninyl)amino]-2,3-dihydro-1-methyl-5-(2-pyridyl)-1H-1,4-benzodiazepin-2-one A solution of 3-[(N-tert-butoxycarbonyl-L-alaninyl)amino]-2,3-dihydro-1-methyl-5-(2-pyridyl)-1H-1,4-benzodiazepin-2-one (3.42 g, 7.82 mmol) in $CH_2Cl_2$ (90 mL) was cooled in an ice bath and treated with TFA (13.2 mL, 172 mmol). The cold bath was removed and the solution stirred at room temperature for four hours. The reaction mixture was washed with 1 M aq. $K_2CO_3$ and the aqueous back-extracted with $CH_2Cl_2$. The combined extracts were washed with $H_2O$, dried ($MgSO_4$) and concentrated to obtain 1.75 g (66% yield) of the title compound as an off-white foam.

MS (IS$^-$) 338 (m/e).

$^1$HNMR (CDCl$_3$): δ=8.76–8.86 (1H, m), 8.63 (1H, m), 8.17 (1H, m), 7.82 (2H, m), 7.60 (1H, m), 7.41 (3H, m), 5.60 (1H, m), 3.63 (1H, m), 3.49 (3H, s), 1.66 (2H, broad), 1.45 (3H, m).

Example C-AF

Synthesis of 3-[(L-Alaninyl)amino]-2,3-dihydro-1-(2-N,N-diethylaminoethyl)-5-(2-pyridyl)-1H-1,4-benzodiazepin-2-one Step A: Synthesis of 3-Amino-2,3-dihydro-1-(2-N,N-diethylaminoethyl)-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-(2-N,N-diethylaminoethyl)-5-(2-pyridyl)-1H-1,4-benzodiazepin-2-one A solution of L-Boc-alanine (1.80 g, 9.50 mmol), HOBt monohydrate (1.28 g, 9.50 mmol), diisopropylethylamine (1.65 mL, 9.50 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.82 g, 9.50 mmol) followed by a solution of 3-amino-2,3-dihydro-1-(2-N,N-diethylaminoethyl)-5-(2-pyridyl)-1H-1,4-benzodiazepin-2-one (3.34 g, 9.50 mmol) dissolved in $CH_2Cl_2$ (25 mL). The cold bath was removed and the solution stirred overnight at room temperature. The reaction mixture was extracted with $H_2O$, 5% aq. $NaHCO_3$, and brine. The remaining $CH_2Cl_2$ solution was dried ($MgSO_4$) and concentrated to a tan foam. The title compound was isolated via column chromatography (2% MeOH/$CH_2Cl_2$ to 10% MeOH/$CH_2Cl_2$) to give 3.53 g (71% yield) of yellow foam.

MS (FD$^+$) 522 (m/z).

$^1$HNMR (CDCl$_3$): δ=8.62 (1H, d), 8.11 (1H, m), 7.80 (2H, m), 7.59 (2H, m), 7.32–7.45 (2H, m), 5.54 (11H, m), 5.02–5.18 (1H, m), 4.38 (11H, m), 4.20 (1H, m), 3.83 (1H, m), 2.62 (2H, t), 2.44 (4H, m), 1.40–1.56 (12H, m), 0.88 (6H, m).

Step C: Synthesis of 3-[(L-Alaninyl)amino]-2,3-dihydro-1-(2-N,N-diethylaminoethyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(2-N,N-diethylaminoethyl)-5-(2-pyridyl)-1H-1,4-benzodiazepin-2-one (3.52 g, 6.73 mmol) was treated with TFA (11.4 mL, 148 mmol) to give 2.61 g (92% yield) the title compound as a light yellow foam.

MS (IS$^+$) 423 (m/e).

$^1$HNMR (CDCl$_3$): δ=8.78–8.93 (1H, m), 8.62 (1H, d), 8.11 (1H, m), 7.80 (2H, m), 7.58 (2H, m), 7.39 (2H, m), 5.58 (1H, m), 4.22 (1H, m), 3.88 (1H, m), 3.61 (1H, m), 2.67 (2H, t), 2.49 (4H, m), 1.73 (2H, broad), 1.42 (3H, m), 0.91 (6H, m).

Example C-AG

Synthesis of 3-[(L-Alaninyl)amino]-2,3-dihydro-1-(3,3-dimethyl-2-oxobutyl)-5-(2-pyridyl)-1H-1,4-benzodiazepin-2-one Step A: Synthesis of 3-Amino-2,3-dihydro-1-(3,3-dimethyl-2-oxobutyl)-5-(2-pyridyl)-1H-1,4-benzodiazepin-2-one The title compound was synthesized as described in *Synth. Commun.*, 26(4), 721–727 (1996).

Step B.: Synthesis of 3-[(N-tert-Butoxycarbonyl-L-alaninyl)amino]-2,3-dihydro-1-(3,3-dimethyl-2-oxobutyl)-5-(2-pyridyl)-1H-1,4-benzodiazepin-2-one A solution of L-Boc-alanine (1.57 g, 8.33 mmol), HOBt monohydrate (1.13 g, 8.33 mmol), diisopropylethylamine (1.45 mL, 8.33 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.60 g, 8.33 mmol) followed by a solution of 3-amino-2,3-dihydro-1-(3,3-dimethyl-2-oxobutyl)-5-(2-pyridyl)-1H-1,4-benzodiazepin-2-one (2.92 g, 8.33 mmol) dissolved in $CH_2Cl_2$ (25 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a yellow foam. The title compound was isolated via column chromatography (20% EtOAc/hexanes to 60% EtOAc/hexanes) to give 4.19 g (96% yield) of light yellow foam.

MS (FD$^+$) 521 (m/z).

$^1$HNMR (CDCl$_3$): δ=8.65 (1H, t), 8.17 (1H, t), 7.90 (1H, t), 7.71–7.85 (1H, m), 7.54 (1H, m), 7.44 (1H, t), 7.37 (1H, d), 7.24–7.32 (1H, m), 7.14 (1H, m), 5.67 (1H, dd), 5.18 (1H, broad), 4.93–5.07 (1H, m), 4.50–4.64 (1H, m), 4.38 (1H, broad), 1.42–1.51 (12H, m), 1.26 (9H, d).

Step C: Synthesis of 3-[(L-Alaninyl)amino]-2,3-dihydro-1-(3,3-dimethyl-2-oxobutyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(3,3-dimethyl-2-oxobutyl)-5-(2-pyridyl)-1H-1,4-benzodiazepin-2-one (4.18 g, 8.01 mmol) was treated with TFA (13.6 mL, 176 mmol) to give 3.14 g (93% yield) the title compound as an off-white foam.

MS (IS$^+$) 422 (m/e).
$^1$HNMR (CDCl$_3$) δ 8.85–8.99 (1H, m), 8.68 (1H, d), 8.20 (1H, t), 7.87 (1H, t), 7.58 (1H, t), 7.42 (2H, m), 7.30 (1H, t), 7.17 (1H, d), 5.72 (1H, m), 5.08 (1H, d), 4.60 (1H, d), 3.66 (1H, m), 1.47 (3H, m), 1.28 (9H, m).

Example C-AH

Synthesis of 3-[(L-Alaninyl)amino]-2,3-dihydro-1-methyl-5-(2-thiazyl)-1H-1,4-benzodiazepin-2-one Step A: Synthesis of 3-Amino-2,3-dihydro-1-methyl-5-(2-thiazyl)-1H-1,4-benzodiazepin-2-one The title compound was synthesized in a manner similar to the procedure described in Synth. Commun., 26(4), 721–727 (1996), starting with 2-(2-aminobenzoyl)thiazole (prepared as described in Tetrahedron, 51(3), 773–786, (1995)).

MS (IS$^+$) 273 (m/e).
$^1$HNMR (CDCl$_3$): δ=7.83–7.94 (2H, m), 7.61 (1H, t), 7.50 (1H, d), 7.34 (2H, m), 4.60 (1H, s), 3.46 (3H, s), 1.97 (2H, broad).

Step B: Synthesis of 3-[(N-tert-Butoxycarbonyl-L-alaninyl)amino]-2,3-dihydro-1-methyl-5-(2-thiazyl)-1H-1,4-benzodiazepin-2-one A solution of L-Boc-alanine (1.85 g, 9.77 mmol), HOBt monohydrate (1.32 g, 9.77 mmol), diisopropylethylamine (1.70 mL, 9.77 mmol) and CH$_2$Cl$_2$ (30 mL) was purged with nitrogen and cooled in an ice bath. To the cold solution was added 1-(3-dimethylaminopropyl)-3-ethylcarbodiimide hydrochloride (1.87 g, 9.77 mmol) followed by a solution of 3-amino-2,3-dihydro-1-methyl-5-(2-thiazyl)-1H-1,4-benzodiazepin-2-one (2.66 g, 9.77 mmol) dissolved in CH$_2$Cl$_2$ (20 mL). The cold bath was removed and the solution stirred overnight at room temperature. The reaction mixture was extracted with H$_2$O, 0.1 N aq. citric acid, 5% aq. NaHCO$_3$, and brine. The remaining CH$_2$Cl$_2$ solution was dried (MgSO$_4$) and concentrated to a light yellow foam. The title compound was crystallized from EtOAc/hexane to give 3.22 g (74% yield) of white crystals, mp. 196–197° C. Anal. Calcd for C$_{21}$H$_{25}$N$_5$O$_4$S: C, 56.87; H, 5.68; N, 15.79. Found: C, 56.74; H, 5.75; N, 15.55.

MS (IS$^-$) 444 m/e.
Step C: Synthesis of 3-[(L-Alaninyl)amino]-2,3-dihydro-1-methyl-5-(2-thiazyl)-1H-1,4-benzodiazepin-2-one The title compound was synthesized using the procedure described in Example C-AE, Step C.

Example C-AI

Synthesis of 3-[(L-Alaninyl)amino]-2,3-dihydro-1-methyl-5-(thiophen-2-yl)-1H-1,4-benzodiazepin-2-one Step A: Synthesis of 3-Amino-2,3-dihydro-1-methyl-5-(2-thiophen-2-yl)-1H-1,4-benzodiazepin-2-one The title compound was synthesized in a manner similar to the procedure described in Synth. Commun., 26(4), 721–727 (1996), starting with 2-(2-aminobenzoyl)thiophene (prepared as described in Collect. Czech. Chem. Commun., 34(2), 468–478, (1969)).

MS (IS$^-$) 272 (m/e).
$^1$HNMR (CDCl$_3$): δ=7.68 (1H, d), 7.60 (1H, t), 7.48 (1H, m), 7.35 (2H, d), 7.28 (1H, m), 7.15 (1H, d), 7.05 (1H, d), 4.50 (1H, broad), 3.45 (3H, s), 2.26 (2H, broad).
Step B: Synthesis of 3-[(N-tert-Butoxycarbonyl-L-alaninyl)amino]-2,3-dihydro-1-methyl-5-(thiophen-2-yl)-1H-1,4-benzodiazepin-2-one The title compound was synthesized in a manner similar to the procedure described in Example C-AH, Step B.

MS (IS$^+$) 443 (m/e).
$^1$HNMR (CDCl$_3$): δ=7.69 (1H, d), 7.61 (2H, m), 7.48 (1H, d), 7.27–7.42 (2H, m), 7.18 (1H, m), 7.05 (1H, m), 5.51 (1H, d), 5.13 (1H, broad), 4.36 (1H, broad), 3.44 (3H, s), 1.38–1.57 (12H, m).
Step C: Synthesis of 3-[(L-Alaninyl)amino]-2,3-dihydro-1-methyl-5-(thiophen-2-yl)-1H-1,4-benzodiazepin-2-one The title compound was synthesized in a manner similar to the procedure described in Example C-AE, Step C.

MS (IS+) 343 (m/e).
$^1$HNMR (CDCl$_3$): δ=8.55 (1H, d), 7.68 (1H, d), 7.59 (1H, m), 7.48 (1H, d), 7.36 (1H, d), 7.31 (1H, d), 7.16 (1H, m), 7.04 (1H, t), 5.54 (1H, d), 3.58 (1H, m), 3.45 (3H, s), 1.41 (3H, d).

Example 5-A

Synthesis of 3-(L-Alaninyl)-amino-2,3-dihydro-1-methyl-5-phenyl-1H-1-benzazepin-2-one Step A—Preparation of 1-Phenyl-1-[2-N-(α-isopropylthio)-N'-(benzyloxycarbonyl)-glycinyl]-aminophenyl]ethylene A solution of α-(isopropylthio)-N-(benzyloxycarbonyl) glycine (1 eq; prepared according to Zoller, V.; Ben-Ishai, D. Tetrahedron 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was re-cooled to 0° C. A solution of 1-phenyl-1-(2-aminophenyl)ethylene (0.9 eq.; Arienti, A.; Bigi, F.; Maggi, R.; Marzi, E.; Moggi, P.; Rastelli, M.; Sartori, G.; Tarantola, F. Tetrahedron 1997, 53, 3795.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous NaHCO$_3$, and brine.

The organic phase was dried over Na$_2$SO$_4$, filtered, and concentrated. The residue was purified via flash chromatography eluting with CH$_2$Cl$_2$ then 90:10 CH$_2$Cl$_2$/ethyl acetate giving a pale yellow oil.

C$_{27}$H$_{28}$N$_2$O$_3$S (MW=460.60); mass spectroscopy (MH$^+$) 461.4. Anal. Calcd for C$_{27}$H$_{28}$N$_2$O$_3$S: C, 70.41; H, 6.13; N, 6.08. Found: C, 70.42; H, 6.05; N, 6.05.
Step B—Preparation of 3-(Benzyloxycarbonyl)-amino-2,3-dihydro-5-phenyl-1H-1-benzazepin-2-one A solution of 1-phenyl-1-[2-N-(α-isopropylthio)-N'-(benzyloxycarbonyl)-glycinyl-aminophenyl]ethylene (1 eq) in acetonitrile under nitrogen was treated with mercury(II) chloride (1.0 equiv.; Aldrich). A white precipitate formed immediately after the mercury(II) chloride had dissolved. The mixture was heated to reflux for 2.5 hours; an additional 0.05 equiv. of mercury(II) chloride was added and refluxing continued for 1 hour. The reaction was cooled to ambient temperature and the mercury salts were filtered washing with methylene chloride. The filtrate was concentrated in vacuo; the resultant residue was taken up in methylene chloride and filtered to remove additional mercury salts. The filtrate was washed with water. The aqueous layer was back-extracted five times with methylene chloride. The combined organics were allowed to stand overnight; additional mercury salts were filtered. The filtrate was dried over $Na_2SO_4$, filtered, and concentrated in vacuo. The crude oil was purified via flash chromatography eluting with a gradient form $CH_2Cl_2$ to 82:18 $CH_2Cl_2$/ethyl acetate giving a tan solid. The solid could be further purified by trituration with diethyl ether which provided a white solid.

$C_{24}H_{20}N_2O_3$ (MW=384.43); mass spectroscopy found (M+H) 385.1. Anal. Calcd for $C_{24}H_{20}N_2O_3 \cdot 0.5H_2O$: C, 73.27; H, 5.38; N, 7.12. Found: C, 73.41; H, 5.13; N, 7.30.

Step C—Preparation of 3-(Benzyloxycarbonyl)-amino-2,3-dihydro-1-methyl-5-phenyl-1H-1-benzazepin-2-one Following General Procedure 4-A and using 3-(benzyloxycarbonyl)-amino-2,3-dihydro-5-phenyl-1H-1-benzazepin-2-one, the title intermediate was prepared as a white solid.

$C_{25}H_{22}N_2O_3$ (MW=398.4); mass spectroscopy found (M+H) 399.2. Anal. Calcd for $C_{25}H_{22}N_2O_3$: C, 75.36; H, 5.57; N, 7.03. Found: C, 75.21; H, 5.57; N, 7.13.

Step D—Preparation of 3-Amino-1,3-dihydro-1-methyl-5-phenyl-2H-1-benzazepin-2-one Following General Procedure 4-B and using 3-(benzyloxycarbonyl)-amino-2,3-dihydro-1-methyl-5-phenyl-1H-1-benzazepin-2-one, the title intermediate was prepared as an amber oil which was used immediately in Step E.

Step E—Preparation of 3-[N'-(tert-Butylcarbamate)-L-alaninyl]-amino-2,3-dihydro-1-methyl-5-phenyl-1H-1-benzazepin-2-one Following General Procedure D using N-Boc Alanine and 3-amino-1,3-dihydro-1-methyl-5-phenyl-2H-1-benzazepin-2-one, the title intermediate was prepared as a white solid.

$C_{25}H_{29}N_3O_4$ (MW=435.57); mass spectroscopy found (M+H) 436.3. $^1H$ NMR (300 MHz, $CDCl_3$) d 7.54 (2H, d, J=4.6 Hz), 7.52–725 (18H, m), 5.90 (1H, d, J=5.3 Hz), 5.88 (1H, d, J=5.3 Hz), 5.1 (1H, bs), 4.9 (1H, bs), 4.60 (2H, m), 4.31 (2H, m), 3.48 (6H, s), 1.48 (9H, s), 1.46 (9H, s), 1.43 (3H, d, J=4.5 Hz), 1.40 (3H, d, J=4.1 Hz).

Step F—Preparation of 3-(L-Alaninyl-amino-2,3-dihydro-1-methyl-5-phenyl-1H-1-benzazepin-2-one Following General Procedure 4-C using 3-[N'-(tert-butylcarbamate)-L-alaninyl]-amino-2,3-dihydro-1-methyl-5-phenyl-1H-1-benzazepin-2-one, the title intermediate was prepared as a white foam. No further purification was necessary.

$C_{20}H_{21}N_3O_2$ (MW=335.40); mass spectroscopy found (M+H) 336.2. Anal. Calcd for $C_{20}H_{21}N_3O_2$: C, 71.62; H, 6.31; N, 12.53. Found: C, 71.78; H, 6.54; N, 12.22.

Example 5-B

Synthesis of 3-(L-Alaninyl)-amino-2,3,4,5-tetrahydro-1-methyl-5-phenyl-1H-1-benzazepin-2-one Step A—Preparation of 3-Amino-2,3,4,5-tetrahydro-1-methyl-5-phenyl-2H-1-benzazepin-2-one A solution of 3-(benzyloxycarbonyl)-amino-2,3-dihydro-1-methyl-5-phenyl-1H-1-benzazepin-2-one (Example 5-A, Steps A–C) in methanol under nitrogen was treated with 10% palladium on carbon (0.4 equiv.). The reaction vessel was placed under a balloon of hydrogen and stirred for 3 hours. The reaction flask was flushed well with nitrogen and the reaction mixture filtered through celite washing with $CH_2Cl_2$. The filtrate was concentrated to a white foam.

$C_{17}H_{18}N_2O$ (MW=266.37); mass spectroscopy found (M+H) 267.1. Anal. Calcd for $C_{17}H_{18}N_2O$: C, 76.66; H, 6.81; N, 10.52. Found: C, 76.56; H, 6.83; N, 10.38.

Step B—Preparation of 3-[N'-(tert-Butylcarbamate)-L-alaninyl]-amino-2,3,4,5-tetrahydro-1-methyl-5-phenyl-1H-1-benzazepin-2-one Following General Procedure D using N-Boc Alanine and 3-amino-2,3,4,5-tetrahydro-1-methyl-5-phenyl-2H-1-benzazepin-2-one, the title intermediate was prepared as a white foam.

$C_{25}H_{31}N_3O_4$ (MW=437.59); mass spectroscopy found (M+H) 438.2. Anal. Calcd for $C_{25}H_{31}N_3O_4$: C, 68.63; H, 7.14; N, 9.60. Found: C, 68.93; H, 7.13; N, 9.49.

Step C—Preparation of 3-(L-Alaninyl)-amino-2,3,4,5-tetrahydro-1-methyl-5-phenyl-1H-1-benzazepin-2-one Following General Procedure 4-C using 3-[N'-(tert-butylcarbamate)-L-alaninyl]-amino-2,3,4,5-tetrahydro-1-methyl-5-phenyl-1H-1-benzazepin-2-one, the title intermediate was prepared as a white foam. No further purification was necesary.

$C_{20}H_{23}N_3O_2$ (MW=337.46); mass spectroscopy found (M+H) 338.2. Anal. Calcd for $C_{20}H_{23}N_3O_2$: C, 71.19; H, 6.87; N, 12.45. Found: C, 71.38; H, 6.83; N, 12.51.

Example 5-C

Synthesis of 3-(L-Alaninyl)-amino-2,3,4,5-tetrahydro-1-methyl-5-phenyl-1H-1-benzazepin-2-one Step A—Preparation of 3-Amino-2,3,4,5-tetrahydro-1-methyl-5-phenyl-2H-1-benzazepin-2-one To a flask containing 300 mL of freshly condensed liquid ammonia at −70° C. was added lithium metal (4.1 equiv.). The dark blue slurry was warmed to −45° C. and treated with a pre-cooled solution of 3-(benzyloxycarbonyl)-amino-2,3-dihydro-1-methyl-5-phenyl-1H-1-benzazepin-2-one (Example 4-AC, Steps A-C) in 30 mL distilled THF. After 10 min a solution of tert-butanol (4.0 equiv.) in distilled THF was added. After an additional 10 min the reaction was quenched with ammonium chloride. The cooling bath w as removed and the ammonia allowed to evaporate overnight. The contents were partitioned between $CH_2Cl_2$ and saturated aqueous $NaHCO_3$. The organic phase was washed with brine, dried over $Na_2SO_4$, filtered, and concentrated. Purified via liquid chromatography eluting with a gradient from 99:1 to 90:10 $CH_2Cl_2$/MeOH.

$C_{17}H_{18}N_2O$ (MW=266.37); mass spectroscopy found (M+H) 267.0.

Step B—Preparation of 3-[N'-(tert-Butylcarbamate)-L-alaninyl]-amino- 2,3,4,5-tetrahydro-1-methyl-5-phenyl-1H-1-benzazepin-2-one Following General Procedure D using N-Boc-alanine and 3-amino-2,3,4,5-tetrahydro-1-methyl-5-phenyl-2H-1-benzazepin-2-one, the title intermediate was prepared as a white foam.

$C_{25}H_{31}N_3O_4$ (MW=437.59); mass spectroscopy found (M+H) 438.2. Anal. Calcd for $C_{25}H_{31}N_3O_4$: C, 68.63; H, 7.14; N, 9.60. Found: C, 68.70; H, 7.15; N, 9.54.

Step C—Preparation of 3-(L-Alaninyl)-amino-2,3,4,5-tetrahydro-1-methyl-5-phenyl-1H-1-benzazepin-2-one Following General Procedure 4-C using 3-[N'-(tert-butylcarbamate)-L-alaninyl]-amino-2,3,4,5-tetrahydro-1-methyl-5-phenyl-1H-1-benzazepin-2-one, the title intermediate was prepared as a white foam. No further purification was necessary.

$C_{20}H_{23}N_3O_2$ (MW=337.46); mass spectroscopy found (M+H) 338.2. Anal. Calcd for $C_{20}H_{23}N_3O_2$: C, 71.19; H, 6.87; N, 12.45. Found: C, 71.32; H, 6.57; N, 12.24.

Example 6

Synthesis of 5-(S)-[N'-(L-Prolyl)-L-alaninyl]-amino-7-methyl-5,7-dihydro-6H-dibenz[b,d]azepin-6-one Step A. Synthesis of N-L-(N'-tert-boc-L-Prolyl)-alanine Methyl Ester N-tert-Boc-L-proline (Aldrich) (5.00 g, 23 mmol) was dissolved in THF (300 mL), under $N_2$. L-alanine methyl ester hydrochloride (3.53 g, 25 mmol), HOBT (3.38 g, 25 mmol), EDC (4.79 g, 25 mmol) and DIPEA (3.23g, 25 mmol) were added. The reaction mixture was stirred at RT overnight. The reaction mixture was stripped to dryness, dissolved in EtOAc, washed with saturated $NaHSO_4$, dilute $NaHCO_3$ and brine, and dried over $Na_2SO_4$. Removal of solvent gave the title compound (6.10 g, 88%) as a white solid.

$C_{14}H_{24}N_2O_5$ (MW=300.4); mass spectroscopy (MH$^+$) 301.

B. Synthesis of N-L-(N'-tert-boc-L-Prolyl)-alanine

The compound prepared in Step A above (5.98 g, 20 mmol) was dissolved in 1,4-dioxane (154 mL). LiOHH$_2$O (0.84 g, 20 mmol) in (H$_2$O 25 mL) was added. The reaction mixture was stirred at RT for 1.5 hr. The reaction mixture was adjusted to pH=3 with a saturated aqueous $NaHSO_4$ solution, which then was evaporated to remove most of the 1,4-dioxane. The residue was extracted with EtOAc and dried over $Na_2SO_4$. Removal of solvent gave the title compound (4.98 g, 87%) as a white solid.

$C_{13}H_{22}N_2O_5$ (MW=286.37); mass spectroscopy (MH$^+$) 287.

Step C. Synthesis of 5-(S)-[N'-(N''-tert-boc-L-Prolyl)-L-alaninyl]-amino-7-methyl-5,7-dihydro-6H-dibenz[b,d]azepin-6-one The compound prepared in Step B above (0.50 g, 1.75 mmol) was dissolved in THF (46 mL), under $N_2$. 5-(S)-amino-7-methyl-5,7-dihydro-6H-dibenz[b,d]azepin-6-one hydrochloride (Example 3A) (0.44 g, 1.59 mmol), HOBT (0.24 g, 1.75 mmol), EDC (0.34 g, 1.75 mmol) and DIPEA (0.23g, 1.75 mmol) were added. The reaction mixture was stirred at RT overnight. The reaction mixture was stripped to dryness, dissolved in EtOAc, washed with saturated $NaHSO_4$, dilute $NaHCO_3$ and brine, dried over $Na_2SO_4$. Removal of solvent gave the title compound (0.76 g, 94%) as a white solid.

$C_{28}H_{30}N_2O_7$ (MW=506.60); mass spectroscopy (MH$^+$) 507.

Step D. Synthesis of 5-(S)-[N'-(L-Prolyl)-L-alaninyl]-amino-7-methyl-5,7-dihydro-6H-dibenz[b,d]azepin-6-one The compound made above (0.70 g, 1.38 mmol) was dissolved in 4M HCl in 1,4-dioxane solution (40 mL), stirred at RT over night. The reaction mixture was stripped to dryness, purified with SCX column [3% (7N NH$_3$ in MeOH)/CH$_2$Cl$_2$] to give the title compound (0.53 g, 95%) as a white solid.

$C_{23}H_{26}N_4O_3$ (MW=406.483); mass spectroscopy (MH$^+$) 407. Accurate mass Calcd for $C_{23}H_{26}N_4O_3$: 407.2083 (MH$^+$); Found: 407.2079. Anal. Calcd for $C_{23}H_{26}N_4O_3$1/2H$_2$O: C, 66.48 H, 6.56 N, 13.49; Found: C, 66.60 H, 6.38 N, 13.35.

Example 7

Synthesis of 5-(S)-[N'-(L-Homoprolyl)-L-alaninyl]-amino-7-methyl-5,7-dihydro-6H-dibenz[b,d]azepin-6-one Step A. Synthesis of N-L-(N'-tert-boc-L-Homoprolyl)-alanine Methyl Ester N-tert-Boc-L-homoproline (BACHEM-CA) (0.80 g, 3.49 mmol) was dissolved in THF (170 mL) maintained under $N_2$. L-alanine methyl ester hydrochloride (0.54 g, 3.84 mmol), HOBT (0.52 g, 3.84 mmol), EDC (0.74 g, 3.84 mmol) and DIPEA (0.50 g, 3.84 mmol) were added. The reaction mixture was stirred at RT overnight. The reaction mixture was stripped to dryness, dissolved in EtOAc, washed with an aqueous saturated $NaHSO_4$ solution, dilute $NaHCO_3$ and brine and dried over $Na_2SO_4$. Removal of solvent gave the title compound (1.06 g, 97%) as a white solid.

$C_{15}H_{26}N_2O_5$ (MW=314.43); mass spectroscopy (MH$^+$) 315.

Step B. Synthesis of N-L-(N'-tert-boc-L-Homoprolyl)-alanine

The compound prepared in Step A above (0.79 g, 2.5 mmol) was dissolved in 1,4-dioxane (19 mL). LiOHH$_2$O (0.10 g, 2.5 mmol) in H$_2$O (3 mL) was then added. The reaction mixture was stirred at RT for 1.5 hours. The reaction mixture was adjusted to pH=3 with an aqueous saturated $NaHSO_4$ solution, which was evaporated to remove most of the 1,4-dioxane. The residue was extracted with EtOAc and dried over $Na_2SO_4$. Removal of solvent gave the title compound (0.71 g, 94%) as a white solid.

$C_{14}H_{24}N_2O_5$ (MW=300.40); mass spectroscopy (MH$^+$) 301.

Step C. Synthesis of 5-(S)-[N'-(N''-tert-boc-L-Homoprolyl)-L-alaninyl]-amino-7-methyl-5,7-dihydro-6H-dibenz[b,d]azepin-6-one The compound prepared in Step B above (0.38 g, 1.27 mmol) was dissolved in THF (36 mL) maintained under $N_2$. 5-(S)-amino-7-methyl-5,7-dihydro-6H-dibenz[b,d]azepin-6-one (Example 3A) (0.30 g, 1.27 mmol), HOBT (0.17 g, 1.27 mmol), and EDC (0.24 g, 1.27 mmol) were added. The reaction mixture was stirred at RT overnight. The reaction mixture was stripped to dryness, dissolved in EtOAc, washed with an aqueous saturated $NaHSO_4$ solution, dilute $NaHCO_3$ and brine, and dried over $Na_2SO_4$. Evaporation and flash chromatography (5% MeOH/CH$_2$Cl$_2$) gave the title compound (0.61 g, 92%) as a white solid.

$C_{29}H_{32}N_2O_7$ (MW=520.63); mass spectroscopy (MH$^+$) 521.

Step D. Synthesis of 5-(S)-[N'-(L-Homoprolyl)-L-alaninyl]-amino-7-methyl-5,7-dihydro-6H-dibenz[b,d]azepin-6-one The compound prepared in Step C above (0.61 g, 1.17 mmol) was dissolved in 4M HCl in 1,4-dioxane solution (30 mL), stirred at RT over night. The reaction mixture was stripped to dryness, washed with Et$_2$O, purified with SCX column [3% (7N NH$_3$ in MeOH)/CH$_2$Cl$_2$] to give the title compound (0.41 g, 83%) as a white solid.

$C_{24}H_{28}N_4O_3$ (MW=420.510); mass spectroscopy (MH$^+$) 421. Anal. Calcd for $C_{24}H_{28}N_4O_3$: C, 68.55 H, 6.71 N, 13.32; Found: C, 68.26 H, 6.73 N, 13.20.

Example 8

Synthesis of 5-(S)-[N'-DL-Homoprolyl)-L-alaninyl]-amino-7-methyl-5,7-dihydro-6H-dibenz[b,d]azepin-6-one Step A. Synthesis of N-tert-boc-DL-Homoproline DL-pipecolinic acid hydrochloride (Aldrich) (1.00 g, 6.0 mmol) was dissolved in $NaHCO_3$ solution ($NaHCO_3$: 1.51 g, 18 mmol; H$_2$O: 25 mL). 1,4-dioxane (15 mL) was added and the reaction solution then stirred at 0° C. Di-t-butyldicarbonate (1.44 g, 6.6 mmol) in 1,4-dioxane (10 mL) was added and the reaction solution was then stirred at RT overnight. Afterwards, the solvent was stripped and water and CH$_2$Cl$_2$ were then added. The aqueous layer was acidified with $NaHSO_4$ to pH=3, extracted with CH$_2$Cl$_2$, washed with brine, and dried over $Na_2SO_4$. Removal of solvent gave the title compound (0.32 g, 23%) as a white solid.

$C_{11}H_{19}NO_4$ (MW=229.31); mass spectroscopy (MH$^+$) 230.

Step B. Synthesis of N-L-(N'-t-boc-DL-Homoprolyl)-alanine Methyl Ester

N-tert-Boc-DL-homoproline (0.32 g, 1.4 mmol) was dissolved in THF (50 mL), under $N_2$. L-alanine methyl ester hydrochloride (0.21 g, 1.5 mmol), HOBT (0.21 g, 1.5 mmol), EDC (0.30 g, 1.5 mmol) and DIPEA (0.27 mL, 1.5 mmol) were then added. The resulting mixture was stirred at RT overnight whereupon the reaction mixture was stripped to dryness, dissolved in EtOAc, washed with an aqueous saturated $NaHSO_4$ solution, dilute $NaHCO_3$ and brine. The resulting organic layer was dried over $Na_2SO_4$. Removal of solvent gave the title compound (0.43 g, 98%).

$C_{15}H_{26}N_2O_5$ (MW=314.43); mass spectroscopy (MH$^+$) 315.

Step C. Synthesis of N-L-(N'-tert-boc-DL-Homoprolyl)-alanine

The compound prepared in Step B above (0.430 g, 1.37 mmol) was dissolved in 1,4-dioxane (10.5 mL). LiOHH$_2$O (0.057 g, 1.37 mmol) in $H_2O$ (1.7 mL) was then added and the resulting reaction mixture was stirred at RT for 1.5 hr. The reaction mixture was adjusted to pH 3 with an aqueous saturated $NaHSO_4$ solution and the resulting reaction mixture was evaporated to remove most of 1,4-dioxane. The residue was extracted with EtOAc and dried over $Na_2SO_4$. Removal of solvent gave the title compound (0.400 g, 95%).

$C_{14}H_{24}N_2O_5$ (MW=300.40); mass spectroscopy (MH$^+$) 301.

Step D. Synthesis of 5-(S)-[N'-(N''-tert-boc-DL-Homoprolyl)-L-alaninyl]-amino-7-methyl-5,7-dihydro-6H-dibenz[b,d]azepin-6-one The compound prepared in Step C above (0.40 g, 1.3 mmol) was dissolved in THF (38 mL) maintained under $N_2$. 5-(S)-amino-7-methyl-5,7-dihydro-6H-dibenz[b,d]azepin-6-one hydrochloride (Example 3A) (0.36 g, 1.3 mmol), HOBT (0.18 g, 1.3 mmol), EDC (0.25 g, 1.3 mmol) and DIPEA (0.23 mL, 1.3 mmol) were then added and the resulting reaction mixture was stirred at RT overnight. The reaction mixture was stripped to dryness, dissolved in EtOAc, washed with an aqueous saturated $NaHSO_4$ solution, dilute $NaHCO_3$ and brine and dried over $Na_2SO_4$. Evaporation and flash chromatography (5% MeOH/CH$_2$Cl$_2$) gave the title compound (0.64 g, 95%) as a white solid.

$C_{29}H_{32}N_2O_7$ (MW=520.63); mass spectroscopy (MH$^+$) 521.

Step E. Synthesis of 5-(S)-[N'-(DL-Homoprolyl)-L-alaninyl]-amino-7-methyl-5,7-dihydro-6H-dibenz[b,d]azepin-6-one The compound prepared in Step D above (0.64 g, 1.2 mmol) was dissolved in a solution of 4M HCl in 1,4-dioxane (30 mL) and then stirred at RT overnight. A solution of 7N NH$_3$ in MeOH was added. Evaporation and flash chromatography (5% MeOH/CH$_2$Cl$_2$) gave the title compound (0.44 g, 87%).

$C_{24}H_{28}N_4O_3$ (MW=420.510); mass spectroscopy (MH$^+$) 421. Anal. Calcd for $C_{24}H_{28}N_4O_3$ with 1/2 H$_2$O: C, 67.11 H, 6.82 N, 13.05; Found: C, 66.78 H, 6.42 N, 12.71.

Example 9

Synthesis of 5-(S)-[N'-(1,2,3,4-Tetrahydroisoquinolin-1-oyl)-L-alaninyl]-amino-7-methyl-5,7-dihydro-6H-dibenz[b,d]azepin-6-one Step A. Synthesis of N-(N'-tert-boc-1,2,3,4-Tetrahydroisoquinolin-1-oyl-L-alanine Methyl Ester N-tert-Boc-1,2,3,4-tetrahydroisoquinoline-1-carboxylic acid (J. Med. Chem., 1993, Vol.36, No.3, pp315) (5.00 g, 18 mmol) was dissolved in THF (240 mL) maintained under $N_2$. L-alanine methyl ester hydrochloride (2.77 g, 20 mmol), HOBT (2.70 g, 20 mmol), EDC (3.83 g, 20 mmol) and DIPEA (2.58 g, 20 mmol) were added and the resulting reaction mixture was stirred at RT overnight.

The reaction mixture was stripped to dryness, dissolved in EtOAc, washed with an aqueous saturated $NaHSO_4$ solution, dilute $NaHCO_3$ and brine, and then dried over $Na_2SO_4$. Removal of solvent gave the title compound (6.40 g, 98%).

$C_{19}H_{26}N_2O_5$ (MW=362.423); mass spectroscopy (MH$^+$) 363.

Step B. Synthesis of N-(N'-tert-boc-1,2,3,4-Tetrahydroisoquinolin-1-oyl)-L-alanine The compound prepared in Step A above (6.09 g, 17 mmol) was dissolved in 1,4-dioxane (127 mL). LiOHH$_2$O (0.71 g, 17 mmol) in $H_2O$ (20 mL) was added and then the resulting reaction mixture was stirred at RT for 1.5 hr. The reaction mixture was adjusted to pH=3 with an aqueous saturated $NaHSO_4$ solution and then the reaction mixture was evaporated to remove most of 1,4-dioxane. The residue was extracted with EtOAc, dried over $Na_2SO_4$. Removal of solvent gave the title compound (5.79 g, 98%).

$C_{18}H_{24}N_2O_5$ (MW=348.44); mass spectroscopy (MH$^+$) 349.

Step C. Synthesis of 5-(S)-[N'-(N''-tert-boc-1,2,3,4-Tetrahydroisoquinolin-1-oyl)-L-alaninyl]-amino-7-methyl-5,7-dihydro-6H-dibenz[b,d]azepin-6-one The compound made above (0.56 g, 1.61 mmol) was dissolved in THF (46 mL) maintained under $N_2$. 5-(S)-amino-7-methyl-5,7-dihydro-6H-dibenz[b,d]azepin-6-one hydrochloride (Example 3A) (0.40 g, 1.46 mmol), HOBT (0.22 g, 1.61 mmol), EDC (0.31 g, 1.61 mmol) and DIPEA (0.28 mL, 1.61 mmol) were then added and the reaction mixture was stirred at RT overnight. The reaction mixture was stripped to dryness, dissolved in EtOAc, washed with an aqueous saturated $NaHSO_4$ solution , dilute $NaHCO_3$ and brine, and then dried over $Na_2SO_4$. Evaporation and flash chromatography (5% MeOH/CH$_2$Cl$_2$) gave the title compound (0.84 g, 100%).

$C_{33}H_{36}N_4O_5$ (MW=568.73); mass spectroscopy (MH$^+$) 569.

Step D. Synthesis of 5-(S)-[N'-(1,2,3,4-Tetrahydroisoquinolin-1-oyl)-L-alaninyl]-amino-7-methyl-5,7-dihydro-6H-dibenz[b,d]azepin-6-one The compound prepared in Step C above (0.84 g, 1.5 mmol) was dissolved in a solution of 4M HCl in 1,4-dioxane (50 mL) and then stirred at RT for 2 hr. Evaporation and flash chromatography [SCX, 4% (7N NH$_3$ in MeOH)/CH$_2$Cl$_2$] gave the title compound (0.65 g, 93%) as a white solid. Two isomers were isolated from the title compound by flash chromatography (silica, 5% MeOH/CH$_2$Cl$_2$).

Isomer 1: $C_{28}H_{28}N_4O_3$ (MW=468.554); mass spectroscopy (MH$^+$) 469. Anal. Calcd for $C_{28}H_{28}N_4O.1/2H_2O$: C, 70.42 H, 6.13 N, 11.73; Found: C, 70.60 H, 5.72 N, 1.79.

Isomer2: $C_{28}H_{28}N_4O_3$ (MW=468.554); mass spectroscopy (MH$^+$) 469.

Anal. Calcd for $C_{28}H_{28}N_4O_3$: C, 71.78 H, 6.02 N, 11.96; Found: C, 71.72 H, 5.91 N, 1.79.

Example 10

Synthesis of 5-(S)-[N'-(Octahydro-indolyl-2-oyl)-L-alaninyl]-amino-7-methyl-5,7-dihydro-6H-dibenz[b,d]azepin-6-one Step A. Synthesis of 5-(S)-[N'-(N"-tert-boc-Octahydro-indolyl-2-oyl)-L-alaninyl]-amino-7-methyl-5 7-dihydro-6H-dibenz[b,d]azepin-6-one Following General Procedure D using N-tert-Boc-octahydro-indolyl-2-carboxylic acid (BaChem) and (S)-5-(L-alaninyl)-amino-7-methyl-5,7-dihydro-6H-dibenz[b,d]azepin-6-one (Example 3-B), the title compound was prepared.

$C_{32}H_{40}N_4O_5$ (MW=560.691); mass spectroscopy (MH$^+$) 561.

Step B. Synthesis of 5-(S)-[N'-(Octahydro-indolyl-2-oyl)-L-alaninyl]-amino-7-methyl-5,7-dihydro-6H-dibenz[b,d]azepin-6-one Following General Procedure 4-N using the compound prepared in Step A above, the title compound was prepared after passing through an SCX column [4% MeOH(7N NH$_3$)/CH$_2$Cl$_2$].

$C_{27}H_{32}N_4O_3$ (MW=460.575); mass spectroscopy (MH$^+$) 461. Anal. Calcd for $C_{27}H_{32}N_4O_3$ with 1/2 H$_2$O: C, 69.05 H, 7.10 N, 11.93; Found: C, 68.66 H, 7.05 N, 11.79.

Example 11

Synthesis of 5-{N'-[cis-4-(3-Methylbutyl)-L-prolyl]-L-alaninyl}-amino-7-methyl-5,7-dihydro-6H-dibenz[b,d]azepin-6-one Step A. Synthesis of 5-{N'-[cis-4-(3-Methylbutyl)-N"-tert-Boc-L-prolyl]-L-alaninyl}-amino-7-methyl-5,7-dihydro-6H-dibenz[b,d]azepin-6-one Following General Procedure D using cis-4-(3-methylbutyl)-N-(tert-Boc-L-proline (J. Am.Chem.Soc., Vol.120, No.16, 1998, pp3899) and 5-(L-alaninyl)-amino-7-methyl-5,7-dihydro-6H-dibenz[b,d]azepin-6-one (Example 3-B), the title compound was prepared.

$C_{33}H_{44}N_4O_5$ (MW=576.81); mass spectroscopy (MH$^+$) 577.

Step B. Synthesis of 5-{N'-[cis-4-(3-Methylbutyl)-L-prolyl]-L-alaninyl}-amino-7-methyl-5,7-dihydro-6H-dibenz[b,d]azepin-6-one Following General Procedure 4-N using the compound prepared in Step A above, the title compound was prepared as a free base, which was purified with flash chromatography [4% MeOH (7N NH$_3$)/CH$_2$Cl$_2$].

$C_{28}H_{36}N_4O_3$ (MW=476.617); mass spectroscopy (MH$^+$) 477. Anal. Calcd for $C_{28}H_{36}N_4O_3$: C, 70.56 H, 7.61 N, 11.75; Found: C, 70.66H, 7.45 N, 11.55.

Example 12

Synthesis of 5-{N'-[trans-4-(3-Methylbutyl)-L-prolyl]-L-alaninyl}-amino-7-methyl-5,7-dihydro-6H-dibenz[b,d]azepin-6-one Step A. Synthesis of 5-{N'-[trans-4-(3-Methylbutyl)-N"-tert-Boc-L-prolyl]-L-alaninyl}-amino-7-methyl-5,7-dihydro-6H-dibenz[b,d]azepin-6-one Following General Procedure D using trans-4-(3-methylbutyl)-N-(tert-Boc-L-proline (J. Am.Chem.Soc., Vol.120, No.16, 1998, pp3899) and 5-(L-alaninyl)-amino-7-methyl-5,7-dihydro-6H-dibenz[b,d]azepin-6-one (Example 3-B), the title compound was prepared.

$C_{33}H_{44}N_4O_5$ (MW=576.81); mass spectroscopy (MH$^+$) 577.

Step B. Synthesis of 5-{N'-[trans-4-(3-Methylbutyl)-L-prolyl]-L-alaninyl}-amino-7-methyl-5,7-dihydro-6H-dibenz[b,d]azepin-6-one Following General Procedure 4-N using the compound made above, the title compound was prepared as a free base, which was purified with flash chromatography [4% MeOH (7N NH$_3$)/CH$_2$Cl$_2$].

Exact mass spectroscopy: Calc. for $C_{28}H_{37}N_4O_3$: 477.2866; Found 477.2871. Anal. Calcd for $C_{21}H_{36}N_4O_3$ with 1 H$_2$O: C, 67.99 H, 7.76 N, 11.33; Found: C, 67.82 H, 7.60 N, 11.26.

Example 13

Synthesis of 5-(S)-[N'-(Decahydro-quinolyl-2-oyl)-L-alaninyl]-amino-7-methyl-5,7-dihydro-6H-dibenz[b,d]azepin-6-one Step A: Synthesis of Decahydro-quinoline-2-carboxylic Acid Hydrochloride A mixture of PtO$_2$ (25 wt. %) and 2-quinolinecarboxylic acid (Aldrich) in acetic acid was hydrogenated at RT under 60 Psi overnight. The reaction mixture was stripped to dryness. Concentrated HCl was added and stripped to dryness to give the title compound as a white solid.

$C_{10}H_{17}NO_2$ (free base, MW=183.26); mass spectroscopy (MH$^+$) 184.

Step B: Synthesis of N-tert-boc-Decahydroquinoline-2-carboxylic Acid

The compound made above (1.0 equiv.) was dissolved in tert-butylalcohol and 2N NaOH. Di-tert-butyldicarbonate (1.2 equiv.) was added, stirred at RT for 8.5 h. The reaction mixture was evaporated and then extracted with EtOAc. The aqueous layer was acidified with 2N HCl and extracted with EtOAc, dried. Removal of the solvent gave the title compound.

$C_{15}H_{25}NO_4$ (MW=283.41); mass spectroscopy (MH$^+$) 284.

Step C: Synthesis of 5-(S)-[N'-(N"-tert-boc-Decahydroquinolyl-2-oyl)-L-alaninyl]-amino-7-methyl-5,7-dihydro-6H-dibenz[b,d]azepin-6-one Following General Procedure D using the compound made above and (S)-5-(L-alaninyl)-amino-7-methyl-5,7-dihydro-6H-dibenz[b,d]azepin-6-one (Example 3-B), the title compound was prepared.

$C_{33}H_{42}N_4O_5$ (MW=574.79); mass spectroscopy (MH$^+$) 575.

Step D: Synthesis of 5-(S)-[N'-(Decahydroquinolyl-2-oyl)-L-alaninyl]-amino-7-methyl-5,7-dihydro-6H-dibenz[b,d]azepin-6-one Following the General Procedure of Step B of Example 1-C using the compound made above, the title compound was prepared as a free base, which was purified with flash chromatography [silica, 4% MeOH (7N NH$_3$)/CH$_2$Cl$_2$] to give two mixtures.

Mixture 1: $C_{28}H_{34}N_4O_3$ (MW=474.602); mass spectroscopy (MH$^+$) 475. Anal. Calcd for $C_{28}H_{34}N_4O_3$ with 1/2 H$_2$O: C, 69.54 H, 7.31, N, 11.59; Found: C, 69.40 H, 7.68, N, 11.46.

Mixture 2: $C_{28}H_{34}N_4O_3$ (MW=474.602); mass spectroscopy (MH$^+$) 475. Anal. Calcd for $C_{28}H_{34}N_4O_3$ with 1/3 H$_2$O: C, 69.97 H, 7.29, N, 11.66; Found: C, 70.09 H, 6.96, N, 11.52.

Example 14

Synthesis of 5-[N'-(Decahydro-quinolyl-2-oyl)-L-alaninyl]-amino-7-methyl-5,7-dihydro-6H-dibenz[b,d]azepin-6-one Step A: Synthesis of 5-[N'-(N"-tert-boc-Decahydroquinolyl-2-oyl)-L-alaninyl]-amino-7-methyl-5,7-dihydro-6H-dibenz[b,d]azepin-6-one Following General Procedure D using N-tert-Boc-decahydroquinoline-2-carboxylic acid (Example 13-B above) and 5-(L-alaninyl)-amino-7-methyl-5,7-dihydro-6H-dibenz[b,d]azepin-6-one (Example 3-B), the title compound was prepared.

$C_{33}H_{42}N_4O_5$ (MW=574.79); mass spectroscopy (MH$^+$) 575.

Step B: Synthesis of 5-[N'-(Decahydro-quinolyl-2-oyl)-L-alaninyl]-amino-7-methyl-5,7-dihydro-6H-dibenz[b,d]azepin-6-one Following the General Procedure of Step B of Example 1-C using the compound made above, the title compound was prepared as a free base, which was purified with flash chromatography [silica, 4% MeOH (7N NH$_3$)/CH$_2$Cl$_2$] to give two fractions.

Fraction 1: $C_{28}H_{34}N_4O_3$ (MW=474.602); mass spectroscopy (MH$^+$) 475. Anal. Calcd for $C_{28}H_{34}N_4O_3$ with 2/3 H$_2$O: C, 69.10 H, 7.33, N, 11.52; Found: C, 68.96 H, 7.06, N, 11.46.

Fraction 2: $C_{28}H_{34}N_4O_3$ (MW=474.602); mass spectroscopy (MH$^+$) 475. Anal. Calcd for $C_{28}H_{34}N_4O_3$ with 1/2 H$_2$O: C, 69.54 H, 7.31, N, 11.59; Found: C, 69.42 H, 7.30, N, 11.43.

Accurate mass Calcd for $C_{28}H_{34}N_4O_3$: 475.2709 (MH$^+$); Found: 475.2729.

Example 15

Synthesis of 5-{N'-[(S)-Indolyl-2-oyl]-L-alaninyl}-amino-7-methyl-5,7-dihydro-6H-dibenz[b,d]azepin-6-one Step A: Synthesis of N-tert-boc-(S)-2-Indolinecarboxylic Acid A mixture of (S)-(−)-indoline-2-carboxylic acid (Aldrich) (1 equiv.) and DIEA (1 equiv.) in CH$_2$Cl$_2$ was stirred at 0° C. Di-tert-butyldicarbonate in CH$_2$Cl$_2$ was added, stirred at 0° C. for 2 h. The reaction mixture was concentrated, acidified with NaHSO$_4$, extracted with EtOAc, washed with brine, dried. Evaporation and flash chromatography (silica, 10% MeOH/CH$_2$Cl$_2$) gave the title compound.

$C_{14}H_{17}NO_4$ (MW=263.32); mass spectroscopy (MH$^+$) 264.

Step B: Synthesis of 5-{N'-[N"-tert-boc-(S)-Indolyl-2-oyl]-L-alaninyl}-amino-7-methyl-5,7-dihydro-6H-dibenz[b,d]azepin-6-one Following General Procedure D using the compound made above and 5-(L-alaninyl)-amino-7-methyl-5,7-dihydro-6H-dibenz[b,d]azepin-6-one (Example 3-B), the title compound was prepared.

$C_{32}H_{34}N_4O_5$ (MW=554.70); mass spectroscopy (MH$^+$) 555.

Step C: Synthesis of 5-{N'-[(S)-Indolyl-2-oyl]-L-alaninyl}-amino-7-methyl-5,7-dihydro-6H-dibenz[b,d]azepin-6-one Following the General Procedure of Step B of Example 1-C using the compound made above, the title compound was prepared as a free base, which was purified with flash chromatography (silica, 4% MeOH/CH$_2$Cl$_2$) to give the title compound.

Accurate mass Calcd for $C_{27}H_{26}N_4O_3$: 455.2083 (MH$^+$); Found: 455.2080. $^1$H nmr (CDCl$_3$): δ=3.35 (s, 1.5H), 3.34 (s, 1.5H), 1.68–1.41 (m, 3H).

Example 16

Synthesis of 5-(S)-{N'-[(S)-Indolyl-2-oyl]-L-alaninyl}-amino-7-methyl-5,7-dihydro-6H-dibenz[b,d]azepin-6-one Step A: Synthesis of 5-(S)-{N'-[N"-tert-boc-(S)-Indolyl-2-oyl]-L-alaninyl}-amino-7-methyl-5,7-dihydro-6H-dibenz[b,d]azepin-6-one Following General Procedure D using N-tert-Boc-(S)-2-indolinecarboxylic acid (Example 15- A, above) and (S)-5-(L-alaninyl)-amino-7-methyl-5,7-dihydro-6H-dibenz[b,d]azepin-6-one (Example 3-B), the title compound was prepared.

$C_{32}H_{34}N_4O_5$ (MW=554.70); mass spectroscopy (MH$^+$) 555.

Step B: Synthesis of 5-(S)-{N'-[(S)-Indolyl-2-oyl]-L-alaninyl}-amino-7-methyl-5,7-dihydro-6H-dibenz[b,d]azepin-6-one Following the General Procedure of Step B of Example 1-C using the compound made above, the title compound was prepared as a free base, which was purified with flash chromatography (silica, 4% MeOH/CH$_2$Cl$_2$) to give the title compound.

Accurate mass Calcd for $C_{27}H_{26}N_4O_3$: 455.2083 (MH$^+$); Found: 455.2070. $^1$H nmr (CDCl$_3$): δ 3.35 (s, 3H), 1.43 (d, 3H).

Example 17

Synthesis of 5-[N'-(L-trans-4-Hydroxyprolyl)-L-alaninyl]-amino-7-methyl-5,7-dihydro-6H-dibenz[b,d]azepin-6-one Step A: Synthesis of 5-[N'-(N"-tert-boc-L-trans-4-Hydroxyprolyl)-L-alaninyl]-amino-7-methyl-5,7-dihydro-6H-dibenz[b,d]azepin-6-one Following General Procedure D using N-α-tert-Boc-L-trans-4-hydroxyproline (novabiochem) and 5-(L-alaninyl)-amino-7-methyl-5,7-dihydro-6H-dibenz[b,d]azepin-6-one (Example 3-B), the title compound was prepared.

$C_{28}H_{34}N_4O_6$ (MW=522.66); mass spectroscopy (M$^+$ CH$_3$COO)— 581.

Step B: Synthesis of 5-[N'-(L-trans-4-Hydroxyprolyl)-L-alaninyl]-amino-7-methyl-5,7-dihydro-6H-dibenz[b,d]azepin-6-one Following the General Procedure of Step B of Example 1-C using the compound made above, the title compound was prepared as a free base, which was purified by reverse phase HPLC and SCX column to give two diastereomers of the title compound.

Isomer 1: Accurate mass Calcd for $C_{23}H_{26}N_4O_4$: 423.2032 (MH$^+$); Found: 423.2009. $^1$H nmr (CDCl$_3$): δ=3.35 (s, 1.5H), 3.50 (s, 3H), 1.42 (d, 3H).

Isomer 2: Accurate mass Calcd for $C_{23}H_{26}N_4O_4$: 423.2032 (MH$^+$); Found: 423.2012. $^1$H nmr (CDCl$_3$): δ=3.35 (s, 1.5H), 3.50 (s, 3H), 1.45 (d, 3H).

Example 18

Synthesis of 5-(S)-[N'-(1,2,3,4-Tetrahydroquinolyl-2-oyl)-L-alaninyl]-amino-7-methyl-5,7-dihydro-6H-dibenz[b,d]azepin-6-one Step A: Synthesis of 1,2,3,4-Tetrahydroquinoline-2-carboxylic Acid A mixture of PtO$_2$ (25 wt. %) and 2-quinolinecarboxylic acid (Aldrich) in acetic acid was hydrogenated at RT under 60 Psi overnight. The reaction mixture was stripped to dryness to give the title compound.

$C_{10}H_{11}NO_2$ (MW=177.22); mass spectroscopy (MH$^+$) 178.

Step B: Synthesis of N-tert-boc-1,2,3,4-Tetrahydroquinoline-2-carboxylic Acid

The compound made above (1.0 equiv.) was dissolved in tert-butyl alcohol and 2N NaOH. Di-tert-butyldicarbonate (1.2 equiv.) was added, stirred at RT overnight. The reaction mixture was evaporated, extracted with EtOAc. The aqueous layer was acidified with 2N HCl and extracted with EtOAc, dried. Evaporation and flash chromatography (silica, 10% MeOH/CH$_2$Cl$_2$) gave the title compound.

C$_{15}$H$_{19}$NO$_4$ (MW=277.35); mass spectroscopy (MH$^+$) 278.

Step C: Synthesis of 5-(S)-[N'-(N"-tert-boc-1,2,3,4-Tetrahydroquinolyl-2-oyl)-L-alaninyl]-amino-7-methyl-5,7-dihydro-6H-dibenz[b,d]azepin-6-one Following General Procedure D using the compound made above and (S)-5-(L-alaninyl)-amino-7-methyl-5,7-dihydro-6H-dibenz[b,d]azepin-6-one (Example 3-B), the title compound was prepared, which was purified by flash chromatography (silica, 10% MeOH/CH$_2$Cl$_2$).

C$_{33}$H$_{36}$N$_4$O$_5$ (MW=568.73); mass spectroscopy (MH$^+$) 569.

Step D: Synthesis of 5-(S)-[N'-(1,2,3,4-Tetrahydroquinolyl-2-oyl)-L-alaninyl]-amino-7-methyl-5,7-dihydro-6H-dibenz[b,d]azepin-6-one Following the General Procedure of Step B of Example 1-C using the compound made above, the title compound was prepared as a free base, a mixture of two diastereomers, which was isolated by flash chromatography [silica, 3% MeOH (7N NH$_3$)/CH$_2$Cl$_2$] to give two diastereomers.

Isomer 1: C$_{28}$H$_{28}$N$_4$O$_3$ (MW=468.60); mass spectroscopy (MH$^+$) 469. $^1$H nmr (CDCl$_3$): δ=3.34 (s, 3H), 1.40 (d, 3H).

Isomer 2: Accurate mass Calcd for C$_{28}$H$_{28}$N$_4$O$_3$: 469.2239 (MH$^+$); Found: 469.2234. $^1$H nmr (CDCl$_3$): δ=3.34 (s, 3H), 1.42 (d, 3H).

Example 19

Synthesis of 5-(S)-[N'-(3,3-Dimethylindolyl-2-oyl)-L-alaninyl]-amino-7-methyl-5,7-dihydro-6H-dibenz[b,d]azepin-6-one Step A: Synthesis of ethyl-[N-tert-boc-(S)-3,3,-Dimethylindoline]-2-carboxylate A mixture of ethyl-(S)-3,3-dimethylindoline-2-carboxylate (WO 9635805) (1 equiv.), DIEA (1 equiv.) and Di-tert-butyldicarbonate (1.2 equiv.) in CH$_2$Cl$_2$ was stirred at 0° C. to RT for three days. Evaporation and flash chromatography (silica, EtOAc/hexane, 1:7, v/v) gave the title compound.

C$_{18}$H$_{25}$NO$_4$ (MW=319.399); mass spectroscopy (MH$^+$) 320.

Step B: Synthesis of N-tert-boc-(S)-3,3,-Dimethylindoline-2-carboxylic Acid

The compound made above was mixed with 5% NaOH, MeOH, THF and catalytic amount of TBABr, heated under reflux for 4 h. After most of the solvents were evaporated, ether was added. The aqueous layer was acidified with conc. HCl, extracted with EtOAc, washed with brine, and dried. Removal of the solvent gave the title compound.

C$_{16}$H$_{21}$NO$_4$ (MW=291.345); mass spectroscopy (M−H)$^-$ 290.

Step C: Synthesis of 5-(S)-[N'-(N"-tert-boc-3,3-Dimethylindolyl-2-oyl)-L-alaninyl]-amino-7-methyl-5,7-dihydro-6H-dibenz[b,d]azepin-6-one Following General Procedure D using the compound made above and (S)-5-(L-alaninyl)-amino-7-methyl-5,7-dihydro-6H-dibenz[b,d]azepin-6-one (Example 3-B), the title compound was prepared.

C$_{34}$H$_{38}$N$_4$O$_5$ (MW=582.76); mass spectroscopy (MH$^+$) 583.

Step D: Synthesis of 5-(S)-[N'-(3,3-Dimethylindolyl-2-oyl)-L-alaninyl]-amino-7-methyl-5,7-dihydro-6H-dibenz[b,d]azepin-6-one Following the General Procedure of Step B of Example 1-C using the compound made above, the title compound was prepared as a free base, which was purified with flash chromatography (silica, 4% MeOH/CH$_2$Cl$_2$) to give the title compound.

Isomer 1: Accurate mass Calcd for C$_{29}$H$_{30}$N$_4$O$_3$: 483.2396 (MH$^+$); Found: 483.2401. $^1$H nmr (CDCl$_3$): δ=3.36 (s, 3H), 1.58 (s, 3H), 1.45 (d, 3H), 1.13 (s, 3H).

Isomer 2: Accurate mass Calcd for C$_{29}$H$_{30}$N$_4$O$_3$: 483.2396 (MH$^+$); Found: 483.2397. $^1$H nmr (CDCl$_3$): δ=3.33 (s, 3H), 1.57 (s, 3H), 1.46 (d, 3H), 1.09 (s, 3H).

Example 20

Synthesis of 5-{N'-[(S)-2-Methylindolyl-2-oyl]-L-alaninyl}-amino-7-methyl-5,7-dihydro-6H-dibenz[b,d]azepin-6-one Step A: Synthesis of cis-L-3-(1,1-Dimethylethyl)-9,9a-dihydro-1H,3H-oxazolo[3,4-a]indol-1-one A mixture of (S)-(−)-indoline-2-carboxylic acid (Aldrich) (1.0 equiv.), pivalaldehyde (7.1 equiv.) and molecular sieves in CH$_3$CN was heated under reflux overnight. The reaction mixture was filtered and stripped to dryness to give the title compound.

C$_{14}$H$_{17}$NO$_2$ (MW=231.293); mass spectroscopy (M+H)$^+$ 232.

Step B: Synthesis of cis-(S)-3-(1,1-Dimethylethyl)-9,9a-dihydro-9a-methyl-1H,3H-oxazolo[3,4-a]indol-1-one The compound made above (1.0 equiv.) in THF was cooled to −78° C. LDA (1.2 equiv., 2.0 M in heptane/THF/ethylbenzene) was added dropwise, stirred at −78° C. for 45 min. MeI (1.3 equiv.) was added dropwise. The resulting mixture was stirred at −78° C. overnight. The reaction mixture was warmed to 0° C. Saturated NH4Cl solution and EtOAc were added. EtOAc layer was washed with NaHCO$_3$ and brine, and then dried. Removal of the solvent gave the title compound.

C$_{15}$H$_{19}$NO$_2$ (MW=245.320 ); mass spectroscopy (M+H)$^+$ 246.

Step C: Synthesis of (S)-2-Methylindoline-2-carboxylic Acid

The compound made above was dissolved in MeOH/H$_2$O (6:1, v/v). Silica gel (230–400 mesh, 100 wt %) was added. The reaction mixture was stirred at RT over the weekend. The reaction mixture was stripped to dryness. MeOH was added, filtered. The filtrate was evaporated to give the title compound.

C$_{10}$H$_{11}$NO$_2$ (MW=177.202); mass spectroscopy (M+H)$^+$ 178.

Step D: Synthesis of N-tert-boc-(S)-2-Methylindoline-2-carboxylic Acid

The compound made above (1 equiv.) was dissolved in CH$_2$Cl$_2$. DIEA (1 equiv.) and di-tert-butyldicarbonate (1 equiv.) were added, stirred at 0° C. for 3 h. EtOAc and saturated NaHSO$_4$ were added. The EtOAc layer was washed with brine and dried. Evaporation and flash chromatography (silica, 5% MeOH/CH$_2$Cl$_2$) gave the title compound.

C$_{15}$H$_{19}$NO$_4$ (MW=277.318); mass spectroscopy (M+H)$^+$ 278.

Step E: Synthesis of 5-{N'-[N"-tert-boc-(S)-2-Methylindolyl-2-oyl]-alaninyl}-amino-7-methyl-5,7-dihydro-6H-dibenz[b,d]azepin-6-one Following General Procedure D using the compound made above and 5-(L-alaninyl)-amino-7-methyl-5,7-dihydro-6H-dibenz[b,d]azepin-6-one (Example 3-B), the title compound was prepared.

C$_{33}$H$_{36}$N$_4$O$_5$ (MW=568.670); mass spectroscopy (MH$^+$) 569.

Step F: Synthesis of 5-{N'-[(S)-2-Methylindolyl-2-oyl]-L-alaninyl}-amino-7-methyl-5,7-dihydro-6H-dibenz[b,d]azepin-6-one Following the General Procedure of Step B of Example 1-C using the compound made above, the title compound was prepared as a free base, which was purified with flash chromatography (silica, 4% MeOH/CH$_2$Cl$_2$) to give the title compound.

Accurate mass Calcd for C$_{28}$H$_{29}$N$_4$O$_3$: 469.2239 (M+H)$^+$; Found: 469.2233. $^1$H nmr (CDCl$_3$): δ=3.34(s, 3H), 1.57 (s, 1.5H), 1.56 (s, 1.5H), 1.46 (d, 1.5H), 1.41 (d, 1.5H).

Example 21

Synthesis of 5-(S)-{N'-[(S)-2-Methylindolyl-2-oyl]-L-alaninyl}-amino-7-methyl-5,7-dihydro-6H-dibenz[b,d]azepin-6-one Step A: Synthesis of 5-(S)-{N'-[N"-tert-boc-(S)-2-Methylindolyl-2-oyl]-L-alaninyl}-amino-7-methyl-5,7-dihydro-6H-dibenz[b,d]azepin-6-one Following General Procedure D using N-tert-Boc-(S)-2-methylindoline-2-carboxylic acid (Example 20-D, above) and (S)-5-(L-alaninyl)-amino-7-methyl-5,7-dihydro-6H-dibenz[b,d]azepin-6-one (Example 3-B), the title compound was prepared.

C$_{33}$H$_{36}$N$_4$O$_5$ (MW=568.670); mass spectroscopy (MH$^+$) 569.

Step B: Synthesis of 5-{N'-[(S)-2-Methylindolyl-2-oyl]-L-alaninyl}-amino-7-methyl-5,7-dihydro-6H-dibenz[b,d]azepin-6-one Following the General Procedure of Step B of Example 1-C using the compound made above, the title compound was prepared as a free base, which was purified with flash chromatography (silica, 4% MeOH/CH$_2$Cl$_2$) to give the title compound.

Accurate mass Calcd for C$_{28}$H$_{29}$N$_4$O$_3$: 469.2239 (M+H)$^+$; Found: 469.2260. $^1$H nmr (CDCl$_3$): δ=3.34 (s, 3H), 1.57 (s, 3H), 1.42 (d, 3H).

Example 22

Synthesis of 5-[N'-(Indole-2-oyl)-L-alaninyl]-amino-7-methyl-5,7-dihydro-6H-dibenz[b,d]azepin-6-one Following General Procedure D using Indole-2-carboxylic acid (Aldrich) and 5-(L-alaninyl)-amino-7-methyl-5,7-dihydro-6H-dibenz[b,d]azepin-6-one (Example 3-B), the title compound was prepared.

Accurate mass Calcd for C$_{27}$H$_{24}$N$_4$O$_3$: 453.1926 (M+H)$^+$; Found: 453.1917. $^1$H nmr (CDCl$_3$): δ=3.53 (s, 1.5H), 3.51 (s, 1.5H), 1.83 (d, 1.5H), 1.67 (d, 1.5H).

Example 23

Synthesis of 1-(S)-[N'-(3,3-Dimethylindolyl-2-oyl)-L-alaninyl]-amino-3-methyl-4,5,6,7-tetrahydro-2H-3-benzazepin-2-one Step A: Synthesis of 1-(S)-[N'-(N"-tert-boc-3,3-Dimethylindolyl-2-oyl)-L-alaninyl]-amino-3-methyl-4,5,6,7-tetrahydro-2H-3-benzazepin-2-one Following General Procedure D using N-tert-Boc-(S)-3,3-dimethylindoline-2-carboxylic acid (Example 19-B, above) and (N)-1-(S)-(L-alaninyl)amino-3-methyl-4,5,6,7-tetrahydro-2H-3-benzazepin-2-one, the single diastereomer was isolated as the first eluting diastereomer from HPLC on a Metasil AQC18 column. Flow rate: 10 ml/min; 1: 214 nm; eluent: CH$_3$CN/0.01% HCl), the title compound was prepared.

C$_{30}$H$_{38}$N$_4$O$_5$ (MW=534.72); mass spectroscopy (M+1)$^+$ 535.

Step B: Synthesis of 1-(S)-[N'-(3,3-Dimethylindolyl-2-oyl)-L-alaninyl]-amino-3-methyl-4,5,6,7-tetrahydro-2H-3-benzazepin-2-one Following the General Procedure of Step B of Example 1-C using the compound made above, the title compound was prepared as a free base, which was purified with flash chromatography [silica, 5% MeOH (7 N NH$_3$)/CH$_2$Cl$_2$) to give the title compounds.

Isomer 1: Accurate mass Calcd for C$_{25}$H$_{31}$N$_4$O$_3$: 435.2396 (MH$^+$); Found: 435.2404. $^1$H nmr (CDCl$_3$):δ=3.02 (s, 3H), 1.58 (s, 3H), 1.50 (d, 3H), 1.11 (s, 3H).

Isomer 2: Accurate mass Calcd for C$_{25}$H$_{31}$N$_4$O$_3$: 435.2396 (MH$^+$); Found: 435.2382. $^1$H nmr (CDCl$_3$): δ=3.02 (s, 3H), 1.58 (s, 3H), 1.50 (d, 3H), 1.10 (s, 3H).

Example 24

Synthesis of 1-(S)-[N'-(1,2,3,4-Tetrahydroquinolyl-2-oyl)-L-alaninyl]-amino-3-methyl-4,5,6,7-tetrahydro-2H-3-benzazepin-2-one Step A: Synthesis of 1-(S)-[N'-(N"-tert-boc-1,2,3,4-Tetrahydroquinolyl-2-oyl)-L-alaninyl]-amino-3-methyl-4,5,6,7-tetrahydro-2H-3-benzazepin-2-one Following General Procedure D using N-tert-Boc-1,2,3,4-tetrahydroquinoline-2-carboxylic acid (Example 18-B, above) and (N)-(S)-1-(L-alaninyl)amino-3-methyl-4,5,6,7-tetrahydro-2H-3-benzazepin-2-one, the single diastereomer was isolated as the first eluting diastereomer from HPLC on a Metasil AQC18 column. Flow rate: 10 ml/min; 1: 214 nm; eluent: CH$_3$CN/0.01% HCl), the title compound was prepared.

C$_{29}$H$_{36}$N$_4$O$_5$ (MW=520.69); mass spectroscopy (M+H)$^+$ 521.

Step B: Synthesis of 1-(S)-[N'-(1,2,3,4-Tetrahydroquinolyl-2-oyl)-L-alaninyl]-amino-3-methyl-4,5,6,7-tetrahydro-2H-3-benzazepin-2-one Following the General Procedure of Step B of Example 1-C using the compound made above, the title compound was prepared as a free base, which was purified by flash chromatography [silica, 5% MeOH (7 N NH$_3$)/CH$_2$Cl$_2$) to give the title compound as a mixture of two diastereomers.

Accurate mass Calcd for C$_{24}$H$_{28}$N$_4$O$_3$: 421.2239 (MH$^+$); Found: 421.2219. $^1$H nmr (CDCl$_3$): δ=3.02 (s, 3H), 1.51–1.42 (m, 3H).

Reverse phase HPLC separation gave the title compounds as hydrochloride salts.

Isomer 1: C$_{24}$H$_{28}$N$_4$O$_3$ (MW=420.510); mass spectroscopy (M+H)$^+$ 421. $^1$H nmr (DMSO-d6): δ=2.90 (s, 3H), 1.30 (d, 3H).

A mixture of isomer 1 and isomer 2: Accurate mass Calcd for C$_{24}$H$_{28}$N$_4$O$_3$: 421.2239 (MH$^+$); Found: 421.2226. $^1$H nmr (DMSO-d6): δ=2.89 (s, 3H), 1.38–1.28 (m, 3H).

Example 25

Synthesis of 3-[(N'-(3-Pyridinoyl)-L-Alaninyl)]amino-2,3-dihydro-1-methyl-5-phenyl-1H-1,4-Benzodiazepin-2-one Following one or more of the general procedures outlined above, using 3-pyridine carboxylic acid and 3-[(L-alaninyl)]amino-2,3-dihydro-1-methyl-5-phenyl-1H-1,4-benzodiazepin-2-one, as described in Example 4-B above, the title compound was prepared. The molecular weight as determined by mass spectrometry (FD) was: 442 (M+H).

Example 26

Synthesis of 5-{N'-(2-Piperidine carboxyl)-L-alaninyl}-amino-7-methyl-5,7-dihydro-6H-dibenz[b,d]azepin-6-one Following one or more of the general procedures outlined above, using 2-piperidine carboxylic acid and 5-(L-alaninyl)-amino-7-methyl-5,7-dihydro-6H-dibenz[b,d]azepin-6-one, as described in Example 3-B, the title compound was prepared.

Example 27

Synthesis of 5-[N'-(Quinolyl-2-oyl)-L-alaninyl]-amino-7-methyl-5,7-dihydro-6H-dibenz[b,d]azepin-6-one Following General Procedure D using quinaldic acid (Aldrich) and 5-(L-alaninyl)-amino-7-methyl-5,7-dihydro-6H-dibenz[b,d]azepin-6-one (Example 3-B), the title compound was prepared.

Anal. Calcd for $C_{28}H_{24}N_4O_3$: C, 72.40; H, 5.21; N, 12.06; Found: C, 72.23; H, 5.20; N, 11.79. Accurate mass Calcd for $C_{28}H_{24}N_4O_3$ ($MH^+$): 465.1926; Found: 465.1918.

Example 28

Cellular Screen for the Detection of Inhibitors of β-Amyloid Production

A compound of formula I above was assayed for its ability to inhibit β-amyloid production in a cell line possessing the Swedish mutation. This screening assay employed cells (K293=human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[8] and Citron et al.[16]. This mutation is commonly called the Swedish mutation and the cells, designated as "293 751 SWE", were plated in Corning 96-well plates at 2–4·10$^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266 [P. Seubert, *Nature* (1992) 359:325–327] against amino acids 13–28 of β-amyloid peptide as described in International Patent Application Publication No. 94/10569[8] and stored at 4° C. overnight. An ELISA assay employing labelled antibody 3D6 [P. Seubert, *Nature* (1992) 359:325–327][17] against amino acids 1–5 of β-amyloid peptide was run the next day to measure the amount of β-amyloid peptide produced.

Cytotoxic effects of the compounds were measured by a modification of the method of Hansen, et al.[18]. To the cells remaining in the tissue culture plate was added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562\ nm}$ and the $OD_{650\ nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compound was assayed for β-amyloid peptide production inhibition activity in cells using this assay. The results of this assay demonstrate that the compounds of formula I inhibit β-amyloid peptide production by at least 30% as compared to the control when employed at 10 μg/mL.

Example 29

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) *Nature* 373:523–527].[19] Depending upon which compound is being tested, the compound is usually formulated at between 1 and 10 mg/mL. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-methyl-cellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25 G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/mL aprotinin, 5 mM EDTA, pH 8.0, 10 μg/mL leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, *Nature* (1992) 359:325–327], is specific to amino acids 13–28 of β-amyloid. The antibody 3D6 [Johnson-Wood et al., *PNAS USA* (1997) 94:1550–1555],[20] which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/mL (11 pM) and shows no cross-reactivity to the endogenous murine β-amyloid peptide at concentrations up to 1 ng/mL.

The configuration of the sandwich ELISA quantitating the level of β-amyloid (aa 1–42) employs the mAb 21F12 [Johnson-Wood et al., *PNAS USA* (1997) 94:1550–1555] (which recognizes amino acids 33–42 of β-amyloid) as the capture antibody. Biotinylated 3D6 is also the reporter antibody in this assay which has a lower limit of sensitivity of ~125 pg/mL (28 pM).

The 266 and 21F12 capture mAbs are coated at 10 μg/mL into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/mL in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 mL Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

Formulations other than those described above can also be used for oral delivery and intravenous delivery to a mammal. For oral delivery, the compound can be mixed with either 100% corn oil or, alternatively, in a solution containing 80% corn oil, 19.5% oleic acid and 0.5% labrafil. The compound can be mixed with the above solutions in concentrations ranging from 1 mg/mL to 10 mg/mL. The compound in solution is preferably administered orally to the mammal at a dose volume of 5 mL/kg of body weight. For IV delivery, the compound is preferably mixed with a solution of 3% ethanol, 3% solutol HS-15 and 94% saline. The compound is preferably mixed with the above solution in concentrations ranging from 0.25 mg/mL to 5 mg/mL. The compound in solution is preferably administered by IV to the mammal at a dose volume of 2 mL/kg of body weight.

From the foregoing description, various modifications and changes in the composition and method will occur to those skilled in the art. All such modifications coming within the scope of the appended claims are intended to be included therein.

What is claimed is:

1. A compound which are represented by formula I or Ia below:

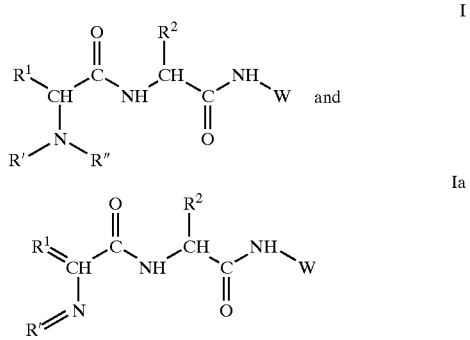

wherein:

$R^1$ together with R' and the carbon and nitrogen atoms attached thereto, respectively, form a nitrogen containing optionally substituted heterocyclic in formula I or a nitrogen containing unsaturated optionally substituted heterocyclic or an optionally substituted heteroaryl group in formula Ia;

R" is selected from the group consisting of hydrogen, alkyl, substituted alkyl and an optionally substituted aryl;

each $R^2$ is independently selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic; and W is a cyclic group selected from the group consisting of:

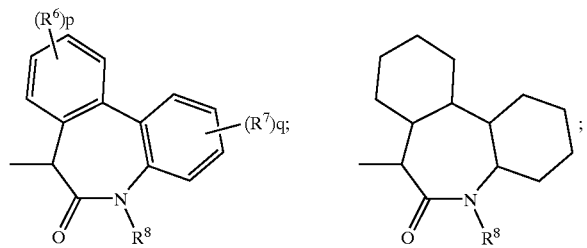

125

-continued

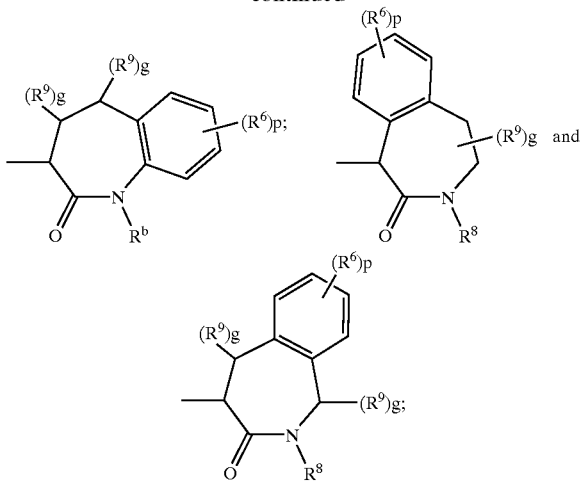

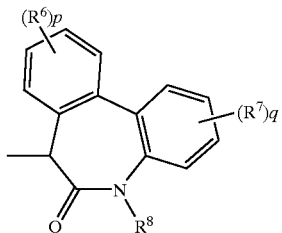

wherein:
each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, optionally substituted aryl, optionally substituted aryloxy, carboxyl, carboxyalkyl, cyano, cycloalkyl, substituted cycloalkyl, halo, optionally substituted heteroaryl, optionally substituted heterocyclic, nitro, thioalkoxy, substituted thioalkoxy, optionally substituted thioaryloxy, optionally substituted thioheteroaryloxy, —SO-alkyl, —SO-substituted alkyl, —SO-optionally substituted aryl, —SO-optionally substituted heteroaryl, —SO$_2$-alkyl, —SO$_2$-substituted alkyl —SO$_2$-optionally substituted aryl, and —SO$_2$-optionally substituted heteroaryl;

each $R^7$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, optionally substituted aryl, optionally substituted aryloxy, carboxyl, carboxyalkyl, cyano, cycloalkyl, substituted cycloalkyl, halo, optionally substituted heteroaryl, optionally substituted heterocyclic, nitro, thioalkoxy, substituted thioalkoxy, optionally substituted thioaryloxy, optionally substituted thioheteroaryloxy, —SO-alkyl, —SO-substituted alkyl, —SO-optionally substituted aryl, —SO-optionally substituted heteroaryl, —SO$_2$-alkyl, —SO$_2$-substituted alkyl, —SO$_2$-optionally substituted aryl, and —SO$_2$-optionally substituted heteroaryl;

$R^8$ is selected from the group consisting of hydrogen, alkyl, substituted alkyl, alkenyl, substituted alkenyl, alkynyl, substituted alkynyl, acyl, optionally substituted aryl, cycloalkyl, substituted cycloalkyl, cycloalkenyl, substituted cycloalkenyl, optionally substituted heteroaryl and optionally substituted heterocyclic;

each $R^9$ is independently selected from the group consisting of alkyl, substituted alkyl, alkenyl, substituted alkenyl, alkynyl, substituted alkynyl, optionally substituted aryl, cycloalkyl, substituted cycloalkyl, cycloalkenyl, substituted cycloalkenyl,

126 optionally substituted heteroaryl and optionally substituted heterocyclic;

g is an integer from 0 to 2; p is an integer from 0 to 4; and q is an integer from 0 to 4; and pharmaceutically acceptable salts thereof.

2. The compound according to claim 1 wherein W has the formula:

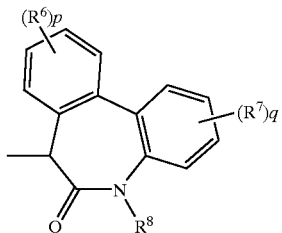

wherein $R^6$, $R^7$, $R^8$, p and q are as defined in claim 1.

3. The compound according to claim 1 wherein W has the formula:

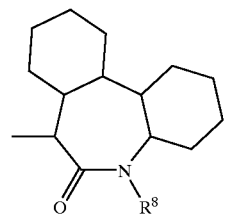

wherein $R^8$ is as defined in claim 1.

4. The compound according to claim 1 wherein W has the formula:

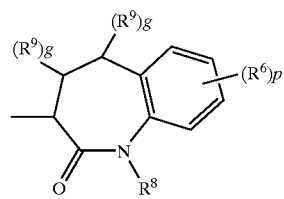

wherein $R^6$, $R^8$, $R^9$, g and p are as defined in claim 1.

5. The compound according to claim 1 wherein W has the formula:

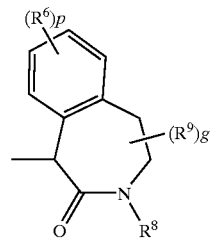

wherein $R^6$, $R^8$, $R^9$, g and p are as defined in claim 1.

6. The compound according to claim 1 wherein W has the formula:

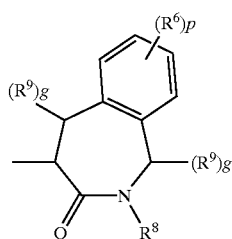

wherein $R^6$, $R^8$, $R^9$, g and p are as defined in claim 1.

7. A pharmaceutical composition comprising a pharmaceutically acceptable carrier and a pharmaceutically effective amount of a compound or mixture of compounds according to claim 2, 3, 4, 5 or 6.

8. A method for inhibiting β-amyloid peptide release and/or its synthesis in a cell which method comprises administering to such a cell an amount of a compound or a mixture of compounds according to claim 2, 3, 4, 5 or 6 effective in inhibiting the cellular release and/or synthesis of β-amyloid peptide.

9. A method for treating a patient with AD in order to inhibit further deterioration in the condition of that patient which method comprises administering to said patient a pharmaceutical composition comprising a pharmaceutically acceptable inert carrier and an effective amount of a compound or a mixture of compounds according to claim 2, 3, 4, 5 or 6.

10. The compound according to claim 1 wherein R" is hydrogen.

11. The compound according to claim 10 wherein $R^1$, R' and the nitrogen and carbon atoms attached thereto form an optionally substituted heterocyclic ring.

12. The compound according to claim 11 wherein said optionally substituted heterocyclic ring is a saturated or unsaturated ring selected from the group consisting of:

monocyclic nitrogen-containing heterocycles optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heterocycles wherein the second cyclic group is selected from the group consisting of aryl, cycloalkyl, cycloalkenyl, heteroaryl and heterocyclic wherein the bicyclic group includes fused bicyclics, bridged bicyclics and spiro bicyclics and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy; and tricyclic heterocycles wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy.

13. The compound according to claim 12 wherein said optionally substituted heterocyclic ring is selected from the group consisting of pyrrolidinyl, 4-hydroxypyrrolidinyl, azetidinyl, thiazolidinyl, piperidinyl, piperizinyl, dihydroindolyl, 2,3-dihydroindol-2-yl, tetrahydroquinolinyl, 1,2,3,4-tetrahydroquinolin-2-yl, morpholinyl, thiomorpholinyl, 4-halopyrrolidinyl, 3-phenylpyrrolidinyl, 4-aminopyrrolidinyl, 3-methoxypyrrolidinyl, 4,4-dimethylpyrrolidinyl and 5,5-dimethylthiazolindin-4-yl.

14. The compound according to claim 10 wherein $R^1$, R' and the nitrogen and carbon atoms attached thereto form an optionally substituted heteroaryl ring.

15. The compound according to claim 14 wherein said optionally substituted heteroaryl ring is selected from the group consisting of:

monocyclic heteroaryls optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heteroaryls wherein the second cyclic group is selected from the group consisting of aryl, cycloalkyl, cycloalkenyl, heteroaryl and heterocyclic wherein the bicyclic group includes fused bicyclics and bridged bicyclics and further wherein each ring is optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second cyclic group is a cycloalkyl, cycloalkenyl or a heterocyclic group, keto and thioketo groups; and tricyclic heteroaryls wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, alkyl, substituted alkyl, alkoxy, substituted alkoxy, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second and/or third cyclic group is a cycloalkyl, cycloalkenyl or a heterocyclic group, keto and thioketo groups.

16. The compound according to claim 15 wherein said optionally substituted heteroaryl group is selected from the group consisting of pyridinyl, 2-quinoxalinyl, indolyl, N-methylindolyl, 3-amino-2-pyrazinyl, 3-amino-5,6-dichloro-2-pyrazinyl, 4-methoxyindolyl and 3-isoquinolinyl.

17. The compound according to claim 1 wherein each $R^2$ is independently selected from the group consisting of alkyl, substituted alkyl, alkenyl, cycloalkyl, optionally substituted aryl, optionally substituted heteroaryl and optionally substituted heterocyclic.

18. The compound according to claim 17 wherein $R^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$-C(O)O-t-butyl, —CH$_2$-C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)═CH$_2$, —CH$_2$CH═CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl and thien-3-yl.

19. The compound according to claim 1 wherein R$^8$ is selected from the group consisting of hydrogen, alkyl, substituted alkyl and cycloalkyl.

20. The compound according to claim 19 wherein R$^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, and cyclohexyl.

21. The compound according to claim 1 wherein R$^9$ is hydrogen, alkyl or substituted alkyl.

22. The compound according to claim 1 wherein R$^9$ is alkyl.

23. A compound selected from the group consisting of:
- 5-(S)-[N'-(L-prolyl)-L-alaninyl]-amino-7-methyl-5,7-dihydro-6H-dibenz[b,d]azepin-one;
- 5-(S)-[N'-(L-homoprolyl)-L-alaninyl]-amino-7-methyl-5,7-dihydro-6H-dibenz[b,d]azepin-one;
- 5-(S)-[N'-(DL-homoprolyl)-L-alaninyl]-amino-7-methyl-5,7-dihydro-6H-dibenz[b,d]azepin-one;
- 5-(S)-[N'-(1,2,3,4-tetrahydroisoquinolin-1-oyl)-L-alaninyl]-amino-7-methyl-5,7-dihydro-6H-dibenz[b,d]azepin-one;
- 5-(S)-[N'-(octahydro-indolyl-2-oyl)-L-alaninyl]-amino-7-methyl-5,7-dihydro-6H-dibenz[b,d]azepin-one;
- 5-{N'-[cis-4-(3-methylbutyl-L-prolyl]-L-alaninyl}-amino-7-methyl-5,7-dihydro-6H-dibenz[b,d]azepin-one;
- 5-{N'-[trans-4-(3-methylbutyl-L-prolyl]-L-alaninyl}-amino-7-methyl-5,7-dihydro-6H-dibenz[b,d]azepin-one;

or a pharmaceutical salt thereof.

24. A pharmaceutical composition comprising a pharmaceutically acceptable carrier and a pharmaceutically effective amount of a compound or mixture of compounds according to claim 1.

25. The pharmaceutical composition according to claim 24 wherein R" is hydrogen.

26. The pharmaceutical composition according to claim 25 wherein R$^1$, R' and the nitrogen and carbon atoms attached thereto form an optionally substituted heterocyclic ring.

27. The pharmaceutical composition according to claim 26 wherein said optionally substituted heterocyclic ring is a saturated or unsaturated ring selected from the group consisting of:

monocyclic nitrogen-containing heterocycles optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heterocycles wherein the second cyclic group is selected from the group consisting of aryl, cycloalkyl, cycloalkenyl, heteroaryl and heterocyclic wherein the bicyclic group includes fused bicyclics, bridged bicyclics and spiro bicyclics and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy; and tricyclic heterocycles wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy.

28. The pharmaceutical composition according to claim 27 wherein said optionally substituted heterocyclic ring is selected from the group consisting of pyrrolidinyl, 4-hydroxypyrrolidinyl, azetidinyl, thiazolidinyl, piperidinyl, piperizinyl, dihydroindolyl, 2,3-dihydroindol-2-yl, tetrahydroquinolinyl, 1,2,3,4-tetrahydroquinolin-2-yl, morpholinyl, thiomorpholinyl, 4-halopyrrolidinyl, 3-phenylpyrrolidinyl, 4-aminopyrrolidinyl, 3-methoxypyrrolidinyl, 4,4-dimethylpyrrolidinyl and 5,5-dimethylthiazolindin-4-yl.

29. The pharmaceutical composition according to claim 25 wherein R$^1$, R' and the nitrogen and carbon atoms attached thereto form an optionally substituted heteroaryl ring.

30. The pharmaceutical composition according to claim 29 wherein said optionally substituted heteroaryl ring is selected from the group consisting of:

monocyclic heteroaryls optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heteroaryls wherein the second cyclic group is selected from the group consisting of aryl, cycloalkyl, cycloalkenyl, heteroaryl and heterocyclic wherein the bicyclic group includes fused bicyclics and bridged bicyclics and further wherein each ring is optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second cyclic group is a cycloalkyl, cycloalkenyl or a heterocyclic group, keto and thioketo groups; and tricyclic heteroaryls wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, alkyl, substituted alkyl, alkoxy, substituted alkoxy, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second and/or third cyclic group is a cycloalkyl, cycloalkenyl or a heterocyclic group, keto and thioketo groups.

31. The pharmaceutical composition according to claim 30 wherein said optionally substituted heteroaryl group is selected from the group consisting of pyridinyl, 2-quinoxalinyl, indolyl, N-methylindolyl, 3-amino-2-pyrazinyl, 3-amino-5,6-dichloro-2-pyrazinyl, 4-methoxyindolyl and 3-isoquinolinyl.

32. The pharmaceutical composition according to claim 24 wherein each $R^2$ is independently selected from the group consisting of alkyl, substituted alkyl, alkenyl, cycloalkyl, optionally substituted aryl, optionally substituted heteroaryl and optionally substituted heterocyclic.

33. The pharmaceutical composition according to claim 32 wherein $R^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl) phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$-C(O)O-t-butyl, —CH$_2$-C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH—Boc, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl and thien-3-yl.

34. The pharmaceutical composition according to claim 24 wherein $R^8$ is selected from the group consisting of hydrogen, alkyl, substituted alkyl and cycloalkyl.

35. The pharmaceutical composition according to claim 34 wherein $R^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, and cyclohexyl.

36. The pharmaceutical composition according to claim 24 wherein $R^9$ is hydrogen, alkyl or substituted alkyl.

37. The pharmaceutical composition according to claim 36 wherein $R^9$ is alkyl.

38. A pharmaceutical composition comprising a pharmaceutically acceptable carrier and a pharmaceutically effective amount of a compound selected from the group consisting of:

5-(S)-[N'-(L-prolyl)-L-alaninyl]-amino-7-methyl-5,7-dihydro-6H-dibenz[b,d]azepin-one;

5-(S)-[N'-(L-homoprolyl)-L-alaninyl]-amino-7-methyl-5,7-dihydro-6H-dibenz[b,d]azepin-one;

5-(S)-[N'-(DL-homoprolyl)-L-alaninyl]-amino-7-methyl-5,7-dihydro-6H-dibenz[b,d]azepin-one;

5-(S)-[N'-(1,2,3,4-tetrahydroisoquinolin-1-oyl)-L-alaninyl]-amino-7-methyl-5,7-dihydro-6H-dibenz[b,d]azepin-one;

5-(S)-[N'-(octahydro-indolyl-2oyl)-L-alaninyl]-amino-7-methyl-5,7-dihydro-6H-dibenz[b,d]azepin-one;

5-{N'-[cis-4-(3-methylbutyl-L-prolyl]-L-alaninyl}-amino-7-methyl-5,7-dihydro-6H-dibenz[b,d]azepin-one;

5-{N'-[trans-4-(3-methylbutyl-L-prolyl]-L-alaninyl}-amino-7-methyl-5,7-dihydro-6H-dibenz[b,d]azepin-one;

or a pharmaceutical salt thereof.

39. A method for inhibiting β-amyloid peptide release and/or its synthesis in a cell which method comprises administering to such a cell an amount of a compound or a mixture of compounds according to formula I or Ia as defined in claim 1 effective in inhibiting the cellular release and/or synthesis of β-amyloid peptide.

40. A method for treating a patient with AD in order to inhibit further deterioration in the condition of that patient which method comprises administering to said patient a pharmaceutical composition comprising a pharmaceutically acceptable inert carrier and an effective amount of a compound of a mixture of compounds of formula I or Ia as defined in claim 1.

41. The method according to claims 39 or 40 wherein R" is hydrogen.

42. The method according to claim 41 wherein $R^1$, R' and the nitrogen and carbon atoms attached thereto form an optionally substituted heterocyclic ring.

43. The method according to claim 42 wherein said optionally substituted heterocyclic ring is a saturated or unsaturated ring selected from the group consisting of:

monocyclic nitrogen-containing heterocycles optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heterocycles wherein the second cyclic group is selected from the group consisting of aryl, cycloalkyl, cycloalkenyl, heteroaryl and heterocyclic wherein the bicyclic group includes fused bicyclics, bridged bicyclics and spiro bicyclics and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy; and tricyclic heterocycles wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, keto, thioketo, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy.

44. The method according to claim 43 wherein said optionally substituted heterocyclic ring is selected from the group consisting of pyrrolidinyl, 4-hydroxypyrrolidinyl, azetidinyl, thiazolidinyl, piperidinyl, piperizinyl, dihydroindolyl, 2,3-dihydroindol-2-yl, tetrahydroquinolinyl, 1,2,3,4-tetrahydroquinolin-2-yl, morpholinyl, thiomorpholinyl, 4-halopyrrolidinyl, 3-phenylpyrrolidinyl, 4-aminopyrrolidinyl, 3-methoxypyrrolidinyl, 4,4-dimethylpyrrolidinyl and 5,5-dimethylthiazolindin-4-yl.

45. The method according to claim 41 wherein $R^1$, $R'$ and the nitrogen and carbon atoms attached thereto form an optionally substituted heteroaryl ring.

46. The method according to claim 45 wherein said optionally substituted heteroaryl ring is selected from the group consisting of:

monocyclic heteroaryls optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy and thioheteroaryloxy;

bicyclic heteroaryls wherein the second cyclic group is selected from the group consisting of aryl, cycloalkyl, cycloalkenyl, heteroaryl and heterocyclic wherein the bicyclic group includes fused bicyclics and bridged bicyclics and further wherein each ring is optionally substituted with 1 to 3 substituents selected from the group consisting of hydroxyl, alkyl, substituted alkyl, alkoxy, substituted alkoxy, amino, substituted amino, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second cyclic group is a cycloalkyl, cycloalkenyl or a heterocyclic group, keto and thioketo groups; and tricyclic heteroaryls wherein the second and/or third cyclic group is independently selected from the group consisting of aryl, cycloalkyl, cycloalkenyl, heteroaryl and heterocyclic wherein the tricyclic group includes fused tricyclics, bridged tricyclics, spiro tricyclics and any combination thereof and further wherein each ring is optionally substituted with 1 to 3 substituents selected from the group consisting of hydroxyl, alkyl, substituted alkyl, alkoxy, substituted alkoxy, aryl, aryloxy, cyano, cycloalkyl, substituted cycloalkyl, halo, heteroaryl, heteroaryloxy, nitro, thiol, thioalkoxy, substituted thioalkoxy, thioaryloxy, thioheteroaryloxy and, in addition, when the second and/or third cyclic group is a cycloalkyl, cycloalkenyl or a heterocyclic group, keto and thioketo groups.

47. The method according to claim 46 wherein said optionally substituted heteroaryl group is selected from the group consisting of pyridinyl, 2-quinoxalinyl, indolyl, N-methylindolyl, 3-amino-2-pyrazinyl, 3-amino-5,6-dichloro-2-pyrazinyl, 4-methoxyindolyl and 3-isoquinolinyl.

48. The method according to claims 39 or 40 wherein each $R^2$ is independently selected from the group consisting of alkyl, substituted alkyl, alkenyl, cycloalkyl, optionally substituted aryl, optionally substituted heteroaryl and optionally substituted heterocyclic.

49. The method according to claim 48 wherein $R^2$ is selected from the group consisting of methyl, ethyl, n-propyl, iso-propyl, n-butyl, iso-butyl, sec-butyl, tert-butyl, —$CH_2CH(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, —$CH_2$-cyclohexyl, —$CH_2CH_2$-cyclopropyl, —$CH_2CH_2$-cyclohexyl, —$CH_2$-indol-3-yl,p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-$(HOOCCH_2O)$-benzyl, 2-aminopyrid-6-yl, p-(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thiophen-2-yl, —$CH_2$(1-methyl)cyclopropyl, —$CH_2$-thiophen-3-yl, thiophen-3-yl, thiophen-2-yl, —$CH_2$-C(O)O-t-butyl, —$CH_2$-C$(CH_3)_3$, —$CH_2CH(CH_2CH_3)_2$, 2-methylcyclopentyl, cyclohex-2-enyl, —CH[CH$(CH_3)_2$]COOCH$_3$, —$CH_2CH_2N(CH_3)_2$, —$CH_2C(CH_3)$=CH$_2$, —$CH_2$CH=CHCH$_3$ (cis and trans), —$CH_2$OH, —CH(OH)CH$_3$, —CH(O-t-butyl)CH$_3$, —$CH_2OCH_3$, —$(CH_2)_4$NH—Boc, —$(CH_2)_4NH_2$, —$CH_2$-pyridyl, pyridyl, —$CH_2$-naphthyl, —$CH_2$-(N-morpholino), p-(N-morpholino-$CH_2CH_2O$)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —$CH_2CH_2SCH_3$, thien-2-yl and thien-3-yl.

50. The method according to claims 39 or 40 wherein $R^8$ is selected from the group consisting of hydrogen, alkyl, substituted alkyl and cycloalkyl.

51. The method according to claim 50 wherein $R^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl and cyclohexyl.

52. The method according to claims 39 or 40 wherein $R^9$ is hydrogen, alkyl or substituted alkyl.

53. The method according to claim 52 wherein $R^4$ is alkyl.

54. The method according to claims 39 or 40 wherein the compound according to formula I or Ia is selected from the group consisting of:

5-(S)-[N'-(L-prolyl)-L-alaninyl]-amino-7-methyl-5,7-dihydro-6H-dibenz[b,d]azepin-one;

5-(S)-[N'-(L-homoprolyl)-L-alaninyl]-amino-7-methyl-5,7-dihydro-6H-dibenz[b,d]azepin-one;

5-(S)-[N'-(DL-homoprolyl)-L-alaninyl]-amino-7-methyl-5,7-dihydro-6H-dibenz[b,d]azepin-one;

5-(S)-[N'-(1,2,3,4-tetrahydroisoquinolin-1-oyl)-L-alaninyl]-amino-7-methyl-5,7-dihydro-6H-dibenz[b,d]azepin-one;

5-(S)-[N'-(octahydro-indolyl-2oyl)-L-alaninyl]-amino-7-methyl-5,7-dihydro-6H-dibenz[b,d]azepin-one;

5-{N'-[cis-4-(3-methylbutyl-L-prolyl]-L-alaninyl}-amino-7-methyl-5,7-dihydro-6H-dibenz[b,d]azepin-one;

5-{N'-[trans-4-(3-methylbutyl-L-prolyl]-L-alaninyl}-amino-7-methyl-5,7-dihydro-6H-dibenz[b,d]azepin-one;

and pharmaceutical salts thereof.

55. A compound selected from the group consisting of 5-(S)-[N'-(decahydro-quinolyl-2-oyl)-L-alaninyl]-amino-7-methyl-5,7-dihydro-6H-dibenz[b,d]azepin-6-one 5-[N'-(decahydro-quinolyl-2-oyl)-L-alaninyl]-amino-7-methyl-5,7-dihydro-6H-dibenz[b,d]azepin-6-one 5-{N'-[(S)-indolyl-2-oyl]-L-alaninyl}-amino-7-methyl-5,7-dihydro-6H-dibenz[b,d]azepin-6-one 5-(S)-{N'-[(S)-indolyl-2-oyl]-L-alaninyl}-amino-7-methyl-5,7-dihydro-6H-dibenz[b,d]azepin-6-one 5-[N'-(L-trans-4-hydroxyprolyl)-L-alaninyl]-amino-7-methyl-5,7-dihydro-6H-dibenz[b,d]azepin-6-one 5-(S)-[N'-(1,2,3,4-tetrahydroquinolyl-2-oyl)-L-alaninyl]-amino-7-methyl-5,7-dihydro-6H-dibenz[b,d]azepin-6-one 5-(S)-[N'-(3,3-dimethylindolyl-2-oyl)-L-alaninyl]-amino-7-methyl-5,7-dihydro-6H-dibenz[b,d]azepin-6-one 5-{N'-[(S)-2-methylindolyl-2-oyl]-L-alaninyl}-amino-7-methyl-5,7-dihydro-6H-dibenz[b,d]azepin-6-one 5-(S)-{N'-[(S)-2-methylindolyl-2-oyl]-L-alaninyl}-amino-7-methyl-5,7-dihydro-6H-dibenz[b,d]azepin-6-one 5-[N'-(indole-2-oyl)-L-alaninyl]-amino-7-methyl-5,7-dihydro-6H-dibenz[b,d]azepin-6-one 1-(S)-[N'-(3,3-dimethylindolyl-2-oyl)-L-alaninyl]-amino-3-methyl-4,5,6,7-tetrahydro-2H-3-benzazepin-2-one 1-(S)-[N'-(1,2,3,4-tetrahydroquinolyl-2-oyl)-L-alaninyl]-amino-3-methyl-4,5,6,7-tetrahydro-2H-3-benzazepin-2-one 3-[(N'-(3-pyridinoyl)-L-alaninyl)]amino-2,3-dihydro-1-methyl-5-phenyl-1H-1,4-benzodiazepin-2-one 5-{N'-(2-piperidine carboxyl)-L-alaninyl}-amino-7-methyl-5,7-dihydro 6H-dibenz[b,d]azepin-6-one (both enantiomers), 5-[N'-(quinolyl-2-oyl)-L-alaninyl]-amino-7-methyl-5,7-dihydro-6H-dibenz[b,d]azepin-6-one and pharmaceutically acceptable salts thereof.

56. A pharmaceutical composition comprising a pharmaceutically acceptable carrier and a pharmaceutically effective amount of a compound selected from the group consisting of:

5-(S)-[N'-(decahydro-quinolyl-2-oyl)-L-alaninyl]-amino-7-methyl-5,7-dihydro-6H-dibenz[b,d]azepin-6-one 5-[N'-(decahydro-quinolyl-2-oyl)-L-alaninyl]-amino-7-methyl-5,7-dihydro-6H-dibenz[b,d]azepin-6-one 5-{N'-[(S)-indolyl-2-oyl]-L-alaninyl}-amino-7-methyl-5,7-dihydro-6H-dibenz[b,d]azepin-6-one 5-(S)-{N'-[(S)-indolyl-2-oyl]-L-alaninyl}-amino-7-methyl-5,7-dihydro-6H-dibenz[b,d]azepin-6-one 5-[N'-(L-trans-4-hydroxyprolyl)-L-alaninyl]-amino-7-methyl-5,7-dihydro-6H-dibenz[b,d]azepin-6-one 5-(S)-[N'-(1,2,3,4-tetrahydroquinolyl-2-oyl)-L-alaninyl]-amino-7-methyl-5,7-dihydro-6H-dibenz[b,d]azepin-6-one 5-(S)-[N'-(3,3-dimethylindolyl-2-oyl)-L-alaninyl]-amino-7-methyl-5,7-dihydro-6H-dibenz[b,d]azepin-6-one 5-{N'-[(S)-2-methylindolyl-2-oyl]-L-alaninyl}-amino-7-methyl-5,7-dihydro-6H-dibenz[b,d]azepin-6-one 5-(S)-{N'-[(S)-2-methylindolyl-2-oyl]-L-alaninyl}-amino-7-methyl-5,7-dihydro-6H-dibenz[b,d]azepin-6-one 5-[N'-(indole-2-oyl)-L-alaninyl]-amino-7-methyl-5,7-dihydro-6H-dibenz[b,d]azepin-6-one 1-(S)-[N'-(3,3-dimethylindolyl-2-oyl) -L-alaninyl]-amino-3-methyl-4,5,6,7-tetrahydro-2H-3-benzazepin-2-one 1-(S)-[N'-(1,2,3,4-tetrahydroquinolyl-2-oyl)-L-alaninyl]-amino-3-methyl-4,5,6,7-tetrahydro-2H-3-benzazepin-2-one 3-[(N'-(3-pyridinoyl)-L-alaninyl)]amino-2,3-dihydro-1-methyl-5-phenyl-1H-1,4-benzodiazepin-2-one 5-{N'-(2-piperidine carboxyl)-L-alaninyl}-amino-7-methyl-5,7-dihydro 6H-dibenz[b,d]azepin-6-one (both enantiomers), 5-[N'-(quinolyl-2-oyl)-L-alaninyl]-amino-7-methyl-5,7-dihydro-6H-dibenz[b,d]azepin-6-one or a pharmaceutically acceptable salt thereof.

57. The method of claims 39 or 40 wherein the compound is selected from the group consisting of:

5-(S)-[N'-(decahydro-quinolyl-2-oyl)-L-alaninyl]-amino-7-methyl-5,7-dihydro-6H-dibenz[b,d]azepin-6-one 5-[N'-(decahydro-quinolyl-2-oyl)-L-alaninyl]-amino-7-methyl-5,7-dihydro-6H-dibenz[b,d]azepin-6-one 5-{N'-[(S)-indolyl-2-oyl]-L-alaninyl}-amino-7-methyl-5,7-dihydro-6H-dibenz[b,d]azepin-6-one 5-(S)-{N'-[(S)-indolyl-2-oyl]-L-alaninyl}-amino-7-methyl-5,7-dihydro-6H-dibenz[b,d]azepin-6-one 5-[N'-(L-trans-4-hydroxyprolyl)-L-alaninyl]-amino-7-methyl-5,7-dihydro-6H-dibenz[b,d]azepin-6-one 5-(S)-[N'-(1,2,3,4-tetrahydroquinolyl-2-oyl)-L-alaninyl]-amino-7-methyl-5,7-dihydro-6H-dibenz[b,d]azepin-6-one 5-(S)-[N'-(3,3-dimethylindolyl-2-oyl)-L-alaninyl]-amino-7-methyl-5,7-dihydro-6H-dibenz[b,d]azepin-6-one 5-{N'-[(S)-2-methylindolyl-2-oyl]-L-alaninyl}-amino-7-methyl-5,7-dihydro-6H-dibenz[b,d]azepin-6-one 5-(S)-{N'-[(S)-2-methylindolyl-2-oyl]-L-alaninyl}-amino-7-methyl-5,7-dihydro-6H-dibenz[b,d]azepin-6-one 5-[N'-(indole-2-oyl)-L-alaninyl]-amino-7-methyl-5,7-dihydro-6H-dibenz[b,d]azepin-6-one 1-(S)-[N'-(3,3-dimethylindolyl-2-oyl)-L-alaninyl]-amino-3-methyl-4,5,6,7-tetrahydro-2H-3-benzazepin-2-one 1-(S)-[N'-(1,2,3,4-tetrahydroquinolyl-2-oyl)-L-alaninyl]-amino-3-methyl-4,5,6,7-tetrahydro-2H-3-benzazepin-2-one 3-[(N'-(3-pyridinoyl)-L-alaninyl)]amino-2,3-dihydro-1-methyl-5-phenyl-1H-1,4-benzodiazepin-2-one 5-{N'-(2-piperidine carboxyl)-L-alaninyl}-amino-7-methyl-5,7-dihydro 6H-dibenz[b,d]azepin-6-one (both enantiomers), 5-[N'-(quinolyl-2-oyl)-L-alaninyl]-amino-7-methyl-5,7-dihydro-6H-dibenz[b,d]azepin-6-one and pharmaceutically acceptable salts thereof.

* * * * *